US012630548B2

(12) United States Patent
McInally et al.

(10) Patent No.: US 12,630,548 B2

(45) Date of Patent: May 19, 2026

(54) AZETIDINE DERIVATIVES FOR THE TREATMENT OF INTEGRIN ASSOCIATED DISEASES

(71) Applicant: The University of Nottingham, Nottingham (GB)

(72) Inventors: Thomas McInally, Nottingham (GB); Simon MacDonald, Hitchin (GB); Christopher Moody, Nottingham (GB); Richard Hatley, Hitchin (GB); Tim Barrett, Stevenage (GB); Morag Watson, Nottingham (GB); Timothy Richie, Nottingham (GB)

(73) Assignee: The University of Nottingham, Nottingham (GB)

( * ) Notice: Subject to any disclaimer, the term of this patent is extended or adjusted under 35 U.S.C. 154(b) by 630 days.

(21) Appl. No.: 18/004,757

(22) PCT Filed: Jul. 8, 2021

(86) PCT No.: PCT/GB2021/051742

§ 371 (c)(1),
(2) Date: Jan. 9, 2023

(87) PCT Pub. No.: WO2022/008918

PCT Pub. Date: Jan. 13, 2022

(65) Prior Publication Data

US 2023/0257375 A1 Aug. 17, 2023

(30) Foreign Application Priority Data

Jul. 10, 2020 (GB) ...................................... 2010626

(51) Int. Cl.
*C07D 471/04* (2006.01)

(52) U.S. Cl.
CPC .................................. *C07D 471/04* (2013.01)

(58) Field of Classification Search
CPC ..................................................... C07D 471/04
See application file for complete search history.

(56) References Cited

U.S. PATENT DOCUMENTS

2013/0303509 A1 11/2013 Hansen et al.
2020/0109141 A1 4/2020 Cha et al.

FOREIGN PATENT DOCUMENTS

| | | | | | |
|---|---|---|---|---|---|
| WO | 9967230 | A1 | | 12/1999 | |
| WO | WO-2005016883 | A2 | * | 2/2005 | ........... C07D 409/06 |
| WO | 2008125215 | A1 | | 10/2008 | |
| WO | 2015048819 | A1 | | 4/2015 | |
| WO | 2018089355 | A1 | | 5/2018 | |
| WO | 2018089358 | A1 | | 5/2018 | |
| WO | 2018119087 | A1 | | 6/2018 | |
| WO | 2020076862 | A1 | | 4/2020 | |

OTHER PUBLICATIONS

Procopiou, et al.; Journal of Medicinal Chemistry; v61, pp. 8417-8443; 2018 (Year: 2018).*

Hatley, et al.; Angewandte Chemie International Edition, v57, pp. 3298-3321; 2018 (Year: 2018).*

Procopiou, P.A. et al., Discovery of (S)-3-(3-(,5-Dimethyl-1H-phrazol-1-ylphenyl)-4-((R)-3-(2-(5,6,7,8-tetrahydro-1,8-naphthyridin-2-yl)ethyl)pyrrolidin-1-yl)butanoic Acid, a Nonpeptidic [alpha]v[beta]6 Integrin Inhibitor for the Inhaled Treatment of Idopathic Pulmonary Fibrosis, Jounral of Medicinal Chemistry, vol. 61, No. 18, 2018, pp. 8417-8443, XP055703577.

GB Application No. GB20210626.6 Search Report dated Dec. 11, 2020, 5 pages.

PCT Application No. PCT/GB2021/051742, International Search Report dated Sep. 23, 2021, 3 pages.

IN Application No. 202317007510, Examination Report dated Jan. 28, 2026.

Kern et al., Robust Synthesis of N Sulfonylazetidine Building Blocks Via Ring Contraction of a-Bromo N-Sulfonylpyrrolidinones, Organic Letters, 16(23), 6104-6107 dated Nov. 14, 2014.

* cited by examiner

*Primary Examiner* — Jeffrey S Lundgren
*Assistant Examiner* — W. Justin Youngblood
(74) *Attorney, Agent, or Firm* — Lathrop GPM LLP; Laura A. Labeots

(57) ABSTRACT

The invention relates to novel compounds of formula (I), the compounds being capable of acting as $a_v\beta_6$ integrin antagonists, their use in the treatment of disease, their methods of manufacture and compositions comprising said compounds for such purposes (I) wherein $R^1$ is selected from: $R^{1a}$, —C(O)$R^{1a}$, —C(O)O$R^{1a}$ —C(O)NH$R^{1a}$, —C(O)N($R^{1a}$)$_2$, —$SO_2R^{1a}$, wherein $R^{1a}$ are each independently selected from: alkyl, alkenyl, alkynyl, aryl, heteroaryl, alkylaryl or alkylheteroaryl, each of which may be optionally substituted; $R^2$ is selected from: hydrogen, halogen, optionally substituted alkyl or optionally substituted alkoxyl; $R^{2a}$ are each independently selected from: hydrogen, halogen, optionally substituted alkyl or optionally substituted alkoxyl; $R^3$ is selected from: hydrogen, optionally substituted alkyl or optionally substituted alkoxyl; $R^4$ is hydroxyl; $Ar^1$ is an optionally substituted heteroaryl or bicyclic heteroaryl; and L is a linker; or a pharmaceutically acceptable salt thereof.

(I)

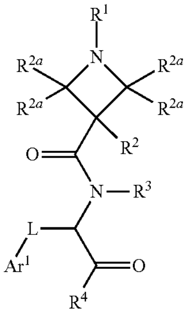

11 Claims, 19 Drawing Sheets

Peak Results

| | Retention Time (min) | Area (µV*sec) | % Area | Width @ 50% |
|---|---|---|---|---|
| 1 | 2.50 | 1009271 | 48.2 | 0.12369 |
| 2 | 3.00 | 1085053 | 51.8 | 0.25092 |

Peak Results

| | Retention Time (min) | Area (µV*sec) | % Area | Width @ 50% |
|---|---|---|---|---|
| 1 | 2.47 | 1260096 | 78.6 | 0.12691 |
| 2 | 3.02 | 342828 | 21.4 | 0.25923 |

Peak Results

| | Retention Time (min) | Area (µV*sec) | % Area | Width @ 50% |
|---|---|---|---|---|
| 1 | 2.38 | 8685863 | 100.0 | 0.10949 |

Peak Results

| | Retention Time (min) | Area (µV*sec) | % Area | Width @ 50% |
|---|---|---|---|---|
| 1 | 2.59 | 10053 | 0.3 | 0.09373 |
| 2 | 2.99 | 4006779 | 99.7 | 0.23871 |

AZETIDINE DERIVATIVES FOR THE TREATMENT OF INTEGRIN ASSOCIATED DISEASES

CROSS REFERENCE TO RELATED APPLICATIONS

This application is a national stage filing under 35 U.S.C. § 371 of International Patent Application No. PCT/GB2021/051742, filed Jul. 8, 2021, which claims priority to Great Britain Patent Application No. GB 2010626.6, filed Jul. 10, 2020. The contents of the above patent applications are incorporated herein by reference in their entireties.

FIELD OF INVENTION

The invention relates to novel compounds capable of acting as $\alpha_v\beta_6$ integrin antagonists, their use in the treatment of disease, their methods of manufacture and compositions comprising said compounds for such purposes.

BACKGROUND

Integrins are cell adhesion receptors made up of a group of heterodimeric glycoprotein complexes formed from α and β subunits. They have roles in signal transduction pathways. Integrins often function in conjunction with other receptors to control cell interactions and cooperate with a range of ligands, such as vitronectin and laminin.

Integrin receptors are known to play a role in the aetiology of a range of different diseases. Of particular interest are RGD-integrins (containing an arginine-glycine-aspartic acid motif within their sequence). For example, the $\alpha_v\beta_3$ is known as an important drug target because its abnormal expression has been linked to diseases such as angiogenesis, cancer and the inhibition of bone resorption in vivo.

D. B. Whitman et al., *Bioorg. Med. Chem. Lett.* 2004, 14, 4411-4415 describes compounds that are effective $\alpha_v\beta_3$ receptor antagonists, believed to be effective at treating osteoporosis. Similarly, US 2018/0008583 discloses a range of compounds which are considered to be effective at treating various cancers as a result of binding $\alpha_v\beta_3$ and $\alpha_v\beta_5$ integrin receptors. WO2018/089355 identifies a range of azetidine-containing compounds, used to treat a wide range of diseases, which are suspected antagonists of any $\alpha_v\beta_1$, $\alpha_v\beta_3$, $\alpha_v\beta_5$, $\alpha_v\beta_6$ and $\alpha_v\beta_8$ integrins. Further, WO2015/048819 discloses a range of compounds effective at binding to $\alpha_v\beta_1$, which may be considered to be effective at treating various forms of fibrosis. However, the binding affinity of compounds to different receptors can vary greatly between compounds. Moreover, compounds effective at binding one receptor are not necessarily effective at binding another.

Attempts have been made in the past to target these integrins with a view to enhancing disease treatment. For instance, WO2016/046230 discloses various compounds suitable for targeting these proteins. In addition, WO2016/04624, WO2014/154725 and WO2016/046225 show similar results.

However, despite such endeavors, there is still a demand for novel, alternative compounds capable of providing effective treatments for various integrin regulated diseases and/or providing improved efficacy in treating a range of known conditions.

The invention is intended to overcome or at least ameliorate this problem.

SUMMARY OF INVENTION

There is provided, in a first aspect of the invention, a compound according to formula (I):

(I)

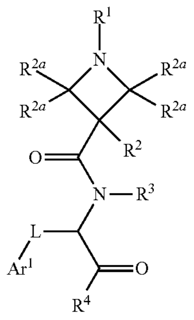

wherein $R^1$ is selected from: $R^{1a}$, —C(O)$R^{1a}$, —C(O)O$R^{1a}$ —C(O)NH$R^{1a}$, —C(O)N($R^{1a}$)$_2$, —$SO_2R^{1a}$, wherein $R^{1a}$ are each independently selected from: alkyl, alkenyl, alkynyl, aryl, heteroaryl, alkylalkoxy, alkylaryl or alkylheteroaryl, each of which may be optionally substituted; $R^2$ is selected from: hydrogen, halogen or optionally substituted alkyl; $R^{2a}$ are each independently selected from: hydrogen or an optionally substituted alkyl; $R^3$ is selected from: hydrogen or optionally substituted alkyl; $R^4$ is hydroxyl; $Ar^1$ is an optionally substituted heteroaryl or bicyclic heteroaryl; and L is a linker. Pharmaceutically acceptable salts of said compounds are also envisaged.

The inventors have discovered that compounds of formula (I) are particularly effective at binding to the $\alpha_v\beta_6$ receptor. Without being bound by theory, it is hypothesised that the rigidity of the four-membered ring structure plays an important part in the observed efficacy of these compounds.

The term "alkyl" is intended to take its usual meaning in the art. In particular, it may be that the alkyl group is optionally substituted and may be a $C_1$ to $C_{12}$ alkyl group wherein one or more of the hydrogens may be replaced with a halogen, such as fluorine or chlorine (often fluorine), to form, for instance, a mono- or di-haloalkyl such as —$CHF_2$. Typically, the alkyl groups will have a length in the range of $C_1$ to $C_{10}$, more typically $C_1$ to $C_8$, even more typically $C_1$ to $C_7$, more typically still $C_1$ to $C_6$, and usually $C_1$ to $C_4$. The alkyl groups may be cyclic, branched or linear (though are often linear) and will often be selected from: methyl, ethyl and propyl. Similarly, the term "alkoxy" is intended to take its usual meaning in the art. That is to say, an alkyl group as described above, bonded via an oxygen atom. The term "alkylalkoxy" is intended to refer to an alkyl group (as defined above) which is attached to an alkoxy group (as defined above). The alkoxy may be attached to any of the alkyl carbons, though usually it is attached at the terminal carbon. The alkyl group present in the alkylalkoxy is typically in the range of $C_1$ to $C_{10}$ in length; more typically in the range of $C_1$ to $C_8$ in length; even more typically in the range of $C_1$ to $C_4$ in length; and most typically either $C_1$ or $C_2$ in length.

The term "alkenyl" is intended to take its usual meaning in the art. In particular, it may be that the alkenyl group is an alkyl group as defined above comprising one or more carbon-carbon double bonds. Typically, the alkenyl group will comprises one double bond. Sometimes the alkenyl group will include two or three double bonds.

The term "alkynyl" is intended to take its usual meaning in the art. In particular, it may be that the alkynyl group is an alkyl group as defined above comprising one or more carbon-carbon triple bonds. Typically, the alkynyl group will comprises one triple bond. Sometimes the alkynyl group will include two or three triple bonds.

The term "aryl" is intended to take its usual meaning in the art. Typically, the ring structures will be wholly aromatic. This term is also intended to cover fused ring structures comprising two or more rings. This may include fused rings comprising two, three, four, five or six rings. Fused aryl ring structures may contain non-aromatic rings in combination with at least one aromatic or partially aromatic ring. The rings may be selected from three- to eight-membered rings. Often the rings will be selected from four-, five-, six- and seven-membered rings. Even more typically, the rings will be five- or six-membered rings. Typically the aryl groups will comprise at least one six-membered ring. As mentioned above, the aryl groups may include one or more optional substituents. Typical substituents that are included as replacements for one or more hydrogen atoms include, but are not limited to: halogens (such as chlorine and fluorine, usually fluorine), hydroxy, alkyl, alkoxy, alkenyl, alkynyl, carboxylic acids, amines, amides, cyano, sulfonyl groups (e.g. $SO_2Me$) or combinations thereof. There is no particular limitation on the number of substituents, though typically there will be four or fewer substituents per ring, more typically three or fewer substituents per ring, even more typically two or fewer substituents per ring. Usually, only one substituent is present per ring.

The term "heteroaryl" is intended to take its usual meaning in the art. In particular, it refers to an aryl group as defined above wherein one or more of the ring carbons is replaced by a heteroatom, typically selected from: nitrogen, sulfur or a combination thereof. Often, the heteroatoms will be selected from nitrogen, oxygen or a combination thereof; and most typically, the heteroatom will be nitrogen. Typically less than four heteroatoms per ring are employed, more typically two or fewer heteroatoms are employed. The majority of heteroaryl substituents contain two heteroatoms.

The term "alkylaryl" is intended to take its usual meaning in the art. In particular, it may refer to an alkyl group, as described above, which is covalently bonded to an aryl group, also as defined above. The aryl group may be bonded to any of the alkyl carbons but typically it is bonded to the terminal carbon. Similarly, the term "alkylheteroaryl" is intended to take its usual meaning in the art. In particular, it may refer to an alkyl group, as described above, which is covalently bonded to a heteroaryl group, also as defined above. The heteroaryl group may be bonded to any of the alkyl carbons but typically it is bonded to the terminal carbon. The alkyl group present in the alkylaryl or alkylheteroaryl is typically in the range of $C_1$ to $C_{10}$ in length; more typically in the range of $C_1$ to $C_8$ in length; even more typically in the range of $C_1$ to $C_4$ in length; and most typically either $C_1$ or $C_2$ in length.

Reference to "halogens" herein is intended to encompass, fluorine, chlorine, bromine, iodine and combinations thereof; typically fluorine, chlorine, bromine and combinations thereof; more typically fluorine, chlorine and combinations thereof; and most typically fluorine.

As used herein, the term "optionally substituted" is intended to take its usual meaning in the art. That is to say, one or more hydrogens are replaced with another species. Unless specified otherwise herein, the optional substituents (which may be the same or different where multiple substituents are present) include, but are not limited to: halogens, such as fluorine and chlorine; lower alkyl species, such as linear, branched or cyclic $C_1$ to $C_4$ alkyl groups; lower alkoxy groups, such as $C_1$ to $C_4$ alkoxy groups (for instance —OMe); saturated or unsaturated cycloalkyls, such as $C_1$-$C_6$ cycloalkyls, often $C_6$ cycloalkyls in which one or more carbons may optionally be substituted with a heteroatom such as oxygen or nitrogen, or combinations thereof. Other optional substituents include hydroxy, cyano, nitro, amine, $—CONR^{11}R^{12}$, $—OR^{13}$, $—SO_2R^{13}$, $—OSO_2R^{13}$, wherein $R^{11}$ and $R^{12}$, each independently represent H or $C_{1-6}$ alkyl, wherein said $R^{11}$ and $R^{12}$ groups may be optionally substituted by one or more substituents which may be the same or different, and which are selected from the group consisting of halogen, hydroxy, $C_{1-6}$ alkyl, $C_{1-6}$ alkoxy, cyano, amino, ═O or trifluoromethyl and wherein $R^{13}$ represents optionally substituted $C_{1-6}$ alkyl, such as halo or amino-substituted alkyl, or optionally substituted aryl.

The "pharmaceutically acceptable salts" described herein are those that would be familiar to one skilled in the art i.e. any salt form that can safely be administered to a patient. Said salts may be acidic or basic and may be organic or inorganic. Typical inorganic salts include alkali metal salts and alkali earth metal salts e.g. lithium, sodium, potassium, magnesium, calcium and the like.

Further the invention is not limited to one particular form of the compound. Various polymorphs of the compounds are contemplated, including both crystal forms and amorphous forms of said compounds. Moreover, complexes comprising said compounds, together with one or more waters of hydration or other solvents are also envisaged.

In some embodiments, $R^1$ is selected from: $R^{1a}$, $—C(O)R^{1a}$, $—C(O)OR^{1a}$ or $—SO_2R^{1a}$. It may be that $R^1$ is $—C(O)OR^{1a}$ or $—SO_2R^{1a}$. In some instances, $R^1$ is $—SO_2R^{1a}$. $R^{1a}$ is selected from: alkyl, alkenyl, aryl, heteroaryl, alkylalkoxy, alkylaryl or alkylheteroaryl, each of which may be optionally substituted. In some embodiments, $R^{1a}$ is an alkyl or alkenyl group such as an optionally substituted cycloalkyl or an optionally substituted cycloalkenyl. In such cases, $R^{1a}$ is often an optionally substituted cycloalkyl comprising 4 to 8 carbons, typically 5 or 7 carbons and most often 6 carbons. On the other hand, $R^{1a}$ may be an optionally substituted cycloalkenyl, comprising 4 to 8 carbons, typically 5 or 7 carbons and most often 6 carbons and one or more double bonds.

Alternatively, $R^{1a}$ may be an aryl or heteroaryl group as described above. In such embodiments, $R^{1a}$ typically comprises at least one ring structure, typically comprising 5 to 10 atoms in the ring, more typically 5 or 6 atoms in the ring and most often 6 atoms in the ring. Sometimes $R^{1a}$ comprises an aryl or heteroaryl group with 5 atoms in the ring. Often, $R^{1a}$ comprises one or more rings selected from: pyrazoyl, thienyl, furyl, pyridyl, imidazolyl, phenyl, naphthyl, quinolinyl or combinations thereof each of which may be optionally substituted. Usually, $R^{1a}$ comprises phenyl, pyrazoyl, thienyl or combinations thereof each of which may be optionally substituted. Often, $R^{1a}$ comprises phenyl, pyrazoyl or combinations thereof, each of which may be optionally substituted; and usually, $R^{1a}$ comprises a single ring, although bicyclic structures such as indane are possible, however, when present as a single ring structure this is typically an optionally substituted phenyl, or optionally substituted pyridine.

Similarly, $R^{1a}$ may also be an alkylalkoxy, alkylaryl or alkylheteroaryl group, more typically an alkylaryl or alkylheteroaryl.

Typically, less than three substituents are provided per ring structure. Typical aryl substituents are as described above. In some embodiments, $R^{1a}$ is an optionally substituted phenyl, with substituents such as a $C_1$ to $C_4$ alkyl (typically methyl or ethyl), and at least partially fluorinated $C_1$ to $C_4$ alkyl (typically methyl or $CF_3$), a $C_1$ to $C_4$ alkoxyl (typically methoxy), an at least partially fluorinated $C_1$ to $C_4$ alkoxyl, —$OCF_3$ fluorine, chlorine, sulfonyl (e.g. $SO_2Me$), aryl, amide, nitrile, ether, heteroaryl or combinations thereof. Often, where optional substituents are present, four or fewer substituents are provided, more typically three or fewer, more typically still two or fewer substituents are provided, and most typically one or two.

Often, $R^2$ is selected from hydrogen, halogen, hydroxy, optionally substituted alkyl, or optionally substituted alkoxy. In some cases, $R^2$ is selected from hydrogen or optionally substituted alkyl. Where $R^2$ is an optionally substituted alkyl and/or an optionally substituted alkoxy, it will typically be a $C_1$ to $C_6$ alkyl or alkoxy group, more typically a $C_1$ to $C_4$ alkyl or alkoxy group, and most typically a $C_1$ to $C_3$ alkyl or alkoxy group. Typically, $R^2$ is selected from hydrogen, hydroxy, fluorine, methyl, ethyl, methoxy, ethoxy or combinations thereof. In some instances, $R^2$ is selected from hydrogen, methyl, ethyl or combinations thereof; and most typically, $R^2$ is selected from hydrogen, methyl or combinations thereof. Further, $R^2$ may also be hydrogen.

In some cases, $R^{2a}$ are each independently selected from hydrogen or optionally substituted alkyl. Where $R^{2a}$ is an optionally substituted alkyl, it will typically be a $C_1$ to $C_6$ alkyl or alkoxy group, more typically a $C_1$ to $C_4$ alkyl or alkoxy group, and most typically a $C_1$ to $C_3$ alkyl or alkoxy group. Typically, $R^{2a}$ are each independently selected from hydrogen, methyl, ethyl or combinations thereof. Most typically, $R^{2a}$ are each independently selected from hydrogen, methyl or combinations thereof. Further, $R^{2a}$ may also be hydrogen. Often, at least two $R^{2a}$ groups are identical; more typically at least three are identical; and most typically, all four $R^{2a}$ groups are identical.

Often, $R^3$ is selected from hydrogen, optionally substituted alkyl or optionally substituted alkoxy. In some cases, $R^3$ is selected from hydrogen or optionally substituted alkyl. Where $R^3$ is an optionally substituted alkyl and/or an optionally substituted alkoxy, it will typically be a $C_1$ to $C_6$ alkyl group, more typically a $C_1$ to $C_4$ alkyl group, and most typically a $C_1$ to $C_3$ alkyl group. Typically, $R^3$ is selected from hydrogen, methyl, ethyl or combinations thereof. In some instances, $R^3$ is selected from hydrogen, methyl, ethyl or combinations thereof; and most typically, $R^3$ is selected from hydrogen, methyl or combinations thereof. Further, $R^3$ may also be hydrogen.

$R^4$ is hydroxy. Without being bound by theory, it is believed that the —OH group, or the deprotonated —$O^-$ group, plays an important role in binding, or coordinating with, key components of integrins. Accordingly, in an alternative embodiment, the hydrogen of said hydroxy group may be replaced by a suitable counter ion, such as sodium or potassium (i.e. —$O^-Na^+$ or —$O^-K^+$).

The term "linker" is also intended to take its usual meaning in the art. This is a group than covalently connects species $Ar^1$ to the rest of the compound shown in formula (I) above. There is no fixed length for said linker and, as one skilled in the art would appreciate, the spacing between group $Ar^1$ and the rest of the molecule can be varied by changing the length of the linker. The length of the linker varies from two bond lengths to 20 bond lengths, more typically in the range of 2 to 12 bond lengths, and even more typically 3 to 7 bond lengths.

Often, the linker is selected from any of formulae (II) to (VIII):

(II)

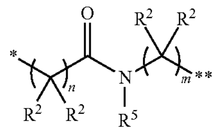

(III)

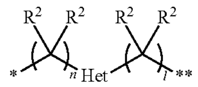

(IV)

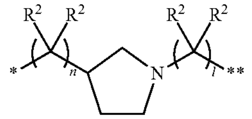

(V)

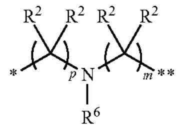

(VI)

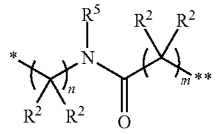

(VII)

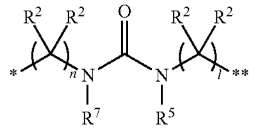

(VIII)

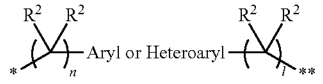

wherein

Het is a 4, 5, 6 or 7 membered saturated heterocycle containing N, O, S or C linked through either N or C, typically selected from: azetidine, pyrrolidine, piperidine, piperazine, morpholine, thiomorpholine, homomorpholine, homopiperazine, azepane; $R^2$ is as described above; $R^5$, $R^6$ and $R^7$ are each independently selected from: hydrogen or optionally substituted alkyl; l, m, n and p are each independently an integer in the range of 0 to 10. The positions indicated with '*' and '**' represent the left-hand side and the right-hand side of the linker respectively as drawn above for formula (I). Accordingly, the linkers are typically orientated such that the left-hand side of the linker (*) is attached to $Ar^1$ (the tetrahydronaphthyridine) in formula (I). In formula (VIII), the "Aryl or Heteroaryl" are as previously defined and may be substituted.

Where $R^2$ is part of the linker (i.e. forms part of any of formulae (II) to (VIII), typically $R^2$ will be selected from hydrogen, halogen, hydroxy, or optionally substituted alkyl. In some cases, $R^2$ is selected from hydrogen or optionally substituted alkyl. Where $R^2$ is an optionally substituted alkyl it will typically be a $C_1$ to $C_6$ alkyl group, more typically a $C_1$ to $C_4$ alkyl group, and most typically a $C_1$ to $C_3$ alkyl group. Typically, $R^2$ is selected from hydrogen, hydroxy, fluorine, methyl, ethyl, or combinations thereof. In some instances, $R^2$ is selected from hydrogen, methyl, ethyl or combinations thereof; and most typically, $R^2$ is selected from hydrogen, methyl or combinations thereof. Further, $R^2$ may also be hydrogen. Typically, $R^5$, $R^6$ and $R^7$ are each independently selected from hydrogen, optionally substituted alkyl or optionally substituted alkoxy. In some cases, $R^5$, $R^6$ and $R^7$ are each independently selected from hydrogen or optionally substituted alkyl. The alkyl or alkoxy group will typically be a $C_1$ to $C_6$ alkyl or alkoxy group, more typically a $C_1$ to $C_4$ or alkoxy group, and most typically a $C_1$ to $C_3$ or alkoxy group. Typically, $R^5$, $R^6$ and $R^7$ are each independently selected from hydrogen, methyl, ethyl or combinations thereof. In some instances, $R^5$, $R^6$ and $R^7$ are each independently selected from hydrogen, methyl, ethyl or combinations thereof; and most typically, $R^5$, $R^6$ and $R^7$ are each independently selected from hydrogen, methyl or combinations thereof. $R^5$, $R^6$ and $R^7$ may each independently also be hydrogen.

In formula (VII), $R^5$ and $R^7$ may be joined together. Typically, where $R^5$ and $R^7$ are joined together, they will form an optionally substituted ring structure. Typically this will comprise a four-, five-, six-, seven- or eight-membered ring; most commonly it will be a five- or six-membered ring. Typically, the ring will form an optionally substituted cycloalkyl ring, though one or more alkenyl groups may be included within the ring structure.

It is typically the case that "l" and "m" are each independently an integer in the range of 1 to 9, more typically 1 to 6, even more typically 1 to 4, and more typically still 1 to 3. Usually, "l" is 1 or 2; and often "l" is 2. In some instances, "m" is 1 or 2; and is often 1. As regards "p" and "n", it is typically the case that these are integer values in the range of 1 to 9, more typically 2 to 8, even more typically 3 to 7 and, more typically still four to 6. It may be that "p" is an integer in the range of 4 to 5, and most typically "p" is 5. Often, "n" is an integer in the range of 4 to 5, and most typically "n" is 4. Typically, "q" is 1 or 2; often 2.

In one embodiment, the linker has a structure according to formulae (II), (III), (V) or (VII); more typically formulae (II), (V) or (VII). The linker may have a structure according to formulae (V) or (VII). Typically, compounds of formula (II) or (V) are employed. However, compounds of formula (VI) or formula (VIII) may also be employed. Where the linker is of formula (II), (V), (VI) or (VII) the N—R unit (i.e. for formula (II) the N—$R^5$ unit, for formula (V) the N—$R^6$ unit, for formula (VI) the N—$R^5$ unit and for formula (VII) either or both of the N—$R^5$ and the N—$R^7$ unit) will often be of the structure:

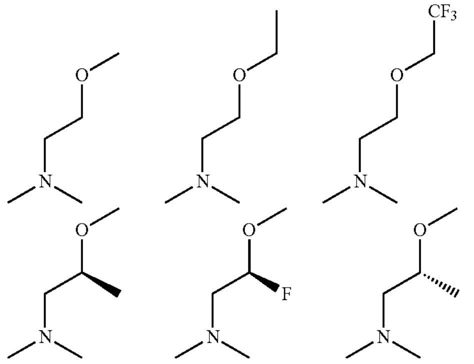

-continued

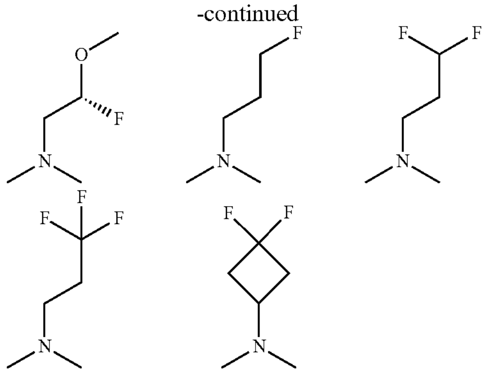

Although, as noted above, often $R^6$ will be hydrogen, or an alkyl, often the alkyl will be methyl, ethyl or propyl.

Although $Ar^1$ may comprise a single optionally substituted heteroaryl ring structure, $Ar^1$ may also be a fused ring structure comprising at least one optionally substituted heteroaryl (as described above). Typically, $Ar^1$ comprises at least one partially or completely aromatic ring structure. $Ar^1$ typically includes two ring structures. Often the rings structures are five- or six-membered rings; more typically, both are six-membered rings. Further, $Ar^1$ typically comprises one aromatic ring and one non-aromatic ring. Typically, the aromatic ring is an optionally substituted heterocyclic species, usually optionally substituted pyridine; and the non-aromatic rings is usually a non-aromatic heterocycle which may comprise one or more heteroatoms selected from nitrogen, oxygen, sulfur and combinations thereof. The non-aromatic ring may be selected from: piperidine, piperazine, thiane, dithiane, tetrahydropyranyl, dioxane, morpholine or thiomorpholine, each of which may be optionally substituted. Typically, the non-aromatic group is an optionally substituted piperidine. The optionally substituted aryl or optionally substituted heteroaryl species of $Ar^1$ are typically selected from: pyridine, pyridazine, pyrimidine, pyrazine, pyrrole, furan, thiophene or combinations thereof, each of which may be optionally substituted. Typically, the heteroaryl species of $Ar^1$ are selected from: pyridine, pyrimidine and pyrazine. Most typically, the optionally substituted heteroaryl species of $Ar^1$ is pyridine.

Typically, $Ar^1$ is able to function as a bidentate ligand. Without being bound by theory, the inventors believe that the presence of two donor atoms in the $Ar^1$ group, is useful in bringing out about effective binding to integrins. As such, $Ar^1$ typically comprises at least two donor atoms, ideally wherein said donor atoms are within at least two bond lengths of one another. Usually, $Ar^1$ will be composed of two ring structures, each comprising a donor atom, typically nitrogen. Said rings may be fused together and may include additional rings attached or fused thereto. Some examples of suitable $Ar^1$ groups are shown WO2018/089353 on pages 3 and 5 with respect to the "Arginine mimetic moiety" labelled as "$R^1$" therein.

For instance, $Ar^1$ may have a structure according to formula (IXa) to (IXi) shown below:

(IXa)

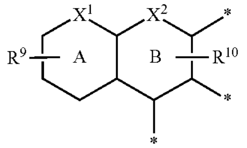

-continued (IXb)

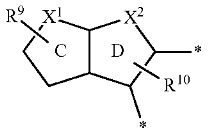

(IXc)

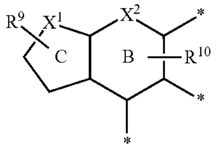

(IXd)

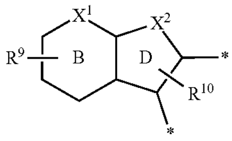

(IXe)

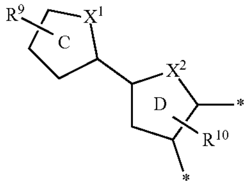

(IXf)

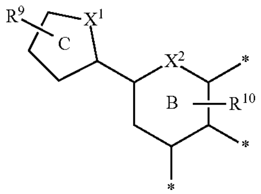

(IXg)

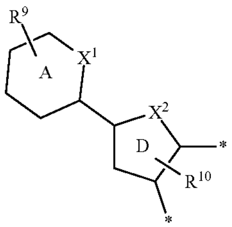

(IXh)

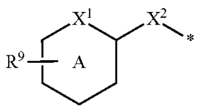

(IXi)

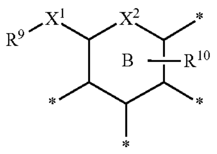

wherein $X^1$ and $X^2$ are each independently a donor atom, typically nitrogen;

* represents a possible connection point between $Ar^1$ and the linker described above; rings A to D are each independently an aromatic heterocycle or a non-aromatic heterocycle, with the proviso that at least one ring is aromatic;

$R^9$ and $R^{10}$ are each independently selected from: hydrogen, halogen, optionally substituted alkyl, optionally substituted alkoxy, optionally substituted alkenyl, optionally substituted alkynyl, optionally substituted aryl, optionally substituted alkylalkoxy, optionally substituted heteroaryl, optionally substituted alkylaryl or optionally substituted alkylheteroaryl, or combinations thereof. Often $R^9$ and $R^{10}$ are each independently selected from hydrogen, halogen, optionally substituted alkyl and optionally substituted alkoxy, often $R^9$ and $R^{10}$ are each independently hydrogen or halogen. Each group includes only a single connection point to the linker moiety at the * position.

Typically, a compound of formulae (IXa) to (IXd) is employed; more typically a compound of formulae (IXa).

Often, $Ar^1$ will be selected one of the groups according to formulae (Xa) to (Xr):

(Xa)

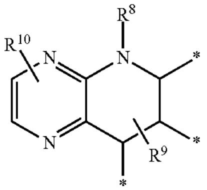

(Xb)

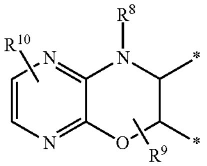

(Xc)

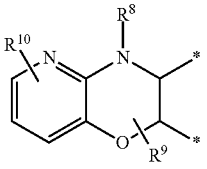

(Xd)

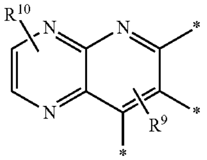

(Xe)

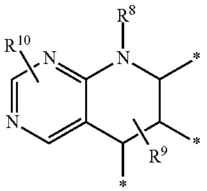

(Xf)

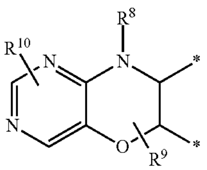

-continued (Xg)

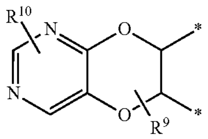

(Xh)

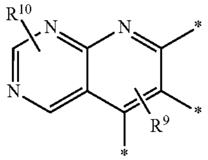

(Xi)

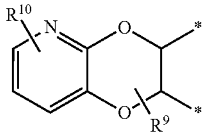

(Xj)

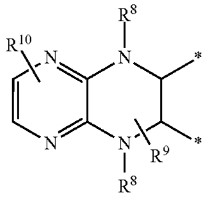

(Xk)

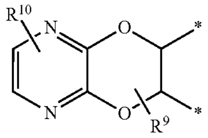

(Xl)

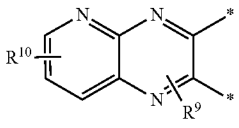

(Xm)

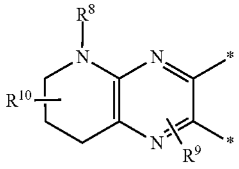

(Xn)

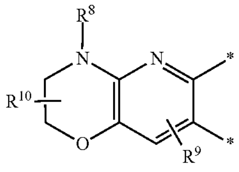

(Xo)

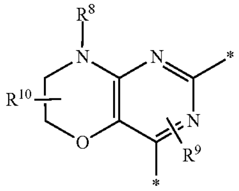

-continued (Xp)

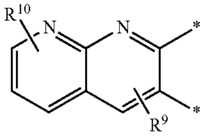

(Xq)

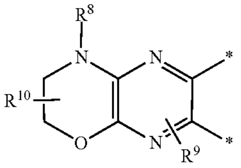

(Xr)

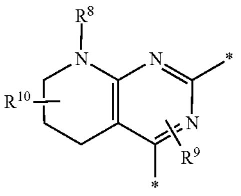

wherein $R^8$ is selected from: hydrogen or optionally substituted alkyl, often hydrogen; and $R^9$ and $R^{10}$ are as described above.

It is often the case that $Ar^1$ is a group according to formulae (XIa), (XIb) or (XIc), often of formula (XIa):

(XIa)

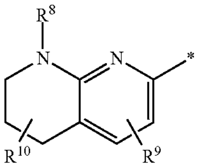

(XIb)

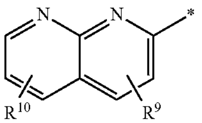

(XIc)

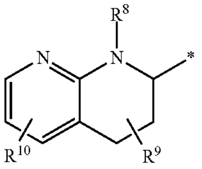

wherein $R^8$, $R^9$ and $R^{10}$ are as described above;

and * denotes a connection point to the linker.

Where $R^8$ is an optionally substituted alkyl, the alkyl will typically be a $C_1$ to $C_6$ alkyl group, more typically a $C_1$ to $C_4$ alkyl group, and most typically a $C_1$ to $C_3$ alkyl group. Typically, $R^8$ is selected from hydrogen, methyl, ethyl or combinations thereof. In some instances, $R^8$ is selected from hydrogen, methyl, ethyl or combinations thereof; and most typically, $R^8$ is selected from hydrogen, methyl or combinations thereof. Further, $R^8$ may also be hydrogen.

As regards $R^9$ and $R^{10}$, each are typically independently selected from: hydrogen, halogen, optionally substituted alkyl, optionally substituted aryl or a combination thereof. More often, $R^9$ and $R^{10}$ are each independently selected from: hydrogen, halogen, optionally substituted alkyl or a combination thereof. In some embodiments, $R^9$ and $R^{10}$ are each independently hydrogen.

The compounds can be provided in enantiomerically pure formats or as mixtures of enantiomers, including racemic mixtures. Typically, the compounds are optically pure, though racemic mixtures are used in some circumstances. The term "enantiomerically pure" is not intended taken literally, as one skilled in the art would understand. Where an optically pure compound is provided, there is typically less than 10% of other enantiomers, diastereomers or other isomers provided, more typically less than 5%, and even more less than 1%.

It may be the case that in the compounds of formula (I), $R^1$ is —$SO_2R^{1a}$, wherein $R^{1a}$ are each independently selected from: alkyl, alkenyl, alkynyl, aryl, heteroaryl, alkylaryl or alkylheteroaryl, each of which may be optionally substituted; $R^2$ is selected from: hydrogen, halogen, optionally substituted alkyl or optionally substituted alkoxyl; $R^{2a}$ are each independently selected from: hydrogen, halogen, optionally substituted alkyl or optionally substituted alkoxyl; $R^3$ is selected from: hydrogen, optionally substituted alkyl or optionally substituted alkoxyl; $R^4$ is hydroxyl; $Ar^1$ is (XIa)

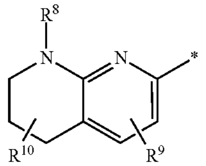

wherein $R^8$ is selected from: hydrogen or optionally substituted alkyl; and $R^9$ and $R^{10}$ are each independently selected from: hydrogen, halogen, optionally substituted alkyl, optionally substituted alkoxy, optionally substituted alkenyl, optionally substituted alkynyl, optionally substituted aryl, optionally substituted alkylalkoxy, optionally substituted heteroaryl, optionally substituted alkylaryl or optionally substituted alkylheteroaryl, or combinations thereof; and L is a linker selected from any of formulae (II), (V) and (VI)

(II)

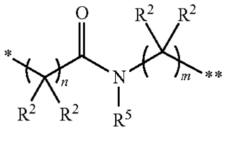

(V)

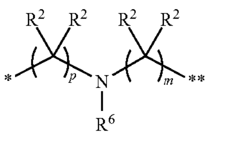

(VI)

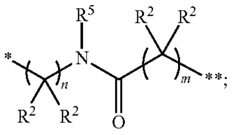

or a pharmaceutically acceptable salt thereof.

In some embodiments, the compound has a structure according to formula (Ia):

(Ia)

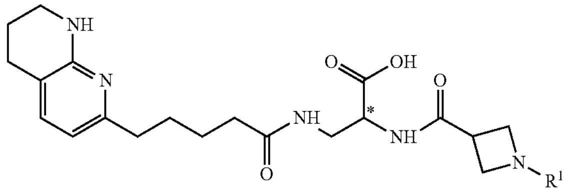

wherein, $R^1$ is as described above.

The compound of this embodiment has one chiral centre (marked as * in formula Ia above). This chiral centre may be either R or S, typically S.

For the avoidance of doubt, the invention also encompasses derivatives of the compounds of the invention and/or prodrugs of the compounds of the invention.

There is provided in a second aspect of the invention, a composition containing the compound according to the first aspect of the invention. As one skilled in the art would appreciate, a variety of excipients and other ingredients may be added to a compound according to the first aspect of the invention in order to modify the physical properties of the composition or formulation containing the compound. This may be done for a variety of reasons, such as: to improve compound stability (both in vitro and/or in vivo), enhance the solubility of the compound, or improve delivery of the compound to a particular part of the body. Typical additives that may be introduced into the compositions of the invention include, but are not limited to: solvents, surfactants, bulking agents, buffers, flavourings, pharmaceutically acceptable carriers, diluents or fillers, binders, disintegrants, lubricants, colouring agents and preservatives.

The compounds of the invention can be used to treat a wide range of conditions, some of which are more suitable for administration via one route than another. As such, whilst there is no particular limitation on the type of composition or formulation that is employed in the present invention, it is typically the case that the composition is adapted for: oral, inhalation, injection, transdermal delivery, topical, sub-lingual, ocular, rectal, vaginal or parenteral administration routes. Of these methods, oral administration and inhalation are most preferred. In particular, where diseases of the lungs require treatment, it is often desirable to employ an inhalation formulation. In some instances a combination of routes may be employed. The compounds of the present invention have been found to be particularly suitable for oral administration.

The compound is typically provided in a composition in a therapeutically effective amount. It will be appreciated by one skilled in the art that a "therapeutically effective amount" is generally a concentration sufficient to bring about a detectable lessening of a disease i.e. it brings about at least some mitigation of a diseases symptoms and/or the disease itself. Typically, it excludes dosages that adversely affect a patient.

The compound may be present in the composition at a range of dosages. Moreover, as one skilled in the art, different dosages may often be required for treating different diseases, different patients and under different dosage regimens. Often the dosage will be a daily dose. However, typically the compound is present in an amount in the range 0.01 to 3000 mg (or pharmaceutical salt thereof), more typically in the range of 100 to 2000 mg. Dosages provided herein are with respect to oral administration. The compound is typically provided with a purity of at least 80%, more typically, at least 90% and even more typically at least 95%.

There is no particular limitation on how the composition is formulated and the composition may be formulated as a solid e.g. a powder, tablet or capsule as would be familiar to one skilled in the art. Alternatively a liquid formulation may be employed depending on the method of delivery e.g. for ocular delivery or topical application.

The composition of the invention may also be provided with additional pharmaceutically active agents, for instance other anti-fibrotic medication or anticancer medication.

There is also provided in a third aspect of the invention, a compound according to the first aspect of the invention, or composition according to the second aspect of the invention, for use in therapy. In particular, for use in the treatment of integrin associated diseases. As explained above, the binding and interaction of compounds with integrins is considered important in the regulation of many biological functions. Moreover, interrupting or otherwise influencing these integrins in many circumstances can offer a valuable treatment for a range of disorders. In the present case, the compound of the first aspect of the invention is effective at binding to several integrins. In particular, the compounds are typically effective at binding at least $\alpha_v\beta_6$ integrins, specifically as $\alpha_v\beta_6$ integrins antagonists. The compounds may also be effective at binding other integrins, such as one or more of $\alpha_v\beta_1$, $\alpha_v\beta_3$, $\alpha_v\beta_5$ and $\alpha_v\beta_8$.

The diseases which the compounds are suitable for use in treating are not especially limited and may be selected from any of the following: cancer, ischemic diseases, fibrosis, osteoporosis, and restenosis. The diseases which the compounds of the invention are particularly effective at treating include cancer and fibrosis. There is no particular restriction on the kind of cancer or fibrosis that the compounds of the invention can be used to treat. Fibrosis generally covers diseases resulting from the formation of excessive connective tissue in the body. Examples of fibrotic diseases that the compounds and compositions of the invention are particularly effective at treating include, but are not limited to: pulmonary fibrosis (e.g. cystic fibrosis, idiopathic pulmonary fibrosis, non-specific interstitial pneumonia, progressive massive fibrosis and ARDS associated fibrosis, and the like), renal fibrosis (e.g. diabetic nephropathy, lupus nephritis, IgA nephropathy, drug or hypertension induced nephropathy, focal segmental glomerulosclerosis, and the like), liver fibrosis (e.g., virus-induced fibrosis, autoimmune hepatitis, cirrhosis, alcoholic liver disease, non-alcoholic fatty liver disease, congenital hepatic fibrosis, sclerosing cholangitis, and the like), dermatological fibrosis (hypertrophic scars, scleroderma, keloids, dermatomyositis, eosinophilic fasciitis, Dupytrens contracture, Ehlers-DAnlos syndrome, Peyronie's disease, epidermolysis bullosa dystrophica, oral submucous fibrosis, or the like), ocular fibrosis (age-related macular degeneration, diabetic macular oedema, dry, glucoma), cardiac fibrosis (congenital heart failure, atherosclerosis, myocardial infarction, endomyocardial fibrosis, hypertrophic cardiomyopathy), Crohn's disease, myelofibrosis, uterine leiomyomas or combinations thereof. In particular, the compounds of the invention are for treating idiopathic pulmonary fibrosis.

In relation to cancer, there is no particular restriction in the type of cancer that the compounds of the invention may be effective at treating. Typically, the cancer is cancer of the: skin, lungs, liver, breast, colon, cervix, pancreas or ovaries.

Whilst reference is made herein to "treatment" of disease, the invention also encompasses prophylactic applications against said diseases and disorders.

There is provided in a fourth aspect of the invention, a method of making a compound according to the first aspect of the invention, comprising the steps of:

i) reacting a first compound of formula (XII):

(XII)

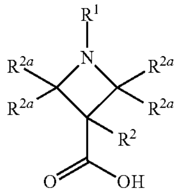

with a second compound according to formula (XIII):

(XIII)

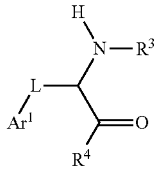

wherein $R^1$, $R^2$, $R^3$, $R^4$ where $R^4$ here is a protected carboxylic acid such as an ester, L and $Ar^1$ are as described above as per the first aspect of the invention. One example of a synthetic route where L is as in structure (II) is shown below. It is taken to one skilled in the art that variations in this route are applicable to other examples and claims herein.

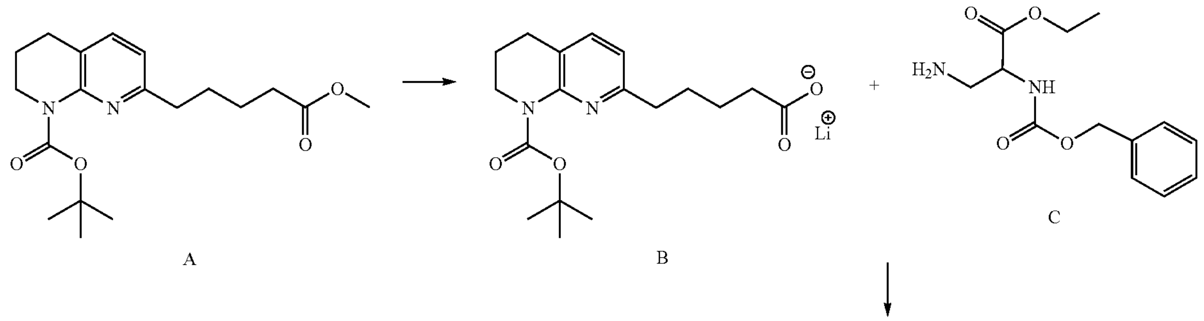

A B C

-continued

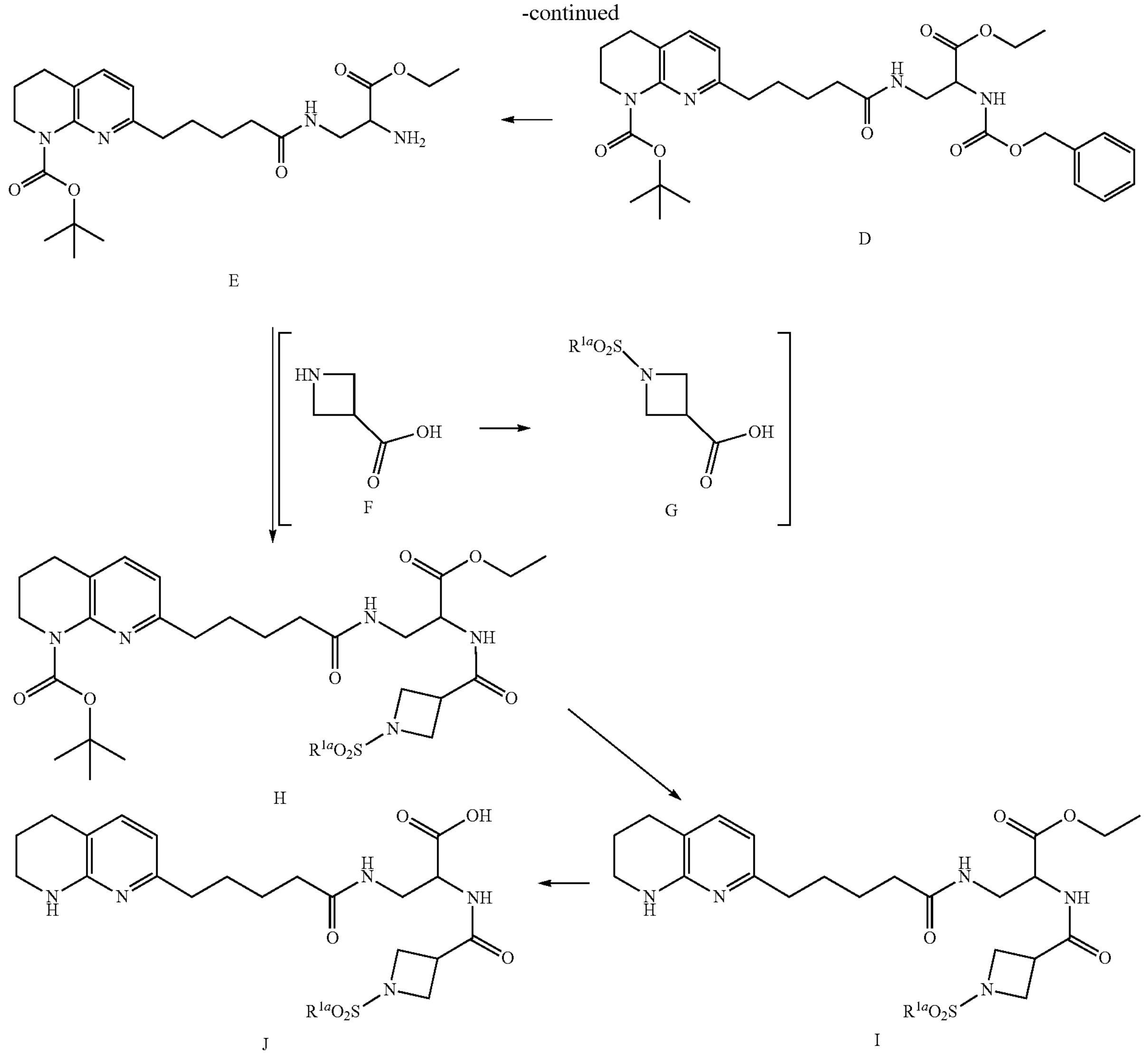

Intermediate B can be prepared by the reaction of intermediate A with an aqueous base e.g. lithium hydroxide or sodium hydroxide in a mixture of a suitable alcohol solvent such as methanol or an ether solvent such as tetrahydrofuran and water at room temperature.

Intermediate D can be prepared by the reaction of intermediate B with commercially available intermediate C in the presence of a suitable coupling agent such as T3P, or HATU or EDC·HCl in the presence of a suitable base such NMM or NEM in a suitable solvent such as THF, acetonitrile or DMF at room temperature.

Intermediate E can be prepared by the reaction of intermediate D in the presence of a hydrogenation catalyst such as Pd on activated carbon in a ratio of 10% in the presence of hydrogen at a pressure of 15 to 45 psi in a suitable solvent. Alternatively intermediate E can be prepared by the reaction of intermediate D in the presence of a hydrogen transfer reagent such as ammonium formate and a catalyst such as Pd on activated carbon in a ratio of 10% in an alcoholic solvent such as ethanol at a suitable temperature such as 60° C.-80° C.

Intermediate G can be prepared from a commercially available intermediate F and a suitable reagent such as a sulfonyl chloride in the presence of a suitable base such as aqueous sodium hydroxide in a mixture of ether and at a temperature between 0° C. and 20° C.

Intermediate H can be prepared by the reaction of intermediates E and G in the presence of a suitable coupling agent such as T3P or HATU or EDC·HCl in the presence of a suitable base such NMM or NEM in a suitable solvent at a temperature between 0° C. and 20° C.

Intermediate I can be prepared by the reaction of intermediate H with a reagent such as trifluoroacetic acid in a suitable solvent such as dichloromethane at a temperature between 0° C. and 20° C.

Compounds such as that shown in formula J can be prepared by the reaction of intermediate I in the presence of a suitable base such as aqueous sodium hydroxide in a suitable alcohol solvent such as ethanol at a temperature between 0° C. and 20° C.

Often, the linker is typically as described above in relation to the first aspect of the invention.

As one skilled in the art will appreciate, there are a number of different synthetic routes to the intermediate compounds described above in the fourth aspect of the invention. Moreover, there are a range of reaction conditions that can be employed to in order to perform the steps described above. The steps of the method of the fourth aspect of the invention do not necessarily need to be performed in sequential order, and the method may include one or more purification stages at any or all steps of the synthetic process. One skilled in the art would appreciate the necessary filtration techniques required to isolate the intermediates and compounds of the invention.

In a yet further aspect of the invention, there is provided a method of treating an integrin associated disease as described above according to the third aspect of the invention, comprising the step of administering a compound according to the first aspect of the invention or a composition according to the second aspect of the invention to a patient.

In order that it may be more readily understood, the invention will now be described with respect to the figures and to the following illustrative examples, however the invention is not limited to these Examples.

EXAMPLES

Figure 1:
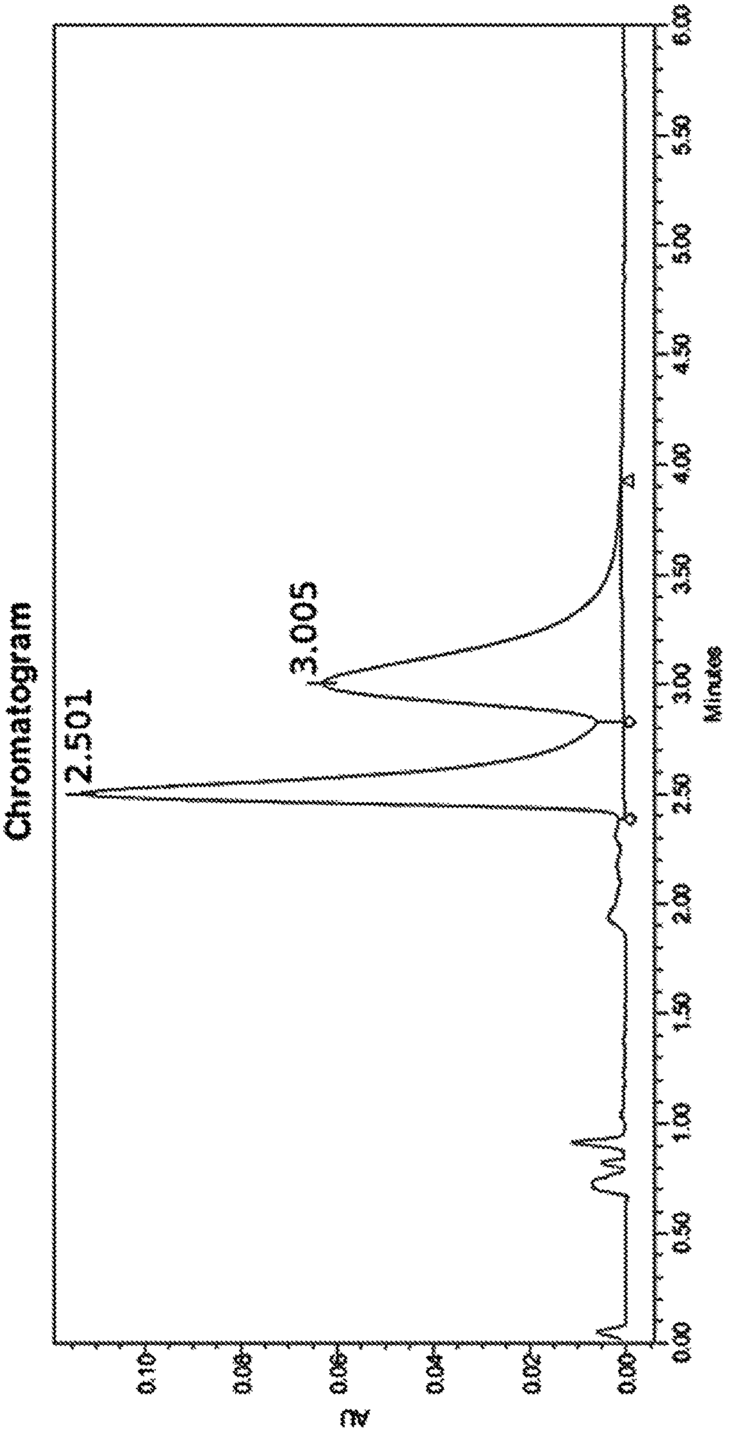
FIG. 1 is a chiral analysis using Supercritical Fluid Chromatography of the racemic product of Example 4.

NMR spectra were recorded on a Bruker AVII+ (600 MHz), Bruker AV-500 (500 MHz), Bruker DPX-400 (400 MHz), Bruker AV-400 (400 MHz) or Bruker DPX-300 (300 MHz) spectrometer as dilute solutions at ambient temperature. The chemical shifts are quoted in ppm (parts per million) and the multiplicity denoted by: s (singlet), d (doublet), dt (double triplet), t (triplet), td (triple doublet), tdd (triple double doublet), q (quartet), quin (quintet) and m (multiplet). In some spectra minor impurity or residual solvent peaks are evident; only peaks attributable to the product are reported. In many spectra, exchangeable protons (e.g. NH, $NH_2$, CONH, OH, $CO_2H$) are not observed.

Mass spectra were recorded on a Bruker MicroTOF system using electrospray ionisation (ESI) techniques, electrospray ionisation operating in positive and negative ion mode.

Compounds were routinely analysed by liquid chromatography mass spectrometry (LCMS). Typical conditions were as follows.

LC Conditions:

The UPLC analysis was conducted on an Acquity UPLC CSH C18 column (50 mm×2.1 mm i.d. 1.7 μm packing diameter) at 40° C. The solvents employed were:

A=10 mM Ammonium bicarbonate in water adjusted to pH 10 with ammonia solution.

B=Acetonitrile.

The gradient employed was:

| Time (min) | Flow Rate (mL/min) | % A | % B |
|---|---|---|---|
| 0.00 | 1 | 97 | 3 |
| 0.05 | 1 | 97 | 3 |
| 1.50 | 1 | 5 | 95 |
| 1.90 | 1 | 5 | 95 |
| 2.00 | 1 | 97 | 3 |

The UV detection was a summed signal from wavelength of 210 nm to 350 nm. Injection volume: 0.3 μL MS Conditions MS: Waters ZQ Ionisation Mode: Alternate-scan Positive and Negative Electrospray Scan Range: 100 to 1000 AMU Scan Time: 0.27 seconds Inter scan Delay: 0.10 seconds Purification Conditions Example 36 was purified by reversed phase preparative HPLC (Reveleris, 0-100% MeCN in 10% aqueous ammonium carbonate).

Mass Directed Auto-Preparative reverse phase HPLC (MDAP) was used for the following Examples under the following conditions.

For Examples 23-32: Waters XSelect CSH C18 19×100 mm 5 m column using acetonitrile water with an ammonium carbonate modifier, or by using an Xterra RP18 prep column, eluting with ammonium carbonate modified MeCN:$H_2O$ (15-55%) for 20 min.

For Example 33: Xterra RP18 prep column, eluting with ammonium carbonate modified MeCN:$H_2O$ (25-55%) for 30 min For Examples 34 and 35: a Xbridge prep C18 column, eluting with ammonium carbonate modified MeCN:$H_2O$ (25-55%) for 30 min For Examples 37-40: Waters XSelect CSH C18 19×100 mm 5 m column using acetonitrile water with an ammonium carbonate modifier.

Other compounds were purified by flash chromatography as described in the following paragraph.

Flash chromatography was performed on Puriflash silica columns and aminopropyl silica columns. Petrol ether refers to light petroleum, bp 40-60° C.

Isolation of some examples was carried out using Waters Oasis HLB using mixtures of water:methanol as eluent.

Reagents were obtained from standard commercial suppliers (e.g. Fluka, Fluorochem, Sigma-Aldrich, Acros) and used without purification unless otherwise stated.

Abbreviations

EtOAc Ethyl acetate
MeCN Acetonitrile
EtOH Ethanol
MeOH Methanol
EDC·HCl 1-Ethyl-3-(3-dimethylaminopropyl)carbodiimide Hydrochloride
HOBt 1-Hydroxybenzotriazole Hydrate
NMM 4-Methylmorpholine
NEM 4-Ethylmorpholine
DMAP 4-Dimethylaminopyridine
HATU (1-[Bis(dimethylamino)methylene]-1H-1,2,3-triazolo[4,5-b]pyridinium 3-oxide hexafluorophosphate Route 1

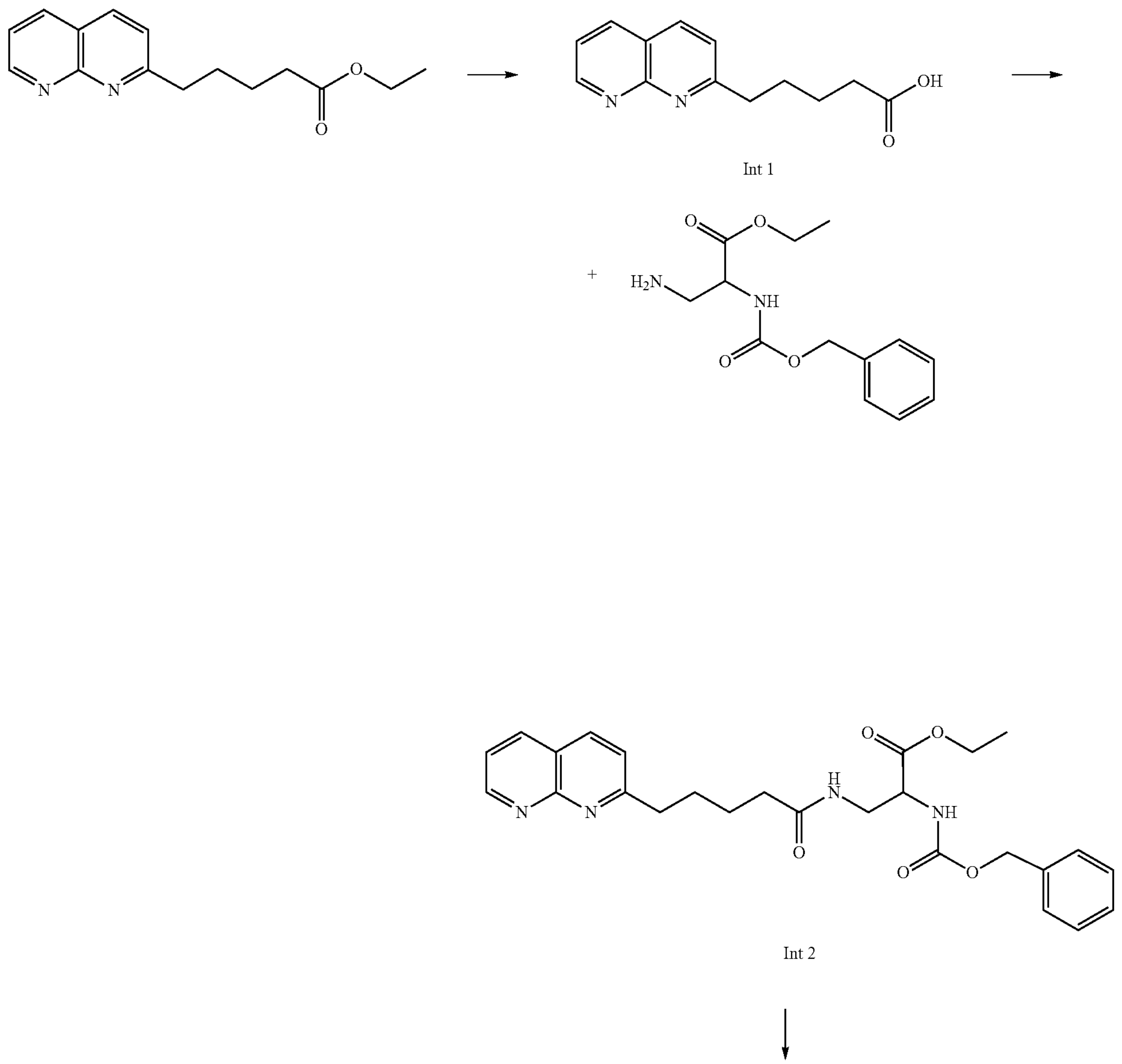

Int 1

Int 2

-continued

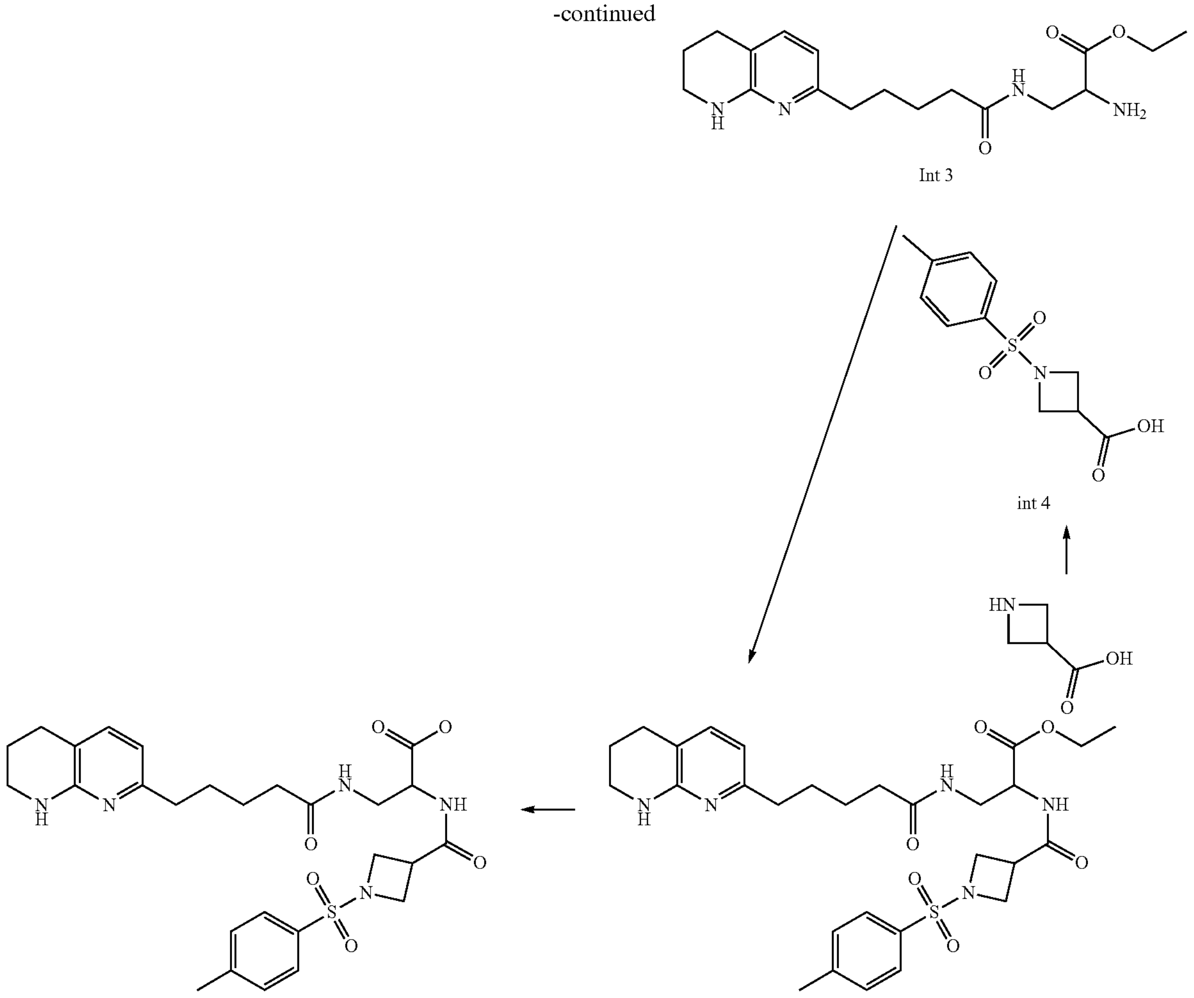

Int 3 int 4

Int 5

Example 1: 3-(5-(5,6,7,8-Tetrahydro-1,8-naphthyridin-2-yl)pentanamido)-2-(1-(4-methylbenzenesulfonyl)azetidine-3-carboxamido)propanoic acid (a) Intermediate 1: 5-(1,8-naphthyridin-2-yl)pentanoic acid

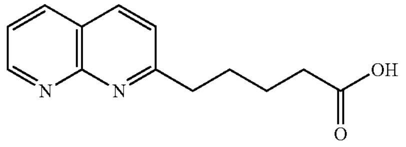 [SMILES: O=C(O)CCCCc1ccc2cccnc2n1]

Ethyl 5-(1,8-naphthyridin-2-yl)pentanoate (5 g, 20.47 mmol) (CAS: 678986-15-7 *Bioorg. Med. Chem. Lett.* 2004, 14, 1049-1052) was dissolved in THF (100 mL) and water (25 mL). LiOH (1 g, 41.75 mmol) was added and stirred at room temperature for 18 h. The solvent was evaporated, the residue dissolved in brine (60 mL) and 2M hydrochloric acid (15 mL) added dropwise to pH=4. A precipitated solid was collected via filtration and dried in a vacuum desiccator for 36 h to give intermediate 1 (2.9 g). $^{1}H$ NMR (400 MHz; DMSO-$d_6$) δ 12.1 (br, 1H), 9.07 (dd, 1H), 8.42 (dd, 1H), 8.35 (d, 1H), 7.55 (m, 2H), 2.96 (t, 2H), 2.27 (t, 2H), 1.79 (quin, 2H), 1.57 (quin, 2H). HRMS $[M+H]^+$ calculated for $C_{13}H_{14}N_2O_2$+H 231.1134, found 231.1151.

(b) Intermediate 2: ethyl 3-(5-(1,8-naphthyridin-2-yl)pentanamido)-2-((benzyloxycarbonyl)amino)propanoate

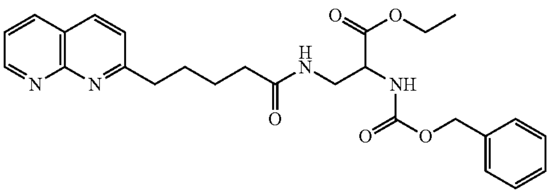 [SMILES: CCOC(=O)C(CNC(=O)CCCCc1ccc2cccnc2n1)NC(=O)OCc1ccccc1]

Intermediate 1 (0.5 g, 2.17 mmol) was dissolved in dry MeCN (20 mL). Ethyl 3-amino-2-((benzyloxycarbonyl)amino)propanoate hydrochloride (0.580 g, 2.17 mmol) (CAS: 179237-70-8, WO9610022). HOBt (0.290 g, 2.17 mmol), EDC·HCl (0.572 g, 2.6 mmol) and NMM (0.72 mL, 6.51 mmol) were added and the reaction mixture stirred at room temperature for 22 h. The solvent was removed to give an orange oil which was dissolved in dichloromethane (50 mL) and washed with saturated aqueous sodium hydrogen carbonate (50 mL). The organic layer was dried and the solvent removed under reduced pressure to give an orange oil. This was purified on a 40 g silica column using EtOAc:EtOH (0-10%) as the eluent to give a clear/green oil. LCMS showed the sub-title compound plus impurity minor peak. The oil was dissolved in dichloromethane and loaded onto an amino propyl 28 g column and eluted with EtOAc:EtOH (12:1) to give a clear oil (335 mg). Further elution with EtOH (3×200 mL) gave intermediate 2 as a clear oil (combined yield, 0.632 g). $^{1}H$ NMR (400 MHz; $CD_3OD$) δ 9.07 (d, 1H), 8.16 (d, 1H), 8.08 (d, 1H), 7.75 (br, 1H), 7.73 (d, 1H), 7.36 (d, 1H), 7.28 (s, 5H), 6.80 (d, 1H), 5.03 (s, 2H), 4.50-4.45 (m, 1H), 4.16 (q, 2H), 3.81 (br, 2H), 3.07 (t, 2H), 2.34 (t, 2H), 1.95 (quin, 2H), 1.74 (q, 2H), 1.23 (t, 3H). HRMS $[M+H]^+$ calculated for $C_{26}H_{30}N_4O_5$+H 479.2294, found 479.2076.

(c) Intermediate 3: ethyl 2-amino-3-(5-(5,6,7,8-tetrahydro-1,8-naphthyridin-2-yl)pentanamido)propanoate

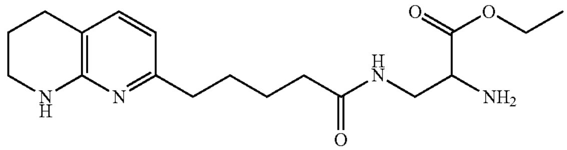 [SMILES: CCOC(=O)C(N)CNC(=O)CCCCc1ccc2c(n1)NCCC2]

Intermediate 2 (632 mg, 1.26 mmol) was dissolved into EtOH (20 mL) and Pd/C (100 mg, 0.94 mmol) was added. The reaction mixture was evacuated under reduced pressure and placed under nitrogen. The reaction mixture was evacuated under reduced pressure and placed under a hydrogen balloon. The reaction mixture was stirred at room temperature for 58 h, and filtered. The filtrate was collected and solvent removed to give intermediate 3 as clear green oil (350 mg). $^{1}H$ NMR (270 MHz; $CDCl_3$) δ 7.14 (d, 1H), 6.60 (s, 1H), 6.35 (d, 1H), 6.17 (br, 1H), 4.29 (q, 2H), 3.71-3.64 (m, 1H), 3.61 (dd, 1H), 3.43 (t, 2H), 3.38-3.32 (m, 1H), 2.71 (t, 2H), 2.26 (t, 2H), 2.60 (t, 2H), 1.19 (quin, 2H), 1.74-1.67 (m, 4H), 1.28 (t, 3H). HRMS $[M+H]^+$ calculated for $C_{18}H_{28}N_4O_3$+H 349.2240, found 349.2237.

(d) Intermediate 4: 1-(4-methylbenzenesulfonyl)azetidine-3-carboxylic acid

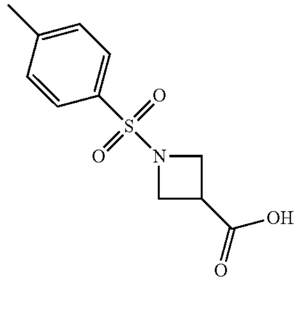 [SMILES: Cc1ccc(S(=O)(=O)N2CC(C(=O)O)C2)cc1]

3-Azetidine carboxylic acid (1 g, 9.9 mmol) was dissolved in ether:water (1:1, 40 mL). 4-toluenesulfonyl chloride (1.88 g, 9.9 mmol) and NaOH (79.9 mL, 19.8 mmol) were added to the solution which was stirred vigorously for 24 h. Ether:water (1:1, 20 mL) was added and the aqueous layer acidified with 2M hydrochloric acid to pH=2, and extracted with EtOAc (3×50 mL). The organic layer was collected and the solvent removed to give intermediate 4 as a colourless solid (1.5 g). $^{1}H$ NMR (400 MHz; $CDCl_3$) δ 7.7 (d, 2H), 7.4 (d, 2H), 4.0 (m, 4H), 3.3 (tt, 1H), 2.5 (s, 3H). HRMS $[M+Na]^+$ calculated for $C_{11}H_{13}NO_4S$+Na 278.0463, found 278.0448.

(e) Intermediate 5: ethyl 3-(5-(5,6,7,8-tetrahydro-1,8-naphthyridin-2-yl)pentanamido)-2-(1-(4-methylbenzenesulfonyl)azetidine-3-carboxamido)propanoate

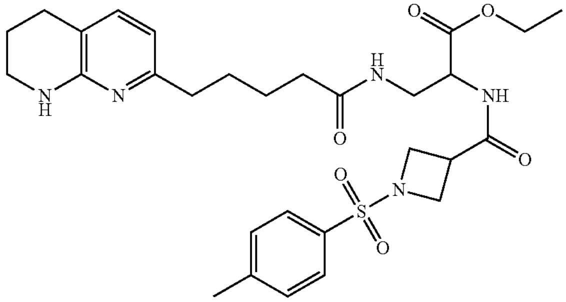 [SMILES: CCOC(=O)C(CNC(=O)CCCCc1ccc2c(n1)NCCC2)NC(=O)C1CN(S(=O)(=O)c2ccc(C)cc2)C1]

Intermediate 3 (300 mg, 0.86 mmol) was dissolved in dry MeCN (15 mL). DMAP (104 mg, 0.86 mmol), EDC·HCl (220 mg, 1.0 mmol), intermediate 4 (219 mg, 0.86 mmol) and NEM (0.29 mL, 1.7 mmol) were added. The reaction mixture was stirred at room temperature for 48 h and the solvent removed to give a yellow oil which was dissolved in dichloromethane (30 mL) and washed with saturated aqueous sodium hydrogen carbonate (3×50 mL). The organic layer was collected, dried and the solvent removed to give a yellow oil. This was purified via column chromatography using a 12 g silica column EtOAc:EtOH (0-8%) as the eluent to give the intermediate 5 as a colourless solid (170 mg).

$^{1}H$ NMR (400 MHz; Acetic acid-$d_4$) δ 7.74 (d, 2H), 7.46 (d, 1H), 7.43 (d, 2H), 6.50 (d, 1H), 4.66 (dd, 1H), 4.15 (m, 2H), 3.88 (t, 4H), 3.66 (dd, 1H), 3.58 (dd, 1H), 3.49 (t, 2H), 3.33 (quin, 1H), 2.77 (t, 2H), 2.72 (2H, br s), 2.45 (3H, s), 2.28 (t, 2H) 1.91 (br, 2H), 1.65 (br, 4H), 1.22 (t, 3H). HRMS $[M+H]^+$ calculated for $C_{29}H_{39}N_5O_6S$+H 586.2699, found 586.2693.

(f) Example 1: 3-(5-(5,6,7,8-tetrahydro-1,8-naphthyridin-2-yl)pentanamido)-2-(1-(4-methylbenzenesulfonyl)azetidine-3-carboxamido)propanoic acid

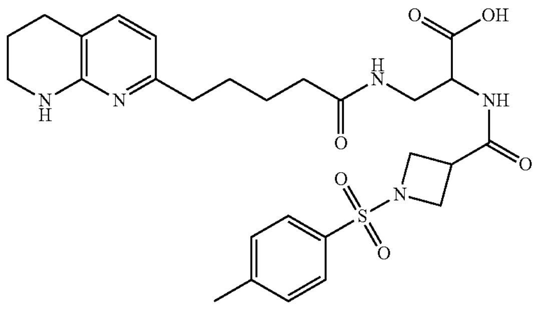 [SMILES: Cc1ccc(S(=O)(=O)N2CC(C(=O)NC(CNC(=O)CCCCc3ccc4c(n3)NCCC4)C(=O)O)C2)cc1]

Intermediate 5 (130 mg, 0.22 mmol) was dissolved in EtOH (4 mL), 2M NaOH (0.4 mL, 0.88 mmol) was added, and the reaction mixture stirred for 24 h. The solvent was removed to give a cream solid. This was dissolved in water 5 mL and loaded onto a 12 g Oasis cartridge and eluted with water:MeOH, (0-50%) to give 3-(5-(5,6,7,8-tetrahydro-1,8-naphthyridin-2-yl)pentanamido)-2-(1-(4-methylbenzenesulfonyl)azetidine-3-carboxamido)propanoic acid as colourless solid (102 mg). $^1$H NMR (400 MHz; $CD_3OD$) δ 7.65 (d, 2H), 7.39 (d, 2H), 7.08 (d, 1H), 6.31 (d, 1H), 4.19 (dd, 1H), 3.80-3.69 (m, 4H), 3.52 (dd, 1H), 3.38-3.34 (m, 1H), 3.25 (m, 2H), 3.12 (m, 1H), 2.63 (t, 2H), 2.45 (t, 2H), 2.39 (s, 3H), 2.10 (t, 2H), 1.81 (quin, 2H), 1.56-1.50 (m, 4H). HRMS $[M+H]^+$ calculated for $C_{27}H_{35}N_5O_6S$+H 558.2386, found 558.2376.

Example 2: 2-(1-(4-Fluorobenzenesulfonyl)azetidine-3-carboxamido)-3-(5-(5,6,7,8-tetrahydro-1,8-naphthyridin-2-yl)pentanamido)propanoic acid (a) Intermediate 6: 1-(4-fluorobenzenesulfonyl)azetidine-3-carboxylic acid

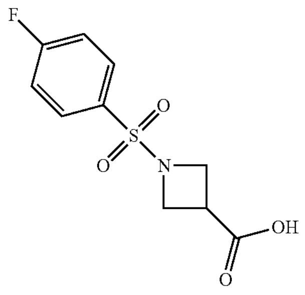 [SMILES: O=C(O)C1CN(S(=O)(=O)c2ccc(F)cc2)C1]

Prepared by the method of intermediate 4 using 4-fluorobenzenesulfonyl chloride to give intermediate 6 as a colourless solid (970 mg). $^1$H NMR (400 MHz; $CDCl_3$) δ 7.9 (m, 2H), 7.3 (m, 2H), 4.1 (t, 4H), 3.3 (m, 1H). HRMS $[M+H]^+$ calculated for $C_{10}H_{10}FNO_4S$+H 260.0393, found 260.0391.

(b) Intermediate 7: ethyl 2-(1-(4-fluorobenzenesulfonyl)azetidine-3-carboxamido)-3-(5-(5,6,7,8-tetrahydro-1,8-naphthyridin-2-yl)pentanamido)propanoate

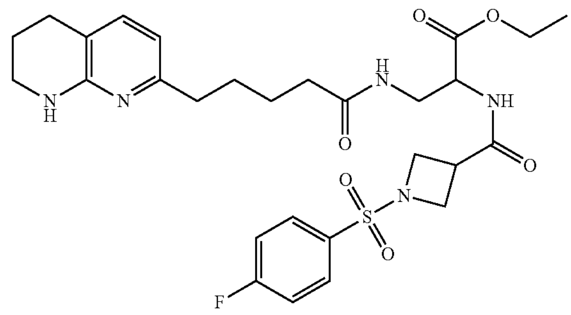 [SMILES: CCOC(=O)C(CNC(=O)CCCCc1ccc2c(n1)NCCC2)NC(=O)C1CN(S(=O)(=O)c2ccc(F)cc2)C1]

Prepared by the method of intermediate 5 using intermediate 6 (372 mg, 1.44 mmol) and intermediate 3 (500 mg, 1.43 mmol) to give intermediate 7 as a colourless gum (140 mg). $^1$H NMR (400 MHz; $CDCl_3$) δ 7.85 (m, 2H), 7.26 (m, 2H), 7.12 (d, 1H) 6.47 (d, 1H), 4.54 (ddd, 1H), 4.21 (m, 2H), 3.92 (m, 4H), 3.76 (m, 1H), 3.55 (m, 1H), 3.49 (t, 2H), 3.31 (m, 1H), 2.72 (t, 2H), 2.61 (s, 2H), 2.29 (m, 1H), 2.18 (s, 1H), 2.03 (d, 1H), 1.96 (m, 2H), 1.69 (s, 3H), 1.26 (t, 3H). HRMS $[M+H]^+$ calculated for $C_{28}H_{36}FN_5O_6S$+H 590.2449, found 590.2477.

(c) Example 2: 2-(1-(4-fluorobenzenesulfonyl)azetidine-3-carboxamido)-3-(5-(5,6,7,8-tetrahydro-1,8-naphthyridin-2-yl)pentanamido)propanoic acid

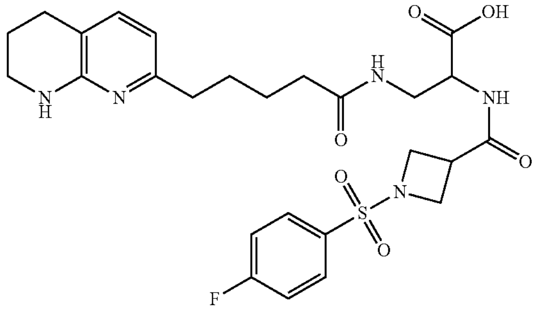 [SMILES: O=C(CCCCc1ccc2c(n1)NCCC2)NCC(NC(=O)C1CN(S(=O)(=O)c2ccc(F)cc2)C1)C(=O)O]

Prepared by the method of Example 1(f) using intermediate 7 (140 mg, 0.243 mmol) to give 2-(1-(4-fluorobenzenesulfonyl)azetidine-3-carboxamido)-3-(5-(5,6,7,8-tetrahydro-1,8-naphthyridin-2-yl)pentanamido)propanoic acid as a colourless gum (60 mg). $^1$H NMR (500 MHz; $CD_3OD$) δ 7.92 (m, 2H), 7.40 (dd, 3H), 6.49 (d, 1H), 4.27 (t, 1H), 3.87 (m, 4H), 3.48 (m, 4H), 3.29 (m, 1H), 2.78 (t, 2H), 2.63 (t, 2H), 2.23 (quin, 2H), 1.95 (m, 2H), 1.67 (m, 4H). HRMS $[M+H]^+$ calculated for $C_{26}H_{32}FN_5O_6S$+H 562.2136, found 562.2159.

Example 3: 3-(5-(5,6,7,8-Tetrahydro-1,8-naphthyridin-2-yl)pentanamido)-2-(1-(2-methylbenzenesulfonylazetidine-3-carboxamido)propanoic acid (a) Intermediate 8: 1-(2-methylbenzenesulfonyl)azetidine-3-carboxylic acid

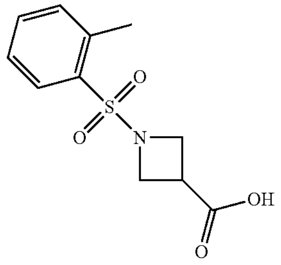 [SMILES: Cc1ccccc1S(=O)(=O)N1CC(C(=O)O)C1]

Prepared by the method of intermediate 4 using 2-toluenesulfonyl chloride (0.72 mL, 4.95 mmol) and 3-azetidinecarboxylic acid (500 mg, 4.95 mmol) to give intermediate 8 as a colourless solid (695 mg). $^1$H NMR (400 MHz; $CDCl_3$) δ 7.97 (dt, 1H), 7.51 (td, 1H), 7.35 (t, 2H), 4.20-4.03 (m, 4H), 3.43 (tt, 1H), 2.67 (s, 3H).

(b) Intermediate 9: ethyl 3-(5-(5,6,7,8-tetrahydro-1,8-naphthyridin-2-yl)pentanamido)-2-(1-(2-methylbenzenesulfonyl)azetidine-3-carboxamido)propanoate

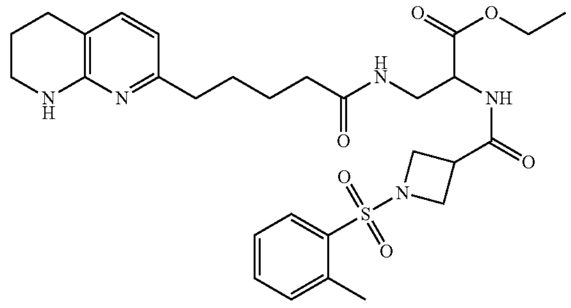 [SMILES: CCOC(=O)C(CNC(=O)CCCCc1ccc2c(n1)NCCC2)NC(=O)C1CN(S(=O)(=O)c2ccccc2C)C1]

Prepared by the method of intermediate 5 using intermediate 8 (368 mg, 1.44 mmol) and intermediate 3 (500 mg, 1.43 mmol) to give intermediate 9 (330 mg) that was used directly in the next step.

(c) Example 3: 3-(5-(5,6,7,8-tetrahydro-1,8-naphthyridin-2-yl)pentanamido)-2-(1-(2-methylbenzenesulfonyl)azetidine-3-carboxamido)propanoic acid

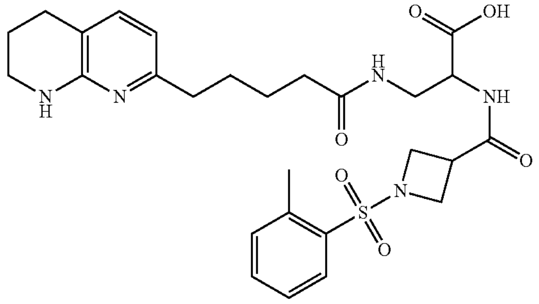 [SMILES: Cc1ccccc1S(=O)(=O)N1CC(C(=O)NC(CNC(=O)CCCCc2ccc3c(n2)NCCC3)C(=O)O)C1]

Prepared by the method of Example 1(f) using intermediate 9 (300 mg, 0.513 mmol) to give 3-(5-(5,6,7,8-tetrahydro-1,8-naphthyridin-2-yl)pentanamido)-2-(1-(2-methylbenzenesulfonyl)azetidine-3-carboxamido)propanoic acid (150 mg).

$^1$H NMR (400 MHz; $CD_3OD$) δ 7.90 (dd, 1H), 7.54 (td, 1H), 7.45 (dt, 1H), 7.43-7.34 (m, 2H), 6.50 (d, 1H), 4.39-4.27 (m, 1H), 4.10-3.98 (m, 2H), 3.93 (ddd, 2H), 3.57 (dd, 2H), 3.50-3.39 (m, 3H), 2.78 (t, 2H), 2.70-2.59 (m, 5H), 2.31-2.16 (m, 2H), 1.98-1.87 (m, 2H), 1.74-1.59 (m, 4H).

Example 4: 3-(5-(5,6,7,8-Tetrahydro-1,8-naphthyridin-2-yl)pentanamido)-2-(1-(3-methylbenzenesulfonyl)azetidine-3-carboxamido)propanoic acid (a) Intermediate 10: 1-(3-methylbenzenesulfonyl)azetidine-3-carboxylic acid

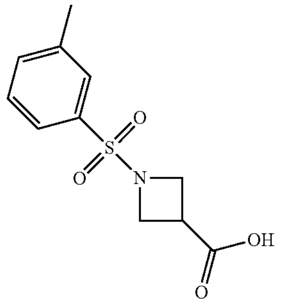 [SMILES: Cc1cccc(S(=O)(=O)N2CC(C(=O)O)C2)c1]

Prepared by the method of intermediate 4 using 3-toluenesulfonyl chloride (0.73 mL, 4.95 mmol) and 3-azetidinecarboxylic acid (500 mg, 4.95 mmol) to give intermediate 10 as a flaky, colourless solid (940 mg). $^1$H NMR (400 MHz; $CDCl_3$) δ 7.69-7.64 (m, 2H), 7.49-7.46 (m, 2H), 4.00 (quin, 4H), 3.29 (m, 1H), 2.47 (s, 3H). HRMS $[M-H]^+$ calculated for $C_{11}H_{13}NO_4S$-H 254.0487, found 254.0485.

(b) Intermediate 11: ethyl 3-(5-(5,6,7,8-tetrahydro-1,8-naphthyridin-2-yl)pentanamido)-2-(1-(3-methylbenzenesulfonyl)azetidine-3-carboxamido)propanoate

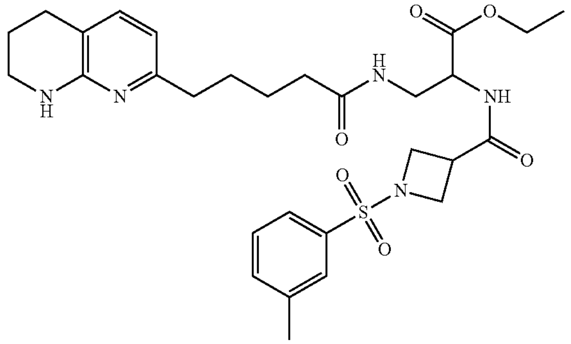 [SMILES: CCOC(=O)C(CNC(=O)CCCCc1ccc2c(n1)NCCC2)NC(=O)C1CN(S(=O)(=O)c2cccc(C)c2)C1]

Prepared by the method of intermediate 5 using intermediate 10 (367.6 mg, 1.44 mmol) and intermediate 3 (500 mg, 1.43 mmol) to give intermediate 11 as a colourless, web-like solid (220 mg). $^1$H NMR (400 MHz; DMSO-$d_6$) δ 8.27 (d, 1H), 7.85 (t, 1H), 7.62-7.57 (m, 2H), 7.03 (d, 1H), 6.25 (d, 1H), 4.24 (q, 1H), 4.02 (q, 2H), 3.83-3.70 (m, 4H), 3.33 (m, 2H), 3.26-3.18 (m, 3H), 2.60 (t, 2H), 2.44 (s, 3H), 2.40 (t, 2H), 2.02 (t, 2H), 1.75 (t, 2H), 1.54-1.42 (m, 4H), 1.13 (t, 3H). HRMS $[M+H]^+$ calculated for $C_{29}H_{39}N_5O_6S$+H 586.2699, found 586.2705.

(c) Example 4: 3-(5-(5,6,7,8-tetrahydro-1,8-naphthyridin-2-yl)pentanamido)-2-(1-(3-methylbenzenesulfonyl)azetidine-3-carboxamido)propanoic acid

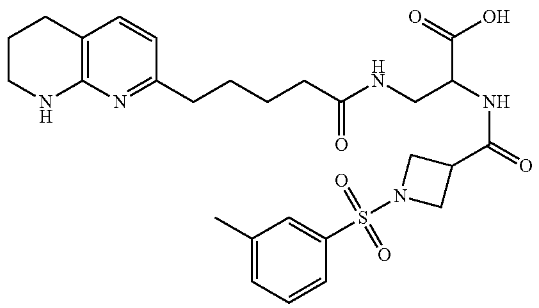 [SMILES: Cc1cccc(S(=O)(=O)N2CC(C(=O)NC(CNC(=O)CCCCc3ccc4c(n3)NCCC4)C(=O)O)C2)c1]

Prepared by the method of Example 1(f) using intermediate 11 to give 3(5,6,7,8-tetrahydro-1,8-naphthyridin-2-yl) pentanamido)-2-(1-(3-methylbenzenesulfonyl)azetidine-3-carboxamido)propanoic acid as a clear, colourless glass (95 mg). $^1$H NMR (400 MHz; $CD_3OD$) δ 7.68-7.64 (m, 2H), 7.56-7.54 (m, 2H), 7.45 (d, 1H), 6.51 (d, 1H), 4.28 (t, 1H), 3.97-3.86 (m, 4H), 3.55-3.53 (m, 2H), 3.46 (t, 2H), 3.30-3.24 (m, 1H), 2.79 (t, 2H), 2.66 (t, 2H), 2.49 (s, 3H), 2.23 (t, 2H), 1.94 (quin, 2H), 1.68 (m, 4H). HRMS $[M+H]^+$ calculated for $C_{27}H_{35}N_5O_6S+H$ 558.2386, found 558.2404.

Example 5: 2-(1-(3-Fluorobenzenesulfonyl)azetidine-3-carboxamido)-3-(5-(5,6,7,8-tetrahydro-1,8-naphthyridin-2-yl)pentanamido)propanoic acid (a) Intermediate 12: 3-(3-fluorobenzenesulfonyl) cyclobutane-1-carboxylic acid

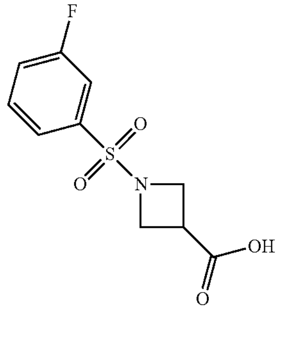 [SMILES: O=C(O)C1CN(S(=O)(=O)c2cccc(F)c2)C1]

Prepared by the method of intermediate 4 using 3-fluorobenzenesulfonyl chloride (936 mg, 4.95 mmol) and 3-azetidinecarboxylic acid (500 mg, 4.95 mmol) to give intermediate 12 as a colourless glass (1.08 g). $^1$H NMR (400 MHz; $CDCl_3$) δ 7.68 (dt, 1H), 7.60 (m, 2H), 7.40 (tdd, 1H), 4.04 (m, 4H), 3.34 (tt, 1H). HRMS $[M-H]^-$ calculated for $C_{10}H_{10}FNO_4S-H$ 258.0236, found 258.0242.

(b) Intermediate 13: ethyl 2-(1-(3-fluorobenzenesulfonyl)azetidine-3 carboxamido)-3-(5-(5,6,7,8-tetrahydro-1,8-naphthyridin-2-yl)pentanamido)propanoate

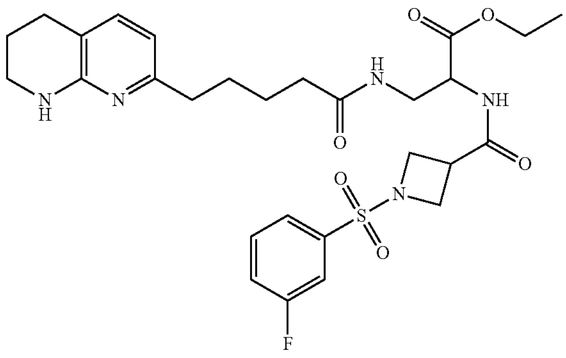 [SMILES: CCOC(=O)C(CNC(=O)CCCCc1ccc2c(n1)NCCC2)NC(=O)C1CN(S(=O)(=O)c2cccc(F)c2)C1]

A solution of intermediate 12 (372 mg, 1.43 mmol) and intermediate 3 (500 mg, 1.43 mmol in acetonitrile (150 mL) was cooled to 3° C. and propylphosphonic anhydride (>50 wt. % in ethyl acetate, 1.2 mL, 2.00 mmol) and N,N-diisopropylethylamine (0.5 mL, 3.44 mmol) added by dropwise addition. The reaction mixture was stirred at room temperature under an atmosphere of nitrogen for 24 h. The solvent was removed under reduced pressure, and the resulting residue dissolved in saturated aqueous hydrogen carbonate (75 mL) and extracted with dichloromethane (4×50 mL). The organic extracts were combined and washed with brine, dried over $MgSO_4$, filtered and the solvent removed under reduced pressure. Silica gel chromatography, eluting with ethyl acetate and triethylamine (98:2 to 91:9) gave intermediate 13 as a colourless gum (400 mg). $^1$H NMR (400 MHz; $CDCl_3$) δ 7.94 (d, 1H), 7.63 (dt, 1H), 7.55 (m, 2H), 7.35 (tdd, 1H), 7.13 (m, 1H), 6.33 (d, 1H), 4.46 (d, 1H), 4.14 (dd, 2H), 3.93 (m, 4H), 3.61 (m, 2H), 3.40 (t, 2H), 3.25 (m, 1H), 2.71 (t, 2H), 2.53 (m, 2H), 2.20 (t, 2H), 1.90 (m, 2H), 1.66 (m, 4H), 1.23 (t, 3H). HRMS $[M+H]^+$ calculated for $C_{28}H_{36}FN_5O_6S+H$ 590.2449, found 590.2475.

(c) Example 5: 2-(1-(3-fluorobenzenesulfonyl)azetidine-3-carboxamido)-3-(5-(5,6,7,8-tetrahydro-1,8-naphthyridin-2-yl)pentanamido)propanoic acid

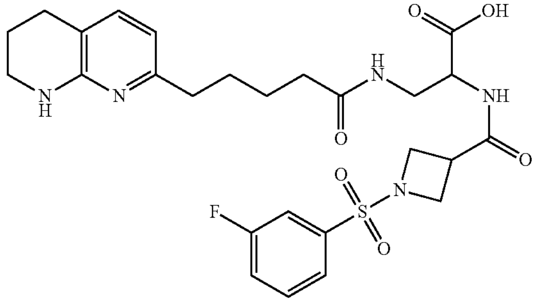 [SMILES: O=C(CCCCc1ccc2c(n1)NCCC2)NCC(NC(=O)C1CN(S(=O)(=O)c2cccc(F)c2)C1)C(=O)O]

Prepared by the method of Example 1(f) using intermediate 13 to give 2-(1-(3-fluorobenzenesulfonyl)azetidine-3-carboxamido)-3-(5-(5,6,7,8-tetrahydro-1,8-naphthyridin-2- yl)pentanamido)propanoic acid as a colourless gum (180 mg). $^1$H NMR (400 MHz; $CD_3OD$) δ (400 MHz, MeOD) 7.93-7.06 (m, 5H), 6.42 (d, 1H), 4.40-4.20 (m, 2H), 4.08-3.78 (m, 4H), 3.71-3.35 (m, 4H), 3.34-3.13 (m, 2H), 2.73 (t, 2H), 2.57 (t, 2H), 2.18 (heptet, 2H), 1.89 (quin, 2H), 1.73-1.55 (m, 4H), 1.42-1.18 (m, 2H). HRMS $[M+H]^+$ calculated for $C_{26}H_{32}FN_5O_6S$+H 562.2136, found 562.2164.
Route 2
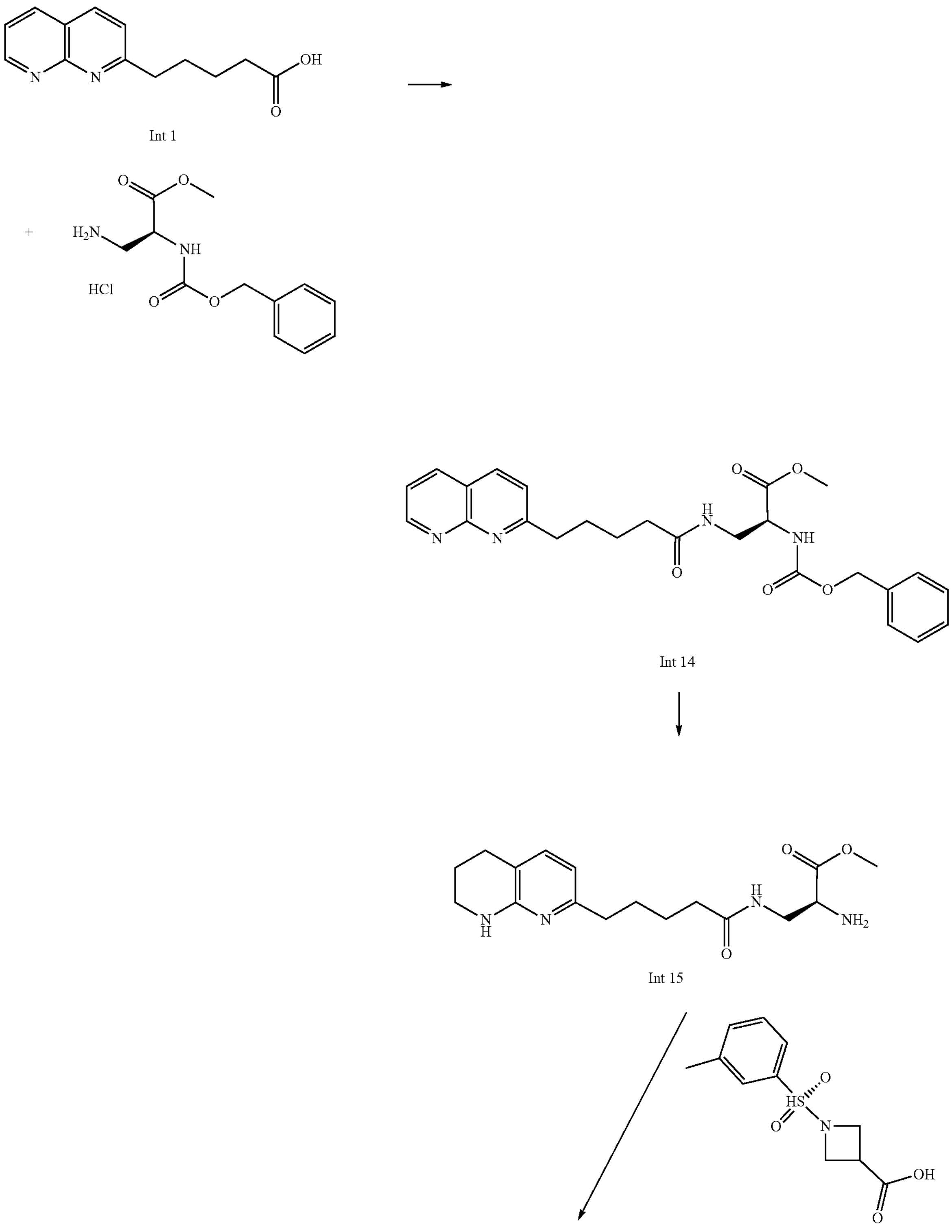
Int 1
Int 14
Int 15
Int 10

-continued

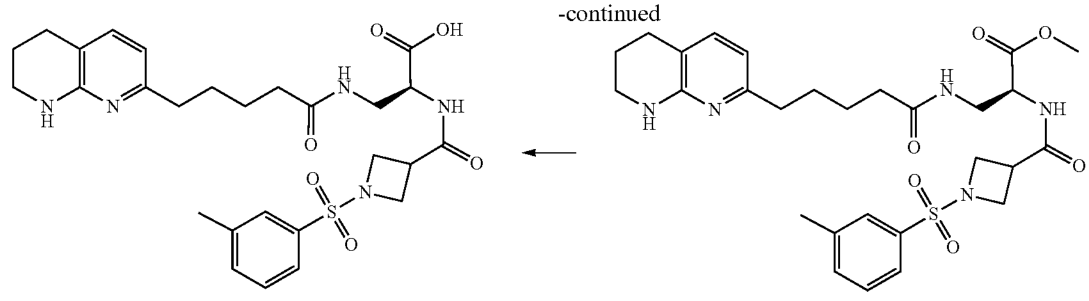

Int 16

Example 6A: (S)-3-(5-(5,6,7,8-Tetrahydro-1,8-naphthyridin-2-yl)pentanamido)-2-(1-(3-methylbenzenesulfonyl)azetidine-3-carboxamido)pentanoic acid (a) Intermediate 14: methyl (S)-3-(5-(1,8-naphthyridin-2-yl)pentanamido)-2-(2-phenylacetamido)propanoate

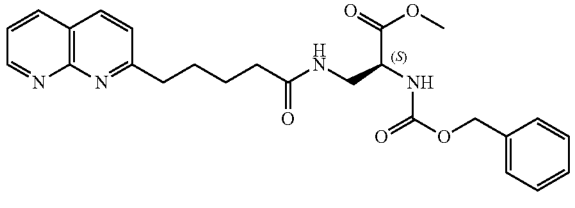

To a stirred solution of intermediate 1 (6.85 g, 29.7 mmol) was added HOBT·$H_2O$ (5.6 g, 35.6 mmol) and EDC·HCl (6.79 g, 35.6 mmol). After 5 min, methyl 2-(S)-[N-carbobenzyloxy]amino-3-aminopropionate hydrochloride (8.6 g, 29.7 mmol) (CAS: 35761-27-4) and N,N-diisopropylethylamine (12.2 mL, 71.2 mmol) were added and the resultant solution stirred at room temperature for 18 h. The solution was concentrated to approx. 20 mL and water (100 mL) added and extracted with dichloromethane (5×100 mL). The combined organic phase was washed with sodium hydrogen carbonate (3×100 mL), brine (140 mL), dried and concentrated to give a residue which as purified by chromatography using ethyl acetate:methanol (2.5% to 10%) to give intermediate 14 (13.79 g). $^1$H NMR (400 MHz; $CDCl_3$) δ 9.1 (m, 1H), 8.19 (d, 1H), 8.10 (m, 1H), 7.9 (d, 1H), 7.44 (m 1H), 7.38 (m, 1H), 7.29-7.24 (m, 5H), 6.95 (d, 1H), 5.04 (s, 2H), 4.53 (m, 1H), 3.86 (m, 2H), 3.72 (s, 3H), 3.10 (m, 2H), 2.37 (m, 2H), 1.98 (m, 2H), 1.79 (m, 2H).

(b) Intermediate 15: methyl (S)-2-amino-3-(5-(5,6,7,8-tetrahydro-1,8-naphthyridin-2-yl)pentanamido)propanoate

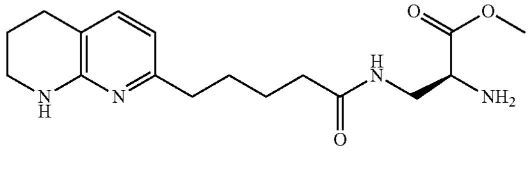 [SMILES: COC(=O)[C@@H](N)CNC(=O)CCCCc1ccc2c(n1)NCCC2]

To a suspension of Pd/C (10%) (4.5 g) in ethyl acetate (20 mL) was added a solution of intermediate 14 (5.8 g, 12.5 mmol) in methanol (100 mL). The suspension was de-gassed three times using argon and placed under an atmosphere of hydrogen and stirred for 18 h. The mixture was filtered, the filtrate evaporated to give intermediate 15 as a pale brown oil which solidified on standing (3.43 g). $^1$H NMR (400 MHz; $CD_3OD$) δ 7.31 (d, 1H), 6.48 (d, 1H), 3.78 (s, 3H), 3.54 (m, 2H), 3.44 (m, 2H), 2.76 (m, 2H), 2.61 (m, 2H), 2.25 (m, 2H), 1.92 (m, 2H), 1.65 (m, 4H).

(c) Intermediate 16: methyl (S)-3-(5-(5,6,7,8-tetrahydro-1,8-naphthyridin-2-yl)pentanamido)-2-(1-(3-methylbenzenesulfonylazetidine-3-carboxamido) pentanoate

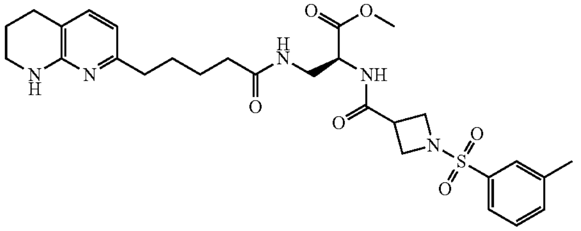 [SMILES: COC(=O)[C@H](CNC(=O)CCCCc1ccc2c(n1)NCCC2)NC(=O)C1CN(S(=O)(=O)c2cccc(C)c2)C1]

To a solution of intermediate 15 (500 mg, 1.30 mmol) in acetonitrile (25 mL) was added intermediate 10 (331.8 mg, 1.30 mmol), propylphosphonic anhydride solution (50% wt % in EtOAc, 1.21 mL, 1.44 mmol) and N,N-diisopropylethylamine (0.66 mL, 1.73 mmol). The solution was stirred at room temperature under nitrogen for 16 h, and the solvent removed under reduced pressure. The resultant oil was dissolved in dichloromethane (50 mL), and washed with saturated sodium hydrogen carbonate (50 mL). The aqueous layer was extracted with dichloromethane (20 mL, then 30 mL). The organic layers were combined and washed with saturated aqueous hydrogen carbonate solution (50 mL). The combined organics were then dried ($MgSO_4$) and the solvent removed under reduced pressure to produce a colourless solid. The crude product was purified by flash chromatography on silica (40 g) eluting using methanol-dichloromethane (5:95) to intermediate 16 as a colourless solid (340 mg). $^1$H NMR (400 MHz; $CDCl_3$) δ 7.68-7.64 (m, 2H), 7.49-7.45 (m, 2H), 7.15 (d, 1H), 6.37 (d, 1H), 4.54 (q, 1H), 3.98-3.89 (m, 4H), 3.73 (s, 3H), 3.65 (d, 2H), 3.44 (t, 2H), 3.20 (quin, 1H), 2.74 (t, 2H), 2.57 (t, 2H), 2.48 (s, 3H), 2.25 (t, 2H), 1.94 (quin, 2H), 1.69-1.60 (m, 4H). HRMS [M−H] calculated for $C_{28}H_{37}N_5O_6S$−H 570.2386, found 570.2368.

(d) Example 6A: (S)-3-(5-(5,6,7,8-tetrahydro-1,8-naphthyridin-2-yl)pentanamido)-2-(1-(3-methylbenzenesulfonyl)azetidine-3-carboxamido)pentanoic acid

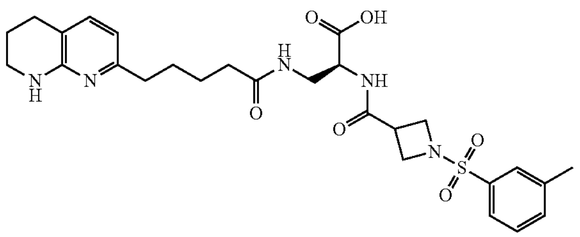 [SMILES: Cc1cccc(S(=O)(=O)N2CC(C(=O)N[C@@H](CNC(=O)CCCCc3ccc4c(n3)NCCC4)C(=O)O)C2)c1]

To a solution of intermediate 16 (150 mg, 0.26 mmol) in ethanol (5 mL) was added aqueous sodium hydroxide solution 2 M (0.26 mL, 0.52 mmol) and stirred at room temperature for 64 h. The solvent was removed under reduced pressure and the resultant colourless solid was dissolved in water (2 mL) and eluted from an Oasis column using water-methanol. Select fractions were combined and the solvent removed under reduced pressure to yield (S)-3-(5-(5,6,7,8-tetrahydro-1,8-naphthyridin-2-yl)pentanamido)-2-(1-(3-methylbenzenesulfonyl)azetidine-3-carboxamido) pentanoic acid as a clear colourless glass (55 mg). $^1H$ NMR (300 MHz; $CD_3OD$) δ 7.68-7.62 (m, 2H), 7.56-7.53 (m, 2H), 7.46 (d, 1H), 6.51 (d, 1H), 4.27 (t, 1H), 3.97-3.86 (m, 4H), 3.53 (d, 2H), 3.46 (t, 2H), 3.28 (quin, 1H), 2.79 (t, 2H), 2.66 (t, 2H), 2.48 (s, 3H), 2.22 (m, 2H), 1.93 (quin, 2H), 1.76-1.60 (m, 4H). HRMS $[M+H]^+$ calculated for $C_{27}H_{35}N_5O_6S+H$ 558.2386, found 558.2368.

The racemic product of Example 4 was subjected to chiral analysis using Supercritical Fluid Chromatography and as expected showed 2 components (FIG. 1).

Figure 2:
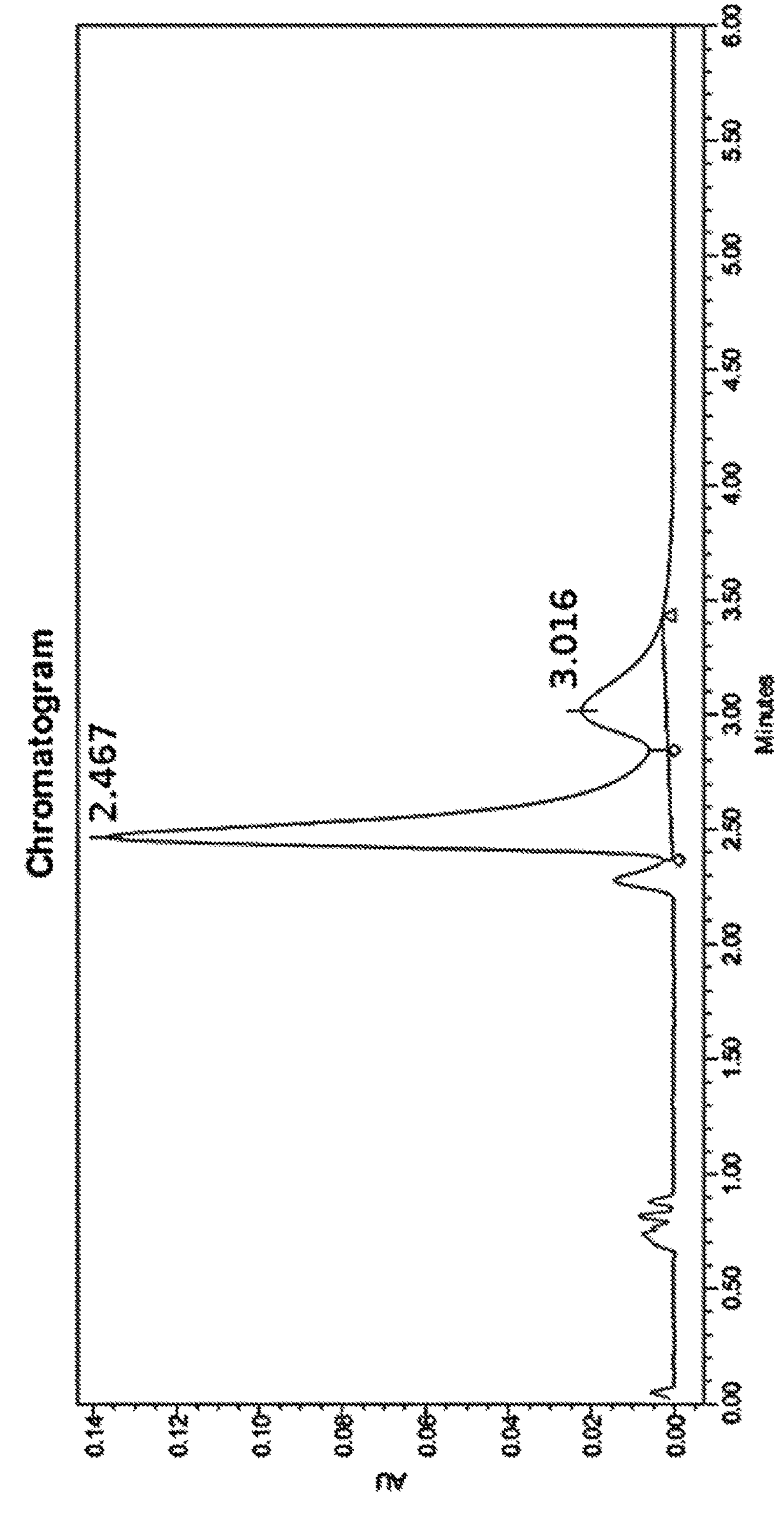
FIG. 2 is a chiral analysis using Supercritical Fluid Chromatography of the chirally enriched product of Example 6.

Chiral Analysis Conditions:

Waters: UPC2
Column Details: Lux C1 (4.6 mm×250 mm, 5 um)
Column Temperature: 40° C.
Flow Rate: 4 mL/min
Detector Wavelength: 210-400 nm
Injection Volume: 1.0 uL
BPR: 125 BarG
Isocratic Conditions: 40:60 MeOH:$CO_2$ The product of Example 6 was subjected to chiral analysis under the same conditions that indicated that the product was not 100% chirally pure but was enriched in the first eluting peak (see FIG. 2). The chromatogram indicated that the first eluting peak was the required S isomer.

Figure 3:
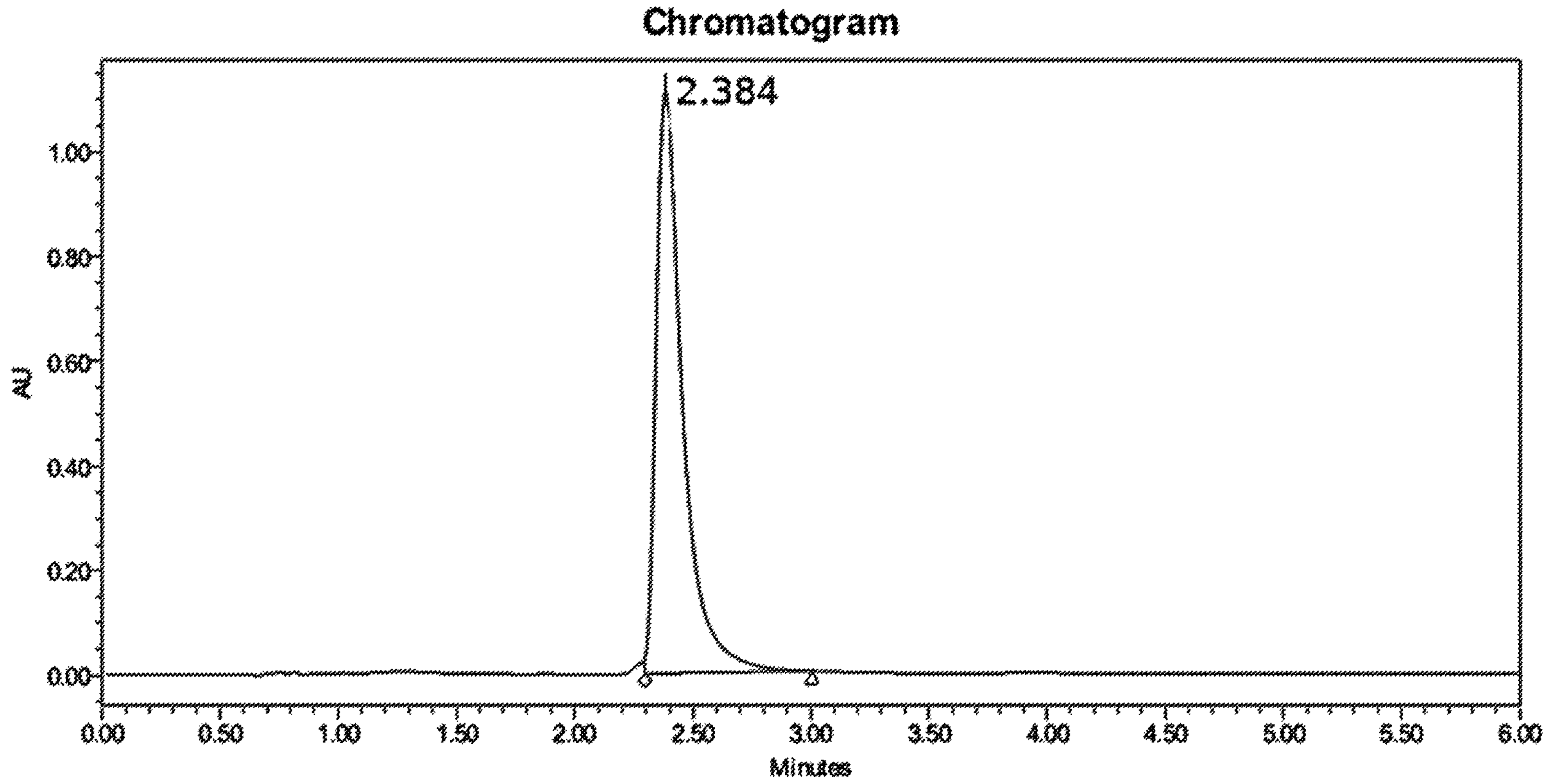
FIG. 3 is the chiral analysis of the first peak (Peak 1, 140.3 mg) of a portion of Example 6 obtained using Supercritical fluid chromatography.
Figure 4:
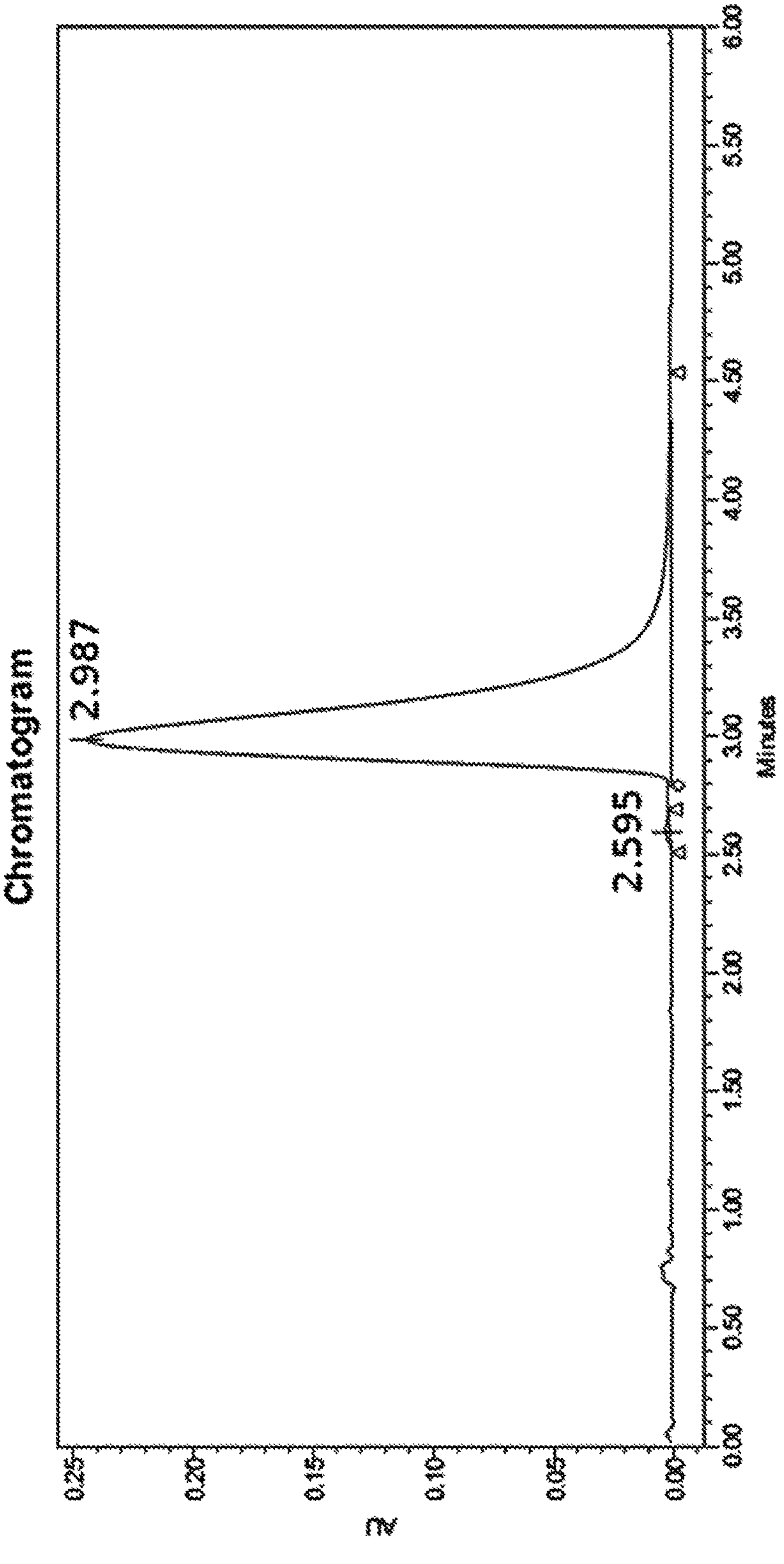
FIG. 4 is the chiral analysis of the second peak (Peak 2, 32.6 mg) of a portion of Example 6 obtained using Supercritical fluid chromatography.

A portion of Example 6 (198 mg) was subjected to chiral purification using Supercritical fluid chromatography to give two products. Peak 1 140.3 mg (FIG. 3) and Peak 2 32.6 mg (FIG. 4).

Chiral Purification Conditions:

Sepiatec 100 Prep SFC
Column Details: Lux C1 (21.2 mm×250 mm, 5 um)
Column Temperature: 40° C.
Flow Rate: 50 mL/min
BPR: 125 BarG
Detector Wavelength: 210 nm
Injection Volume: 500 uL (25 mg)
Isocratic Conditions: 40:60 MeOH:$CO_2$ Peak 1 Example 6A: (S)-3-(5-(5,6,7,8-tetrahydro-1,8-naphthyridin-2-yl)pentanamido)-2-(1-(3-methylbenzenesulfonyl)azetidine-3-carboxamido)pentanoic acid—See FIG. 3.

Peak 2 Example 6B: 6: (R)-3-(5-(5,6,7,8-tetrahydro-1,8-naphthyridin-2-yl)pentanamido)-2-(1-(3-methylbenzenesulfonyl)azetidine-3-carboxamido)pentanoic acid (below)—See FIG. 4.

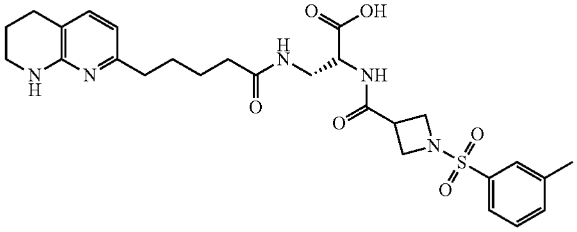

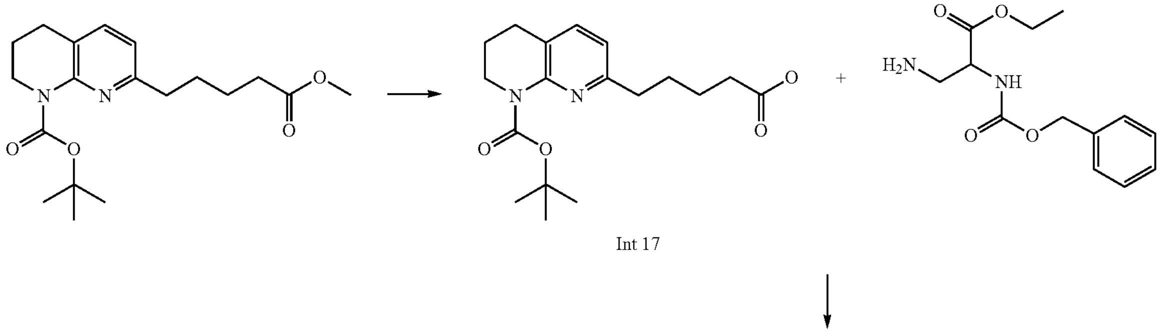

Int 17

-continued
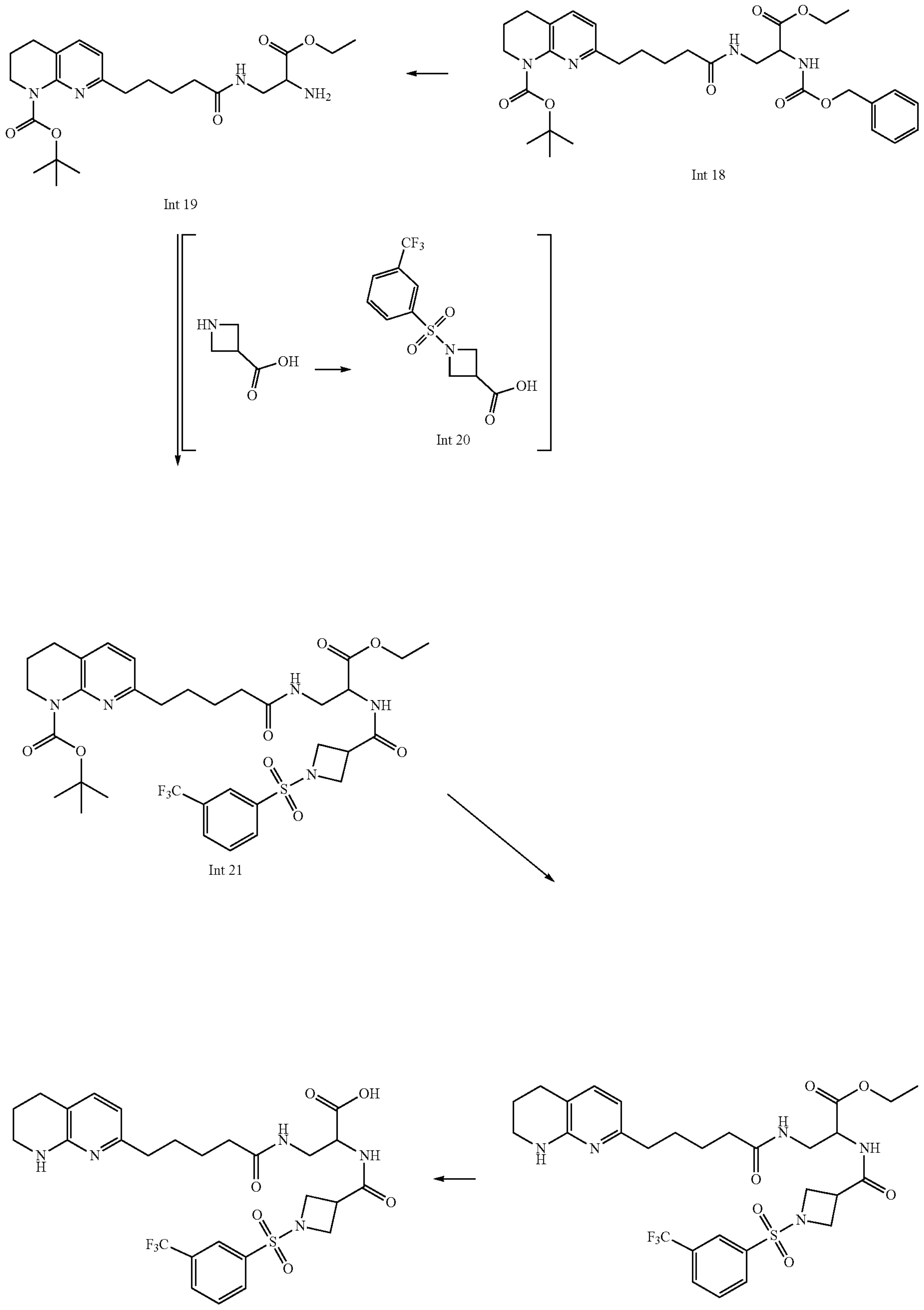
Int 19
Int 18
Int 20
Int 21
Int 22

Example 7: 3-(5-(5,6,7,8-Tetrahydro-1,8-naphthyridin-2-yl)pentanamido)-2-(1-(3-(trifluoromethylbenzenesulfonyl)azetidine-3-carboxamido)propanoic acid (a) Intermediate 17: lithium 5-(8-(tert-butoxycarbonyl)-5,6,7,8-tetrahydro-1,8-naphthyridin-2-yl)pentanoate

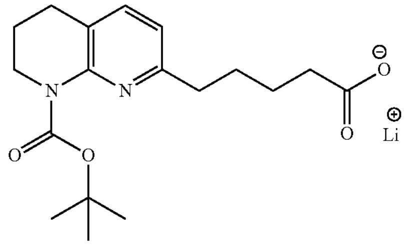 [SMILES: CC(C)(C)OC(=O)N1CCCc2ccc(CCCCC(=O)[O-])nc21 ; [Li+]]

To a solution of tert-butyl 7-(5-methoxycarbonylpentyl)-3,4-dihydro-1,8-naphthyridine-1(2H)-carboxylate (10 g, 28.7 mmol) in tetrahydrofuran (60 mL) and water (20 mL) was added lithium hydroxide monohydrate (1.33 g, 31.6 mmol). The reaction mixture was stirred at room temperature for 36 h and concentrated under reduced pressure and azeotroped with toluene (10×25 mL) to yield intermediate 17 as a cream foam (11.5 g, 118%—solvent residue). $^1$H NMR (300 MHz; $CD_3OD$) δ 7.47 (d, 1H), 6.99 (d, 1H), 3.74 (t, 2H), 2.77 (t, 2H), 2.75 (t, 2H), 2.21 (t, 2H), 1.92 (q, 2H), 1.81-1.64 (m, 4H), 1.52 (s, 9H). HRMS $[M]^-$ calculated for $C_{18}H_{25}N_2O_4$ 333.1820, found 333.1807.

(b) Intermediate 18: 9-tert-butyl 7-(5-((2-((benzyloxycarbonyl)amino)-3-ethoxycarbonylpropyl) amino)-5-oxopentyl)-3,4-dihydro-1,8-naphthyridine-1(2H)-carboxylate

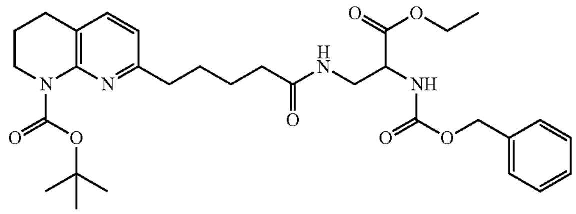 [SMILES: CCOC(=O)C(CNC(=O)CCCCc1ccc2c(n1)N(C(=O)OC(C)(C)C)CCC2)NC(=O)OCc1ccccc1]

To a solution of intermediate 17 (9.77 g, 28.7 mmol) in acetonitrile (500 mL) was added ethyl 3-amino-2-((benzyloxycarbonyl)amino)propanoate (8.67 g, 28.7 mmol). To this solution was added N,N-diisopropylethylamine (9.83 mL, 57.4 mmol) and propylphosphonic anhydride solution (50% w/w in EtOAc, 20.5 mL, 34.44 mmol) at 0° C. over 10 min. The reaction was stirred at room temperature for 24 h and the solvent removed under reduced pressure. The resultant oil was dissolved in dichloromethane (200 mL) and washed with saturated sodium hydrogen carbonate solution (200 mL). The layers were separated and the aqueous layer extracted with dichloromethane (2×200 mL). The organic layers were combined, dried with $MgSO_4$, filtered and the solvent removed under reduced pressure. The resultant oil was separated into 4 batches and purified via flash chromatography on silica cartridges (200 g, 50μ), eluting using methanol-ethyl acetate (5:95), to produce intermediate 18 as a clear colourless oil (10.5 g). $^1$H NMR (300 MHz; $CDCl_3$) δ 7.37-7.30 (m, 6H), 6.82 (d, 1H), 5.09 (s, 2H), 4.35 (m, 1H), 4.15 (t, 2H), 3.75 (q, 2H), 3.68-3.57 (m, 2H), 2.74 (t, 2H), 2.72 (t, 2H), 2.24 (t, 2H), 1.92 (quin, 2H), 1.80-1.64 (m, 4H), 1.53 (s, 9H), 1.25 (t, 3H). HRMS $[M+H]^+$ calculated for $C_{31}H_{42}N_4O_7$+H 583.3132, found 583.3152.

b1) Intermediate 19: tert-butyl 7-(5-((2-amino-3-ethoxycarbonylpropyl)amino)-5-oxopentyl)-3,4-dihydro-1,8-naphthyridine-1(2H)-carboxylate

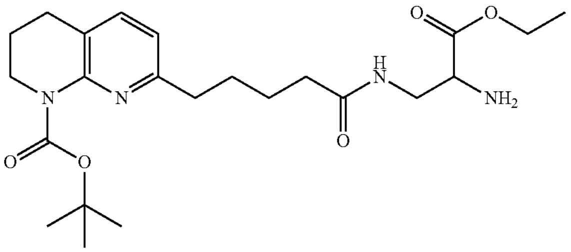 [SMILES: CCOC(=O)C(N)CNC(=O)CCCCc1ccc2c(n1)N(C(=O)OC(C)(C)C)CCC2]

To a solution of intermediate 18 (4.55 g, 7.82 mmol) in ethanol (450 mL) was added palladium on carbon (10% w/w, 455 mg) and placed under nitrogen. The flask was evacuated, placed under hydrogen and stirred at room temperature for 48 h. The hydrogen was evacuated from the flask and replaced with air, the reaction mixture filtered through glass-fibre filter paper and the solid phase washed with ethanol (50 mL) The filtrate was evaporated under reduced pressure to produce intermediate 19 as a clear colourless oil (3.11 g). $^1$H NMR (300 MHz; $CDCl_3$) δ 7.30 (d, 1H), 6.82 (d, 1H), 4.18 (q, 2H), 3.78-3.70 (m, 3H), 3.62-3.28 (m, 4H), 2.73 (m, 4H), 2.25 (t, 2H), 1.93 (quin, 2H), 1.75 (m, 4H), 1.53 (s, 9H), 1.25 (t, 3H). HRMS $[M+H]^+$ calculated for $C_{23}H_{36}N_4O_5$+H 449.2758, found 449.2757.

(c) Intermediate 20: 1-(3-(trifluoromethyl)benzenesulfonyl)azetidine-3-carboxylic acid

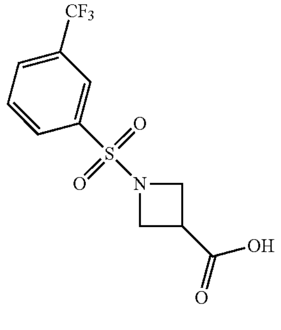 [SMILES: O=C(O)C1CN(S(=O)(=O)c2cccc(C(F)(F)F)c2)C1]

Prepared by the method of intermediate 4 using 3-(trifluoromethyl)benzenesulfonyl chloride (0.69 mL, 4.30 mmol) and azetidine-3-carboxylic acid (500 mg, 4.95 mmol) to produce intermediate 20 as a flaky, white solid (650 mg). $^1$H NMR (500 MHz; $CDCl_3$) δ 8.14 (s, 1H), 8.08 (d, 1H), 7.94 (d, 1H), 7.77 (t, 1H), 4.07 (dt, 4H), 3.39-3.33 (m, 1H). HRMS $[M+H]^+$ calculated for $C_{11}H_{10}F_3NO_4S$+H 310.0361, found 310.0366.

(d) Intermediate 21: tert-butyl 7-(5-((3-ethoxycarbonyl-2-(1-(3-(trifluoromethyl)benzenesulfonyl)azetidine-3-carboxamido)propyl)amino)-5-oxopentyl)-3,4-dihydro-1,8-naphthyridine-1(2H)-carboxylate

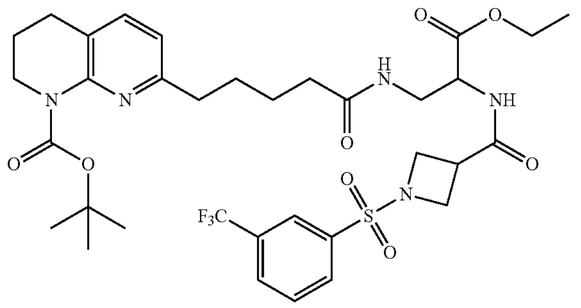 [SMILES: CCOC(=O)C(CNC(=O)CCCCc1ccc2c(n1)N(C(=O)OC(C)(C)C)CCC2)NC(=O)C1CN(S(=O)(=O)c2cccc(C(F)(F)F)c2)C1]

To a solution of intermediate 19 (500 mg, 1.12 mmol) in acetonitrile (30 mL) was added intermediate 20 (364 mg, 1.12 mmol). To this solution was added N,N-diisopropylethylamine (390 μL, 2.24 mmol) and propylphosphonic anhydride (0.80 mL, 1.34 mmol) at 0° C. over 10 min. The reaction was left to stir at room temperature under nitrogen for 48 h. and the solvent removed under reduced pressure. The crude product was dissolved in dichloromethane (25 mL) and washed with saturated sodium hydrogen carbonate solution (25 mL). The layers were separated and the aqueous layer extracted with dichloromethane (2×25 mL). The organics were combined, dried ($MgSO_4$), filtered and the solvent removed under reduced pressure. The resultant oil was purified via flash chromatography on silica (40 g) and eluted using methanol-dichloromethane (5:95) to produce intermediate 21 as a colourless oil (680 mg). $^1H$ NMR (500 MHz; $CDCl_3$) δ 8.07 (s, 1H), 8.01 (d, 1H), 7.88 (d, 1H), 7.72 (t, 1H), 7.33 (d, 1H), 6.83 (d, 1H), 4.33 (td, 1H), 4.08-4.00 (m, 2H), 3.91 (dt, 4H), 3.75-3.71 (m, 2H), 3.59-3.53 (m, 1H), 3.47-3.43 (m, 1H), 3.14 (quin, 1H), 2.74-2.68 (m, 4H), 2.20 (td, 2H), 1.91 (quin, 2H), 1.73-1.59 (m, 4H), 1.49 (s, 9H), 1.15 (t, 3H). HRMS $[M+H]^+$ calculated for $C_{34}H_{44}F_3N_5O_8S$+H 740.2935, found 740.2938.

(e) Intermediate 22: ethyl 3-(5-(5,6,7,8-tetrahydro-1,8-naphthyridin-2-yl)pentanamido)-2-(1-(3-(trifluoromethyl)benzenesulfonyl)azetidine-3-carboxamido)propanoate

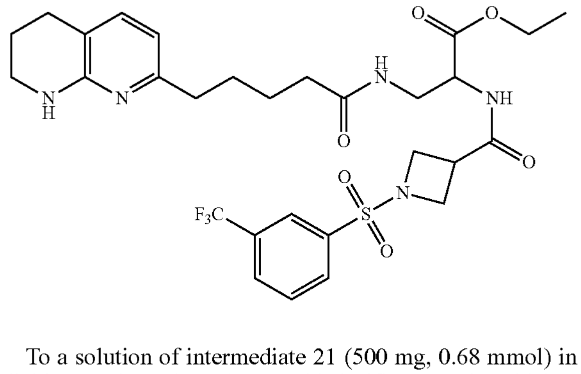

To a solution of intermediate 21 (500 mg, 0.68 mmol) in dichloromethane (3 mL) was added trifluoroacetic acid (2.5 mL). The reaction was stirred at room temperature for 24 h, and toluene (5 mL) added. The solvent was removed under reduced pressure and dissolved in dichloromethane (20 mL) and washed with saturated sodium hydrogen carbonate solution (20 mL). The layers were separated and the aqueous layer extracted with dichloromethane (2×10 mL). The organics were combined, dried ($MgSO_4$), filtered and the solvent removed under reduced pressure to yield intermediate 22 as a white solid (360 mg). $^1H$ NMR (500 MHz; $CDCl_3$) δ 8.11 (s, 1H), 8.05 (d, 1H), 7.91 (t, 1H), 7.75 (t, 1H), 7.18 (d, 1H), 6.37 (d, 1H), 4.47 (m, 1H), 4.16 (m, 2H), 3.97 (m, 4H), 3.63 (m, 2H), 3.44 (t, 2H), 3.21 (quin, 1H), 2.74 (t, 2H), 2.56 (t, 2H), 2.24 (t, 2H), 1.93 (quin, 2H), 1.66 (m, 4H), 1.25 (t, 3H). HRMS $[M+H]^+$ calculated for $C_{29}H_{36}F_3N_5O_6S$+H 640.2411, found 640.2394.

(f) Example 7: 3-(5-(5,6,7,8-tetrahydro-1,8-naphthyridin-2-yl)pentanamido)-2-(1-(3-(trifluoromethyl)benzenesulfonyl)azetidine-3-carboxamido)propanoic acid

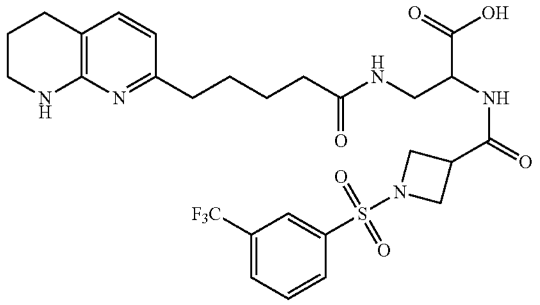 [SMILES: O=C(CCCCc1ccc2c(n1)NCCC2)NCC(NC(=O)C1CN(S(=O)(=O)c2cccc(C(F)(F)F)c2)C1)C(=O)O]

To a solution of Intermediate 22 (150 mg, 0.23 mmol) in ethanol (5 mL) was added aqueous sodium hydroxide solution 2M (0.23 mL, 0.47 mmol). The reaction mixture was stirred at room temperature for 24 h and then the solvent removed under reduced pressure. The crude product was eluted from an Oasis column using methanol-water. Selected fractions of sufficient purity were combined and the solvent removed under reduced pressure to yield 3-(5-(5,6,7,8-tetrahydro-1,8-naphthyridin-2-yl)pentanamido)-2-(1-(3-(trifluoromethyl)benzenesulfonyl)azetidine-3-carboxamido) propanoic acid as a white solid (80 mg). $^1H$ NMR (400 MHz; $CD_3OD$) δ 8.13 (d, 1H), 8.09 (s, 1H), 8.05 (d, 1H), 7.89 (t, 1H), 7.31 (d, 1H), 6.44 (d, 1H), 4.28 (t, 1H), 4.01-3.88 (m, 4H), 3.62-3.57 (m, 1H), 3.51-3.46 (m, 1H), 3.42 (t, 2H), 3.33 (quin, 1H), 2.74 (t, 2H), 2.60 (t, 2H), 2.20 (t, 2H), 1.89 (quin, 2H), 1.69-1.59 (m, 4H). HRMS $[M+H]^+$ calculated for $C_{27}H_{32}F_3N_5O_6S$+H 612.2098, found 612.2066.

Example 8: 3-(5-(5,6,7,8-Tetrahydro-1,8-naphthyridin-2-yl)pentanamido)-2-(1-(3-(trifluoromethoxy)benzenesulfonyl)azetidine-3-carboxamido)propanoic acid (a) Intermediate 23 1-(3-(trifluoromethoxy)benzenesulfonyl)azetidine-3-carboxylic acid

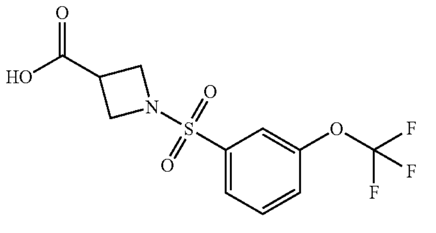 [SMILES: O=C(O)C1CN(S(=O)(=O)c2cccc(OC(F)(F)F)c2)C1]

Prepared by the method of intermediate 4 using 3-(trifluoromethoxy)benzenesulfonyl chloride (0.84 mL, 4.95 mmol) and 3-azetidinecarboxylic acid (500 mg, 4.95 mmol) to give intermediate 23 as a colourless glass (500 mg). $^1$H NMR (500 MHz; $CDCl_3$) δ 7.81 (d, 1H), 7.71 (s, 1H), 7.67 (t, 1H), 7.53 (d, 1H), 4.03 (dt, 4H), 3.36-3.29 (m, 1H). HRMS $[M+H]^+$ calculated for $C_{11}H_{10}F_3NO_5S$+H 326.0305, found 326.0310.

(b) Intermediate 24: tert-butyl 7-(5-((3-ethoxycarbonyl-2-(1-(3-(trifluoromethoxy)benzenesulfonyl)azetidine-3-carboxamido)propyl)amino)-5-oxopentyl)-3,4-dihydro-1,8-naphthyridine-1(2H)-carboxylate

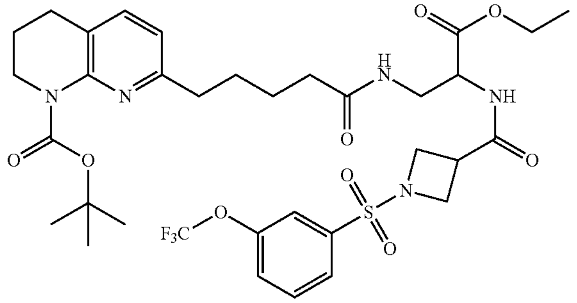 [SMILES: CCOC(=O)C(CNC(=O)CCCCc1ccc2c(n1)N(C(=O)OC(C)(C)C)CCC2)NC(=O)C1CN(S(=O)(=O)c2cccc(OC(F)(F)F)c2)C1]

Prepared by the method of intermediate 21 using intermediate 23 (346 mg, 1.12 mmol). and intermediate 19 (500 mg, 1.12 mmol) to give intermediate 24 (480 mg). $^1$H NMR (500 MHz; $CDCl_3$) δ 7.79 (d, 1H), 7.69 (s, 1H), 7.64 (t, 1H), 7.50 (d, 1H), 7.36 (d, 1H), 6.86 (d, 1H), 4.35 (dt, 1H), 4.13-4.02 (m, 2H), 3.97-3.89 (m, 4H), 3.77 (dt, 2H), 3.62-3.57 (m, 1H), 3.50-3.46 (m, 1H), 3.14 (quin, 1H), 2.79-2.73 (m, 4H), 2.25 (td, 2H), 1.94 (quin, 2H), 1.75 (quin, 2H), 1.65 (quin, 2H), 1.53 (s, 9H), 1.19 (t, 3H). HRMS $[M-H]^-$ calculated for $C_{34}H_{44}F_3N_5O_9S$−H 754.2739, found 754.2731.

(c) Intermediate 25: Ethyl 3-(5-(5,6,7,8-tetrahydro-1,8-naphthyridin-2-yl)pentanamido)-2-(1-(3-trifluoromethoxy)benzenesulfonyl)azetidine-3-carboxamido)propanoate

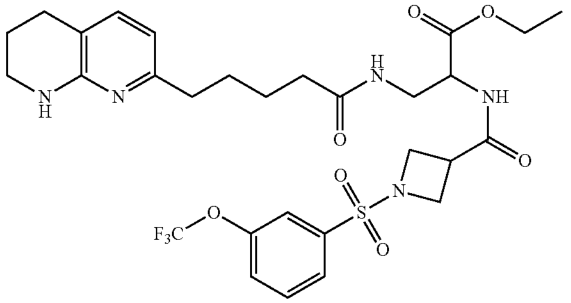 [SMILES: CCOC(=O)C(CNC(=O)CCCCc1ccc2c(n1)NCCC2)NC(=O)C1CN(S(=O)(=O)c2cccc(OC(F)(F)F)c2)C1]

Prepared by the method of intermediate 22 using intermediate 24 (450 mg, 0.60 mmol) to give intermediate 25 as a white solid (380 mg). $^1$H NMR (500 MHz; $CDCl_3$) δ 7.78 (d, 1H), 7.69 (s, 1H), 7.64 (t, 1H), 7.51 (d, 1H), 7.08 (d, 1H), 6.33 (d, 1H), 4.49-4.46 (m, 1H), 4.19-4.12 (m, 2H), 3.97-3.87 (m, 4H), 3.63-3.60 (m, 2H), 3.38 (t, 2H), 3.19 (quin, 1H), 2.70 (t, 2H), 2.49 (t, 2H), 2.19 (t, 2H), 1.89 (quin, 2H), 1.67-1.57 (m, 4H), 1.23 (t, 3H). HRMS $[M+H]^+$ calculated for $C_{29}H_{36}F_3N_5O_7S$+H 656.2360, found 656.2356.

(d) Example 8: 3-(5-(5,6,7,8-tetrahydro-1,8-naphthyridin-2-yl)pentanamido)-2-(1-(3-(trifluoromethoxy)benzenesulfonyl)azetidine-3-carboxamido)propanoic acid

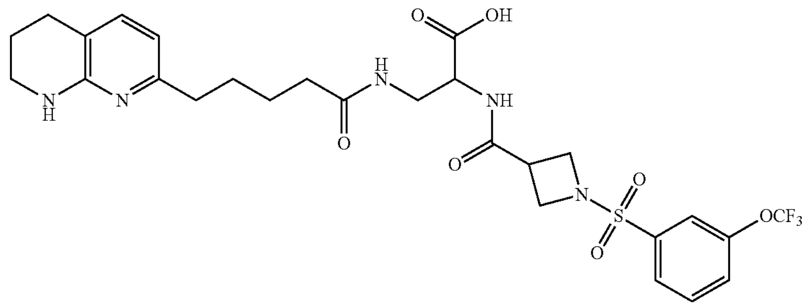 [SMILES: O=C(CCCCc1ccc2c(n1)NCCC2)NCC(NC(=O)C1CN(S(=O)(=O)c2cccc(OC(F)(F)F)c2)C1)C(=O)O]

Prepared by the method of Example 7(f) using intermediate 25 (150 mg, 0.23 mmol) to give 3-(5-(5,6,7,8-tetrahydro-1,8-naphthyridin-2-yl)pentanamido)-2-(1-(3-(trifluoromethoxy)benzenesulfonyl)azetidine-3-carboxamido) propanoic acid as a white solid (100 mg). $^1$H NMR (300 MHz; DMSO-$d_6$) δ 7.95 (d, 1H), 7.86-7.72 (m, 3H), 7.10 (d, 1H), 6.28 (d, 1H), 4.07-4.00 (m, 1H), 3.88-3.73 (m, 5H), 3.34-3.20 (m, 3H), 3.14 (quin, 1H), 2.62 (t, 2H), 2.42 (t, 2H), 2.05-1.99 (m, 2H), 1.76 (quin, 2H), 1.54-1.42 (m, 4H). HRMS $[M+Na]^+$ calculated for $C_{27}H_{32}F_3N_5O_7S$+Na 650.1867, found 650.1850.

Example 9: 2-(1-(Phenylsulfonyl)azetidine-3-carboxamido)-3-(5-(5,6,7,8-tetrahydro-1,8-naphthyridin-2-yl)pentanamido)propanoic acid (b) Intermediate 26: 1-(phenylsulfonyl)azetidine-3-carboxylic acid

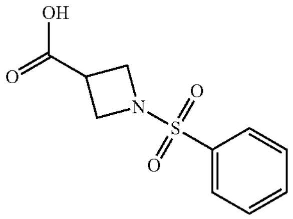 [SMILES: O=C(O)C1CN(S(=O)(=O)c2ccccc2)C1]

Prepared by the method of intermediate 4 using benzenesulfonyl chloride (1.27 mL, 9.9 mmol) and 3-azetidine carboxylic acid (1 g, 9.9 mmol) to give intermediate 26 as a colourless solid (1.99 g). $^1$H NMR (400 MHz; $CD_3OD$) δ 7.90-7.85 (m, 2H), 7.78-7.72 (m, 1H), 7.71-7.66 (m, 2H), 3.99 (t, 2H), 3.93-3.84 (m, 2H), 3.32-3.24 (m, 1H). HRMS $[M]^-$ calculated for $C_{10}H_{11}NO_4S$–H 240.0336, found 240.0336.

(c) Intermediate 27: tert-butyl 7-(5-((3-ethoxycarbonyl-2-(1-(phenylsulfonyl)azetidine-3-carboxamido) propyl)amino)-5-oxopentyl)-3,4-dihydro-1,8-naphthyridine-1(2H)-carboxylate

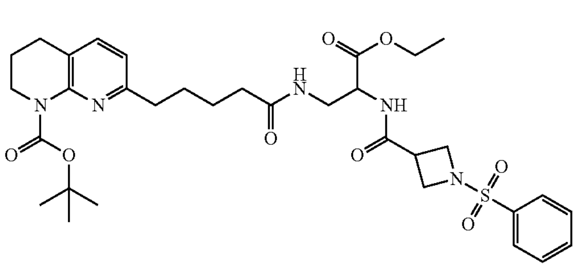 [SMILES: CCOC(=O)C(CNC(=O)CCCCc1ccc2c(n1)N(C(=O)OC(C)(C)C)CCC2)NC(=O)C1CN(S(=O)(=O)c2ccccc2)C1]

To a solution of intermediate 26 (0.24 g, 0.89 mmol) and intermediate 19 (0.4 g, 0.89 mmol) in acetonitrile (10 mL) was added N,N-diisopropylethylamine (0.76 mL, 4.45 mmol) and HATU (0.67 g, 1.78 mmol). Initially the solution was a pale green colour, after a few minutes the solution became a dark brown colour. The solution was stirred under an inert atmosphere at room temperature for 5 h. The resultant dark brown solution was dissolved in ethyl acetate (100 mL) and washed with aqueous sodium hydrogen carbonate solution (saturated, 5×50 mL). The organic layer was separated, dried with magnesium sulfate, filtered and solvent removed under reduced pressure, to produce the crude product as a brown oil. The resultant oil was purified on a silica cartridge, (25 g, 50μ) eluting using 100% ethyl acetate to produce intermediate 27 pale yellow oil (0.42 g). $^1$H NMR (400 MHz; $CDCl_3$) δ 7.82 (d, 2H), 7.62 (t, 1H), 7.56 (t, 2H), 7.34 (d, 1H), 6.84 (d, 1H), 4.35-4.31 (m, 1H), 4.10-3.99 (m, 2H), 3.91-3.84 (m, 4H), 3.78-3.71 (t, 2H), 3.63-3.40 (m, 2H), 3.07 (quin, 1H), 2.76-2.71 (m, 4H), 2.22 (td, 2H), 1.92 (quin, 2H), 1.78-1.60 (m, 4H), 1.51 (s, 9H), 1.17 (t, 3H). HRMS $[M]^+$ calculated for $C_{33}H_{45}N_5O_8S$ 671.2989, found 672.3058.

(d) Intermediate 28: ethyl-2-(1-(phenylsulfonyl) azetidine-3-carboxamido)-3-(5-(5,6,7,8-tetrahydro-1,8-naphthyridin-2-yl)pentanamido)propanoate

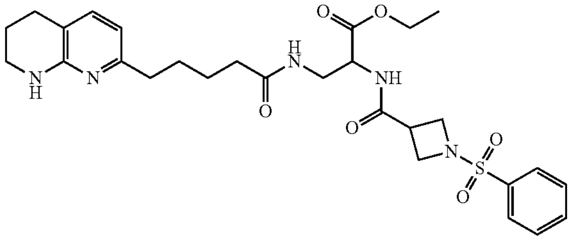 [SMILES: CCOC(=O)C(CNC(=O)CCCCc1ccc2c(n1)NCCC2)NC(=O)C1CN(S(=O)(=O)c2ccccc2)C1]

Prepared by the method in intermediate 22 using intermediate 27 (0.38 g, 0.57 mmol) to give intermediate 28 (0.24 g). $^1$H NMR (400 MHz; $CDCl_3$) δ 7.88-7.85 (m, 2H), 7.69-7.64 (m, 1H), 7.61-7.57 (m, 2H), 7.09 (d, 1H), 6.35 (d, 1H), 4.49 (dt, 1H), 4.20-4.17 (m, 2H), 3.96-3.73 (m, 4H), 3.70-3.56 (m, 2H), 3.41-3.38 (m, 2H), 3.19-3.12 (m, 1H), 2.71 (t, 2H), 2.51 (t, 2H), 2.22-2.20 (m, 2H), 1.94-1.88 (m, 2H), 1.72-1.60 (m, 4H), 1.25 (t, 3H). HRMS $[M+H]^+$ calculated for $C_{28}H_{37}N_5O_6S$+H 572.2537, found 572.2536.

(e) Example 9: 2-(1-(phenylsulfonyl)azetidine-3-carboxamido)-3-(5-(5,6,7,8-tetrahydro-1,8-naphthyridin-2-yl)pentanamido)propanoic acid

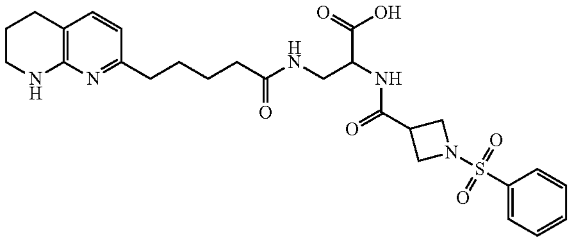 [SMILES: O=C(CCCCc1ccc2c(n1)NCCC2)NCC(NC(=O)C1CN(S(=O)(=O)c2ccccc2)C1)C(=O)O]

Prepared by the method of Example 7(f) using intermediate 28 (0.24 g, 0.42 mol) to produce 2-(1-(phenylsulfonyl) azetidine-3-carboxamido)-3-(5-(5,6,7,8-tetrahydro-1,8-naphthyridin-2-yl)pentanamido)propanoic acid as a colourless solid (0.15 g). $^1$H NMR (400 MHz; $CD_3OD$) δ 7.80 (d, 2H), 7.68 (t, 1H), 7.61 (t, 2H), 7.29 (d, 1H), 6.41 (d, 1H), 4.21 (t, 1H), 3.93-3.77 (m, 4H), 3.55-3.40 (m, 2H), 3.40-3.35 (m, 2H), 3.24-3.14 (m, 1H), 2.70 (t, 2H), 2.55 (t, 2H), 2.22-2.07 (m, 2H), 1.86 (quin, 2H), 1.60-1.59 (m, 4H). HRMS $[M]^+$ calculated for $C_{26}H_{33}N_5O_6S$ 543.2152, found 544.2226.

Example 10: 2-(1-(3,5-Dichlorobenzenesulfonyl) azetidine-3-carboxamido)-3-(5-(5,6,7,8-tetrahydro-1,8-naphthyridin-2-yl)pentanamido)propanoic acid (a) Intermediate 29: 1-(3,5-dichlorobenzenesulfonyl)azetidine-3-carboxylic acid

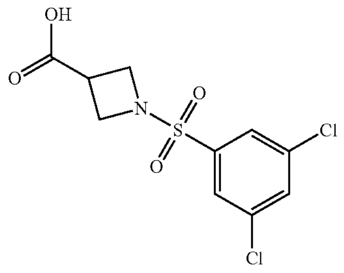 [SMILES: O=C(O)C1CN(S(=O)(=O)c2cc(Cl)cc(Cl)c2)C1]

Prepared by the method of intermediate 4 using 3,5-dichlorobenzenesulfonyl chloride (0.73 g, 1.97 mmol) and 3-azetidine carboxylic acid (0.3 g, 3.97 mmol) to give intermediate 29 as a colourless solid (0.89 g). $^1$H NMR (400 MHz; $CD_3OD$) δ 7.86 (t, 1H), 7.82 (d, 2H), 4.08 (t, 2H), 3.95 (dd, 2H), 3.38-3.30 (m, 1H). HRMS [M−H]-calculated for $C_{10}H_9Cl_2NO_4S$−H 307.9557, found 307.9556.

(b) Intermediate 30: tert-butyl 7-(5-((2-(1-(3,5-dichlorobenzenesulfonyl)azetidine-3-carboxamido)-3-ethoxycarbonylpropyl)amino)-5-oxopentyl)-3,4-dihydro-1,8-naphthyridine-1(2H)-carboxylate

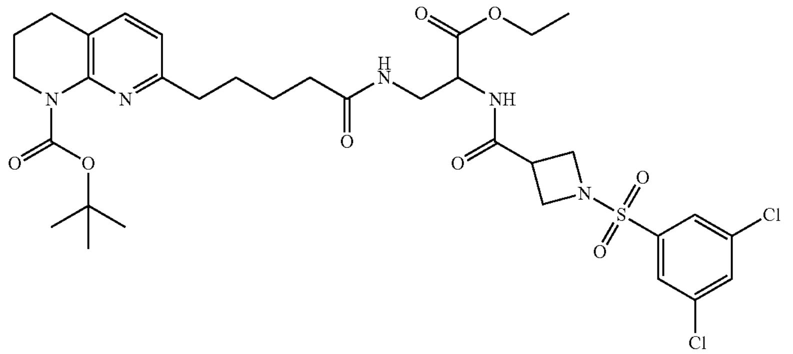 [SMILES: CCOC(=O)C(CNC(=O)CCCCc1ccc2c(n1)N(C(=O)OC(C)(C)C)CCC2)NC(=O)C1CN(S(=O)(=O)c2cc(Cl)cc(Cl)c2)C1]

Prepared by the method of intermediate 21 using intermediate 29 (0.33 g, 1.08 mmol) and intermediate 19 (0.44 g, 0.98 mmol) to give intermediate 30 as a clear oil (0.54 g). $^1$H NMR (400 MHz; $CDCl_3$) δ 7.69 (d, 2H), 7.59 (t, 1H), 7.33 (d, 1H), 6.83 (d, 1H), 4.34 (dt, 1H), 4.07-4.01 (m, 2H), 3.99-3.88 (m, 4H), 6.76-3.73 (m, 2H), 3.63-3.42 (m, 2H), 3.20-3.09 (m, 1H), 2.76-2.71 (m, 4H), 2.28-2.19 (m, 2H), 1.92 (quin, 2H), 1.76-1.61 (m, 4H), 1.51 (s, 9H), 1.17 (t, 3H). HRMS [M+H]$^+$ calculated for $C_{33}H_{43}Cl_2N_5O_8S$+H 740.2288, found 740.2282.

(c) Intermediate 31: ethyl 2-(1-(3,5-dichlorobenzenesulfonyl)azetidine-3-carboxamido)-3-(5-(5,6,7,8-tetrahydro-1,8-naphthyridin-2-yl)pentanamido)propanoate

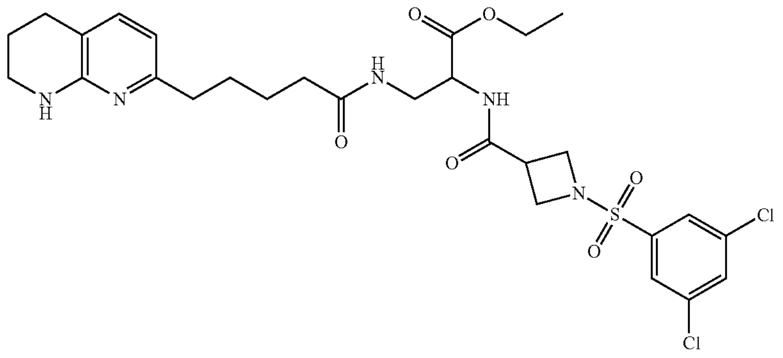 [SMILES: CCOC(=O)C(CNC(=O)CCCCc1ccc2c(n1)NCCC2)NC(=O)C1CN(S(=O)(=O)c2cc(Cl)cc(Cl)c2)C1]

Prepared by the method of intermediate 22 using intermediate 31 (0.51 g, 0.69 mmol) to give intermediate 31 as a colourless solid (0.18 g). $^1$H NMR (400 MHz; $CDCl_3$) δ 7.70 (d, 2H), 7.60 (t, 1H), 7.07 (d, 1H), 6.33 (d, 1H), 4.50 (td, 1H), 4.21-4.15 (m, 2H), 4.05-3.86 (m, 4H), 3.74-3.53 (m, 2H), 3.44-3.32 (m, 2H), 3.19 (quin, 1H), 2.69 (t, 2H), 2.50 (t, 2H), 2.10-1.93 (m, 2H), 1.90 (dt, 2H), 1.75-1.53 (m, 4H), 1.25 (t, 3H). HRMS $[M+H]^+$ calculated for $C_{28}H_{35}Cl_2N_5O_6S+H$ 640.1758, found 640.1755.

(d) Example 10: 2-(1-(3,5-dichlorobenzenesulfonyl)azetidine-3-carboxamido)-3-(5-(5,6,7,8-tetrahydro-1,8-naphthyridin-2-yl)pentanamido)propanoic acid

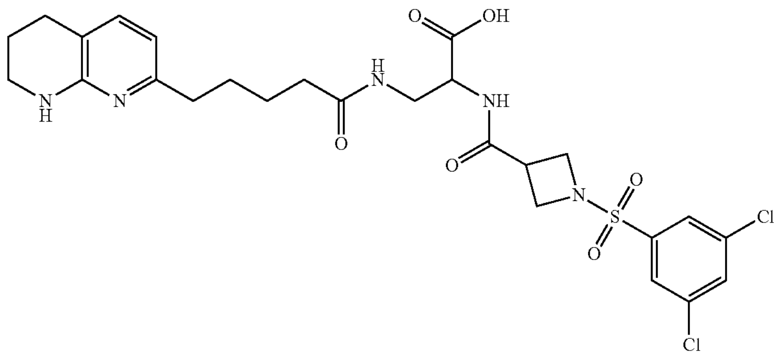 [SMILES: O=C(CCCCc1ccc2c(n1)NCCC2)NCC(NC(=O)C1CN(S(=O)(=O)c2cc(Cl)cc(Cl)c2)C1)C(=O)O]

Prepared by the method of Example 7(f) using intermediate 31 (0.18 g, 0.28 mmol) to give 2-(1-(3,5-dichlorobenzenesulfonyl)azetidine-3-carboxamido)-3-(5-(5,6,7,8-tetrahydro-1,8-naphthyridin-2-yl)pentanamido)propanoic acid as a colourless solid (0.08 g). $^1$H NMR (400 MHz; $CD_3OD$) δ 7.83 (t, 1H), 7.76 (d, 2H), 7.59 (d, 1H), 6.64 (d, 1H), 4.54-4.50 (m, 1H), 4.05-3.85 (m, 4H), 3.73-3.68 (m, 1H), 3.55-3.47 (m, 2H), 3.43-3.36 (m, 2H), 2.82 (t, 2H), 2.72 (t, 2H), 2.28 (t, 2H), 1.95 (quin, 2H), 1.74-1.60 (m, 4H). HRMS $[M+H]^+$ calculated for $C_{26}H_{31}Cl_2N_5O_6S+H$ 612.1445, found 612.1430.

Example 11: 2-(1-(3,5-Dimethylbenzenesulfonyl)azetidine-3-carboxamido)-3-(5-(5,6,7,8-tetrahydro-1,8-naphthyridin-2-yl)pentanamido)propanoic acid (a) Intermediate 32: 1-(3,5-dimethylbenzenesulfonyl)azetidine-3-carboxylic acid

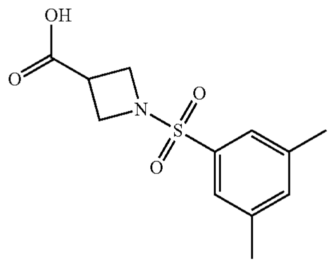 [SMILES: Cc1cc(C)cc(S(=O)(=O)N2CC(C(=O)O)C2)c1]

Prepared by the method of intermediate 4 using 3,5-dimethylbenzenesulfonyl chloride (2.0 g, 9.89 mmol) and azetidine-3-carboxylic acid (1 g, 9.89 mmol) to give intermediate 32 a white solid (1.75 g). $^1$H NMR (400 MHz; $CD_3OD$) δ 7.47 (s, 2H), 7.40 (s, 1H), 3.92 (m, 4H), 3.27 (m, 1H), 2.44 (s, 6H). HRMS $[M+Na]^+$ calculated for $C_{12}H_{15}NO_4S$+Na 292.0619, found 292.0616.

(b) Intermediate 33: tert-butyl 7-(5-((2-(1-(3,5-dimethylbenzenesulfonyl)azetidine-3-carboxamido)-3-ethoxycarbonylpropyl)amino)-5-oxopentyl)-3,4-dihydro-1,8-naphthyridine-1(2H)-carboxylate

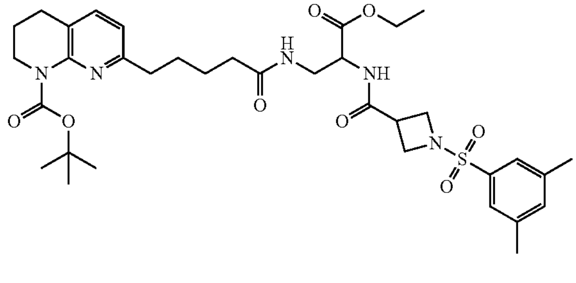 [SMILES: CCOC(=O)C(CNC(=O)CCCCc1ccc2c(n1)N(C(=O)OC(C)(C)C)CCC2)NC(=O)C1CN(S(=O)(=O)c2cc(C)cc(C)c2)C1]

Prepared by the method of intermediate 27 using intermediate 32 (0.4 g, 1.485 mmol) and intermediate 19 (0.6 g, 1.35 mmol) to give intermediate 33 as a brown oil (0.363 g). $^1$H NMR (400 MHz; $CD_3OD$) δ 7.52 (d, 1H), 7.45 (s, 2H), 7.39 (s, 1H), 7.01 (d, 1H), 4.43 (m, 1H), 4.14 (m, 2H), 3.86 (m, 4H), 3.77 (m, 2H), 3.52 (m, 2H), 3.22 (m, 1H), 2.79 (t, 2H), 2.73 (t, 2H), 2.43 (s, 6H), 2.21 (t, 2H), 1.94 (quin, 2H), 1.68 (m, 4H), 1.53 (s, 9H), 1.23 (t, 3H). HRMS $[M+H]^+$ calculated for $C_{35}H_{49}N_5O_8S$+H 700.3380, found 700.3363.

(c) Intermediate 34: ethyl 2-(1-(3,5-dimethylbenzenesulfonyl)azetidine-3-carboxamido)-3-(5-(5,6,7,8-tetrahydro-1,8-naphthyridin-2-yl)pentanamido)propanoate

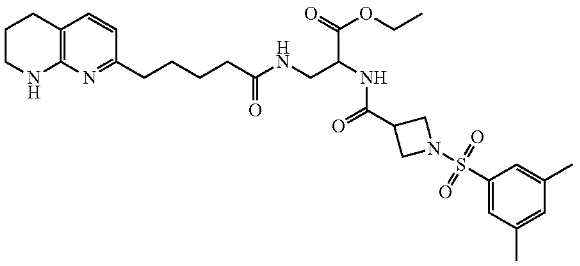 [SMILES: CCOC(=O)C(CNC(=O)CCCCc1ccc2c(n1)NCCC2)NC(=O)C1CN(S(=O)(=O)c2cc(C)cc(C)c2)C1]

Prepared by the method of intermediate 22 using intermediate 33 (0.363 g, 0.052 mmol) to give intermediate 34 as a brown foam (0.2 g). $^1$H NMR (400 MHz; $CD_3OD$) δ 7.45 (s, 2H), 7.38 (s, 1H), 7.29 (d, 1H), 6.46 (d, 1H), 4.47 (dd, 1H), 4.14 (m, 2H), 3.88 (m, 4H), 3.47-3.41 (m, 4H), 3.24 (m, 1H), 2.75 (t, 2H), 2.58 (t, 2H), 2.45 (s, 6H), 2.20 (t, 2H), 1.91 (quin, 2H), 1.63 (m, 4H), 1.24 (t, 3H). HRMS $[M+H]^+$ calculated for $C_{30}H_{41}N_5O_6S$+H 600.2856, found 600.2853.

(d) Example 11: 2-(1-(3,5-dimethylbenzenesulfonyl)azetidine-3-carboxamido)-3-(5-(5,6,7,8-tetrahydro-1,8-naphthyridin-2-yl)pentanamido)propanoic acid

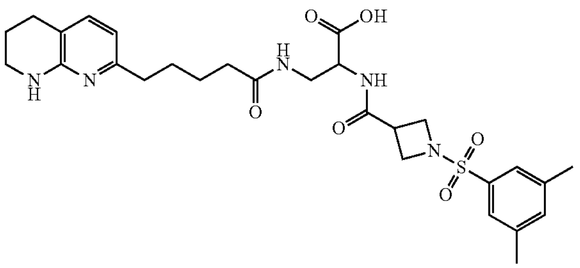 [SMILES: Cc1cc(C)cc(S(=O)(=O)N2CC(C(=O)NC(CNC(=O)CCCCc3ccc4c(n3)NCCC4)C(=O)O)C2)c1]

Prepared by the method of Example 7(f) using intermediate 34 (0.2 g, 0.333 mmol) to give 2-(1-(3,5-dimethylbenzenesulfonyl)azetidine-3-carboxamido)-3-(5-(5,6,7,8-tetrahydro-1,8-naphthyridin-2-yl)pentanamido)propanoic acid, as a white gel. $^1$H NMR (400 MHz; $CD_3OD$) δ 7.61 (m, 1H), 7.45 (m, 2H), 7.40 (s, 1H), 6.67 (d, 1H), 4.54 (m, 1H), 3.89 (m, 4H), 3.74-3.63 (m, 1H), 3.61-3.5 (m, 2H), 3.46-3.41 (m, 1H), 3.29-3.21 (m, 1H), 2.84 (t, 2H), 2.74 (t, 2H), 2.44 (s, 6H), 2.30 (m, 2H), 1.97 (quin, 2H), 1.68 (m, 4H). HRMS $[M+H]^+$ calculated for $C_{28}H_{37}N_5O_6S$+H 572.2543, found 572.2526.

Example 12: 2-(1-(3-(methylsulfonyl)benzenesulfonyl)azetidine-3-carboxamido)-3-(5-(1,2,3,4-tetrahydro-1,8-naphthyridin-2-yl)pentanamido)propanoic acid (a) Intermediate 35: 1-(3-(methylsulfonyl)benzenesulfonyl)azetidine-3-carboxylic acid

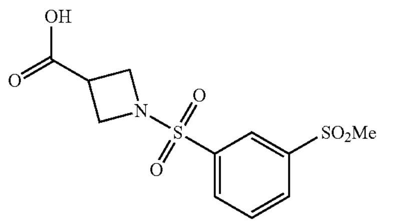 [SMILES: CS(=O)(=O)c1cccc(S(=O)(=O)N2CC(C(=O)O)C2)c1]

Prepared by the method of intermediate 4 using 3-(methylsulfonyl)benzenesulfonyl chloride (0.5 g, 1.97 mmol) and azetidine-3-carboxylic acid (0.2 g, 1.97 mmol) to give intermediate 35 as a white gel (0.35 g,). $^{1}$H NMR (400 MHz; $CD_3OD$) δ 8.39 (s, 1H), 8.33 (d, 1H), 8.21 (d, 1H), 7.96 (t, 1H), 4.00 (m, 4H), 3.30 (m, 1H), 3.24 (s, 3H). HRMS $[M+Na]^+$ calculated for $C_{11}H_{13}NO_6S_2$+Na 342.0082, found 342.0069.

(b) Intermediate 36: tert-butyl 7-(5-((3-ethoxycarbonyl-2-(1-(3-(methylsulfonyl)benzenesulfonyl)azetidine-3-carboxamido)-propyl)amino)-5-oxopentyl)-3,4-dihydro-1,8-naphthyridine-1(2H)-carboxylate

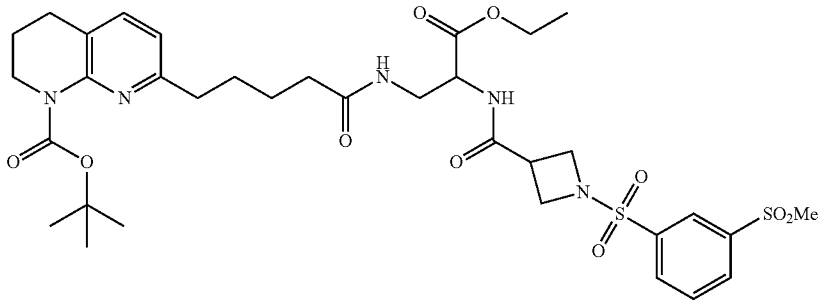 [SMILES: CCOC(=O)C(CNC(=O)CCCCc1ccc2c(n1)N(C(=O)OC(C)(C)C)CCC2)NC(=O)C1CN(S(=O)(=O)c2cccc(S(C)(=O)=O)c2)C1]

Prepared by the method of intermediate 27 using intermediate 35 (0.340 g, 1.07 mmol) and intermediate 19 (0.480 g, 1.07 mmol) to give intermediate 36 as a brown oil (0.418 g). $^{1}$H NMR (400 MHz; $CDCl_3$) δ 8.40 (s, 1H), 8.21 (d, H), 8.12 (d, 1H), 7.81 (t, 2H), 7.49 (d, 1H), 7.39 (d, 1H), 7.02 (m, 1H), 6.88 (d, 1H), 4.30 (m, 1H), 4.00 (m, 6H), 3.77 (m, 2H), 3.53 (m, 2H), 3.13 (s, 4H), 2.76 (m, 4H), 2.24 (m, 2H), 1.95 (quin, 2H), 1.68 (m, 4H), 1.52 (s, 9H), 1.18 (t, 3H). HRMS $[M+H]^+$ calculated for $C_{34}H_{47}N_5O_{10}S_2$+H 750.2843, found 750.2826.

(c) Intermediate 37: ethyl 2-(1-(3-(methylsulfonyl)benzenesulfonyl)azetidine-3-carboxamido)-3-(5-(5,6,7,8-tetrahydro-1,8-naphthyridin-2-yl)pentanamido)propanoate

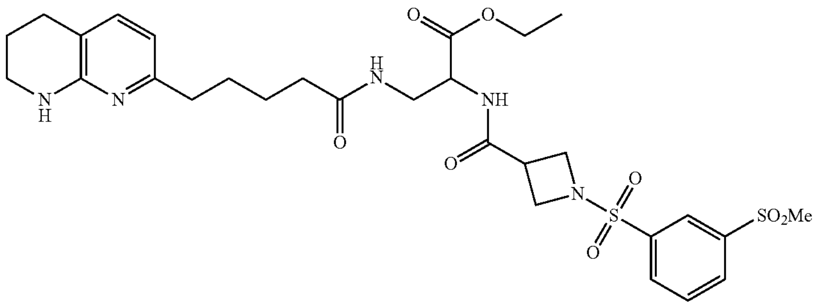 [SMILES: CCOC(=O)C(CNC(=O)CCCCc1ccc2c(n1)NCCC2)NC(=O)C1CN(S(=O)(=O)c2cccc(S(C)(=O)=O)c2)C1]

Prepared by the method of intermediate 22 using intermediate 36 (0.388 g, 0.519 mmol) to give intermediate 37 as a collapsed foam (0.254 g). $^1$H NMR (400 MHz; $CDCl_3$) δ 8.42 (s, 1H), 8.23 (d, 1H), 8.14 (d, 1H), 7.95 (d, 1H), 7.83 (t, 1H), 7.17 (d, 1H), 6.57 (s, 1H), 6.37 (d, 1H), 4.44 (m, 1H), 4.16 (q, 2H), 3.97 (m, 4H), 3.63 (m, 2H), 3.44 (m, 2H), 3.25 (m, 1H), 3.25 (s, 3H), 2.74 (t, 2H), 2.56 (t, 2H), 2.24 (m, 2H), 1.94 (quin, 2H), 1.66 (m, 4H), 1.25 (t, 3H). HRMS $[M+H]^+$ calculated for $C_{29}H_{39}N_5O_8S_2$+H 650.2318, found 650.2308.

(d) Example 12: 2-(1-(3-(methylsulfonyl)benzenesulfonyl)azetidine-3-carboxamido)-3-(5-(1,2,3,4-tetrahydro-1,8-naphthyridin-2-yl)pentanamido)propanoic acid

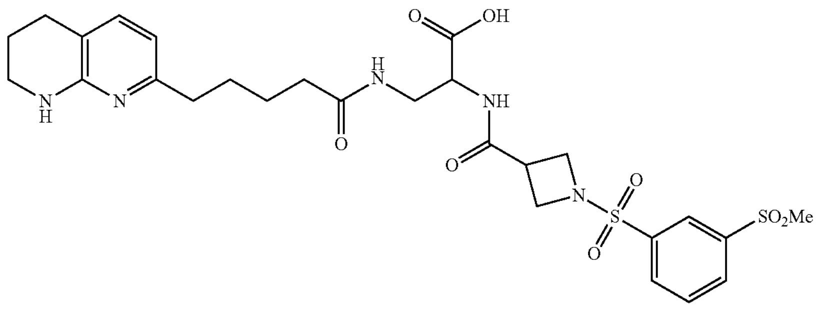 [SMILES: CS(=O)(=O)c1cccc(S(=O)(=O)N2CC(C(=O)NC(CNC(=O)CCCCc3ccc4c(n3)NCCC4)C(=O)O)C2)c1]

Prepared by the method of Example 7(f) using intermediate 37 (254 mg, 0.39 mmol) to give 2-(1-(3-(methylsulfonyl)benzenesulfonyl)azetidine-3-carboxamido)-3-(5-(1,2,3,4-tetrahydro-1,8-naphthyridin-2-yl)pentanamido)propanoic acid as a pale yellow gel (37 mg). $^1$H NMR (400 MHz; $CD_3OD$) δ 8.36 (s, 1H), 8.32 (d, 1H), 8.20 (d, 1H), 7.95 (t, 1H), 7.48 (d, 1H), 6.53 (d, 1H), 4.22 (t, 1H), 3.98 (m, 4H), 3.49 (m, 4H), 3.36 (m, 1H), 3.26 (s, 3H), 2.80 (t, 2H), 2.67 (t, 2H), 2.23 (t, 2H), 1.94 (quin, 2H), 1.69 (m, 4H). HRMS $[M+H]^+$ calculated for $C_{27}H_{35}N_5O_8S_2$+H 622.2005, found 622.1981.

Example 13: 2-(1-(3-Chloro-5-methylbenzenesulfonyl)azetidine-3-carboxamido)-3-(5-(5,6,7,8-tetrahydro-1,8-naphthyridin-2-yl)pentanamido)propanoic acid (a) Intermediate 38: 1-(3-chloro-5-methylbenzenesulfonyl)azetidine-3-carboxylic acid

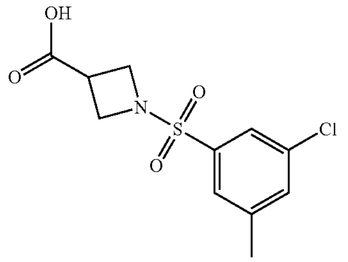 [SMILES: Cc1cc(Cl)cc(S(=O)(=O)N2CC(C(=O)O)C2)c1]

Prepared by the method of intermediate 4 using 3-chloro-5-methylbenzenesulfonyl chloride (0.44 g, 1.96 mmol) and azetidine-3-carboxylic acid (0.2 g, 1.97 mmol) to give intermediate 38 as a colourless oil (0.32 g). $^1$H NMR (400 MHz; $CDCl_3$) δ 7.65-7.62 (m, 1H), 7.62-7.58 (m, 2H), 4.05-4.01 (m, 2H), 3.92-3.88 (m, 2H), 3.38 (quin, 1H), 2.48 (s, 3H). HRMS [M−H] calculated for $C_{11}H_{12}ClNO_4S-H$ 288.0097, found 288.0103.

(b) Intermediate 39: tert-butyl 7-(5-((2-(1-(3-chloro-5-methylbenzenesulfonyl)azetidine-3-carboxamido)-3-ethoxycarbonylpropyl)amino)-5-oxopentyl)-3,4-dihydro-1,8-naphthyridine-1(2H)-carboxylate

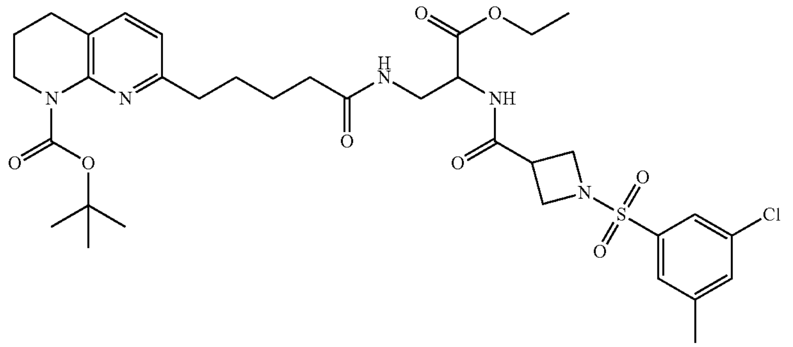 [SMILES: CCOC(=O)C(CNC(=O)CCCCc1ccc2c(n1)N(C(=O)OC(C)(C)C)CCC2)NC(=O)C1CN(S(=O)(=O)c2cc(C)cc(Cl)c2)C1]

Prepared by the method of intermediate 27 using intermediate 38 (0.17 g, 0.59 mmol) and intermediate 19 (0.26 g, 0.59 mmol) to give intermediate 39 as a yellow oil (0.05 g). $^1$H NMR (400 MHz; $CDCl_3$) δ 7.62-7.58 (m, 1H), 7.51-7.50 (m, 1H), 7.41-7.40 (m, 1H), 7.54-7.33 (m, 1H), 6.98-6.87 (m, 1H), 4.39 (dt, 1H), 4.10-3.99 (m, 2H), 3.95-3.84 (m, 4H), 3.82-3.75 (m, 2H), 3.63-3.45 (m, 2H), 3.13 (dt, 1H), 2.79-2.70 (m, 4H), 2.43 (s, 3H), 2.30-2.15 (m, 2H), 1.96 (quin, 2H), 1.76 (quin, 2H), 1.70-1.58 (m, 2H), 1.53 (s, 9H,), 1.19 (t, 3H). HRMS [M+H]$^+$ calculated for $C_{34}H_{46}ClN_5O_8S+H$ 720.2834, found 720.2801.

(c) Example 13: 2-(1-(3-chloro-5-methylbenzenesulfonyl)azetidine-3-carboxamido)-3-(5-(5,6,7,8-tetrahydro-1,8-naphthyridin-2-yl)pentanamido)propanoic acid

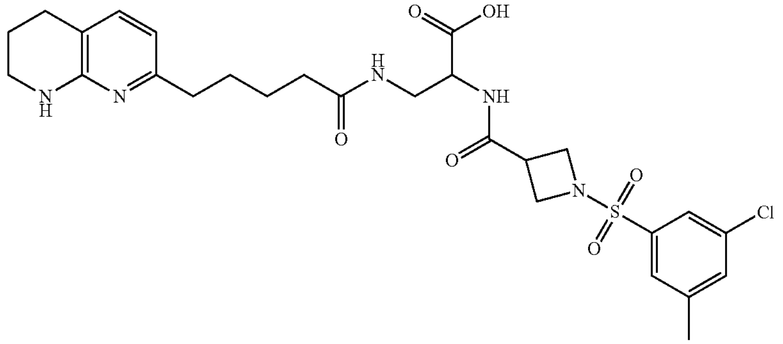 [SMILES: Cc1cc(Cl)cc(S(=O)(=O)N2CC(C(=O)NC(CNC(=O)CCCCc3ccc4c(n3)NCCC4)C(=O)O)C2)c1]

To a solution of intermediate 39 (0.075 g, 0.10 mmol) in dichloromethane (3 mL) was added trifluoroacetic acid (2 mL). The solution was stirred at room temperature under an inert atmosphere for 20 h. Toluene (20 mL) was added to the resultant red reaction mixture and solvent was removed under reduced pressure. The resultant oil was dissolved in ethyl acetate (30 mL) and washed with aqueous sodium hydrogen carbonate solution (saturated, 3x30 mL). The organic layer was dried and filtered. Solvent was removed under reduced pressure to give a red oil which was used without purification or full characterisation. The crude product dissolved in ethanol (5 mL) and sodium hydroxide (2 M, 0.08 mL, 0.16 mmol) added. The reaction mixture was stirred for 4 h. Solvent was removed under reduced pressure and water (20 mL) added. Hydrochloric acid (1 M) was added dropwise until the solution became pH 5. The solution was extracted with dichloromethane (3x30 mL) and the solvent removed to give 2-(1-(3-chloro-5-methylbenzenesulfonyl)azetidine-3-carboxamido)-3-(5-(5,6,7,8-tetrahydro-1,8-naphthyridin-2-yl)pentanamido)propanoic acid as a colourless solid (0.04 g). $^1$H NMR (400 MHz; $CDCl_3$) δ 7.63-7.54 (m, 4H), 6.65 (d, 1H), 4.54-4.46 (m, 1H), 4.01-3.81 (m, 4H), 3.73-3.6 (m, 1H), 3.53-3.45 (m, 3H), 3.40-3.35 (m, 1H), 2.82 (t, 2H), 2.72 (t, 2H), 2.47 (s, 3H), 2.32 (t, 2H), 1.94 (quin, 2H), 1.77-1.58 (m, 4H). HRMS $[M+H]^+$ calculated for $C_{27}H_{34}ClN_5O_6S+H$ 592.1991, found 592.1987.

Example 14: 2-(1-(3-Ethylbenzenesulfonyl)azetidine-3-carboxamido)-3-(5-(5,6,7,8-tetrahydro-1,8-naphthyridin-2-yl)pentanamido)propanoic acid (a) Intermediate 40: 1-(3-ethylbenzenesulfonyl)azetidine-3-carboxylic acid

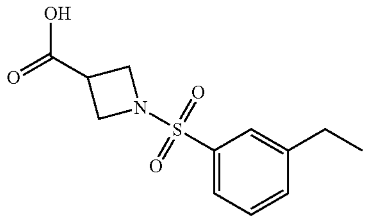 [SMILES: CCc1cccc(S(=O)(=O)N2CC(C(=O)O)C2)c1]

Prepared by the method of intermediate 4 using 3-ethylbenzenesulfonyl chloride (0.365 g, 1.84 mmol) and azetidine-3-carboxylic acid to give intermediate 40 a pale white gel (0.28 g). $^1$H NMR (400 MHz; $CD_3OD$) δ 7.68 (m, 2H), 7.59 (m, 2H), 3.93 (m, 4H), 3.26 (tt, 1H), 2.80 (q, 2H), 1.31 (t, 3H).

(b) Intermediate 41: tert-butyl 7-(5-((3-ethoxycarbonyl-2-(1-(3-ethylbenzenesulfonyl)azetidine-3-carboxamido)propyl)amino)-5-oxopentyl)-3,4-dihydro-1,8-naphthyridine-1(2H)-carboxylate

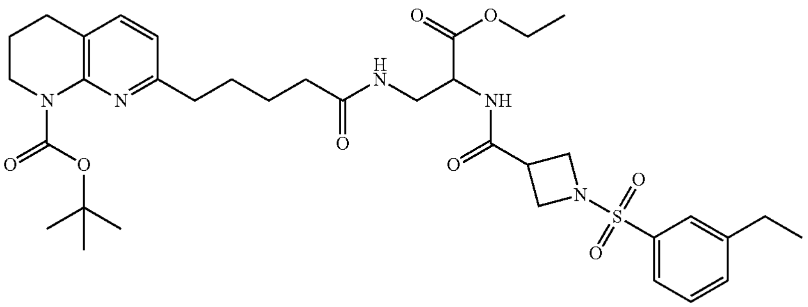 [SMILES: CCOC(=O)C(CNC(=O)CCCCc1ccc2c(n1)N(C(=O)OC(C)(C)C)CCC2)NC(=O)C1CN(S(=O)(=O)c2cccc(CC)c2)C1]

Prepared by the method of intermediate 27 using intermediate 40 (0.280 g, 1.04 mmol) and intermediate 19 (0.466 g, 1.04 mmol to give intermediate 41 as a light brown oil (0.504 g). $^1$H NMR (400 MHz; $CDCl_3$) δ 7.65 (m, 2H), 7.48 (m, 2H), 7.39 (m, 2H), 7.04 (t, 1H), 6.87 (d, 1H), 4.39 (m, 1H), 4.08 (m, 2H), 3.89 (m, 4H), 3.77 (t, 2H), 3.56 (m, 2H), 3.11 (quin, 1H), 2.76 (m, 6H), 2.25 (t, 2H), 1.95 (quin, 2H), 1.70 (m, 4H), 1.53 (s, 9H), 1.29 (t, 3H), 1.20 (t, 3H). HRMS $[M+H]^+$ calculated for $C_{35}H_{49}N_5O_8S$+H 700.3380, found 700.3362.

(c) Intermediate 42: ethyl 2-(1-(3-ethylbenzenesulfonyl)azetidine-3-carboxamido)-3-(5-(5,6,7,8-tetrahydro-1,8-naphthyridin-2-yl)pentanamido)propanoate

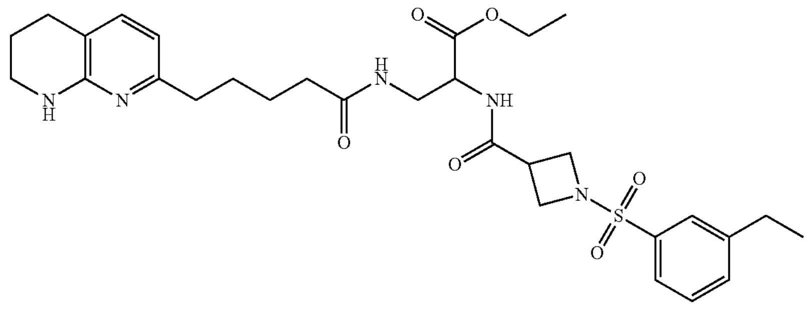 [SMILES: CCOC(=O)C(CNC(=O)CCCCc1ccc2c(n1)NCCC2)NC(=O)C1CN(S(=O)(=O)c2cccc(CC)c2)C1]

Prepared by the method of intermediate 22 using intermediate 41 (0.5 g; 0.72 mmol) to give intermediate 42 as a light brown oil (0.372 g). $^1$H NMR (400 MHz; $CDCl_3$) δ 7.78 (d, 1H), 7.67 (m, 2H), 7.49 (d, 2H), 7.12 (d, 1H), 6.52 (t, 1H), 4.50 (m, 1H), 4.16 (m, 2H), 3.91 (m, 4H), 3.64 (t, 2H), 3.42 (m, 2H), 3.18 (quin, 1H), 2.73 (m, 4H), 2.54 (t, 2H), 2.22 (t, 2H), 1.92 (quin, 2H), 1.67 (m, 4H), 1.29 (t, 3H), 1.25 (t, 3H). HRMS $[M+H]^+$ calculated for $C_{30}H_{41}N_5O_6S$+H 600.2856, found 600.2832.

(d) Example 14: 2-(1-(3-ethylbenzenesulfonyl)azetidine-3-carboxamido)-3-(5-(5,6,7,8-tetrahydro-1,8-naphthyridin-2-yl)pentanamido)propanoic acid

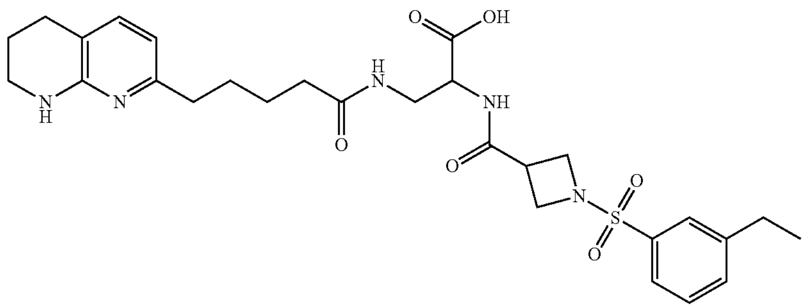 [SMILES: CCc1cccc(S(=O)(=O)N2CC(C(=O)NC(CNC(=O)CCCCc3ccc4c(n3)NCCC4)C(=O)O)C2)c1]

Prepared by the method of Example 7(f) using intermediate 42 (0.37 g, 0.618 mmol) to give 2-(1-(3-ethylbenzenesulfonyl)azetidine-3-carboxamido)-3-(5-(5,6,7,8-tetrahydro-1,8-naphthyridin-2-yl)pentanamido)propanoic acid as a colourless oil (0.13 g). $^1$H NMR (400 MHz; $CD_3OD$) δ 7.67 (m, 2H), 7.58 (m, 2H), 7.28 (d, 1H), 6.53 (d, 1H), 4.28 (t, 1H), 3.92 (m, 4H), 3.53 (m, 2H), 3.47 (t, 2H), 3.28 (m, 1H), 2.80 (m, 4H), 2.68 (t, 2H), 2.24 (m, 2H), 1.94 (quin, 2H), 1.69 (m, 4H), 1.30 (t, 3H). HRMS $[M+H]^+$ calculated for $C_{28}H_{37}N_5O_8S$+H 572.2543, found 572.2514.

Example 15: 2-(3-Methyl-1-(3-methylbenzenesulfonyl)azetidine-3-carboxamido)-3-(5-(5,6,7,8-tetrahydro-1,8-naphthyridin-2-yl)pentanamido)propanoic acid (a) Intermediate 43: methyl 1-(3-methylbenzenesulfonyl)azetidine-3-carboxylate

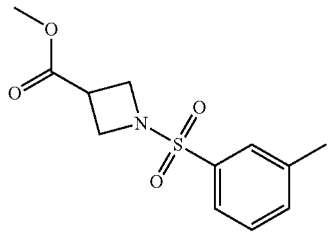 [SMILES: COC(=O)C1CN(S(=O)(=O)c2cccc(C)c2)C1]

Triethylamine (3.3 mL, 24 mmol) was added over 0.25 h to a solution of methyl azetidine-3-carboxylate hydrochloride (1.26 g, 8.3 mmol) and 3-methylbenzenesulfonyl chloride (1.32 g, 8.3 mmol) in dichloromethane (20 mL) and cooled in an ice bath. The resultant cloudy yellow solution was stirred under nitrogen for 21 h. The solution was dissolved in dichloromethane (50 mL) and the organic layer was extracted with aqueous sodium hydrogen carbonate solution (saturated, 4×50 mL). The organic layer was washed with brine (50 mL), dried ($MgSO_4$), filtered and the solvent removed under reduced pressure to yield intermediate 43 as a pale yellow oil (1.66 g). $^1$H-NMR (400 MHz; $CDCl_3$) δ 7.75-7.59 (m, 2H), 7.55-7.43 (m, 2H), 4.08-3.89 (m, 4H), 3.65 (s, 3H), 3.27 (tt, 1H), 2.48 (s, 3H). HRMS $[M+H]^+$ calculated for $C_{12}H_{15}NO_4S$+H 270.0795, found 270.0793.

(b) Intermediate 44: methyl 3-methyl-1-(3-methylbenzenesulfonyl)azetidine-3-carboxylate

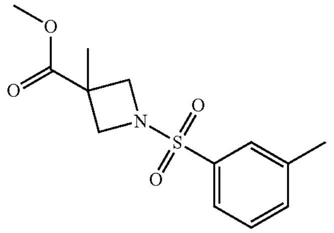 [SMILES: COC(=O)C1(C)CN(S(=O)(=O)c2cccc(C)c2)C1]

Sodium bis(trimethylsilyl)amide (1 M in THF, 10.0 mL, 10 mmol) was added to a solution of intermediate 43 (800 mg, 3.0 mmol) in dry tetrahydrofuran (20 mL) at −72° C. and the resultant pale yellow solution stirred for 0.5 h. Methyl iodide (1.60 ml, 26 mmol) in dry tetrahydrofuran (1.5 mL) was added dropwise to the stirred solution and the resultant solution stirred for 3 h at −72° C. Hydrochloric acid solution (1M, 20 mL) was added to the solution at −72° C. and the aqueous layer was extracted with ethyl acetate (3×30 mL). The separated organic layer was washed with brine (2×50 mL), filtered and the solvent removed under reduced pressure. The oil formed was purified via flash chromatography on a silica cartridge (40 g) eluting using petroleum ether:ethyl acetate (65:35). The fractions containing product were combined and the solvent was removed under reduced pressure to yield intermediate 44 as an orange solid (0.37 g). $^1$H-NMR (400 MHz; $CDCl_3$) δ 7.68-7.60 (m, 2H), 7.50-7.42 (m, 2H), 4.05 (d, 2H), 3.62-3.57 (m, 5H), 2.46 (s, 3H), 1.39 (s, 3H). HRMS $[M+H]^+$ calculated for $C_{13}H_{17}NO_4S$+H 284.0951, found 284.0947.

(c) Intermediate 45: tert-butyl 7-(5-((3-ethoxycarbonyl-2-(3-methyl-1-(3-methylbenzenesulfonyl)azetidine-3-carboxamido)propyl)amino)-5-oxopentyl)-3,4-dihydro-1,8-naphthyridine-1(2H)-carboxylate

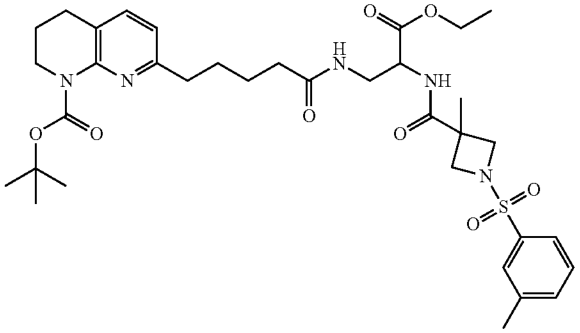 [SMILES: CCOC(=O)C(CNC(=O)CCCCc1ccc2c(n1)N(C(=O)OC(C)(C)C)CCC2)NC(=O)C1(C)CN(S(=O)(=O)c2cccc(C)c2)C1]

Intermediate 44 (370 mg, 1.3 mmol) was added to a solution of THF (10 mL), water (3.5 mL) and methanol (3.5 mL). Lithium hydroxide (45 mg, 1.9 mmol) was added and the resultant pale yellow solution was stirred for 24 h. The reaction mixture was concentrated under reduced pressure and the residual water removed via azeotrope with toluene (5×10 mL) to give lithium 3-methyl-1-(3-methylbenzenesulfonyl)azetidine-3-carboxylate (356 mg) as a white cream collapsed foam.

N,N-Diisopropylethylamine (1.13 mL, 6.6 mmol) and HATU (1000 mg, 2.6 mmol) were slowly added at 0° C. to a solution of intermediate 19 (590 mg, 1.3 mmol) and lithium 3-methyl-1-(3-methylbenzenesulfonyl)azetidine-3-carboxylate (350 mg, 1.3 mmol) in N,N-dimethylformamide (5 mL) under a nitrogen atmosphere. The solution was stirred at room temperature for 68 h. The resultant solution was dissolved in ethyl acetate (100 mL), and the organic layer washed with aqueous sodium hydrogen carbonate solution (saturated, 6×50 mL). The organic layer was washed with brine (50 mL), dried, filtered and the solvent removed under reduced pressure. The crude product was purified via flash chromatography on a silica cartridge (40 g) eluting using ethyl acetate (100%). The fractions containing product were combined and the solvent was removed under reduced pressure to yield intermediate 45 as a pale brown gel (0.630 g). $^1$H-NMR (400 MHz; $CDCl_3$) δ 7.68-7.58 (m, 3H), 7.46-7.38 (m, 2H), 7.33 (d, 1H), 7.24-7.18 (m, 1H), 6.84 (d, 1H), 4.32-4.23 (m, 1H), 4.08-3.99 (m, 4H), 3.79-3.71 (m, 2H), 3.65-3.54 (m, 1H), 3.51 (d, 2H), 3.48-3.40 (m, 1H), 2.78-2.67 (m, 4H), 2.44 (s, 3H), 2.34-2.17 (m, 2H), 1.98-1.87 (m, 2H), 1.84-1.72 (m, 2H), 1.72-1.59 (m, 2H), 1.52 (s, 9H), 1.34 (s, 3H), 1.16 (t, 3H). HRMS $[M+H]^+$ calculated for $C_{35}H_{49}N_5O_8S+H$ 700.3375, found 700.3362.

(d) Intermediate 46: ethyl 2-(3-methyl-1-(3-methylbenzenesulfonyl)azetidine-3-carboxamido)-3-(5-(5,6,7,8-tetrahydro-1,8-naphthyridin-2_yl)pentanamido)propanoate

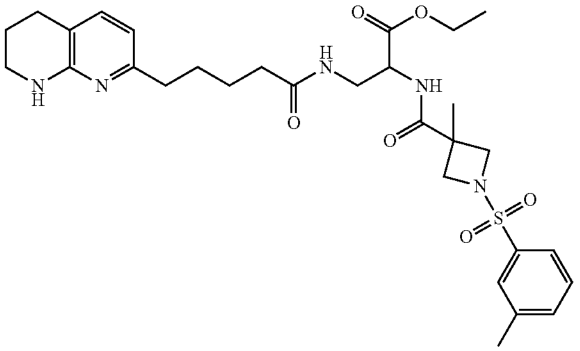 [SMILES: CCOC(=O)C(CNC(=O)CCCCc1ccc2c(n1)NCCC2)NC(=O)C1(C)CN(S(=O)(=O)c2cccc(C)c2)C1]

Prepared by the method of intermediate 22 using intermediate 45 (600 mg, 0.86 mmol) to give intermediate 46 as an orange gel (0.460 g). $^1$H-NMR (400 MHz; $CDCl_3$) δ 7.70-7.57 (m, 3H), 7.46-7.38 (m, 2H), 7.05 (d, 1H), 6.61 (bt, 1H), 6.31 (d, 1H), 4.98 (bs, 1H), 4.43-4.36 (m, 1H), 4.16-4.09 (m, 2H), 4.09-4.02 (m, 2H), 3.62-3.55 (m, 2H), 3.52 (d, 2H), 3.41-3.34 (m, 2H), 2.67 (t, 2H), 2.55-2.48 (m, 2H), 2.43 (s, 3H), 2.23-2.14 (m, 2H), 1.93-1.82 (m, 2H), 1.69-1.56 (m, 4H), 1.36 (s, 3H), 1.29-1.17 (m, 3H). HRMS $[M+H]^+$ calculated for $C_{30}H_{41}N_5O_6S+H$ 600.2856, found 600.2850.

Example 15: 2-(3-methyl-1-(3-methylbenzenesulfonyl)azetidine-3-carboxamido)-3-(5-(5,6,7,8-tetrahydro-1,8-naphthyridin-2-yl)pentanamido)propanoic acid

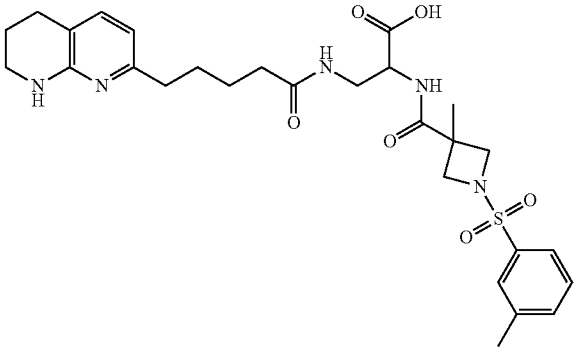 [SMILES: Cc1cccc(S(=O)(=O)N2CC(C)(C(=O)NC(CNC(=O)CCCCc3ccc4c(n3)NCCC4)C(=O)O)C2)c1]

Prepared by the method of Example 7(f) using intermediate 46 (420 mg, 0.70 mmol) to yield 2-(3-methyl-1-(3-methylbenzenesulfonyl)azetidine-3-carboxamido)-3-(5-(5,6,7,8-tetrahydro-1,8-naphthyridin-2-yl)pentanamido) propanoic acid as a yellow oil (0.18 g). $^1$H-NMR (400 MHz; $CD_3OD$) δ 7.67-7.58 (m, 2H), 7.56-7.49 (m, 2H), 7.50-7.44 (m, 1H), 6.51 (d, 1H), 4.28-4.23 (t, 1H), 4.05 (dd, 2H), 3.59-3.40 (m, 6H), 2.77 (t, 2H), 2.69-2.61 (m, 2H), 2.45 (s, 3H), 2.29-2.14 (m, 2H), 1.95-1.86 (m, 2H), 1.75-1.59 (m, 4H), 1.27 (s, 3H). HRMS $[M-H]^-$ calculated for $C_{28}H_{37}N_5O_6S-H$ 570.2392, found 570.2400.

Example 16: 2-(3-Ethyl-1-(3-methylbenzenesulfonyl)azetidine-3-carboxamido)-3-(5-(5,6,7,8-tetrahydro-1,8-naphthyridin-2-yl)pentanamido)propanoic acid (a) Intermediate 47: methyl 3-ethyl-1-(3-methylbenzenesulfonyl)azetidine-3-carboxylate

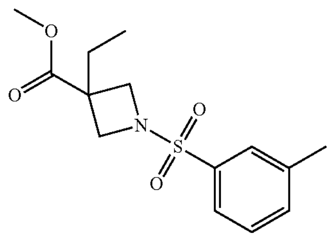 [SMILES: CCC1(C(=O)OC)CN(S(=O)(=O)c2cccc(C)c2)C1]

Prepared by the method of intermediate 44 using intermediate 43 (940 mg, 3.5 mmol) and ethyl iodide (2.75 mL, 34 mmol) to give intermediate 47 as a yellow oil (0.540 g). $^1$H-NMR (400 MHz; $CDCl_3$) δ 7.67-7.60 (m, 2H), 7.46-7.43 (m, 2H), 3.99 (d, 2H), 3.63 (d, 2H), 3.60 (s, 3H), 2.45 (s, 3H), 1.76 (q, 2H), 0.76 (t, 3H). HRMS $[M+H]^+$ calculated for $C_{14}H_{19}NO_4S$+H 298.1113, found 298.1108.

(b) Intermediate 48: tert-butyl 7-(5-((3-ethoxycarbonyl-2-(3-ethyl-1-(3-methylbenzenesulfonyl)azetidine-3-carboxamido)propyl)amino)-5-oxopentyl)-3,4-dihydro-1,8-naphthyridine-1(2H)-carboxylate

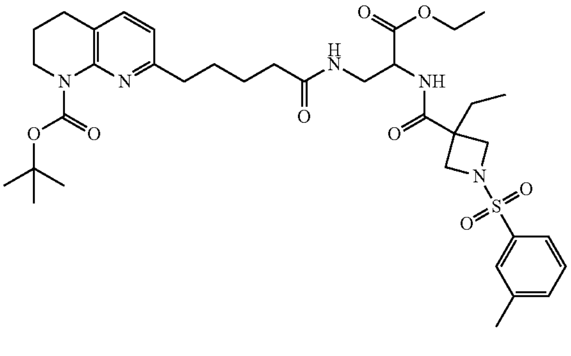 [SMILES: CCOC(=O)C(CNC(=O)CCCCc1ccc2c(n1)N(C(=O)OC(C)(C)C)CCC2)NC(=O)C1(CC)CN(S(=O)(=O)c2cccc(C)c2)C1]

Prepared by the method of intermediate 45 using intermediate 47 (500 mg, 1.7 mmol) and lithium hydroxide (60 mg, 2.5 mmol) to yield lithium 3-ethyl-1-(3-methylbenzenesulfonyl)azetidine-3-carboxylate as a cream collapsed foam (490 mg). A portion (410 mg, 1.4 mmol) and intermediate 19 (544 mg, 1.2 mmol) gave intermediate 48 as a pale brown gel (0.440 g). $^1$H-NMR (400 MHz; $CDCl_3$) δ 7.69-7.57 (m, 3H), 7.46-7.37 (m, 2H), 7.35-7.24 (m, 2H), 6.83 (d, 1H), 4.30-4.21 (m, 1H), 4.07-3.98 (m, 3H), 3.94 (d, 1H), 3.78-3.71 (m, 2H), 3.64-3.49 (m, 3H), 3.48-3.39 (m, 1H), 2.80-2.64 (m, 4H), 2.43 (s, 3H), 2.35-2.16 (m, 2H), 1.98-1.85 (m, 2H), 1.82-1.71 (m, 2H), 1.71-1.59 (m, 4H), 1.51 (s, 9H), 1.14 (t, 3H), 0.75 (t, 3H). HRMS $[M+H]^+$ calculated for $C_{36}H_{51}N_5O_8S$+H 714.3531, found 714.3515.

(c) Intermediate 49: ethyl 2-(3-ethyl-1-(3-methylbenzenesulfonyl)azetidine-3-carboxamido)-3-(5-(5,6,7,8-tetrahydro-1,8-naphthyridin-2-yl)pentanamido)propanoate

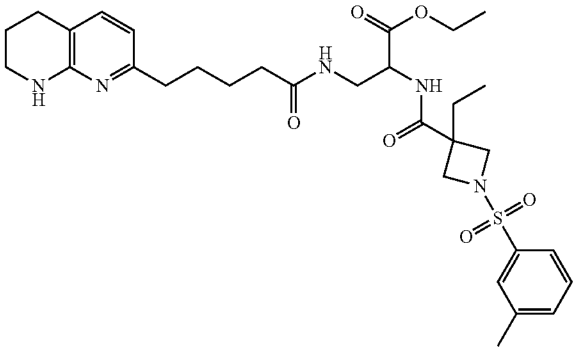 [SMILES: CCOC(=O)C(CNC(=O)CCCCc1ccc2c(n1)NCCC2)NC(=O)C1(CC)CN(S(=O)(=O)c2cccc(C)c2)C1]

Prepared by the method of intermediate 22 using intermediate 48 (440 mg, 0.62 mmol) to give intermediate 49 as a yellow oil (0.29 g). $^1$H-NMR (400 MHz; $CDCl_3$) δ 7.68 (bd, 1H), 7.65-7.57 (m, 2H), 7.44-7.37 (m, 2H), 7.04 (d, 1H), 6.73-6.65 (m, 1H), 6.30 (d, 1H), 5.04 (bs, 1H), 4.42-4.34 (m, 1H), 4.16-4.05 (m, 2H), 4.01 (dd, 2H), 3.61-3.50 (m, 4H), 3.42-3.33 (m, 2H), 2.66 (t, 2H), 2.54-2.47 (m, 2H), 2.42 (s, 3H), 2.24-2.13 (m, 2H), 1.91-1.83 (m, 2H), 1.75-1.55 (6H, m), 1.27-1.16 (m, 3H), 0.76 (t, 3H). HRMS $[M+H]^+$ calculated for $C_{31}H_{43}N_5O_6S$+H 614.3012, found 614.3007.

Example 16: 2-(3-ethyl-1-(3-methylbenzenesulfonyl)azetidine-3-carboxamido)-3-(5-(5,6,7,8-tetrahydro-1,8-naphthyridin-2-yl)pentanamido)propanoic acid

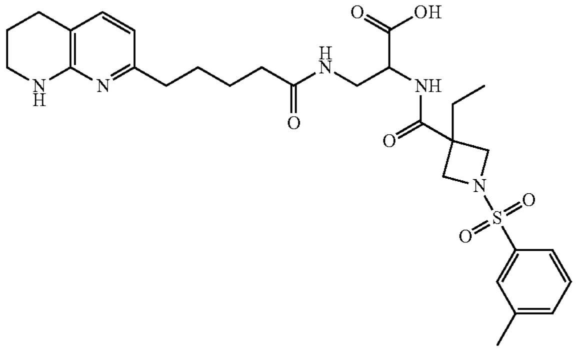 [SMILES: CCC1(C(=O)NC(CNC(=O)CCCCc2ccc3c(n2)NCCC3)C(=O)O)CN(S(=O)(=O)c2cccc(C)c2)C1]

Prepared by the method of Example 7(f) using intermediate 49 (260 mg, 0.42 mmol to yield 2-(3-ethyl-1-(3-methylbenzenesulfonyl)azetidine-3-carboxamido)-3-(5-(5,6,7,8-tetrahydro-1,8-naphthyridin-2-yl)pentanamido) propanoic acid as a yellow oil (0.22 g). $^1$H-NMR (400 MHz; $CD_3OD$) δ 7.65-7.58 (m, 2H), 7.58-7.48 (m, 3H), 6.62 (d, 1H), 4.48 (dd, 1H), 3.99 (dd, 2H), 3.64-3.40 (6H, m), 2.79 (t, 2H), 2.71 (t, 2H), 2.46 (s, 3H), 2.28-2.20 (m, 2H), 2.00-1.85 (m, 2H), 1.75-1.47 (6H, m), 0.69 (t, 3H). HRMS $[M-H]^-$ calculated for $C_{29}H_{39}N_5O_6S$-H 584.2548, found 584.2562.

Example 17: 2-(3-Fluoro-1-(3-methylbenzenesulfonyl)azetidine-3-carboxamido)-3-(5-(5,6,7,8-tetrahydro-1,8-naphthyridin-2-yl)pentanamido)propanoic acid (a) Intermediate 50: methyl 3-fluoro-1-(3-methylbenzenesulfonyl)azetidine-3-carboxylate

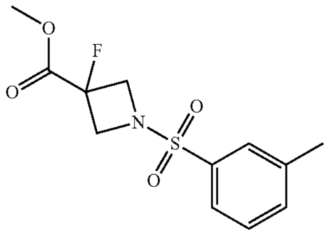 [SMILES: COC(=O)C1(F)CN(S(=O)(=O)c2cccc(C)c2)C1]

Sodium bis(trimethylsilyl)amide (5.2 mL, 5.2 mmol) was added to a solution intermediate 43 (700 mg, 2.6 mmol) in dry tetrahydrofuran (20 mL) at −72° C. and the resultant pale yellow solution stirred for 0.5 h. N-Fluorobenzenesulfonimide (1.23 g, 3.9 mmol) in dry tetrahydrofuran (15 mL) was added to the stirred solution and the resultant solution stirred for 4 h at −72° C. The solution was warmed to room temperature and a white solid precipitated from the solution. The mixture was stirred at room temperature for 15 h. Hydrochloric acid (1M, 30 mL) was added to the resultant solution and the aqueous layer was extracted with ethyl acetate (3×30 mL). The organic layer was washed with brine (2×30 mL), dried, filtered and the solvent removed under reduced pressure to yield a brown oil. The oil formed was purified via flash chromatography on a silica cartridge (40 g), eluting using petroleum ether:ethyl acetate (65:35). The fractions containing product were combined and the solvent was removed under reduced pressure to yield intermediate 50 as a yellow oil (0.250 g). $^1$H-NMR (400 MHz; $CDCl_3$) δ 7.99-7.92 (m, 2H), 7.55-7.43 (m, 2H), 4.27 (ddd, 2H), 4.06 (ddd, 2H), 3.76 (s, 3H), 2.46 (s, 3H). HRMS $[M+H]^+$ calculated for $C_{12}H_{14}FNO_4S$+H 288.0700, found 288.0693.

(b) Intermediate 51: tert-butyl 7-(5-((3-ethoxycarbonyl-2-(3-fluoro-1-(3-methylbenzenesulfonyl)azetidine-3-carboxamido)propyl)amino)-5-oxopentyl)-3,4-dihydro-1,8-naphthyridine-1(2H)-carboxylate

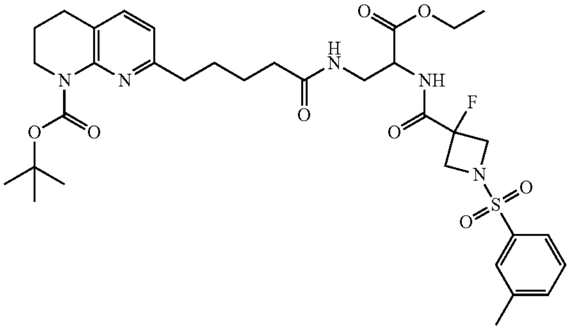 [SMILES: CCOC(=O)C(CNC(=O)CCCCc1ccc2c(n1)N(C(=O)OC(C)(C)C)CCC2)NC(=O)C1(F)CN(S(=O)(=O)c2cccc(C)c2)C1]

Prepared by the method of intermediate 45 using intermediate 50 (100 mg, 0.35 mmol) and lithium hydroxide (12 mg, 0.53 mmol) to yield lithium 3-fluoro-1-(3-methylbenzenesulfonyl)azetidine-3-carboxylate as a pale yellow oil (105 mg), used without purification and reacted with intermediate 19 (202 mg, 0.45 mmol) to give intermediate 51 as a pale brown gel (45 mg). $^1$H-NMR (400 MHz; $CDCl_3$) δ 8.03-7.92 (m, 1H), 7.67-7.57 (m, 2H), 7.48-7.40 (m, 2H), 7.36 (d, 1H), 7.00 (bt, 1H), 6.84 (d, 1H), 4.43-4.36 (m, 1H), 4.25-4.14 (m, 2H), 4.12-4.07 (m, 2H), 4.06-3.89 (m, 2H), 3.78-3.72 (m, 2H), 3.61-3.50 (m, 2H), 2.77-2.68 (m, 4H), 2.43 (s, 3H), 2.27-2.13 (m, 2H), 1.95-1.87 (m, 2H), 1.76-1.68 (m, 2H), 1.65-1.56 (m, 2H), 1.50 (s, 9H), 1.17 (t, 3H). HRMS $[M+H]^+$ calculated for $C_{34}H_{46}FN_5O_8S$+H 704.3124, found 704.3114.

(c) Intermediate 52: ethyl 2-(3-fluoro-1-(3-methylbenzenesulfonyl)azetidine-3-carboxamido)-3-(5-(5,6,7,8-tetrahydro-1,8-naphthyridin-2-yl)pentanamido)propanoate

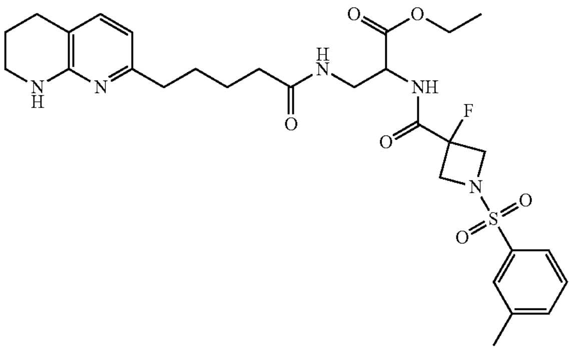 [SMILES: CCOC(=O)C(CNC(=O)CCCCc1ccc2c(n1)NCCC2)NC(=O)C1(F)CN(S(=O)(=O)c2cccc(C)c2)C1]

Prepared by the method of intermediate 22 using intermediate 51 (45 mg, 0.06 mmol) to give intermediate 52 as a yellow oil (30 mg). $^1$H-NMR (400 MHz; $CDCl_3$) δ 7.99-7.92 (m, 1H), 7.71-7.58 (m, 2H), 7.50-7.40 (m, 2H), 7.07 (d, 1H), 6.54 (bs, 1H), 6.31 (d, 1H), 5.51 (bs, 1H), 4.49 (td, 1H), 4.33-3.94 (m, 6H), 3.77-3.52 (m, 2H), 3.45-3.33 (m, 2H), 2.69 (t, 2H), 2.55-2.49 (m, 2H), 2.44 (s, 3H), 2.19 (t, 2H), 1.95-1.84 (m, 2H), 1.69-1.56 (m, 4H), 1.30-1.15 (m, 3H). HRMS $[M+H]^+$ calculated for $C_{29}H_{38}FN_5O_6S$+H 604.2605, found 604.2601.

(d) Example 17: 2-(3-fluoro-1-(3-methylbenzenesulfonyl)azetidine-3-carboxamido)-3-(5-(5,6,7,8-tetrahydro-1,8-naphthyridin-2-yl)pentanamido)propanoic acid

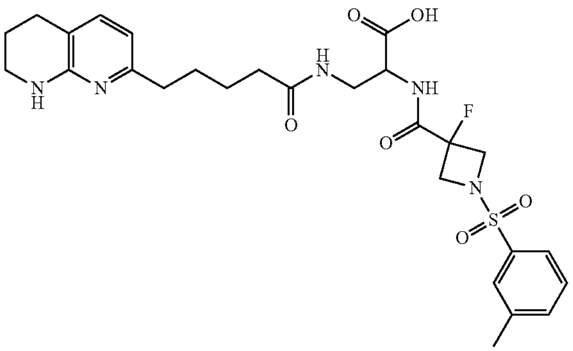 [SMILES: Cc1cccc(S(=O)(=O)N2CC(F)(C(=O)NC(CNC(=O)CCCCc3ccc4c(n3)NCCC4)C(=O)O)C2)c1]

Prepared by the method of Example 7(f) using intermediate 52 (30 mg, 0.05 mmol) to yield 2-(3-fluoro-1-(3-methylbenzenesulfonyl)azetidine-3-carboxamido)-3-(5-(5,6,7,8-tetrahydro-1,8-naphthyridin-2-yl)pentanamido) propanoic acid as a pale yellow oil (25 mg). $^1$H-NMR (400 MHz; $CD_3OD$) δ 7.71-7.62 (m, 2H), 7.59-7.50 (m, 2H), 7.48 (d, 1H), 6.51 (d, 1H), 4.32-4.18 (m, 3H), 4.02-3.87 (m, 2H), 3.60 (qd, 2H), 3.49-3.42 (m, 2H), 2.78 (t, 2H), 2.69-2.59 (m, 2H), 2.47 (s, 3H), 2.24-2.14 (m, 2H), 1.97-1.87 (m, 2H), 1.77-1.55 (m, 4H). HRMS $[M-H]^-$ calculated for $C_{27}H_{34}FN_5O_6S-H$ 574.2141, found 574.2150.

Example 18: 2-(1-((1-Methyl-1H-imidazol-4-yl) sulfonyl) azetidine-3-carboxamido)-3-(5-(5,6,7,8-tetrahydro-1,8-naphthyridin-2-yl)pentanamido) propanoic acid (a) Intermediate 53: methyl 1-((1-methyl-1H-imidazol-4-yl)sulfonyl)azetidine-3-carboxylate

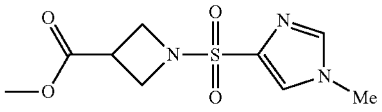 [SMILES: COC(=O)C1CN(S(=O)(=O)c2cn(C)cn2)C1]

Methyl azetidine-3-carboxylate (350 mg, 3.05 mmol) was dissolved in tetrahydrofuran (10 mL). Triethylamine (0.45 mL, 6.10 mmol) was added and the reaction mixture was cooled in an ice bath. 1-Methyl-1H-imidazole-4-sulfonyl chloride (550 mg, 3.05 mmol) was added and the reaction mixture was allowed to return to room temperature and was stirred for 18 h. Triethylamine (0.45 mL, 6.10 mmol) and acetonitrile (2 mL) were added and the reaction mixture was stirred at room temperature for a further 4 h. The reaction mixture was concentrated in vacuo and the residue was dissolved in sodium hydrogen carbonate solution (saturated, 70 mL) and extracted with dichloromethane (5×20 mL). Sodium hydroxide solution (2M, 1 mL) was added to the aqueous which was then extracted with dichloromethane (6×20 mL). The organics were combined and concentrated in vacuo to give intermediate 53 as a white solid (0.440 g).

$^1$H NMR (400 MHz; $CD_3OD$) δ 7.86 (s, 1H), 7.84 (d, 1H), 4.11-4.00 (m, 4H), 3.87 (s, 3H), 3.67 (s, 3H), 3.40-3.31 (m, 1H). HRMS $[M+H]^+$ calculated for $C_9H_{13}N_3O_4S+H$ 260.0705, found 260.0699.

(b) Intermediate 54: lithium 1-((1-methyl-1H-imidazol-4-yl)sulfonyl)azetidine-3-carboxylate

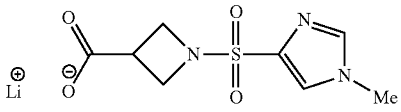 [SMILES: [Li+] ; Cn1cnc(S(=O)(=O)N2CC(C(=O)[O-])C2)c1]

Intermediate 53 (420 mg, 1.62 mmol) was dissolved in tetrahydrofuran (9 mL), methanol (3 mL) and water (3 mL). Lithium hydroxide (78 mg, 3.24 mmol) was added and the reaction mixture stirred at room temperature for 18 h. Toluene (3×5 mL) was added and the reaction mixture was concentrated three times in vacuo to give intermediate 54 as a colourless oil (0.48 g). $^1$H NMR (400 MHz; $CD_3OD$) δ 7.79 (d, 1H), 7.77 (d, 1H), 3.97 (d, 2H), 3.95 (d, 2H), 3.83 (s, 3H), 3.11-3.02 (m, 1H). HRMS $[M-H]^-$ calculated for $C_8H_{10}LiN_3O_4S-H$ 244.0392, found 244.0399.

(c) Intermediate 55: tert-butyl 7-(5-((3-ethoxycarbonyl-2-(1-((1-methyl-1H-imidazol-4-yl)sulfonyl)azetidine-3-carboxamido)propyl)amino)-5-oxopentyl)-3,4-dihydro-1,8-naphthyridine-1(2H)-carboxylate

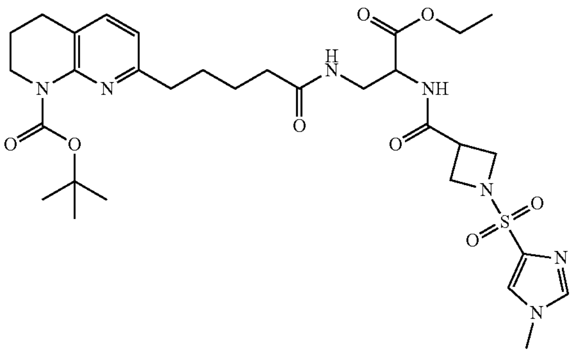 [SMILES: CCOC(=O)C(CNC(=O)CCCCc1ccc2c(n1)N(C(=O)OC(C)(C)C)CCC2)NC(=O)C1CN(S(=O)(=O)c2cn(C)cn2)C1]

Intermediate 19 (300 mg, 0.67 mmol) and Intermediate 54 (147 mg, 0.67 mmol) were dissolved in acetonitrile (10 mL). N—N-diisopropylethylamine (0.32 mL, 3.35 mmol) and HATU (764 mg, 2.01 mmol) were added and the reaction mixture was allowed to return to room temperature and was stirred for 66 h. The reaction mixture was concentrated in vacuo and the residue was partitioned between aqueous sodium hydrogen carbonate solution (saturated, 50 mL) and ethyl acetate (3×40 mL). The organic layer was collected, washed with brine (3×30 mL), dried, filtered and concentrated in vacuo to a yellow oil (760 mg). The crude was then purified via flash chromatography eluting with 0:100-10:80 methanol:ethyl acetate to give intermediate 55 as a yellow oil (350 mg). $^1$H NMR (400 MHz; $CDCl_3$) δ 7.57 (d, 1H), 7.52 (d, 1H), 7.39-7.31 (m, 2H), 6.97 (t, 1H), 6.86 (d, 1H), 4.43-4.37 (m, 1H), 4.14-4.04 (m, 4H), 4.02-3.95 (m, 2H), 3.78 (s, 3H), 3.77-3.72 (m, 2H), 3.65-3.55 (m, 1H), 3.53-3.45 (m, 1H), 3.20-3.06 (m, 1H), 2.78-2.70 (m, 4H), 2.22 (t, 2H), 1.93 (quin, 2H), 1.78-1.69 (m, 2H), 1.68-1.59 (m, 2H), 1.50 (s, 9H), 1.20 (t, 3H). HRMS $[M-H]^-$ calculated for $C_{31}H_{45}N_7O_8S-H$ 674.2978, found 674.2986.

(d) Intermediate 56: ethyl 2-(1-((1-methyl-1H-imidazol-4-yl)sulfonyl)azetidine-3-carboxamido)-3-(5-(5,6,7,8-tetrahydro-1,8-naphthyridin-2-yl)pentanamido)propanoate

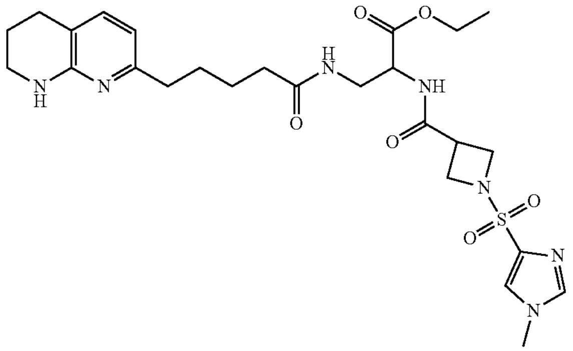 [SMILES: CCOC(=O)C(CNC(=O)CCCCc1ccc2c(n1)NCCC2)NC(=O)C1CN(S(=O)(=O)c2cn(C)cn2)C1]

Prepared by the method of intermediate 22 using intermediate 55 (234 mg, 0.35 mmol) to give intermediate 56 as a yellow oil (0.178 g). $^1$H NMR (400 MHz; $CDCl_3$) δ 7.93 (d, 1H), 7.55 (d, 1H), 7.52 (d, 1H), 7.12 (d, 1H), 6.58 (s, 1H), 6.35 (d, 1H), 5.51 (s, 1H), 4.52-4.45 (m, 1H), 4.21-4.13 (m, 4H), 4.06-3.97 (m, 2H), 3.78 (s, 3H), 3.69-3.63 (m, 2H), 3.44-3.38 (m, 2H), 3.30-3.20 (m, 1H), 2.71 (t, 2H), 2.58-2.51 (m, 2H), 2.27-2.20 (m, 2H), 1.95-1.87 (m, 2H), 1.72-1.61 (m, 4H), 1.26 (t, 3H). HRMS $[M-H]^-$ calculated for $C_{26}H_{37}N_7O_6S$–H 574.2453, found 574.2473.

(e) Example 18: 2-(1-((1-methyl-1H-imidazol-4-yl) sulfonyl) azetidine-3-carboxamido)-3-(5-(5,6,7,8-tetrahydro-1,8-naphthyridin-2-yl)pentanamido) propanoic acid

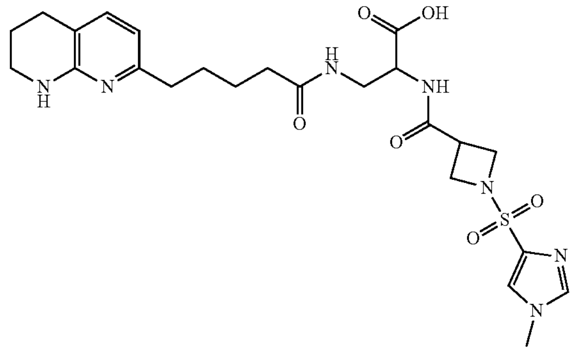 [SMILES: Cn1cnc(S(=O)(=O)N2CC(C(=O)NC(CNC(=O)CCCCc3ccc4c(n3)NCCC4)C(=O)O)C2)c1]

Prepared by the method of Example 7(f) using intermediate 56 (163 mg, 0.28 mmol) to give 2-(1-((1-methyl-1H-imidazol-4-yl)sulfonyl) azetidine-3-carboxamido)-3-(5-(5,6,7,8-tetrahydro-1,8-naphthyridin-2-yl)pentanamido) propanoic acid as a colourless cracked glass (0.123 g). $^1$H NMR (400 MHz; $CH_3OD$) δ 7.81 (s, 1H), 7.79 (d, 1H), 7.22 (d, 1H), 6.40 (d, 1H), 4.29-4.24 (m, 1H), 4.04-3.89 (m, 4H), 3.83 (s, 3H), 3.58 (dd, 1H), 3.46 (dd, 1H), 3.43-3.38 (m, 2H), 3.28-3.19 (m, 1H), 2.72 (t, 2H), 2.59-2.53 (m, 2H), 2.23-2.15 (m, 2H), 1.93-1.85 (m, 2H), 1.68-1.57 (m, 4H). HRMS $[M-H]^-$ calculated for $C_{24}H_{33}N_7O_6S$–H 546.2140, found 546.2159.

Example 19: 2-(1-((1-Methyl-1H-pyrazol-4-yl) sulfonyl)azetidine-3-carboxamido)-3-(5-(5,6,7,8-tetrahydro-1,8-naphthyridin-2-yl)pentanamido)propanoic acid (a) Intermediate 57: give 1-((1-methyl-1H-pyrazol-4-yl)sulfonyl)azetidine-3-carboxylic acid

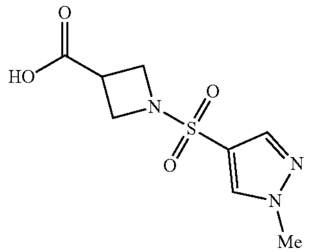 [SMILES: Cn1cc(S(=O)(=O)N2CC(C(=O)O)C2)cn1]

1-Methyl-1H-pyrazole-4-sulfonyl chloride (536 mg, 2.97 mmol) was dissolved in diethyl ether (5 mL) and water (5 mL). Azetidine-3-carboxylic acid (300 mg, 2.97 mmol) and sodium hydroxide solution 2 M (3 mL, 6 mmol) were added and the reaction mixture was stirred at room temperature for 18 h. Diethyl ether (10 mL) was added and the aqueous layer was separated and acidified with hydrochloric acid solution (2 M) to pH 6. Extraction into organic solvent was unsuccessful so the aqueous layer was concentrated in vacuo and the product was triturated with petrol to give intermediate 57 as a sticky white solid (879 mg). $^1$H NMR (400 MHz; $CD_3OD$) δ 8.20 (s, 1H), 7.81 (s, 1H), 3.98 (s, 3H), 3.90-3.76 (m, 4H), 3.14-3.03 (m, 1H). LRMS $[M-H]^-$ calculated for $C_8H_{11}N_3O_4S$–H 244.04, found 244.04.

(b) Intermediate 58: tert-butyl 7-(5-((3-ethoxycarbonyl-2-(1-((1-methyl-1H-pyrazol-4-yl)sulfonyl)azetidine-3-carboxamido)propyl)amino)-5-oxopentyl)-3,4-dihydro-1,8-naphthyridine-1(2H)-carboxylate

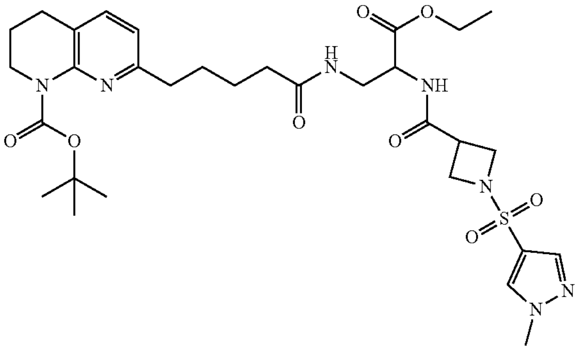 [SMILES: CCOC(=O)C(CNC(=O)CCCCc1ccc2c(n1)N(C(=O)OC(C)(C)C)CCC2)NC(=O)C1CN(S(=O)(=O)c2cnn(C)c2)C1]

Prepared by the method of intermediate 27 using intermediate 19 (300 mg, 0.67 mmol) and intermediate 57 (164 mg, 0.37 mmol) to give intermediate 58 as a yellow oil (0.28 g). $^1$H NMR (400 MHz; $CD_3OD$) δ 8.21 (s, 1H), 7.81 (s, 1H), 7.50 (d, 1H), 6.99 (d, 1H), 4.42 (dd, 1H), 4.21-4.07 (m, 2H), 3.98 (s, 3H), 3.89-3.69 (m, 6H), 3.58 (dd, 1H), 3.45 (dd, 1H), 3.27-3.19 (m, 1H), 2.78 (t, 2H), 2.72 (t, 2H), 2.20 (t, 2H), 1.96-1.89 (m, 2H), 1.75-1.60 (m, 4H), 1.51 (s, 9H), 1.24 (t, 3H). HRMS $[M-H]^-$ calculated for $C_{31}H_{45}N_7O_8S$–H 674.2972, found 674.2978.

(c) Intermediate 59: ethyl 2-(1-((1-methyl-1H-pyrazol-4-yl)sulfonyl)azetidine-3-carboxamido)-3-(5-(5,6,7,8-tetrahydro-1,8-naphthyridin-2-yl)pentanamido) propanoate

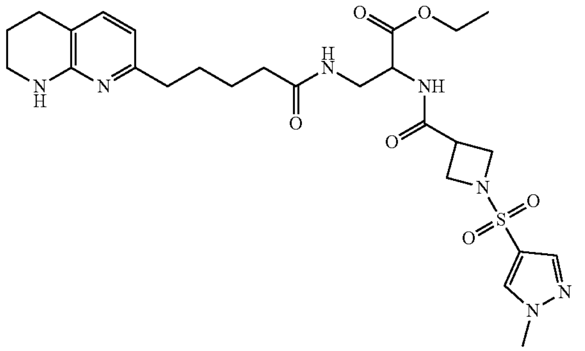 [SMILES: CCOC(=O)C(CNC(=O)CCCCc1ccc2c(n1)NCCC2)NC(=O)C1CN(S(=O)(=O)c2cnn(C)c2)C1]

Prepared by the method of intermediate 22 using intermediate 58 (155 mg, 0.23 mmol) to give intermediate 59 as a yellow oil (0.133 g). $^1H$ NMR (400 MHz; $CDCl_3$) δ 7.86 (s, 1H), 7.83 (d, 1H), 7.81 (s, 1H), 7.10 (d, 1H), 6.34 (d, 1H), 6.30 (s, 1H), 4.49 (td, 1H), 4.18 (qd, 2H), 3.98 (s, 3H), 3.93-3.83 (m, 4H), 3.74-3.65 (m, 1H), 3.64-3.56 (m, 1H), 3.42-3.37 (m, 2H), 3.24-3.15 (m, 1H), 2.70 (t, 2H), 2.55-2.49 (m, 2H), 2.26-2.19 (m, 2H), 1.94-1.86 (m, 2H), 1.69-1.61 (m, 4H), 1.25 (t, 3H). HRMS $[M-H]^-$ calculated for $C_{26}H_{37}N_7O_6S-H$ 574.2453, found 574.2461.

(d) Example 19: 2-(1-((1-methyl-1H-pyrazol-4-yl)sulfonyl)azetidine-3-carboxamido)-3-(5-(5,6,7,8-tetrahydro-1,8-naphthyridin-2-yl)pentanamido)propanoic acid

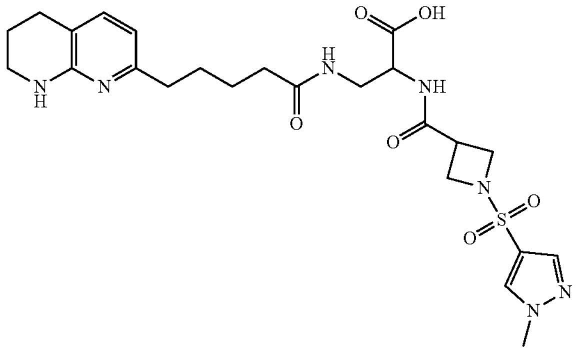 [SMILES: Cn1cc(S(=O)(=O)N2CC(C(=O)NC(CNC(=O)CCCCc3ccc4c(n3)NCCC4)C(=O)O)C2)cn1]

Prepared by the method of Example 7(f) using intermediate 59 (117 mg, 0.20 mmol to give 2-(1-((1-methyl-1H-pyrazol-4-yl)sulfonyl)azetidine-3-carboxamido)-3-(5-(5,6,7,8-tetrahydro-1,8-naphthyridin-2-yl)pentanamido)propanoic acid as a colourless cracked glass (73 mg). $^1H$ NMR (400 MHz; $CD_3OD$) δ 8.22 (s, 1H), 7.82 (s, 1H), 7.34 (d, 1H), 6.45 (d, 1H), 4.26 (t, 1H), 3.99 (s, 3H), 3.89-3.81 (m, 4H), 3.57 (dd, 1H), 3.49 (dd, 1H), 3.45-3.40 (m, 2H), 3.30-3.22 (m, 1H), 2.75 (t, 2H), 2.64-2.57 (m, 2H), 2.27-2.14 (m, 2H), 1.95-1.86 (m, 2H), 1.72-1.59 (m, 4H). HRMS $[M-H]^-$ calculated for $C_{24}H_{33}N_7O_6S-H$ 546.2140, found 546.2141.

Example 20: 2-(1-((5-Chlorothiophen-2-yl)sulfonyl)azetidine-3-carboxamido)-3-(5-(5,6,7,8-tetrahydro-1,8-naphthyridin-2-yl)pentanamido)propanoic acid (a) Intermediate 60: methyl 1-((5-chlorothiophen-2-yl)sulfonyl)azetidine-3-carboxylate

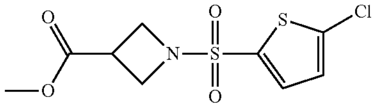 [SMILES: COC(=O)C1CN(S(=O)(=O)c2ccc(Cl)s2)C1]

Prepared by the method of intermediate 53 using methyl azetidine-3-carboxylate (265 mg, 1.75 mmol) and 5-chlorothiophene-2-sulfonyl chloride (500 mg, 2.30 mmol) to give intermediate 60 as an orange oil (0.63 g). $^1H$ NMR (400 MHz; $CDCl_3$) δ 7.44 (d, 1H), 7.06 (d, 1H), 4.10-3.97 (m, 4H), 3.68 (s, 3H), 3.36-3.27 (m, 1H).

(b) Intermediate 61: lithium 1-((5-chlorothiophen-2-yl)sulfonyl)azetidine-3-carboxylate

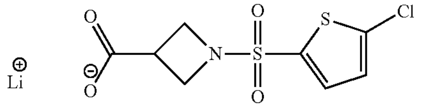 [SMILES: [Li+] ; O=C([O-])C1CN(S(=O)(=O)c2ccc(Cl)s2)C1]

Prepared by the method of intermediate 54 using intermediate 60 (630 mg, 2.13 mmol) and lithium hydroxide (102 mg, 4.26 mmol) to give intermediate 61 as a pink solid (0.69 g). $^1H$ NMR (400 MHz; $CD_3OD$) δ 7.51 (d, 1H), 7.21 (d, 1H), 3.94 (m, 4H), 3.13 (tt, 1H).

(c) Intermediate 62: tert-butyl 7-(5-((2-(1-((5-chlorothiophen-2-yl)sulfonyl)azetidine-3-carboxamido)-3-ethoxycarbonylpropyl)amino)-5-oxopentyl)-3,4-dihydro-1,8-naphthyridine-1(2H)-carboxylate

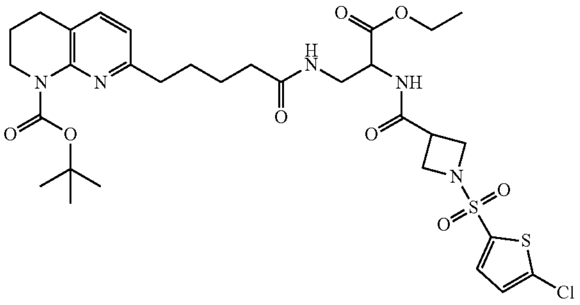 [SMILES: CCOC(=O)C(CNC(=O)CCCCc1ccc2c(n1)N(C(=O)OC(C)(C)C)CCC2)NC(=O)C1CN(S(=O)(=O)c2ccc(Cl)s2)C1]

Prepared by the method of intermediate 55 using intermediate 61 (185 mg, 0.67 mmol) and intermediate 19 (300 mg, 0.67 mmol) to give intermediate 62 as a yellow oil (0.37 g). $^1H$ NMR (400 MHz; $CDCl_3$) δ 7.46 (s, 1H), 7.41 (d, 1H), 7.35 (s, 1H), 7.03 (d, 1H), 6.96-6.88 (m, 2H), 4.43-4.37 (m, 1H), 4.15-4.04 (m, 2H), 3.99-3.88 (m, 4H), 3.82-3.77 (m, 2H), 3.63-3.47 (m, 2H), 3.23-3.11 (m, 1H), 2.81-2.74 (m, 4H), 2.24 (td, 2H), 1.98-1.92 (m, 2H), 1.80-1.72 (m, 2H), 1.69-1.60 (m, 2H), 1.53 (s, 9H), 1.20 (t, 3H). HRMS $[M+H]^+$ calculated for $C_{31}H_{42}ClN_5O_8S_2+H$ 712.2236, found 712.2224.

(d) Intermediate 63: ethyl 2-(1-((5-chlorothiophen-2-yl)sulfonyl)azetidine-3-carboxamido)-3-(5-(5,6,7,8-tetrahydro-1,8-naphthyridin-2-yl)pentanamido)propanoate

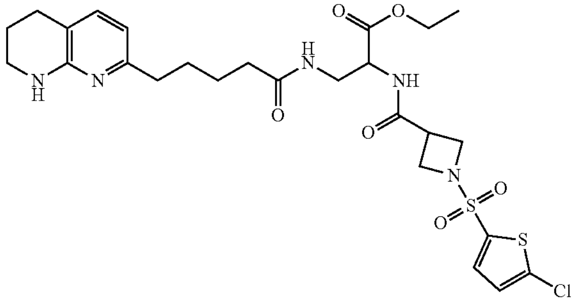 [SMILES: CCOC(=O)C(CNC(=O)CCCCc1ccc2c(n1)NCCC2)NC(=O)C1CN(S(=O)(=O)c2ccc(Cl)s2)C1]

Prepared by the method of intermediate 22 using intermediate 62 (370 mg, 0.52 mmol) to give intermediate 63 as a yellow oil (0.186 g). $^1$H NMR (400 MHz; $CDCl_3$) δ 7.89 (d, 1H), 7.42 (d, 1H), 7.15 (d, 1H), 7.04 (d, 1H), 6.36 (d, 1H), 4.55-4.48 (m, 1H), 4.17 (qd, 2H), 4.04-3.90 (m, 4H), 3.70-3.62 (m, 2H), 3.45-3.40 (m, 2H), 3.30-3.20 (m, 1H), 2.72 (t, 2H), 2.58-2.51 (m, 2H), 2.29-2.20 (m, 2H), 1.96-1.88 (m, 2H), 1.70-1.63 (m, 4H), 1.25 (t, 3H). HRMS $[M-H]^-$ calculated for $C_{26}H_{34}ClN_5O_6S_2$– H 610.1566, found 610.1567.

(e) Example 20: 2-(1-((5-chlorothiophen-2-yl)sulfonyl)azetidine-3-carboxamido)-3-(5-(5,6,7,8-tetrahydro-1,8-naphthyridin-2-yl)pentanamido)propanoic acid

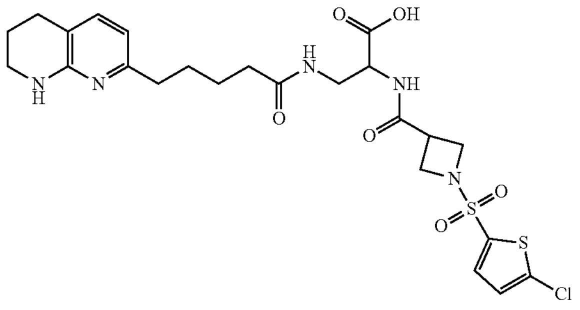 [SMILES: O=C(CCCCc1ccc2c(n1)NCCC2)NCC(NC(=O)C1CN(S(=O)(=O)c2ccc(Cl)s2)C1)C(=O)O]

Prepared by the method of Example 7(f) using intermediate 63 (186 mg, 0.30 mmol) to give 2-(1-((5-chlorothiophen-2-yl)sulfonyl)azetidine-3-carboxamido)-3-(5-(5,6,7,8-tetrahydro-1,8-naphthyridin-2-yl)pentanamido)propanoic acid as a yellow cracked glass (0.165 g). $^1$H NMR (400 MHz; $CD_3OD$) δ 7.59 (d, 1H), 7.53 (d, 1H), 7.24 (d, 1H), 6.65 (d, 1H), 4.56-4.49 (m, 1H), 4.02-3.92 (m, 4H), 3.74-3.60 (m, 1H), 3.53-3.49 (m, 2H), 3.49-3.43 (m, 1H), 3.42-3.36 (m, 1H), 2.82 (t, 2H), 2.73 (t, 2H), 2.31-2.25 (m, 2H), 1.98-1.94 (m, 2H), 1.75-1.60 (m, 4H). HRMS $[M-H]^-$ calculated for $C_{24}H_{30}ClN_5O_6S_2$–H 582.1253, found 582.1257.

Example 21: 2-(1-(Pyridin-3-ylsulfonyl)azetidine-3-carboxamido)-3-(5-(5,6,7,8-tetrahydro-1,8-naphthyridin-2-yl)pentanamido)propanoic acid (a) Intermediate 64: methyl 1-(pyridin-3-ylsulfonyl)azetidine-3-carboxylate

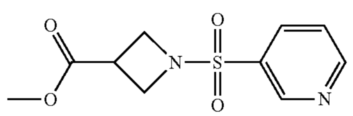 [SMILES: COC(=O)C1CN(S(=O)(=O)c2cccnc2)C1]

Prepared by the method of intermediate 53 using methyl azetidine-3-carboxylate (269 mg, 2.34 mmol) and pyridine-3-sulfonyl chloride (500 mg, 2.34 mmol) to give intermediate 64 as a yellow oil (250 mg). $^1$H NMR (400 MHz; $CDCl_3$) δ 9.06 (d, 1H), 8.88 (dd, 1H), 8.14 (dt, 1H), 7.54 (ddd, 1H), 4.11-4.03 (m, 2H), 4.00-3.93 (m, 2H), 3.63 (s, 3H), 3.36-3.26 (m, 1H).

(b) Intermediate 65: lithium 1-(pyridin-3-ylsulfonyl)azetidine-3-carboxylate

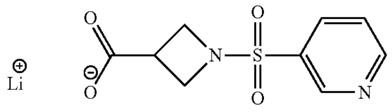 [SMILES: [Li+] ; O=C([O-])C1CN(S(=O)(=O)c2cccnc2)C1]

Prepared by the method of intermediate 54 using intermediate 64 (181 mg, 0.71 mmol) and Lithium hydroxide (34 mg, 1.42 mmol) to give intermediate 65 as a white solid (0.160 g). $^1$H NMR (400 MHz; $CD_3OD$) δ 8.97 (dd, 1H), 8.84 (dd, 1H), 8.26 (ddd, 1H), 7.70 (ddd, 1H), 3.99-3.92 (m, 2H), 3.92-3.85 (m, 2H), 3.15-3.05 (m, 1H). HRMS $[M-H]^-$ calculated for $C_9H_{10}N_2O_4S$–H 241.0289, found 241.0294.

(c) Intermediate 66: tert-butyl 7-(5-((3-ethoxycarbonyl-2-(1-(pyridin-3-ylsulfonyl)azetidine-3-carboxamido)propyl) amino)-5-oxopentyl)-3,4-dihydro-1,8-naphthyridine-1(2H)-carboxylate

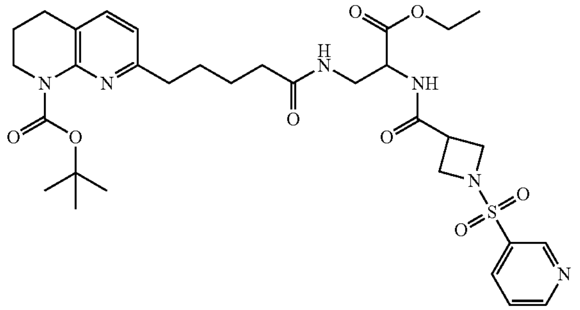 [SMILES: CCOC(=O)C(CNC(=O)CCCCc1ccc2c(n1)N(C(=O)OC(C)(C)C)CCC2)NC(=O)C1CN(S(=O)(=O)c2cccnc2)C1]

Prepared by the method of intermediate 55 using intermediate 65 (151 mg, 0.61 mmol) and intermediate 19 (274 mg, 0.61 mmol) to give intermediate 66 (170) mg as a yellow oil. $^1$H NMR (400 MHz; $CDCl_3$) δ 9.03 (dd, 1H), 8.85 (dd, 1H), 8.14-8.10 (ddd, 1H), 7.52 (ddd, 1H), 7.42 (s, 2H), 6.96 (s, 1H), 6.90 (d, 1H), 4.39-4.32 (m, 1H), 4.18-4.02 (m, 2H), 4.00-3.88 (m, 4H), 3.81-3.73 (m, 2H), 3.61-3.43 (m, 2H), 3.20-3.11 (m, 1H), 2.81-2.70 (m, 4H), 2.28-2.18 (m, 2H), 2.00-1.90 (m, 2H), 1.80-1.70 (m, 2H), 1.70-1.60 (m, 2H), 1.53 (s, 9H), 1.18 (t, 3H). HRMS $[M-H]^-$ calculated for $C_{32}H_{44}N_6O_8S$–H 671.2863, found 671.2914.

(d) Intermediate 67: ethyl 2-(1-(pyridin-3-ylsulfonyl)azetidine-3-carboxamido)-3-(5-(5,6,7,8-tetrahydro-1,8-naphthyridin-2-yl)pentanamido)propanoate

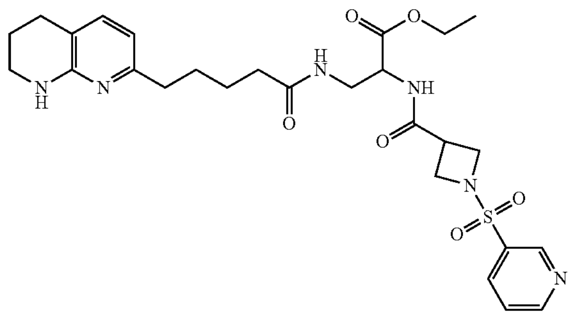 [SMILES: CCOC(=O)C(CNC(=O)CCCCc1ccc2c(n1)NCCC2)NC(=O)C1CN(S(=O)(=O)c2cccnc2)C1]

Prepared by the method of intermediate 22 using intermediate 66 (160 mg, 0.24 mmol) to give intermediate 67 as a yellow oil (0.112 g). $^1$H NMR (400 MHz; $CDCl_3$) δ 9.05 (dd, 1H), 8.86 (dd, 1H), 8.13 (ddd, 1H), 7.87 (d, 1H), 7.52 (ddd, 1H), 7.09 (d, 1H), 6.39-3.60 (m, 2H), 4.51-4.42 (m, 1H), 4.25-4.10 (m, 2H), 4.02-3.90 (m, 4H), 3.71-3.62 (m, 1H), 3.62-3.53 (m, 1H), 3.43-3.35 (m, 2H), 3.24-3.14 (m, 1H), 2.73-2.67 (m, 2H), 2.57-2.48 (m, 2H), 2.25-2.18 (m, 2H), 1.97-1.87 (m, 2H), 1.72-1.59 (m, 4H), 1.24 (t, 3H). HRMS $[M-H]^-$ calculated for $C_{27}H_{36}N_6O_6S$−H 571.2344, found 571.2345.

(e) Example 21: 2-(1-(pyridin-3-ylsulfonyl)azetidine-3-carboxamido)-3-(5-(5,6,7,8-tetrahydro-1,8-naphthyridin-2-yl)pentanamido)propanoic acid

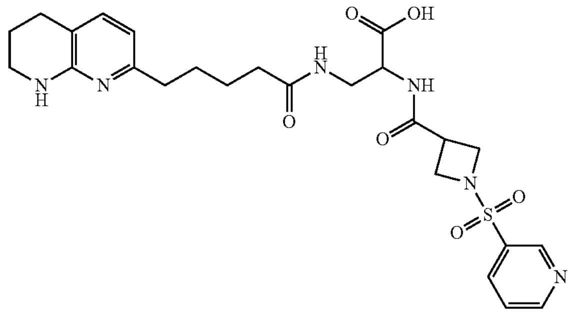 [SMILES: O=C(CCCCc1ccc2c(n1)NCCC2)NCC(NC(=O)C1CN(S(=O)(=O)c2cccnc2)C1)C(=O)O]

Prepared by the method of Example 7(f) using intermediate 67 (112 mg, 0.20 mmol) to give 2-(1-(pyridin-3-ylsulfonyl)azetidine-3-carboxamido)-3-(5-(5,6,7,8-tetrahydro-1,8-naphthyridin-2-yl)pentanamido)propanoic acid as a colourless cracked glass (56 mg). $^1$H NMR (400 MHz; $CD_3OD$) δ 8.98 (s, 1H), 8.85 (d, 1H), 8.26 (dt, 1H), 7.70 (dd, 1H), 7.36 (d, 1H), 6.46 (d, 1H), 4.26-4.20 (m, 1H), 3.99-3.89 (m, 4H), 3.58-3.47 (m, 2H), 3.46-3.40 (m, 2H), 3.33-3.29 (m, 1H), 2.75 (t, 2H), 2.61 (t, 2H), 2.23-2.15 (m, 2H), 1.95-1.86 (m, 2H), 1.71-1.58 (m, 4H). HRMS $[M-H]^-$ calculated for $C_{25}H_{32}N_6O_6S$−H 543.2031, found 543.2029.

Example 22: 2-(1-((1,2-Dimethyl-1H-imidazol-4-yl)sulfonyl)azetidine-3-carboxamido)-3-(5-(5,6,7,8-tetrahydro-1,8-naphthyridin-2-yl)pentanamido)propanoic acid (a) Intermediate 68: methyl 1-((1,2-dimethyl-1H-imidazol-4-yl)sulfonyl)azetidine-3-carboxylate

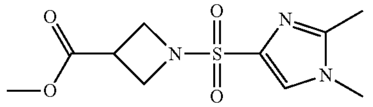

Prepared by the method of intermediate 53 using methyl azetidine-3-carboxylate (389 mg, 2.57 mmol) and 1,2-dimethyl-1H-imidazole-4-sulfonyl chloride (500 mg, 2.57 mmol) to give intermediate 68 as colourless crystals (0.670 g). $^1$H NMR (400 MHz; $CDCl_3$) δ 7.43 (s, 1H), 4.18-4.06 (m, 4H), 3.67 (s, 3H), 3.65 (s, 3H), 3.28 (tt, 1H), 2.41 (s, 3H). HRMS $[M+H]^+$ calculated for $C_{10}H_{15}N_3O_4S$+H 274.0856, found 274.0854.

(b) Intermediate 69: lithium 1-((1,2-dimethyl-1H-imidazol-4-yl)sulfonyl)azetidine-3-carboxylate

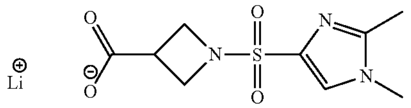 [SMILES: [Li+] ; Cc1nc(S(=O)(=O)N2CC(C(=O)[O-])C2)cn1C]

Prepared by the method of intermediate 54 using intermediate 68 (500 mg, 1.83 mmol) and lithium hydroxide (88 mg, 3.66 mmol) to give intermediate 69 as a white solid (0.52 g). $^1$H NMR (400 MHz; $CD_3OD$) δ 7.67 (s, 1H), 3.99-3.90 (m, 4H), 3.71 (s, 3H), 3.11-3.01 (m, 1H), 2.41 (s, 3H). HRMS $[M-H]^-$ calculated for $C_9H_{13}N_3O_4S$ 258.0554, found 258.0562.

(c) Intermediate 70: tert-butyl 7-(5-((2-(1-((1,2-dimethyl-1H-imidazol-4-yl)sulfonyl)azetidine-3-carboxamido)-3-ethoxycarbonylpropyl)amino)-5-oxopentyl)-3,4-dihydro-1,8-naphthyridine-1(2H)-carboxylate

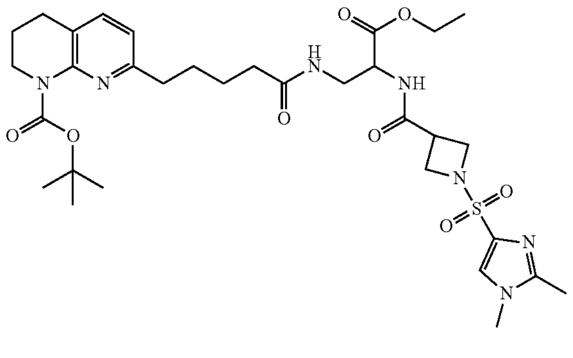 [SMILES: CCOC(=O)C(CNC(=O)CCCCc1ccc2c(n1)N(C(=O)OC(C)(C)C)CCC2)NC(=O)C1CN(S(=O)(=O)c2cn(C)c(C)n2)C1]

Prepared by the method of intermediate 55 using intermediate 69 (178 mg, 0.67 mmol) and intermediate 19 (300 mg, 0.67 mmol) to intermediate 70 as a yellow oil (0.330 g). $^1$H NMR (400 MHz; $CDCl_3$) δ 7.43 (s, 1H), 7.36 (d, 1H), 7.30 (d, 1H), 7.01 (t, 1H), 6.86 (d, 1H), 4.42-4.36 (m, 1H), 4.15-3.92 (m, 6H), 3.78-3.73 (m, 2H), 3.64 (s, 3H), 3.62-3.55 (m, 1H), 3.53-3.45 (m, 1H), 3.16-3.06 (m, 1H), 2.78-2.70 (m, 4H), 2.40 (s, 3H), 2.23 (t, 2H), 1.97-1.89 (m, 2H), 1.78-1.69 (m, 2H), 1.69-1.59 (m, 2H), 1.51 (s, 9H), 1.20 (t, 3H). HRMS [M−H]$^-$ calculated for $C_{32}H_{47}N_7O_8S$–H 688.3134, found 688.3138.

(d) Intermediate 71: ethyl 2-(1-((1,2-dimethyl-1H-imidazol-4-yl)sulfonyl)azetidine-3-carboxamido)-3-(5-(5,6,7,8-tetrahydro-1,8-naphthyridin-2-yl)pentanamido)propanoate

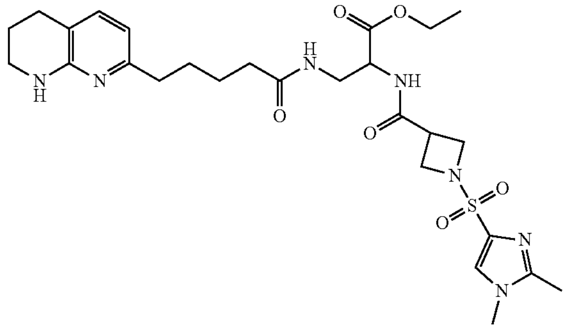 [SMILES: CCOC(=O)C(CNC(=O)CCCCc1ccc2c(n1)NCCC2)NC(=O)C1CN(S(=O)(=O)c2cn(C)c(C)n2)C1]

Prepared by the method of intermediate 22 using intermediate 70 (310 mg, 0.45 mmol) to give intermediate 71 as a yellow oil (0.297 g). $^1$H NMR (400 MHz; $CDCl_3$) δ 7.75 (d, 1H), 7.44 (s, 1H), 7.11 (d, 1H), 6.55 (s, 1H), 6.34 (d, 1H), 4.53-4.47 (m, 1H), 4.21-4.14 (m, 2H), 4.14-4.08 (m, 2H), 4.05-3.95 (m, 2H), 3.72-3.59 (m, 5H), 3.44-3.38 (m, 2H), 3.27-3.17 (m, 1H), 2.71 (t, 2H), 2.56-2.50 (m, 2H), 2.41 (s, 3H), 2.26-2.19 (m, 2H), 1.94-1.87 (m, 2H), 1.70-1.60 (m, 4H), 1.26 (t, 3H). HRMS [M−H]$^-$ calculated for $C_{27}H_{39}N_7O_6S$–H 588.2604, found 588.2610.

(e) Example 22: 2-(1-((1,2-dimethyl-1H-imidazol-4-yl)sulfonyl)azetidine-3-carboxamido)-3-(5-(5,6,7,8-tetrahydro-1,8-naphthyridin-2-yl)pentanamido)propanoic acid

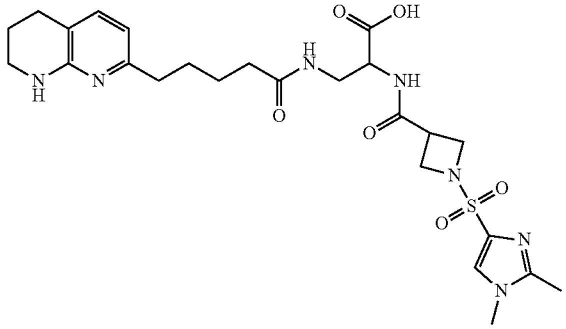 [SMILES: Cc1nc(S(=O)(=O)N2CC(C(=O)NC(CNC(=O)CCCCc3ccc4c(n3)NCCC4)C(=O)O)C2)cn1C]

Prepared by the method of Example 7(f) using intermediate 71 (270 mg, 0.46 mmol) to give 2-(1-((1,2-dimethyl-1H-imidazol-4-yl)sulfonyl)azetidine-3-carboxamido)-3-(5-(5,6,7,8-tetrahydro-1,8-naphthyridin-2-yl)pentanamido) propanoic acid as a colourless cracked glass (0.140 g). $^1$H NMR (400 MHz; $CD_3OD$) δ 7.68 (s, 1H), 7.14 (d, 1H), 6.37 (d, 1H), 4.26 (dd, 1H), 4.02-3.85 (m, 4H), 3.71 (s, 3H), 3.59 (dd, 1H), 3.43 (dd, 1H), 3.40-3.36 (m, 2H), 3.25-3.17 (m, 1H), 2.70 (t, 2H), 2.54-2.49 (m, 2H), 2.41 (s, 3H), 2.20-2.15 (m, 2H), 1.91-1.84 (m, 2H), 1.65-1.55 (m, 4H). HRMS [M−H]$^-$ calculated for $C_{25}H_{35}N_7O_6S$–H 560.2291, found 560.2278.

Route 4

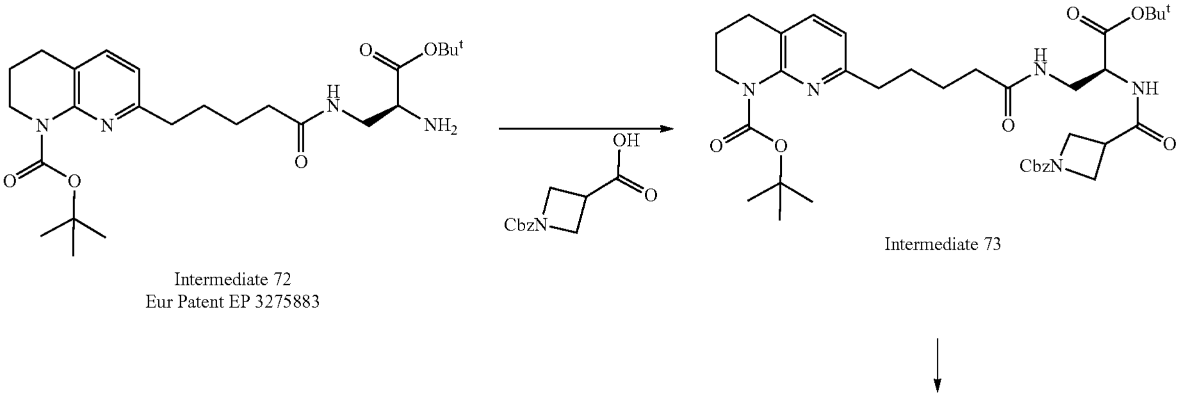

Intermediate 72
Eur Patent EP 3275883

Intermediate 73

-continued

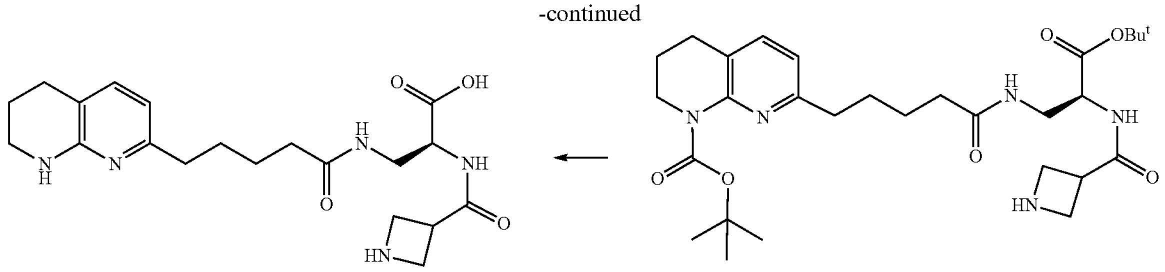

Intermediate 75 Intermediate 74

Example 23: (S)-2-(1-(3,5-Dichlorobenzenesulfonyl)azetidine-3-carboxamido)-3-(5-(5,6,7,8-tetrahydro-1,8-naphthyridin-2-yl)pentanamido)propanoic acid (a) Intermediate 73: tert-Butyl (S)-7-(5-((2-(1-((benzyloxy)carbonyl)azetidine-3-carboxamido)-3-(tert-butoxy)-3-oxopropyl)amino)-5-oxopentyl)-3,4-dihydro-1,8-naphthyridine-1(2H)-carboxylate

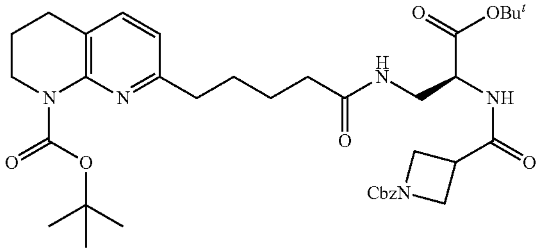

Figure 5:
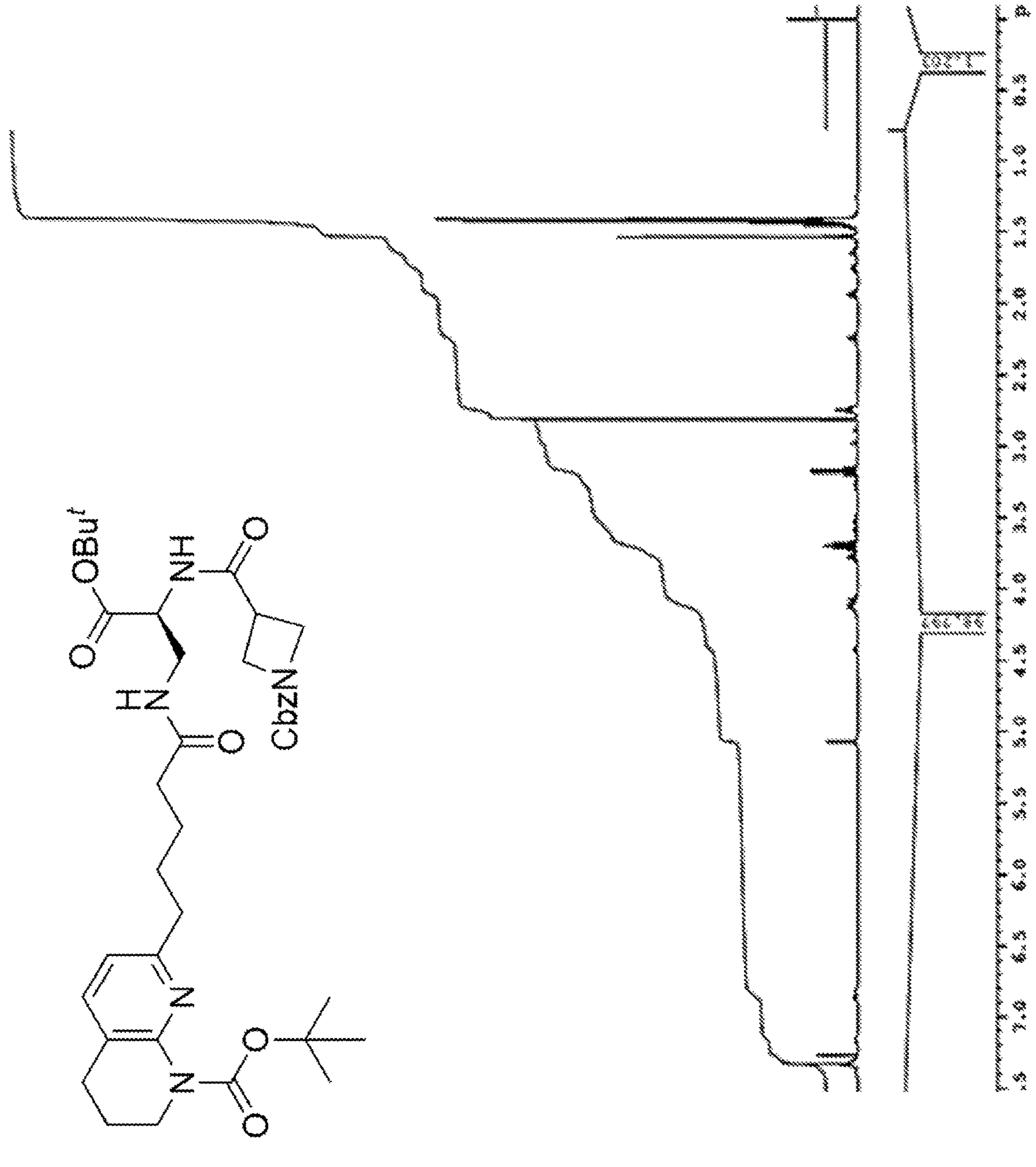
FIG. 5 is a $^1H$ NMR spectra (400 MHz; DMSO-$d_6$) of Intermediate 73.

In a 500 mL round bottomed flask was added, 1-((benzyloxy)carbonyl)azetidine-3-carboxylic acid (2.78 g, 11.82 mmol), intermediate 72 (Eur Pat EP 3275883) (5.12 g, 10.74 mmol), HATU (4.49 g, 11.82 mmol), dichloromethane (100 mL) and DIPEA (7 mL, 40.1 mmol) and stirred at room temperature for 30 min. LCMS showed the reaction had gone to completion. The reaction mixture was diluted with water (200 mL) and brine (50 mL) and extracted with dichloromethane (2×150 mL). The organic layers were combined and concentrated in vacuo to give the crude product as brown oil. The crude product was loaded onto a 120 g flash silica column and purified by 0-25% EtOH: EtOAc for 35 min. The relevant fractions were concentrated in vacuo to give intermediate 73 (10 g) as a yellow oil used without further purification. MS $[M+H]^+$ calculated for $C_{37}H_{51}N_5O_8$+H 694.38, found 694.6. $^1$H NMR (400 MHz; DMSO-$d_6$) is as shown in FIG. 5.

(b) Intermediate 74: tert-Butyl (S)-7-(5-((2-(azetidine-3-carboxamido)-3-(tert-butoxy)-3-oxopropyl)amino)-5-oxopentyl)-3,4-dihydro-1,8-naphthyridine-1(2H)-carboxylate

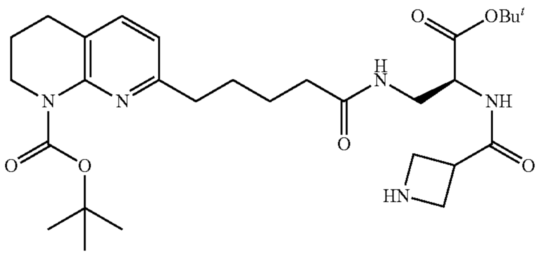

To 10% Pd/C (1.534 g, 1.441 mmol) was added intermediate 73 (10 g, 14.41 mmol) in ethanol (144 mL) and stirred in the presence of $H_2$ gas overnight (16 h). The reaction mixture was filtered over Celite and flushed with ethanol (3×200 mL) and concentrated in vacuo to give intermediate 74 as a yellow oil used without further purification. MS $[M+H]^+$ calculated for $C_{29}H_{45}N_5O_6$+H 560.34, found 560.3.

(c) Intermediate 75: (S)-2-(Azetidine-3-carboxamido)-3-(5-(5,6,7,8-tetrahydro-1,8-naphthyridin-2-yl)pentanamido)propanoic acid

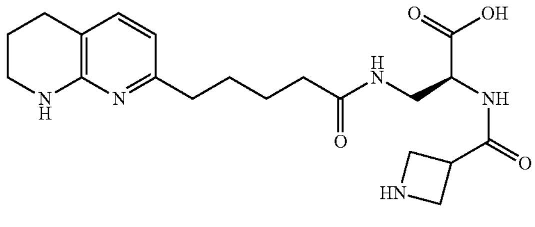 [SMILES: O=C(CCCCc1ccc2c(n1)NCCC2)NC[C@H](NC(=O)C1CNC1)C(=O)O]

Intermediate 74 (4.56 g, 8.14 mmol), was dissolved in dichloromethane (80 mL). To the reaction mixture was added TFA (15 mL, 195 mmol) and stirred at 20° C. for 6 h. LCMS showed the reaction had gone to completion and was concentrated in vacuo. The crude product was purified using 120 g $C_{18}$ column, eluting with ammonium carbonate modified MeCN:$H_2O$ (0-25%) for 35 min. The relevant fractions were concentrated in vacuo to give an impure white solid. The crude product was re-purified using 120 g $C_{18}$ column, eluting with ammonium carbonate modified MeCN:$H_2O$ (0-25%) for 50 min. The relevant fractions were concentrated in vacuo to give intermediate 75 (1.03 g) as a white solid. $^1$H NMR (400 MHz; $CD_3OD$) δ 7.20 (d, 1H), 6.40 (d, 1H), 4.36 (dd, 1H), 4.26-4.18 (m, 1H), 4.18-4.08 (m, 3H), 3.74 (d, 1H), 3.71 (d, 1H), 3.68-3.59 (m, 1H), 3.50 (dd, 1H), 3.43-3.39 (m, 2H), 2.73 (t, 2H), 2.56 (t, 2H), 2.22 (t, 2H), 1.94-1.86 (m, 2H), 1.69-1.60 (m, 4H). MS $[M+H]^+$ calculated for $C_{20}H_{30}N_5O_4$+H 404.23, found 404.2.

Example 23: (S)-2-(1-(3,5-Dichlorobenzenesulfonyl)azetidine-3-carboxamido)-3-(5-(5,6,7,8-tetrahydro-1,8-naphthyridin-2-yl)pentanamido)propanoic acid

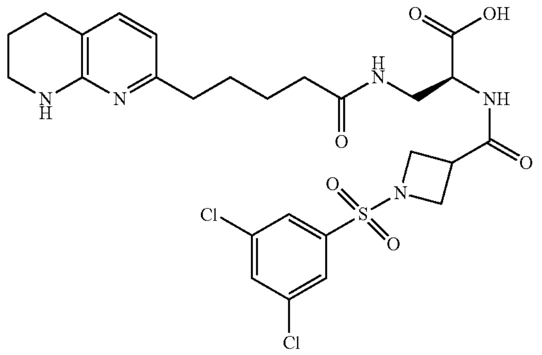 [SMILES: O=C(CCCCc1ccc2c(n1)NCCC2)NC[C@H](NC(=O)C1CN(S(=O)(=O)c2cc(Cl)cc(Cl)c2)C1)C(=O)O]

A solution of intermediate 75 (50 mg, 0.124 mmol), THF (1 mL) and $Na_2CO_3$ (180 μL, 0.180 mmol) was cooled to 0° C. 3,5-Dichlorobenzenesulfonyl chloride (9 μL, 0.124 mmol) was added to the reaction mixture and the suspension was stirred at 0° C. for 1 h. LCMS showed the reaction had gone to completion. The reaction mixture was acidified with 2 M HCl (100 μL), then purified using Xterra RP18 prep column, eluting with ammonium carbonate modified MeCN: $H_2O$ (15-55%) for 20 min. The relevant fractions were concentrated in vacuo to give (S)-2-(1-(3,5-dichlorobenzenesulfonyl)azetidine-3-carboxamido)-3-(5-(5,6,7,8-tetrahydro-1,8-naphthyridin-2-yl)pentanamido)propanoic acid (55.1 mg) as a white solid. $^1$H NMR (400 MHz; DMSO-$d_6$) δ 8.09 (t, 1H), 8.05 (d, 1H), 7.85-7.80 (m, 2H), 7.80-7.75 (m, 1H), 7.32 (br. s., 1H), 7.14 (d, 1H), 6.31 (d, 1H), 4.21-4.13 (m, 1H), 3.95-3.87 (m, 2H), 3.85-3.78 (m, 2H), 3.42-3.30 (m, 2H), 3.27 (t, 2H), 3.21-3.13 (m, 1H), 2.63 (t, 2H), 2.44 (t, 2H), 2.04 (qd, 2H), 1.77 (quin, 2H), 1.57-1.43 (m, 4H). MS $[M+H]^+$ calculated for $C_{26}H_{31}Cl_2N_5O_6S$+H 612.14, found 612.1.

Examples 24-32

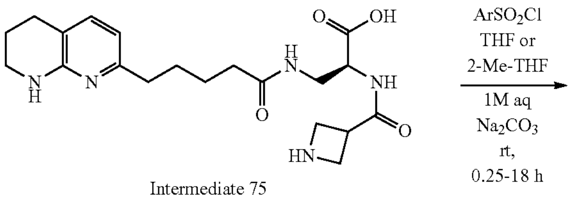

Intermediate 75

-continued

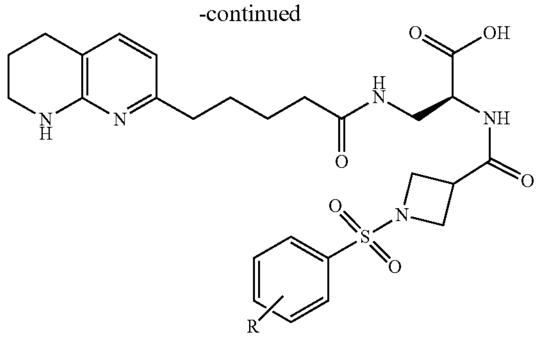

Examples 34-32

Examples 24-32 were prepared by the method of Example 23 using arenesulfonyl chlorides where the R group is listed in the Table below. Crude products were purified either by mass directed reverse phase HPLC on Waters XSelect CSH C18 19×100 mm 5 m column using acetonitrile-water with an ammonium carbonate modifier or by using an Xterra RP18 prep column, eluting with ammonium carbonate modified MeCN:$H_2O$ (15-55%) for 20 min.

| Example number | R | Yield/% | MF & MWt | $MH^+$ observed | MH− observed |
|---|---|---|---|---|---|
| 24 | 3,5-$Me_2$ | 14 | $C_{28}H_{37}N_5O_6S$ 571.7 | 572.5 | 570.5 |
| 25 | 3-Cl-5-Me | 24 | $C_{27}H_{34}ClN_5O_6S$ 591.5, 593.5 | 592.5, 594.5 | 590.5, 592.4 |
| 26 | 3-Et | 15 | $C_{28}H_{37}N_5O_6S$ 571.7 | 572.5 | 572.5 |
| 27 | 3-Cl | 64 | $C_{26}H_{32}ClN_5O_6S$ 577, 579 | 578, 580 | 576, 578 |
| 28 | 3-OMe | 14 | $C_{27}H_{35}N_5O_7S$ 573.7 | 574.5 | 572.5 |
| 29 | 3-$CHF_2$ | 33 | $C_{27}H_{33}F_2N_5O_6S$ 593.6 | 594.3 | 592.4 |
| 30 | 3-$^c$Pr | 75 | $C_{29}H_{37}N_5O_6S$ 583.2 | 584.2 | 582.2 |
| 31 | 3,4-$(CH_2)_3$— | 26 | $C_{29}H_{37}N_5O_6S$ 583.2 | 584.1 | 582.06 |
| 32 | 3,4-$(OMe)_2$ | 26 | $C_{28}H_{37}N_5O_8S$ 603.7 | 604.05 | 602.05 |

Figure 6:
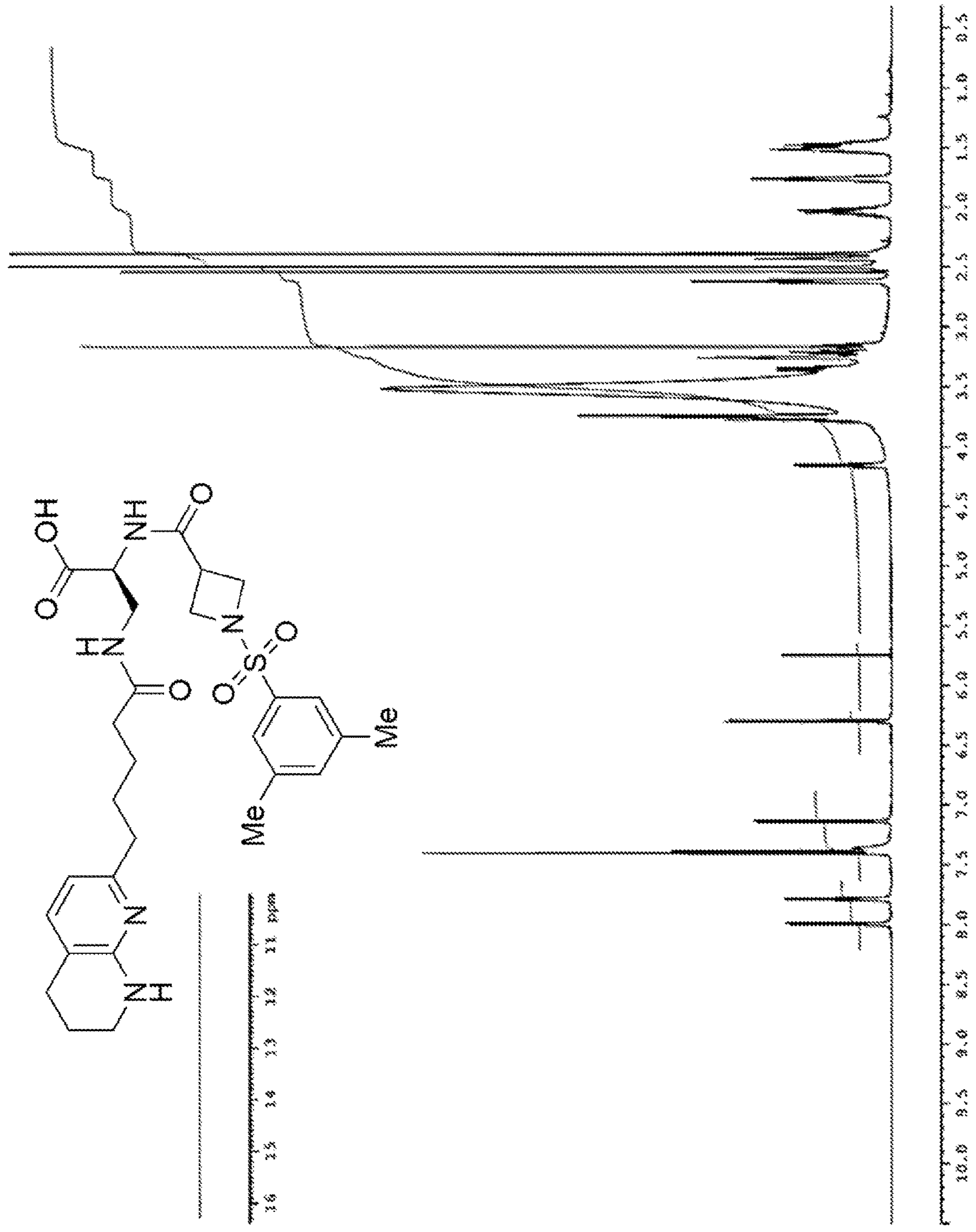
FIG. 6 is a $^1H$ NMR (600 MHz; DMSO-$d_6$) of Example 24.

Example 24: (S)-2-(1-(3,5-Dimethyl benzenesulfonyl)azetidine-3-carboxamido)-3-(5-(5,6,7,8-tetrahydro-1,8-naphthyridin-2-yl)pentanamido)propanoic acid $^1$H NMR (600 MHz; DMSO-$d_6$) is as shown in FIG. 6.

Figure 7:
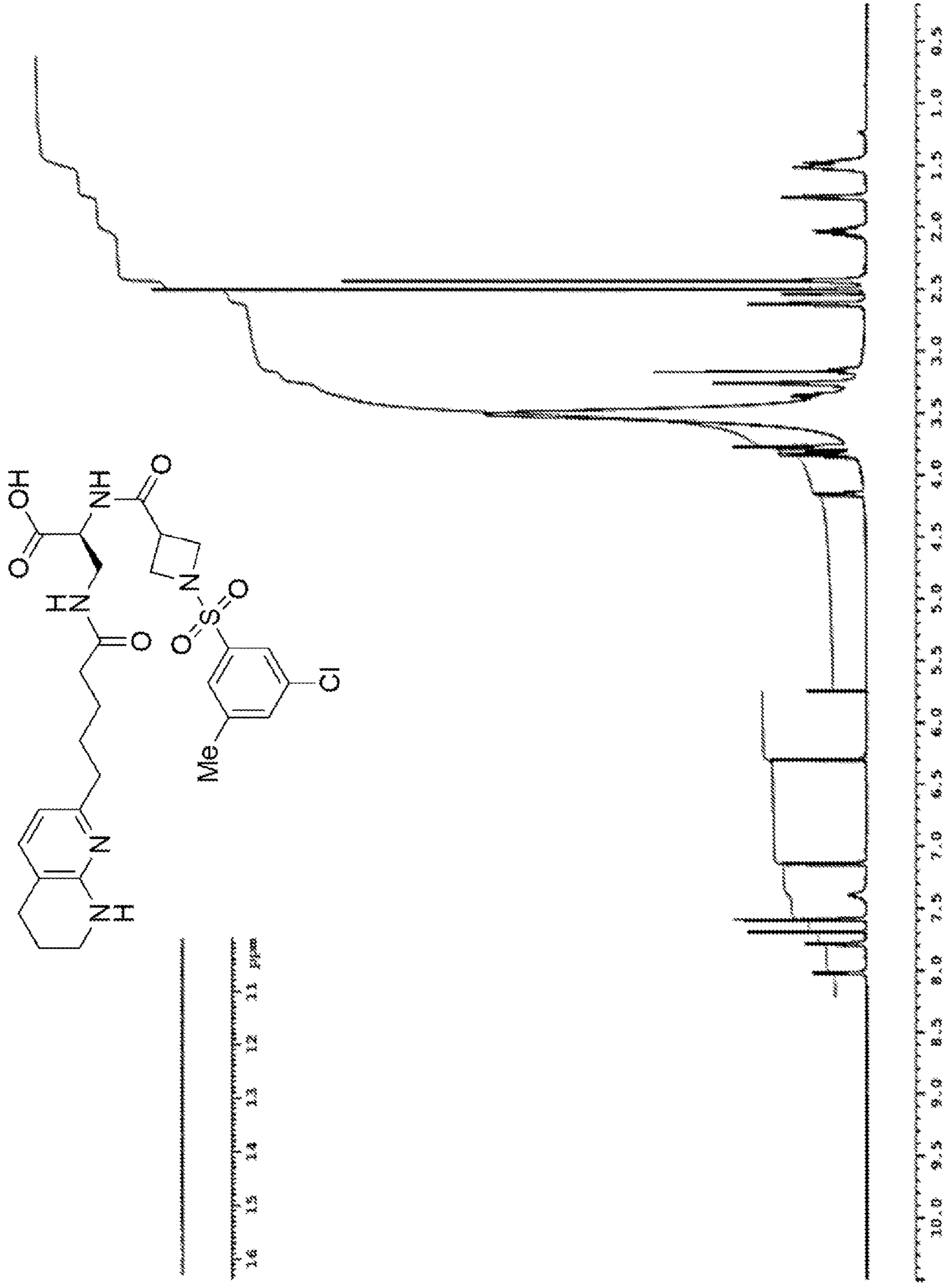
FIG. 7 is a $^1H$ NMR (600 MHz; DMSO-$d_6$) of Example 25.

Example 25: (S)-2-(1-(3-Chloro-5-methyl benzenesulfonyl)azetidine-3-carboxamido)-3-(5-(5,6,7,8-tetrahydro-1,8-naphthyridin-2-yl)pentanamido)propanoic acid $^1$H NMR (600 MHz; DMSO-$d_6$) is as shown in FIG. 7.

Figure 8:
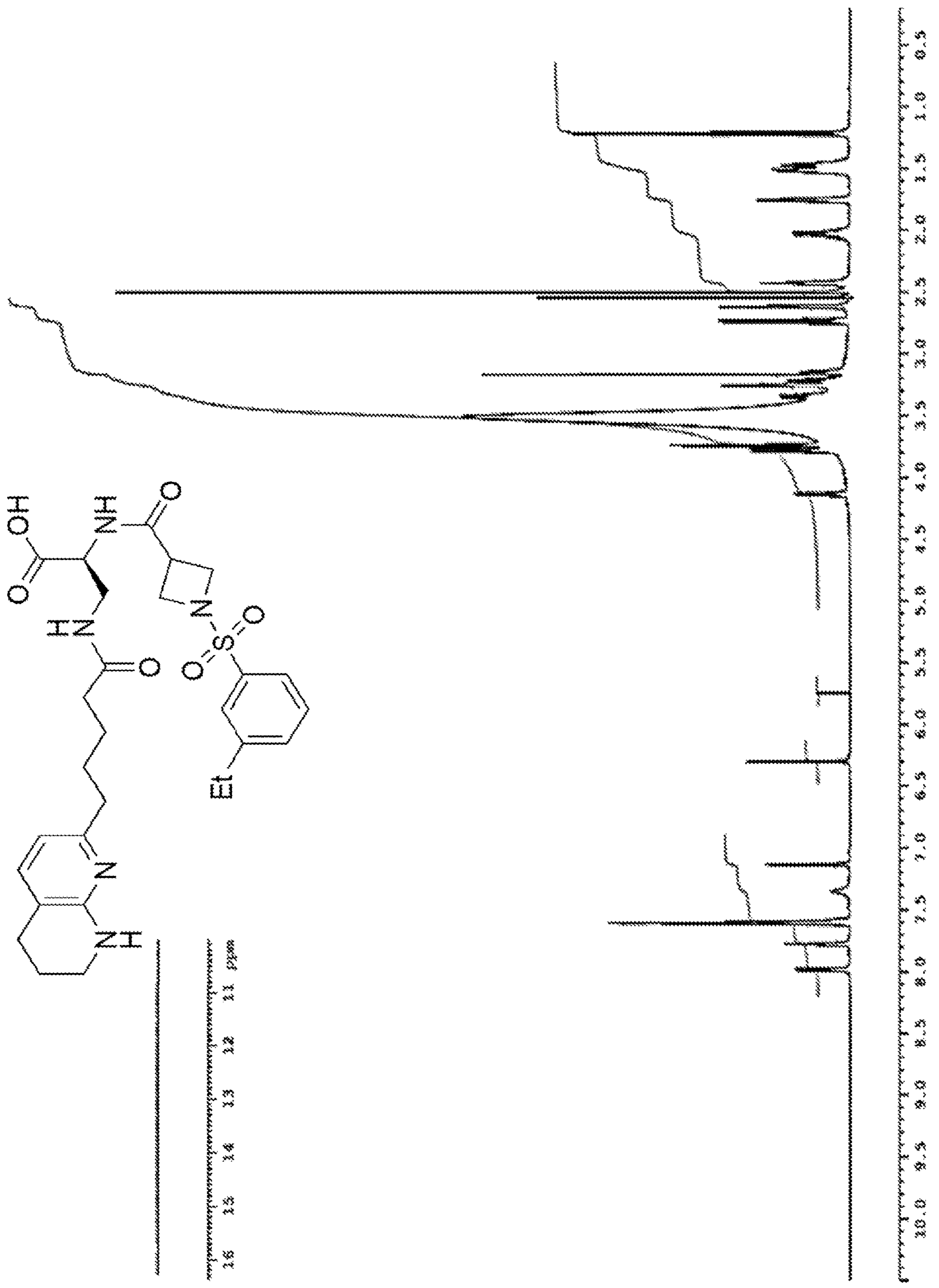
FIG. 8 is a $^1H$ NMR (600 MHz; DMSO-$d_6$) of Example 26.

Example 26: (S)-2-(1-(3-Ethylbenzenesulfonyl)azetidine-3-carboxamido)-3-(5-(5,6,7,8-tetrahydro-1,8-naphthyridin-2-yl)pentanamido)propanoic acid $^1$H NMR (600 MHz; DMSO-$d_6$) is as shown in FIG. 8.

Example 27: (S)-2-(1-(3-Chlorobenzenesulfonyl)azetidine-3-carboxamido)-3-(5-(5,6,7,8-tetrahydro-1,8-naphthyridin-2-yl)pentanamido)propanoic acid

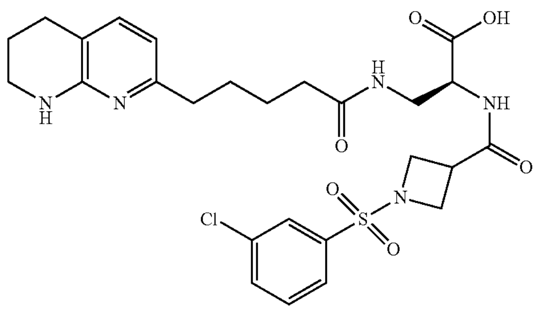 [SMILES: O=C(CCCCc1ccc2c(n1)NCCC2)NC[C@H](NC(=O)C1CN(S(=O)(=O)c2cccc(Cl)c2)C1)C(=O)O]

$^1$H NMR (400 MHz; $CDCl_3$) δ 10.12 (br. s., 1H), 7.86 (t, 1H), 7.80-7.73 (m, 1H), 7.68-7.61 (m, 1H), 7.59-7.50 (m, 1H), 7.27 (s, 1H), 7.03 (d, 1H), 6.97 (br. s., 1H), 6.31 (d, 1H), 4.38-4.29 (m, 1H), 4.05-3.93 (m, 4H), 3.61-3.52 (m, 1H), 3.49 (t, 3H), 3.32-3.20 (m, 1H), 2.80-2.66 (m, 3H), 2.61-2.50 (m, 1H), 2.36-2.21 (m, 2H), 1.99-1.90 (m, 2H), 1.89-1.78 (m, 1H), 1.75-1.59 (m, 3H).

Figure 9:
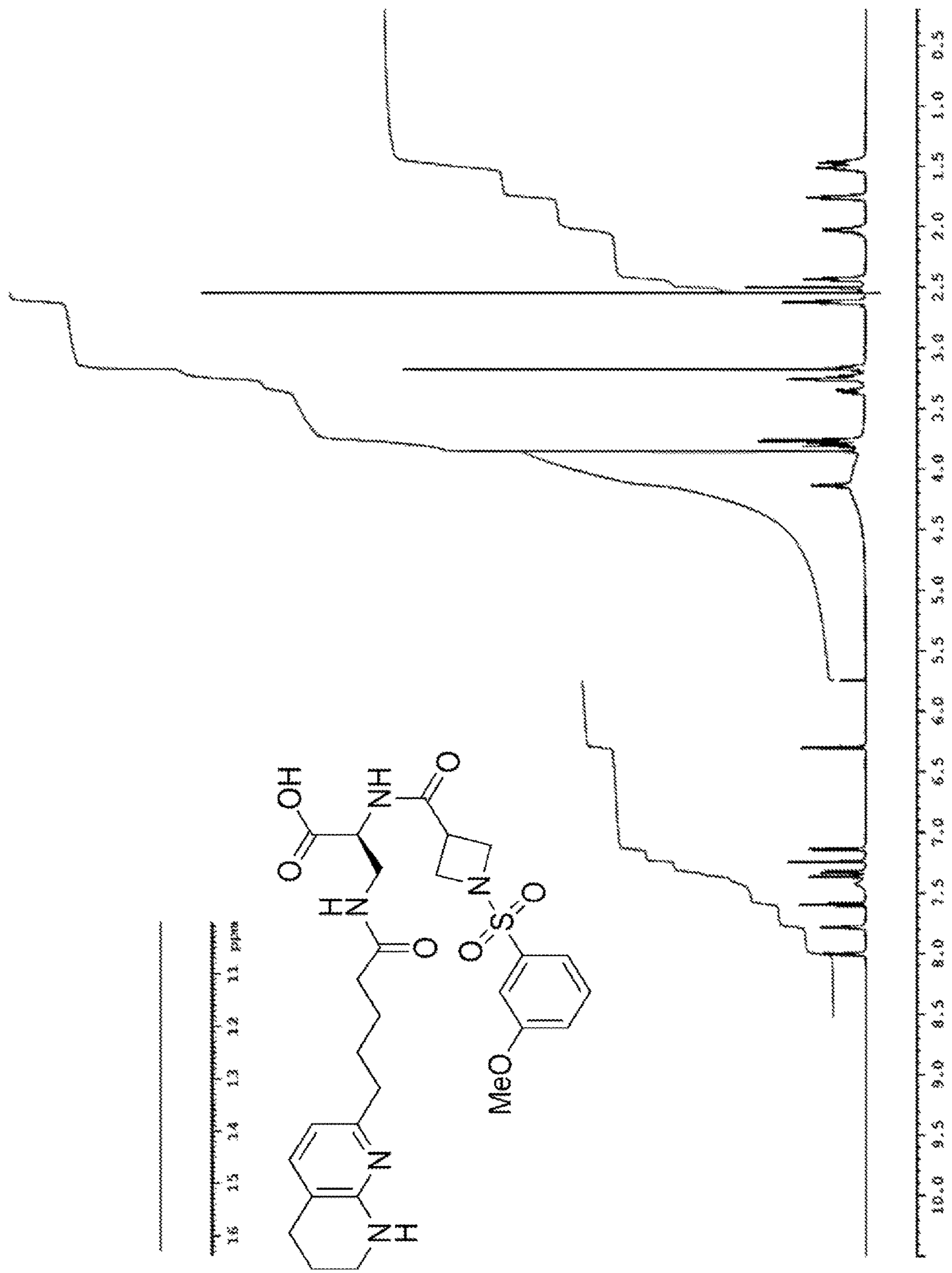
FIG. 9 is a $^1H$ NMR (600 MHz; DMSO-$d_6$) of Example 28.

Example 28: (S)-2-(1-(3-Methoxybenzenesulfonyl)azetidine-3-carboxamido)-3-(5-(5,6,7,8-tetrahydro-1,8-naphthyridin-2-yl)pentanamido)propanoic acid $^1$H NMR (600 MHz; DMSO-$d_6$) is as shown in FIG. 9.

Example 29: (S)-2-(1-(3-(Difluoromethyl)benzenesulfonyl)azetidine-3-carboxamido)-3-(5-(5,6,7,8-tetrahydro-1,8-naphthyridin-2-yl)pentanamido)propanoic acid

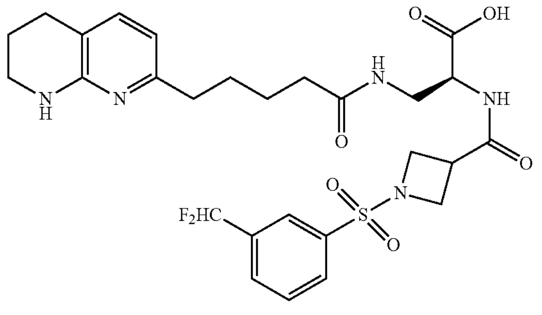 [SMILES: O=C(CCCCc1ccc2c(n1)NCCC2)NC[C@H](NC(=O)C1CN(S(=O)(=O)c2cccc(C(F)F)c2)C1)C(=O)O]

$^1$H NMR (400 MHz; $CDCl_3$) δ 9.25 (br. s., 1H), 8.03-7.91 (m, 2H), 7.80 (d, 1H), 7.75-7.64 (m, 2H), 7.63-7.53 (m, 1H), 7.34 (d, 1H), 6.75 (t, 1H), 6.39 (d, 1H), 4.37 (br. s., 1H), 4.04-3.86 (m, 4H), 3.61-3.43 (m, 4H), 3.30-3.18 (m, 1H), 2.75 (t, 2H), 2.71-2.56 (m, 2H), 2.25 (br. s., 2H), 1.99-1.87 (m, 2H), 1.66 (br. s., 4H).

Example 30: (S)-2-(1-(3-Cyclopropylbenzenesulfonyl)azetidine-3-carboxamido)-3-(5-(5,6,7,8-tetrahydro-1,8-naphthyridin-2-yl)pentanamido)propanoic acid

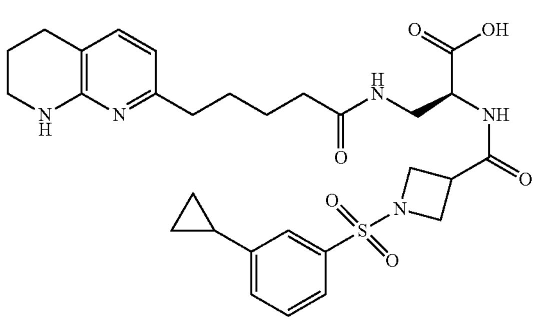 [SMILES: O=C(CCCCc1ccc2c(n1)NCCC2)NC[C@H](NC(=O)C1CN(S(=O)(=O)c2cccc(C3CC3)c2)C1)C(=O)O]

$^1$H NMR (400 MHz; $CDCl_3$) δ 10.30-10.08 (m, 1H), 7.64 (d, 1H), 7.58-7.54 (m, 1H), 7.52-7.44 (m, 1H), 7.38 (s, 1H), 7.27 (m, 1H), 6.97-6.87 (m, 1H), 6.82-6.70 (m, 1H), 6.31 (d, 1H), 4.33 (td, 1H), 4.04-3.90 (m, 4H), 3.60 (td, 1H), 3.50 (t, 2H), 3.36 (d, 1H), 3.28-3.15 (m, 1H), 2.80-2.69 (m, 3H), 2.62-2.49 (m, 1H), 2.39-2.21 (m, 2H), 2.07-1.83 (m, 4H), 1.74-1.60 (m, 3H), 1.11-1.02 (m, 2H), 0.84-0.75 (m, 2H).

Figure 10:
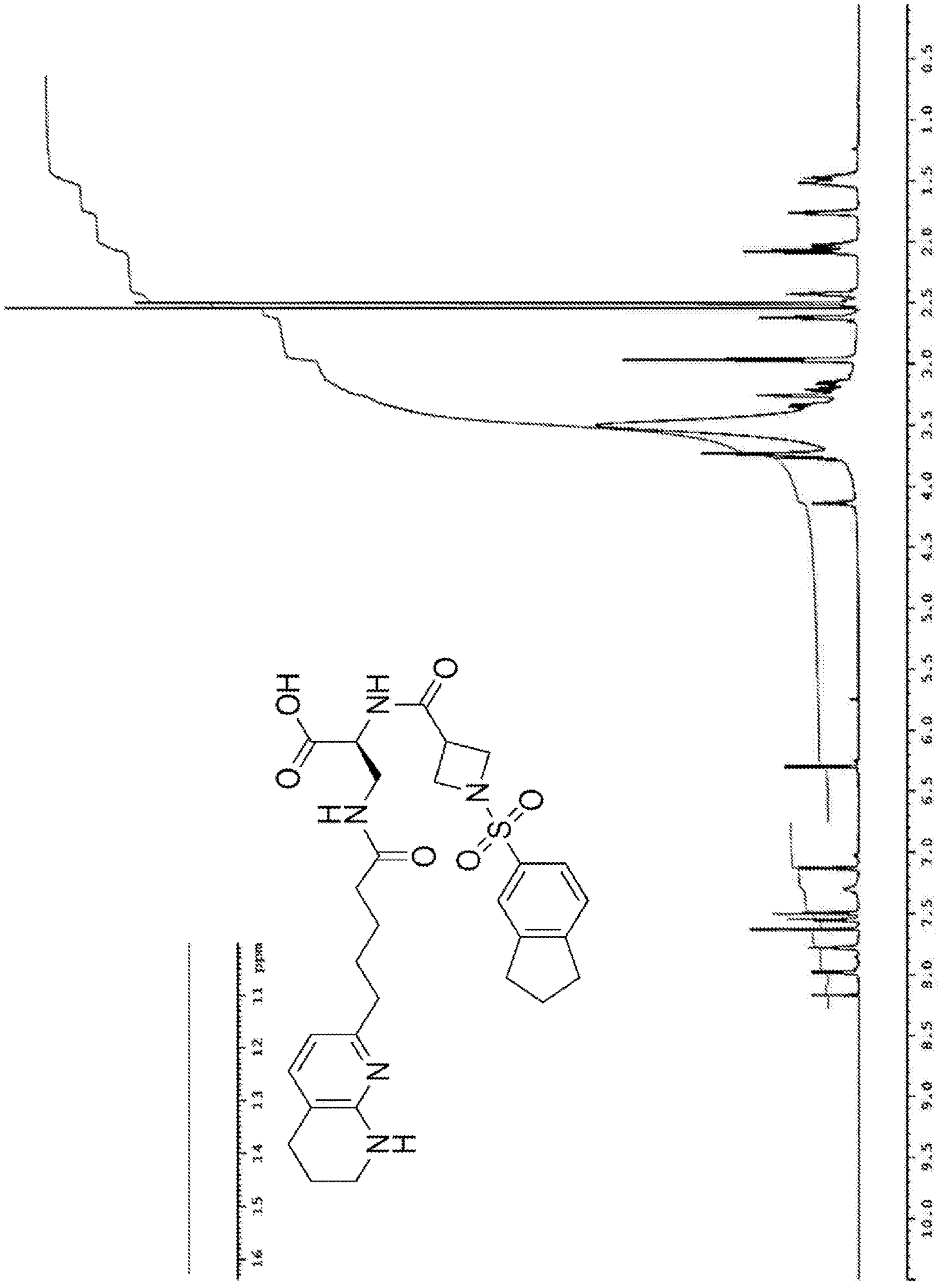
FIG. 10 is a $^1H$ NMR (600 MHz; DMSO-$d_6$) of Example 31.

Example 31: (S)-2-(1-((2,3-Dihydro-1H-inden-5-yl)sulfonyl)azetidine-3-carboxamido)-3-(5-(5,6,7,8-tetrahydro-1,8-naphthyridin-2-yl)pentanamido)propanoic acid $^1$H NMR (600 MHz; DMSO-$d_6$) is as shown in FIG. 10.

Figure 11:
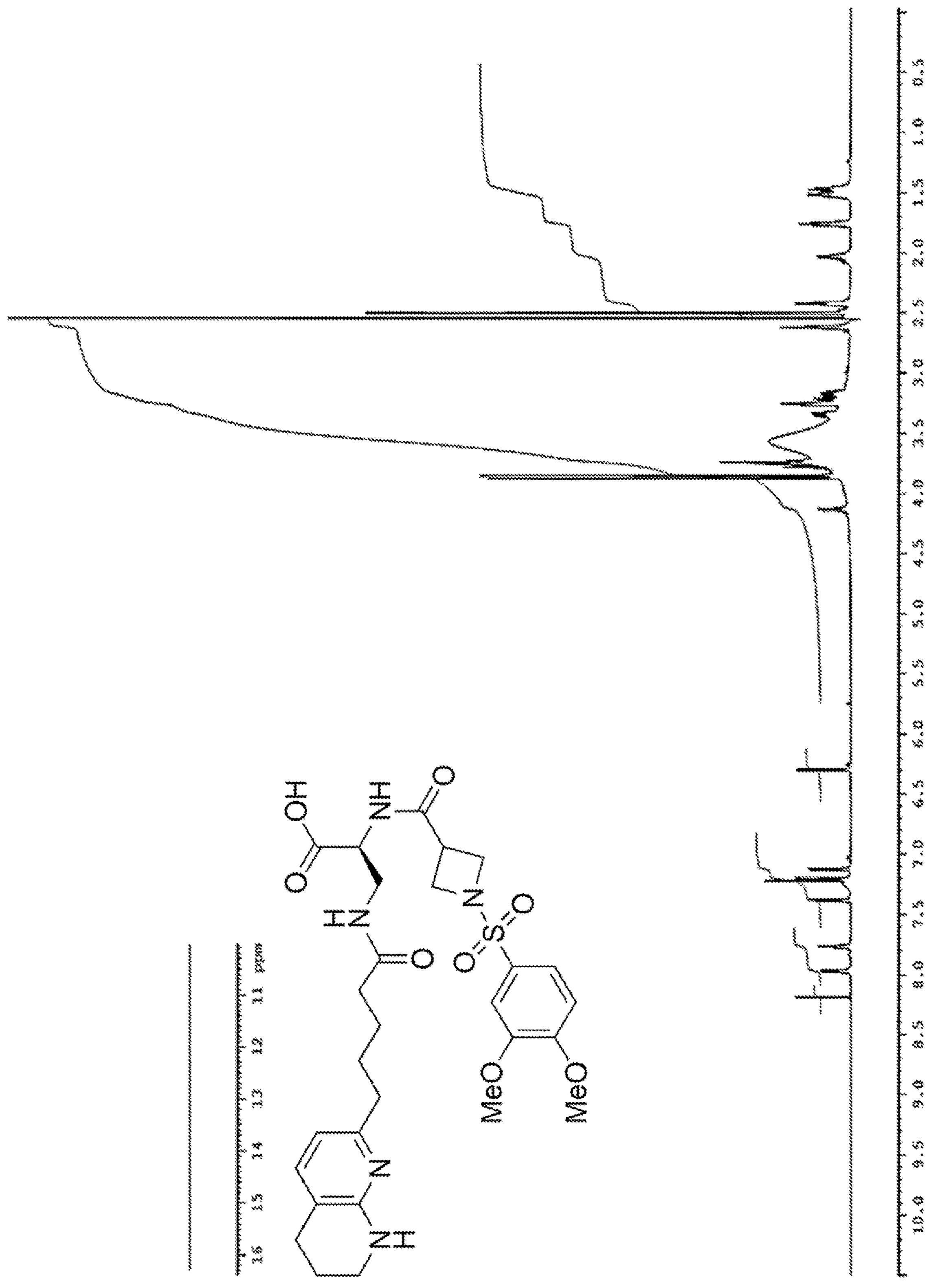
FIG. 11 is a $^1H$ NMR (600 MHz; DMSO-$d_6$) of Example 32.

Example 32: (S)-2-(1-(3,4-Dimethoxybenzenesulfonyl)azetidine-3-carboxamido)-3-(5-(5,6,7,8-tetrahydro-1,8-naphthyridin-2-yl)pentanamido)propanoic acid $^1$H NMR (600 MHz; DMSO-$d_6$) is as shown in FIG. 11.

Example 33: (S)-2-(1-((3-(3,6-Dihydro-2H-pyran-4-yl)benzenesulfonyl)azetidine-3-carboxamido)-3-(5-(5,6,7,8-tetrahydro-1,8-naphthyridin-2-yl)pentanamido)propanoic acid (a) Intermediate 76: tert-Butyl (S)-7-(5-((2-(1-(3-bromobenzenesulfonyl)azetidine-3-carboxamido)-3-(tert-butoxy)-3-oxopropyl)amino)-5-oxopentyl)-3,4-dihydro-1,8-naphthyridine-1(2H)-carboxylate

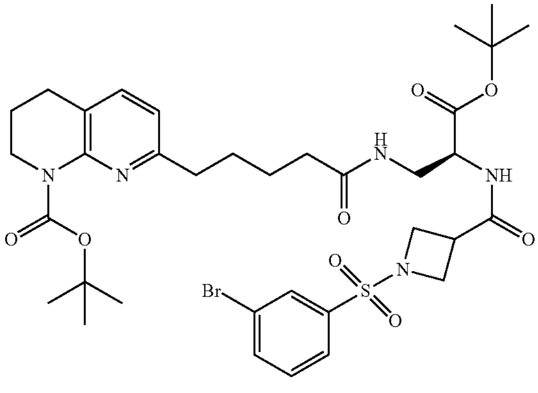 [SMILES: CC(C)(C)OC(=O)[C@H](CNC(=O)CCCCc1ccc2c(n1)N(C(=O)OC(C)(C)C)CCC2)NC(=O)C1CN(S(=O)(=O)c2cccc(Br)c2)C1]

A solution of intermediate 74 (820 mg, 1.465 mmol), $Na_2CO_3$ (3.6 mL, 3.60 mmol) and THF (21 mL) was cooled to 0° C. To the reaction mixture was added, 3-bromobenzenesulfonyl chloride (412 mg, 1.612 mmol) and stirred at 0° C. for 10 min. The reaction mixture was acidified with 2 M HCl (3 mL) and concentrated in vacuo before being diluted with water (20 mL) and brine (5 mL). The aqueous layer was extracted with EtOAc (3×25 mL) and the organic layers were combined and concentrated in vacuo to give intermediate 76 (990 mg) as a light yellow oil which was used without further purification. MS $[M+H]^+$ calculated for $C_{35}H_{48}Br^{79}N_5O_8S+H$ 778.24, found 778.4

Example 33: (S)-2-(1-((3-(3,6-Dihydro-2H-pyran-4-yl)benzenesulfonyl)azetidine-3-carboxamido)-3-(5-(5,6,7,8-tetrahydro-1,8-naphthyridin-2-yl)pentanamido)propanoic acid

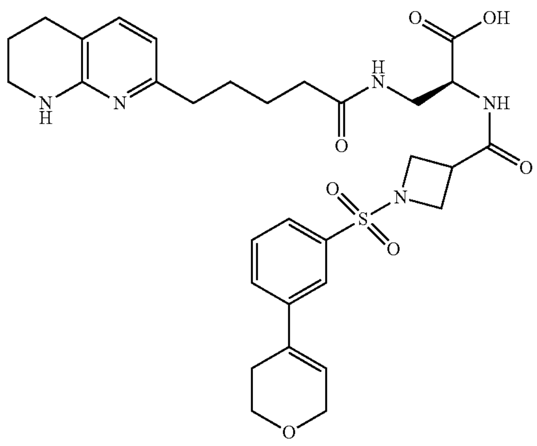 [SMILES: O=C(CCCCc1ccc2c(n1)NCCC2)NC[C@H](NC(=O)C1CN(S(=O)(=O)c2cccc(C3=CCOCC3)c2)C1)C(=O)O]

A solution of intermediate 76 (120.2 mg, 0.154 mmol), 2'-(dimethylamino)-2-biphenylyl-palladium(II) chloride dinorbornylphosphine complex (8.65 mg, 0.015 mmol), 2-(3,6-dihydro-2H-pyran-4-yl)-4,4,5,5-tetramethyl-1,3,2-dioxaborolane (64.9 mg, 0.309 mmol), $K_2CO_3$ (64.0 mg, 0.463 mmol) in THF (0.7 mL) and water (0.7 mL) was purged with $N_2$ gas and heated in the microwave at 100° C. for 1 h. The reaction mixture was filtered through Celite and washed with EtOAc (3×10 mL) and concentrated in vacuo to give the crude product as an orange gum that was dissolved in dichloromethane (2 mL). TFA (0.3 mL, 3.89 mmol) was added and left to stir at room temperature overnight (16 h). Further TFA (0.18 mL, 2.336 mmol) was added and the reaction mixture was left to stir at room temperature for 7 h. The reaction mixture was concentrated in vacuo to give a black oil. The crude mixture was purified using a Xterra RP18 prep column, eluting with ammonium carbonate modified $MeCN:H_2O$ (25-55%) for 30 min. The relevant fractions were concentrated in vacuo to give (S)-2-(1-((3-(3,6-dihydro-2H-pyran-4-yl)benzenesulfonyl)azetidine-3-carboxamido)-3-(5-(5,6,7,8-tetrahydro-1,8-naphthyridin-2-yl)pentanamido)propanoic acid (27.9 mg) as a colourless solid. $^1H$ NMR (400 MHz; $CDCl_3$) δ 10.12 (br. s. 1H), 7.86 (t, 1H), 7.75 (d, 1H), 7.70-7.64 (m, 1H), 7.61-7.53 (m, 1H), 7.27 (s, 1H), 7.11 (br. s. 1H), 7.02 (d, 1H), 6.35-6.22 (m, 2H), 4.39-4.27 (m, 3H), 4.04-3.91 (m, 6H), 3.58-3.44 (m, 4H), 3.24 (quin, 1H), 2.80-2.66 (m, 3H), 2.61-2.50 (m, 3H), 2.3-2.21 (m, 2H), 1.99-1.89 (m, 2H), 1.86-1.76 (m, 1H), 1.7-1.57 (m, 3H). MS $[M+H]^+$ calculated for $C_{31}H_{39}N_5O_7S+H$ 626.2, found 626.4

Example 34: (S)-2-(1-(3-(Piperazin-1-yl)benzenesulfonyl)azetidine-3-carboxamido)-3-(5-(5,6,7,8-tetrahydro-1,8-naphthyridin-2-yl)pentanamido)propanoic acid

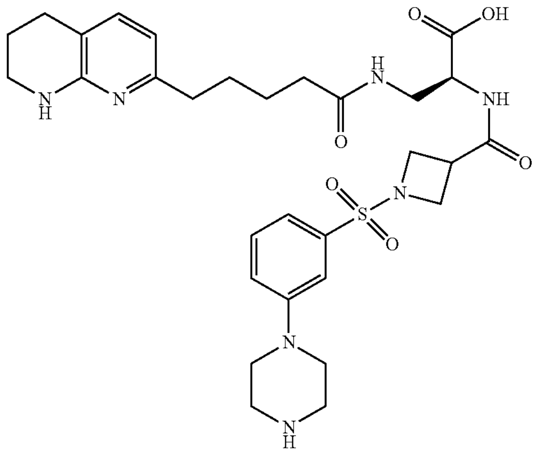 [SMILES: O=C(CCCCc1ccc2c(n1)NCCC2)NC[C@H](NC(=O)C1CN(S(=O)(=O)c2cccc(N3CCNCC3)c2)C1)C(=O)O]

To a solution of intermediate 76 (94.2 mg, 0.121 mmol), RuPhosPdG4 (Sigma Aldrich) (16.3 mg, 0.019 mmol), $Cs_2CO_3$ (164.3 mg, 0.504 mmol), in toluene (1.2 mL) was added piperazine (72.2 mg, 0.838 mmol). The reaction mixture was purged with $N_2$ gas and heated in the microwave at 100° C. for 4 h. LCMS showed starting material was still present so further piperazine (52.1 mg, 0.605 mmol) was added and the reaction mixture was heated in the microwave at 100° C. for 3 h. The reaction mixture was filtered and washed with MeOH (3×10 mL). The reaction mixture was concentrated in vacuo to give a yellow gum that was dissolved in dichloromethane (2 mL) and TFA (0.3 mL, 3.89 mmol) was added. The reaction mixture was stirred at room temperature overnight (16 h). The reaction mixture was concentrated in vacuo to give an orange solid which was purified using a Xbridge prep C18 column, eluting with ammonium carbonate modified $MeCN:H_2O$ (25-55%) for 30 min. The relevant fractions were combined and concentrated in vacuo to give (S)-2-(1-(3-(piperazin-1-yl)benzenesulfonyl)azetidine-3-carboxamido)-3-(5-(5,6,7,8-tetrahydro-1,8-naphthyridin-2-yl)pentanamido)propanoic acid (10.5 mg) as a white solid. $^1H$ NMR (400 MHz; $CD_3OD$) δ 7.54 (dd, 1H), 7.38-7.28 (m, 4H), 6.44 (d, 1H), 4.18 (t, 1H), 3.97-3.91 (m, 2H), 3.91-3.84 (m, 2H), 3.55-3.45 (m, 6H), 3.45-3.39 (m, 2H), 3.29-3.22 (m, 5H), 2.79-2.72 (m, 2H), 2.59 (t, 2H), 2.23-2.17 (m, 2H), 1.95-1.88 (m, 2H), 1.70-1.60 (m, 4H). MS $[M+H]^+$ calculated for $C_{30}H_{41}N_7O_6S+H$ 628.2, found 628.4

Example 35: (S)-2-(1-((3-(2-(Dimethylamino)ethoxy)benzenesulfonyl)azetidine-3-carboxamido)-3-(5-(5,6,7,8-tetrahydro-1,8-naphthyridin-2-yl)pentanamido)propanoic acid

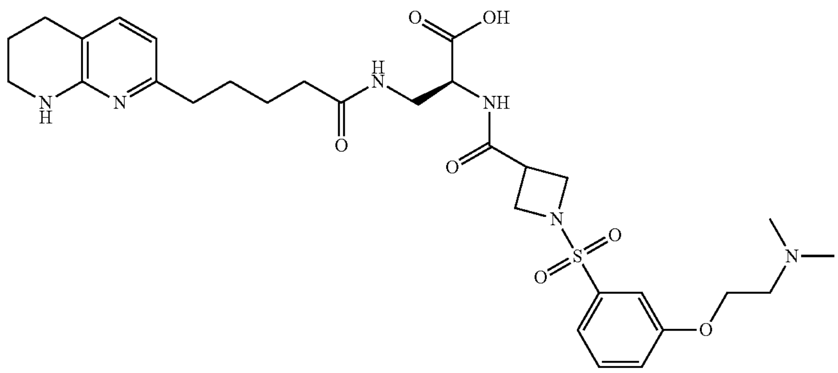 [SMILES: CN(C)CCOc1cccc(S(=O)(=O)N2CC(C(=O)N[C@@H](CNC(=O)CCCCc3ccc4c(n3)NCCC4)C(=O)O)C2)c1]

To a solution of intermediate 76 (103.2 mg, 0.133 mmol), RockPhosPdG3 (Sigma Aldrich) (11.11 mg, 0.013 mmol), $Cs_2CO_3$ (71.2 mg, 0.219 mmol), in toluene (1.3 mL) was added 2-(dimethylamino)ethan-1-ol (0.053 mL, 0.530 mmol). The reaction mixture was purged with $N_2$ gas and heated in the microwave at 100° C. for 4 h. The reaction mixture was filtered and washed with MeOH (3×10 mL). The reaction mixture was concentrated in vacuo to give an orange gum that was dissolved in dichloromethane (3.00 mL) and TFA (0.26 mL, 3.37 mmol) was added. The reaction mixture was stirred at room temperature overnight (16 h). Further TFA (0.3 mL, 3.89 mmol) was added and the reaction mixture was left to stir at room temperature for 4 h. The reaction mixture was concentrated in vacuo to give a yellow solid which was purified using a Xbridge prep C18 column, eluting with ammonium carbonate modified MeCN: $H_2O$ (25-55%) for 30 min. The relevant fractions were combined and concentrated in vacuo to give (S)-2-(1-((3-(2-(dimethylamino)ethoxy)benzenesulfonyl)azetidine-3-carboxamido)-3-(5-(5,6,7,8-tetrahydro-1,8-naphthyridin-2-yl)pentanamido)propanoic acid (8.5 mg) as a white solid. $^1H$ NMR (400 MHz; $CDCl_3$) δ 10.06 (br. s., 1H), 7.54-7.36 (m, 3H), 7.26 (s, 1H), 7.25-7.19 (m, 1H), 7.02 (br. s., 1H), 6.96-6.87 (m, 1H), 6.31 (d, 1H), 4.36-4.26 (m, 1H), 4.17 (t, 2H), 4.05-3.91 (m, 4H), 3.61-3.53 (m, 1H), 3.52-3.39 (m, 3H), 3.22 (quin, 1H), 2.81 (t, 2H), 2.75 (t, 3H), 2.62-2.49 (m, 1H), 2.43-2.36 (m, 6H), 2.34-2.17 (m, 2H), 2.00-1.89 (m, 2H), 1.89-1.77 (m, 1H), 1.74-1.57 (m, 3H). MS $[M+H]^+$ calculated for $C_{30}H_{42}N_6O_7S+H$ 631.76, found 631.4.

Route 5

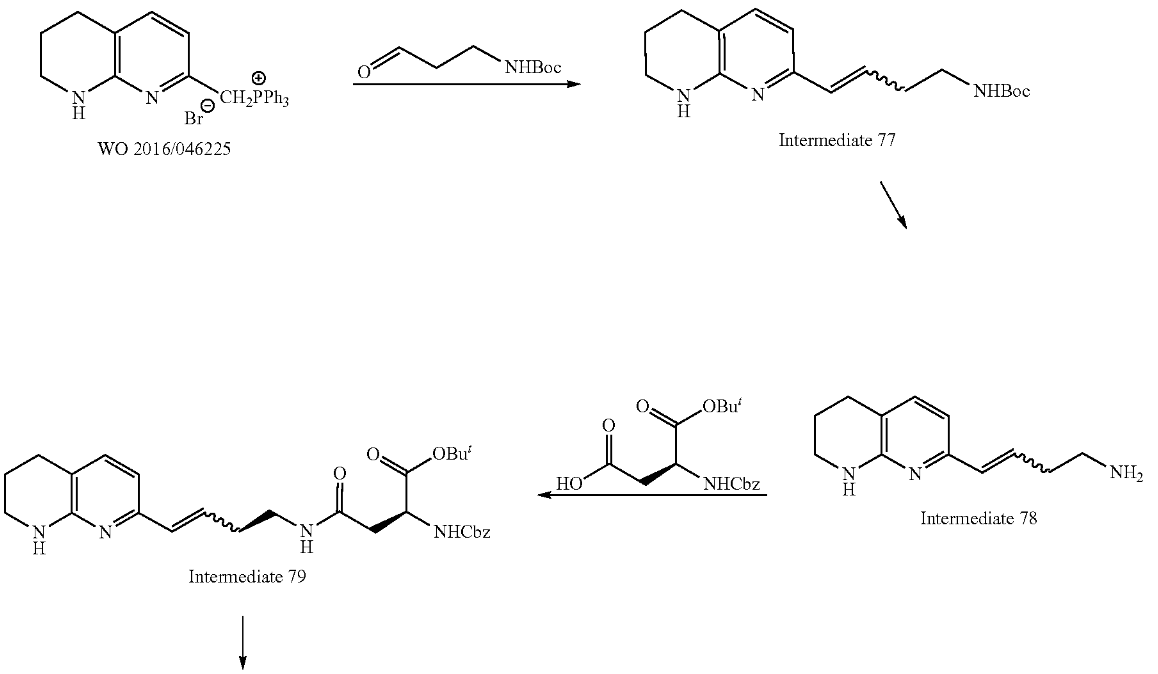
WO 2016/046225
Intermediate 77
Intermediate 78
Intermediate 79

-continued

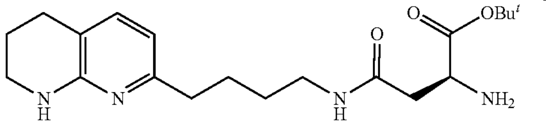

Intermediate 80

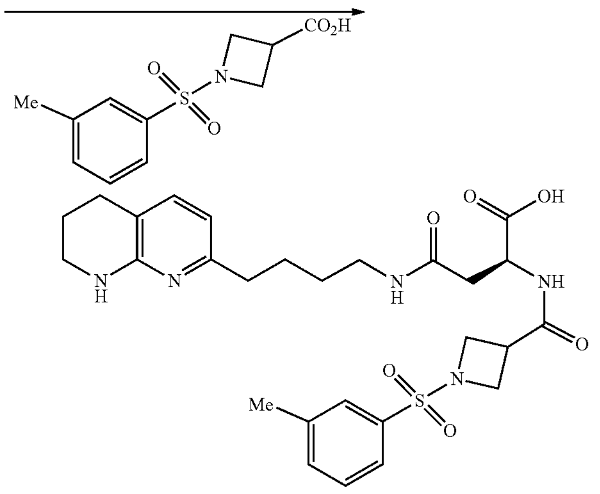

Example 36

Example 36: N4-(4-(5,6,7,8-Tetrahydro-1,8-naphthyridin-2-yl)butyl)-N2-(1-(3-methylbenzenesulfonyl)azetidine-3-carbonyl)-L-asparagine Intermediate 77: tert-Butyl (4-(5,6,7,8-tetrahydro-1,8-naphthyridin-2-yl)but-3-en-1-yl)carbamate

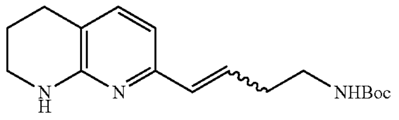 [SMILES: CC(C)(C)OC(=O)NCCC=Cc1ccc2c(n1)NCCC2]

Figure 12:
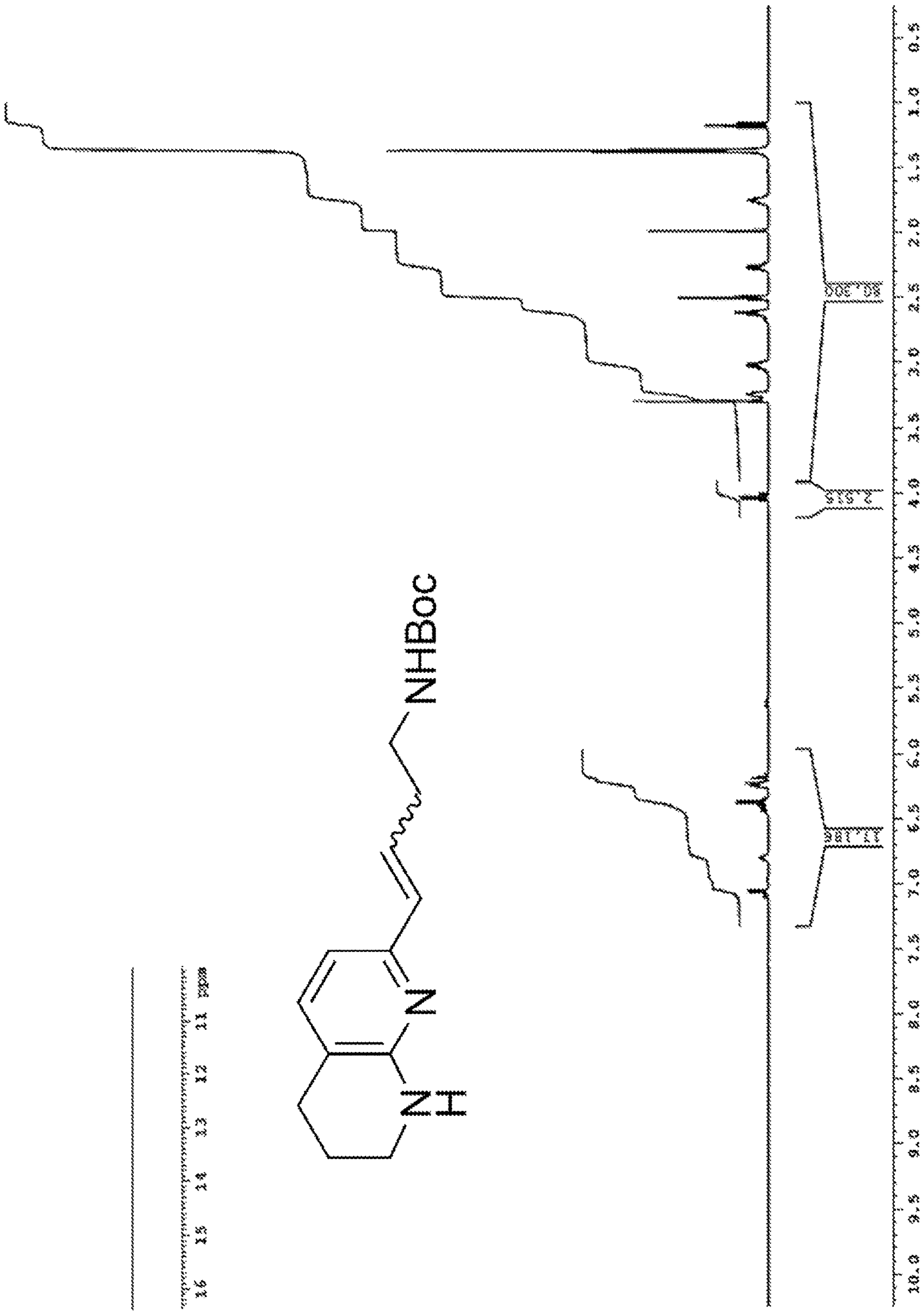
FIG. 12 is a $^1H$ NMR (400 MHz; DMSO-$d_6$) of Intermediate 77.

To a stirring mixture of triphenyl((5,6,7,8-tetrahydro-1,8-naphthyridin-2-yl)methyl)phosphonium bromide (WO 2016/046225) (6.71 g, 13.71 mmol) and sodium tert-butoxide (2 M in THF) (8.91 mL, 17.82 mmol) in dichloromethane (25 mL), tert-butyl (3-oxopropyl)carbamate (2.5 g, 13.71 mmol) were added and stirred at room temperature (5 min). LCMS showed substantial desired product. The mixture was further stirred (2.5 h) then left overnight (16 h). The mixture was dissolved in dichloromethane (~30 mL); Florisil (10 g) was added, the mixture concentrated in vacuo and dry loaded, and purified by column chromatography (340 g silica cartridge, 30-100% EtOAc in cyclohexane). The purest product fractions were concentrated in vacuo to afford intermediate 77 (3.36 g) as a mixture of geometric isomers as a yellow gum used without further purification. MS $[M+H]^+$ calculated for $C_{17}H_{25}N_3O_2$+H 304.20, found 304.2. $^1H$ NMR (400 MHz; DMSO-$d_6$) as shown in FIG. 12.

Intermediate 78: (E)-4-(5,6,7,8-Tetrahydro-1,8-naphthyridin-2-yl)but-3-en-1-amine

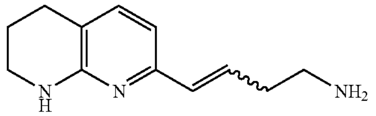 [SMILES: NCCC=Cc1ccc2c(n1)NCCC2]

To a solution of intermediate 77 (3.36 g, 9.86 mmol) in dichloromethane (10 mL) was added trifluoroacetic acid (7 mL, 91 mmol) and the resulting yellow solution stirred at room temperature (2 h). LCMS showed the desired intermediate 78 as a mixture of regioisomers used without further purification. MS $[M+H]^+$ calculated for $C_{12}H_{17}N_3$+H 204.15, found 204.2.

Intermediate 79: tert-Butyl (E)-N2-((benzyloxy)carbonyl)-N4-(4-(5,6,7,8-tetrahydro-1,8-naphthyridin-2-yl)but-3-en-1-yl)-L-asparaginate

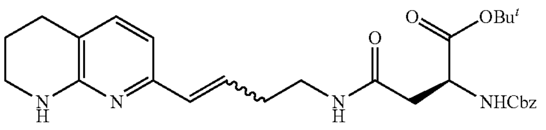

2,4,6-Tripropyl-1,3,5,2,4,6-trioxatriphosphinane 2,4,6-trioxide (0.320 mL, 0.537 mmol) was added to a solution of N-benzyloxycarbonyl-(L)-aspartic acid mono-tert-butyl ester (combi-Blocks) (165 mg, 0.537 mmol) in ethyl acetate (3 mL) and stirred (20° C., 30 min). Triethylamine (0.6 mL, 4.30 mmol) was added to a solution of intermediate 78 (332 mg, 0.735 mmol) in ethyl acetate (3 mL) and stirred (30 min), then heated to reflux (90° C.). The previous mixture of activated acid in ethyl acetate was added and stirred (1 min). The mixture was cooled to room temperature with stirring (1 h). The mixture was washed with water (2×20 mL) and the aqueous layers combined and extracted with ethyl acetate (~10 mL). The organic layers were combined and washed with aqueous ammonium carbonate (~5 mL) then passed through a hydrophobic frit and the solvent evaporated under a stream of nitrogen (40° C.) to afford intermediate 79 (210 mg) used without further purification. MS $[M+H]^+$ calculated for $C_{28}H_{36}N_4O$+H 509.27, found 509.2

Intermediate 80: tert-Butyl N4-(4-(5,6,7,8-tetrahydro-1,8-naphthyridin-2-yl)butyl)-L-asparaginate

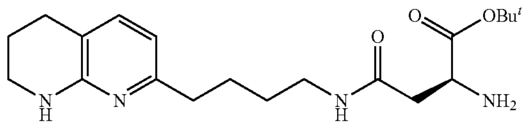

A solution of intermediate 79 (210 mg, 0.413 mmol) in methanol (10 mL) was hydrogenated using H-Cube technology (5 bar, 30° C., 1 mL/min, palladium on carbon (10%) (43.9 mg, 0.413 mmol). The product solution was concentrated in vacuo affording intermediate 80 (126 mg), used without purification. MS $[M+H]^+$ calculated for $C_{20}H_{32}N_4O_3$+H 377.25, found 377.3.

Example 36: N4-(4-(5,6,7,8-Tetrahydro-1,8-naphthyridin-2-yl)butyl)-N2-(1-(3-methylbenzenesulfonyl)azetidine-3-carbonyl)-L-asparagine

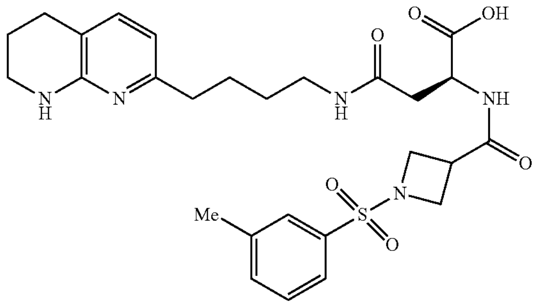 [SMILES: Cc1cccc(S(=O)(=O)N2CC(C(=O)N[C@@H](CC(=O)NCCCCc3ccc4c(n3)NCCC4)C(=O)O)C2)c1]

Figure 13:
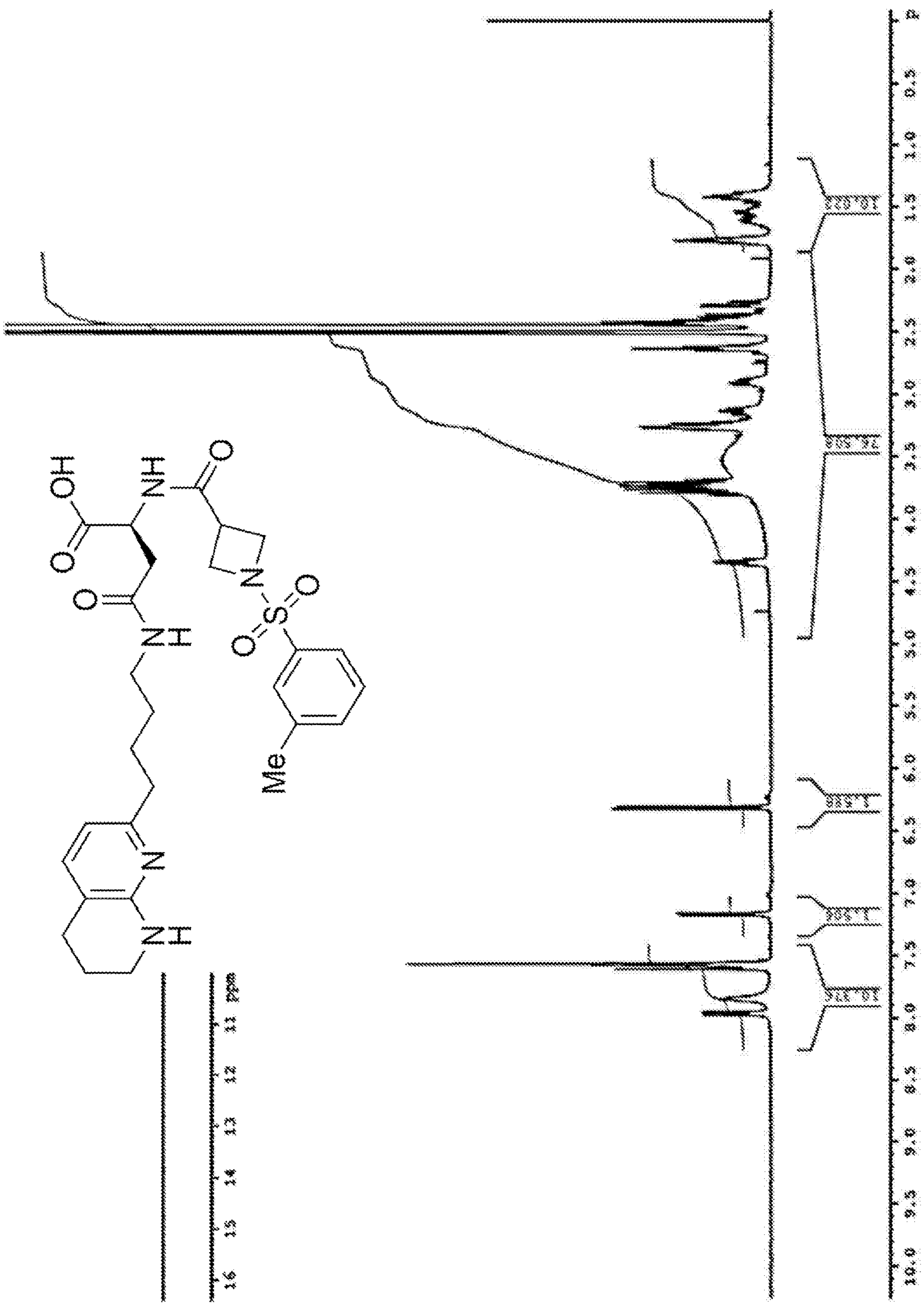
FIG. 13 is a $^1H$ NMR (400 MHz; DMSO-$d_6$) of Example 36.

A solution of intermediate 10 (26.1 mg, 0.102 mmol), HATU (45.3 mg, 0.119 mmol) and DIPEA (0.054 mL, 0.311 mmol) in DMF (0.4 mL) was stirred at room temperature (15 min). Intermediate 80 (1.45 mL, 0.104 mmol) was added to the previous solution as a 0.0716 M suspension in (DMF (2.9 mL) and stirred at room temperature (20° C., 1.5 h). LCMS showed that starting material remained. Additional HATU (13 mg, 0.034 mmol) and intermediate 10 (6 mg, 0.024 mmol) and DIPEA (0.02 mL, 0.115 mmol) were added and the mixture stirred overnight (16 h). The reaction mixture was evaporated under a stream of nitrogen (40° C.). Trifluoroacetic acid (0.200 mL, 2.60 mmol) was added to a solution of the residue in dichloromethane (1.0 mL) and stirred (20° C., 19 h). Additional trifluoroacetic acid (0.200 mL, 2.60 mmol) was added and stirred (16 h). The mixture was concentrated to dryness under a stream of nitrogen. The sample was purified by reversed phase HPLC (Reveleris, 0-100% MeCN in 10% aqueous ammonium carbonate) The appropriate fractions were combined and concentrated to dryness in vacuo to give N4-(4-(5,6,7,8-tetrahydro-1,8-naphthyridin-2-yl)butyl)-N2-(1-(3-methylbenzenesulfonyl) azetidine-3-carbonyl)-L-asparagine (23.9 mg) as a yellow solid. MS $[M+H]^+$ calculated for $C_{27}H_{35}N_5O_6S$+H 558.23, found 558.3. $^1$H NMR (400 MHz; DMSO-$d_6$) is as shown in FIG. 13.

Route 6

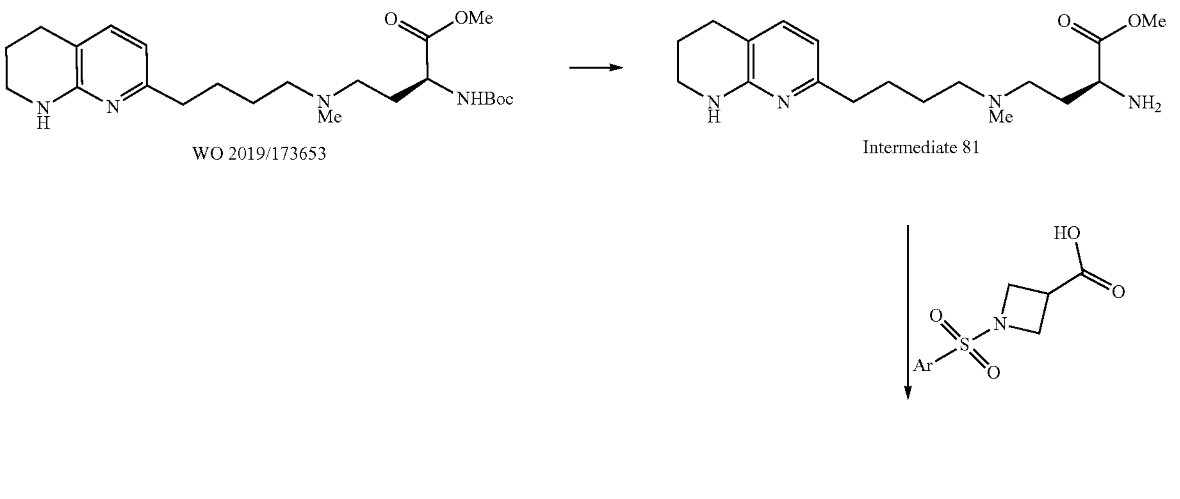

-continued

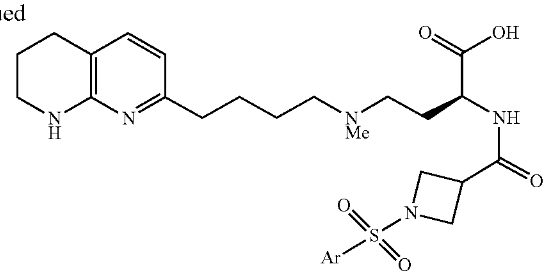

Examples 37-38

Example 37: (S)-4-(Methyl(4-(5,6,7,8-tetrahydro-1,8-naphthyridin-2-yl)butyl)amino)-2-(1-(3-methylbenzenesulfonyl)azetidine-3-carboxamido)butanoic acid

(a) Intermediate 81: Methyl (S)-2-amino-4-(methyl(4-(5,6,7,8-tetrahydro-1,8-naphthyridin-2-yl)butyl)amino)butanoate

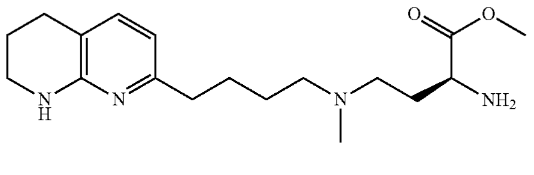 [SMILES: COC(=O)[C@@H](N)CCN(C)CCCCc1ccc2c(n1)NCCC2]

Figure 14:
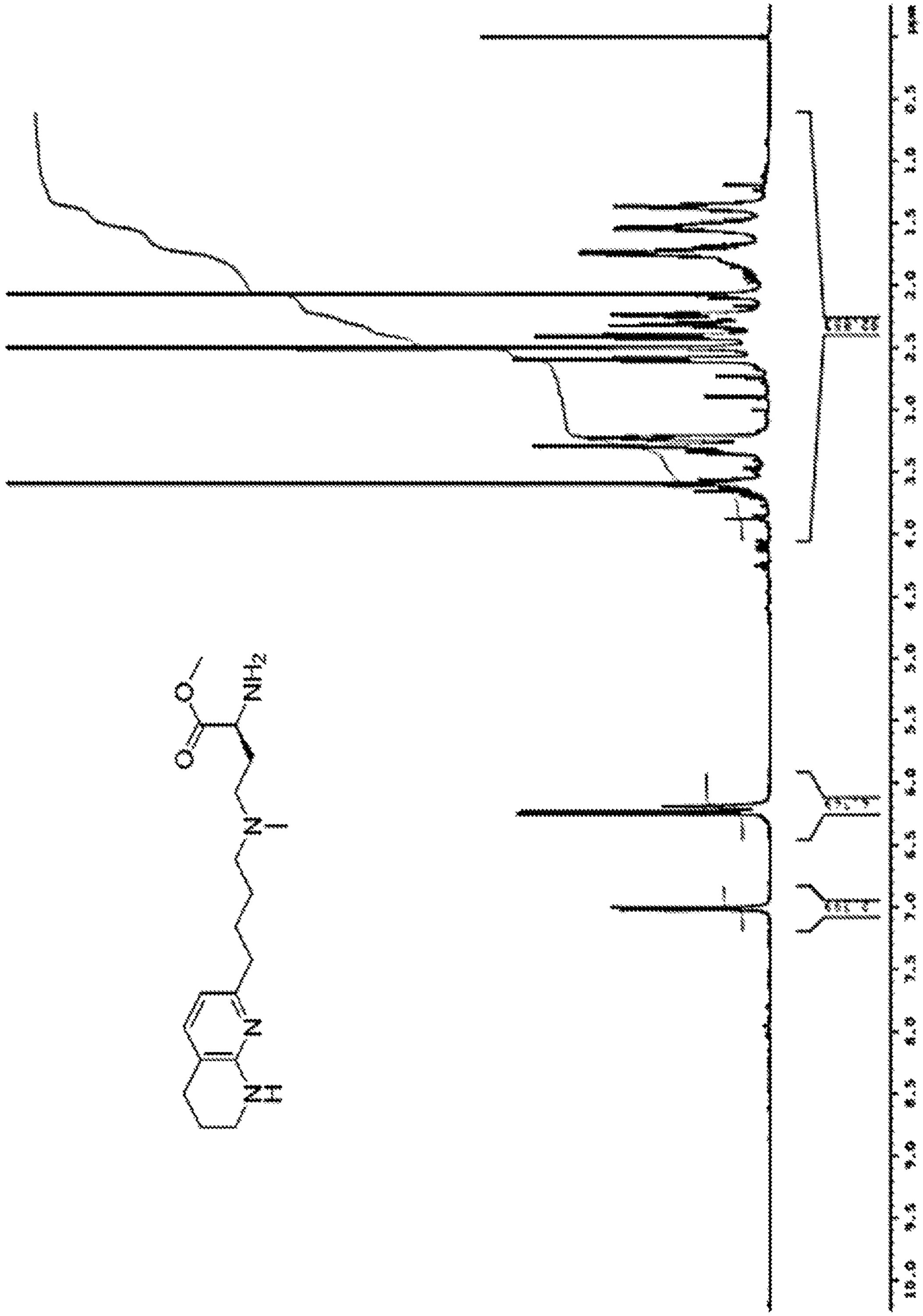
FIG. 14 is a $^1H$ NMR (400 MHz; DMSO-$d_6$) of Intermediate 81.

To a stirred solution of methyl (S)-2-((tert-butoxycarbonyl)amino)-4-(methyl(4-(5,6,7,8-tetrahydro-1,8-naphthyridin-2-yl)butyl)amino)butanoate (715 mg, 0.987 mmol) (WO201973653 page 108) in dichloromethane (5 mL) was added hydrochloric acid (4 M in 1,4-dioxane) (2 mL, 8.00 mmol) and the resulting orange solution stirred at room temperature for 3 h. LCMS showed that the reaction had gone to near completion. The reaction mixture was left stirring for a further 30 min then washed with saturated aqueous $NaHCO_3$ (20 mL) and saturated aqueous NaCl (20 mL). LCMS of the aqueous showed that it contained product. The aqueous was extracted with dichloromethane (3×10 mL) and EtOAc (3×10 mL). The combined organics were passed through a hydrophobic frit and concentrated in vacuo to give a yellow gum that was dissolved in trifluoroacetic acid (1 mL, 12.98 mmol) and stirred at room temperature for 16 h. The reaction mixture was concentrated in vacuo to give an orange oil which was dissolved in MeOH (20 mL) and passed through an amino-propyl ion exchange column (50 g), eluting with MeOH. The appropriate fractions were combined and concentrated in vacuo to give intermediate 81 (265 mg), as an orange gum. MS $[M+H]^+$ calculated for $C_{18}H_{30}N_4O_2$+H 335.23, found 335.3. $^1H$ NMR (400 MHz; DMSO-$d_6$) is as shown in FIG. 14.

Example 37: (S)-4-(Methyl(4-(5,6,7,8-tetrahydro-1,8-naphthyridin-2-yl)butyl)amino)-2-(1-(3-methylbenzenesulfonyl)azetidine-3-carboxamido)butanoic acid

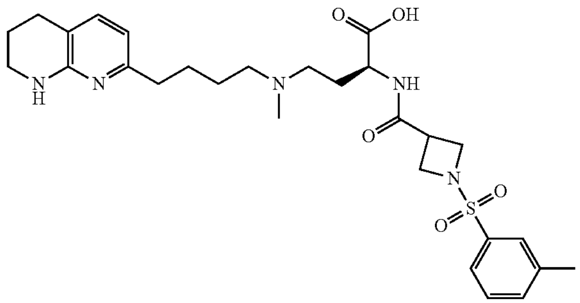 [SMILES: Cc1cccc(S(=O)(=O)N2CC(C(=O)N[C@@H](CCN(C)CCCCc3ccc4c(n3)NCCC4)C(=O)O)C2)c1]

Figure 15:
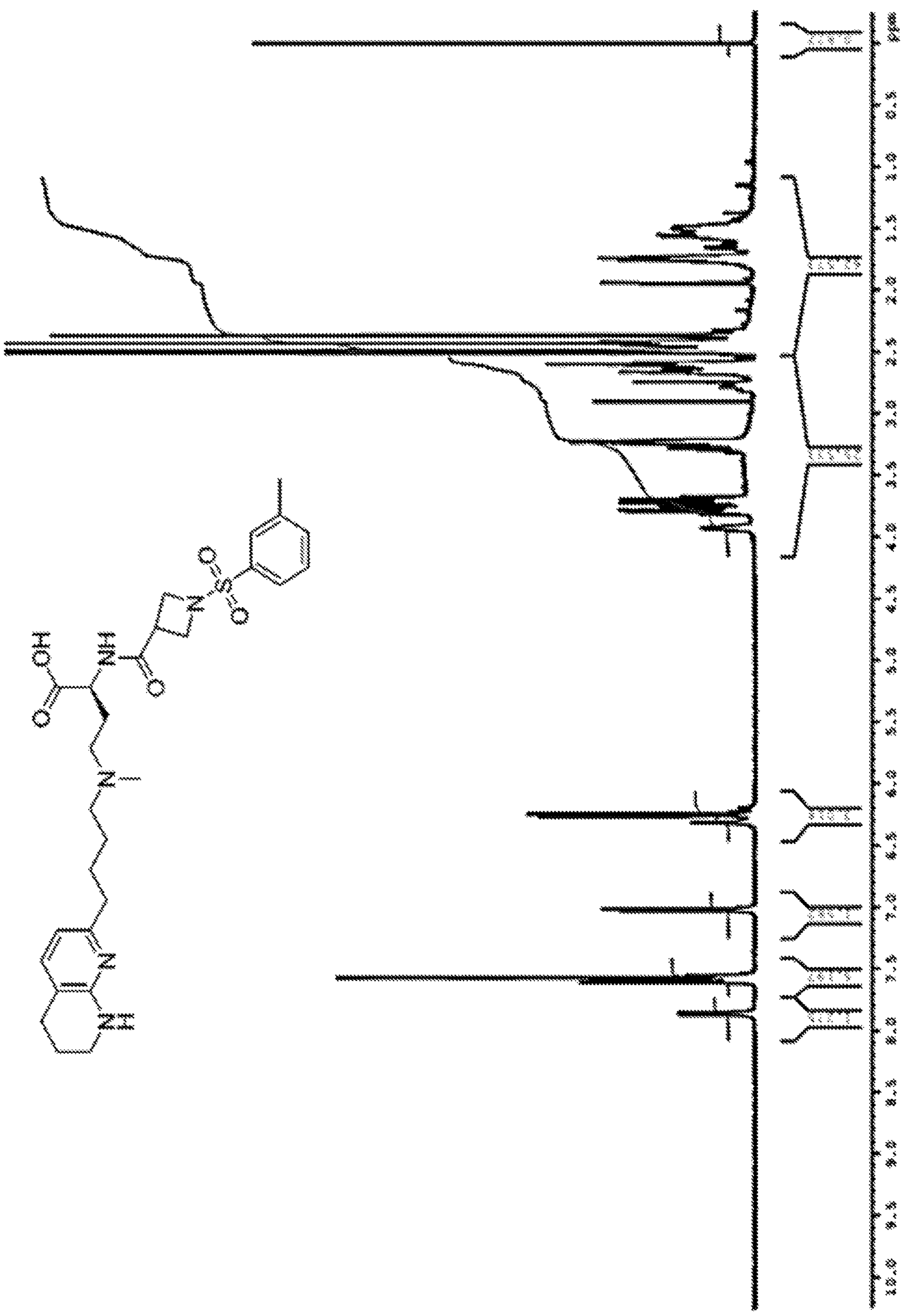
FIG. 15 is a $^1H$ NMR (400 MHz; DMSO-$d_6$) of Example 37.

A solution of intermediate 10 (65.2 mg, 0.255 mmol), HATU (115 mg, 0.187 mmol) and DIPEA (0.148 mL, 0.851 mmol) in dichloromethane (0.4 mL) was stirred for 15 min then intermediate 81 (219 mg, 0.170 mmol) in DMF (0.4 mL) added. The resulting solution was stirred at room temperature for 1 h. LCMS showed that the amide coupling had gone to completion, giving the desired methyl ester intermediate. The reaction mixture was concentrated in vacuo then re-dissolved in a mixture of methanol (0.3 mL) and sodium hydroxide (2 M) (0.3 mL, 0.600 mmol). The resulting mixture was stirred at room temperature for 66 h. LCMS showed no reaction progression. The mixture was concentrated in vacuo to remove the DMF and MeOH then re-dissolved in methanol (0.3 mL) and sodium hydroxide (2 M) (0.3 mL, 0.600 mmol). The reaction was stirred at room temperature for 8 h. The reaction mixture was concentrated in vacuo then dissolved in DMSO (0.2 mL) and purified by MDAP. The appropriate fractions were combined and concentrated in vacuo to give (S)-4-(methyl(4-(5,6,7,8-tetrahydro-1,8-naphthyridin-2-yl)butyl)amino)-2-(1-(3-methylbenzenesulfonyl)azetidine-3-carboxamido)butanoic acid (27 mg) as a white solid. MS $[M+H]^+$ calculated for $C_{28}H_{39}N_5O_5S$+H 558.2, found 558.3. $^1H$ NMR (400 MHz; DMSO-$d_6$) is as shown in FIG. 15.

Example 38: (S)-4-(Methyl(4-(5,6,7,8-tetrahydro-1,8-naphthyridin-2-yl)butyl)amino)-2-(1-(phenylsulfonyl)azetidine-3-carboxamido)butanoic acid

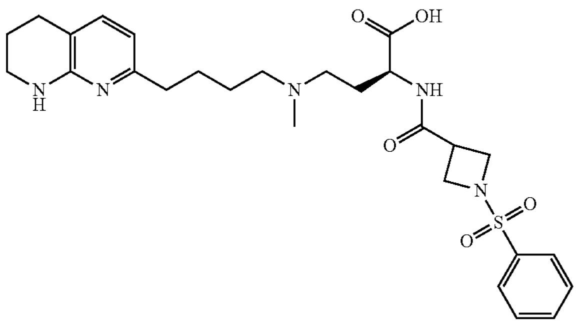 [SMILES: CN(CCCCc1ccc2c(n1)NCCC2)CC[C@H](NC(=O)C1CN(S(=O)(=O)c2ccccc2)C1)C(=O)O]

Figure 16:
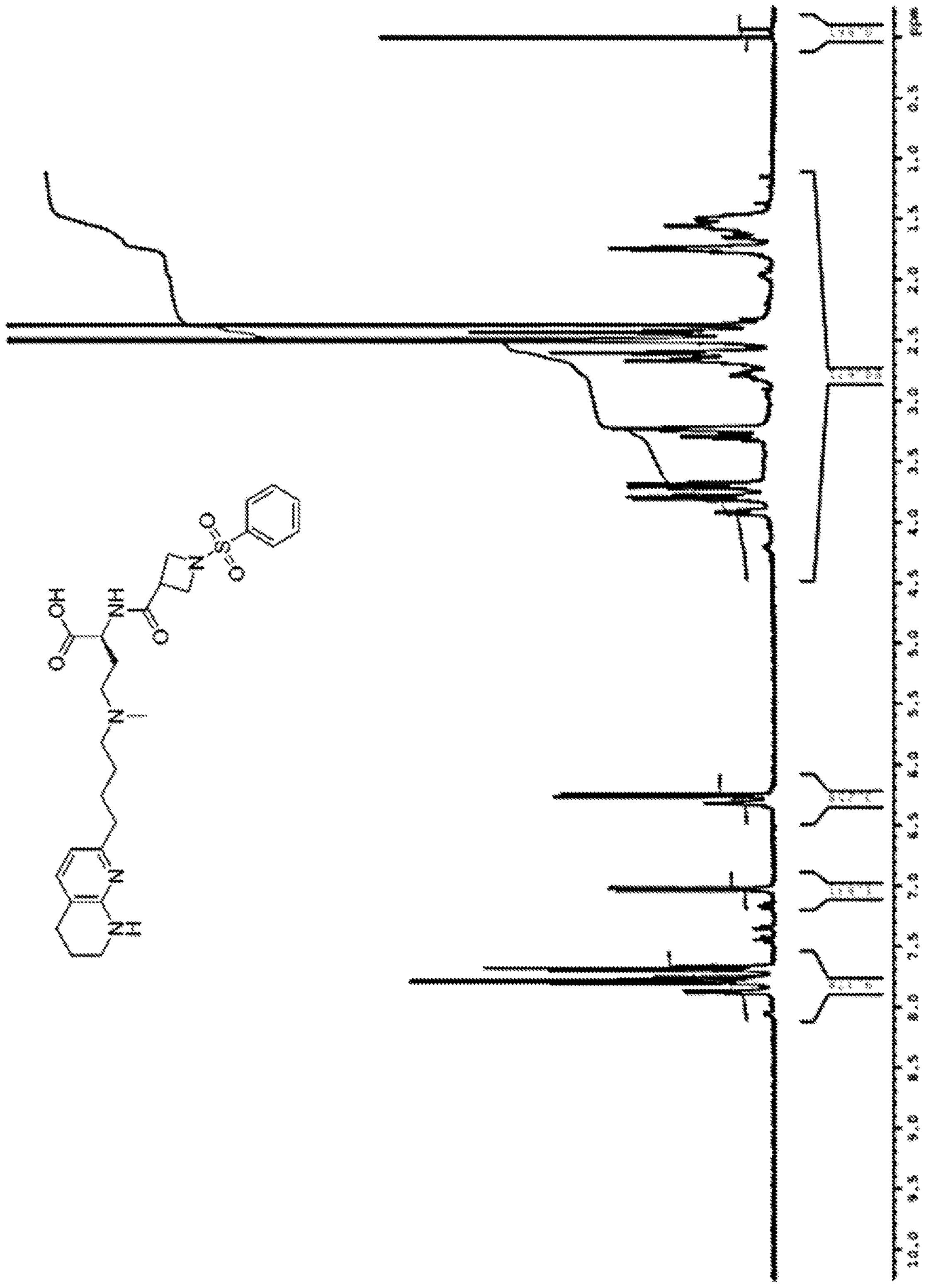
FIG. 16 is a $^1H$ NMR (400 MHz; DMSO-$d_6$) of Example 38.

A solution of intermediate 26 (61.6 mg, 0.255 mmol), HATU (115 mg, 0.187 mmol) and DIPEA (0.148 mL, 0.851 mmol) in dichloromethane (0.4 mL) was stirred for 15 min then intermediate 81 (219 mg, 0.170 mmol) and DMF (0.4 mL) added. The resulting solution was stirred at room temperature for 1 h. LCMS showed that the amide coupling had gone to completion, giving the desired methyl ester intermediate. The reaction mixture was concentrated in vacuo then re-dissolved in methanol (0.3 mL) and sodium hydroxide (2 M) (0.3 mL, 0.600 mmol) added. The resulting mixture was stirred at room temperature for 66 h, concentrated in vacuo to remove the DMF and MeOH and re-dissolved in methanol (0.3 mL) and sodium hydroxide (2 M) (0.3 mL, 0.600 mmol). The reaction mixture was stirred at room temperature for 8 h, concentrated in vacuo, dissolved in DMSO (0.2 mL) and purified by MDAP. The appropriate fractions were combined and concentrated in vacuo to give (S)-4-(methyl(4-(5,6,7,8-tetrahydro-1,8-naphthyridin-2-yl)butyl)amino)-2-(1-(phenylsulfonyl)azetidine-3-carboxamido)butanoic acid (59 mg), as a white solid. MS $[M+H]^+$ calculated for $C_{27}H_{37}N_5O_5S+H$ 544.25, found 544.3. $^1H$ NMR (400 MHz; DMSO-$d_6$) is as shown in FIG. 16.

Route 7

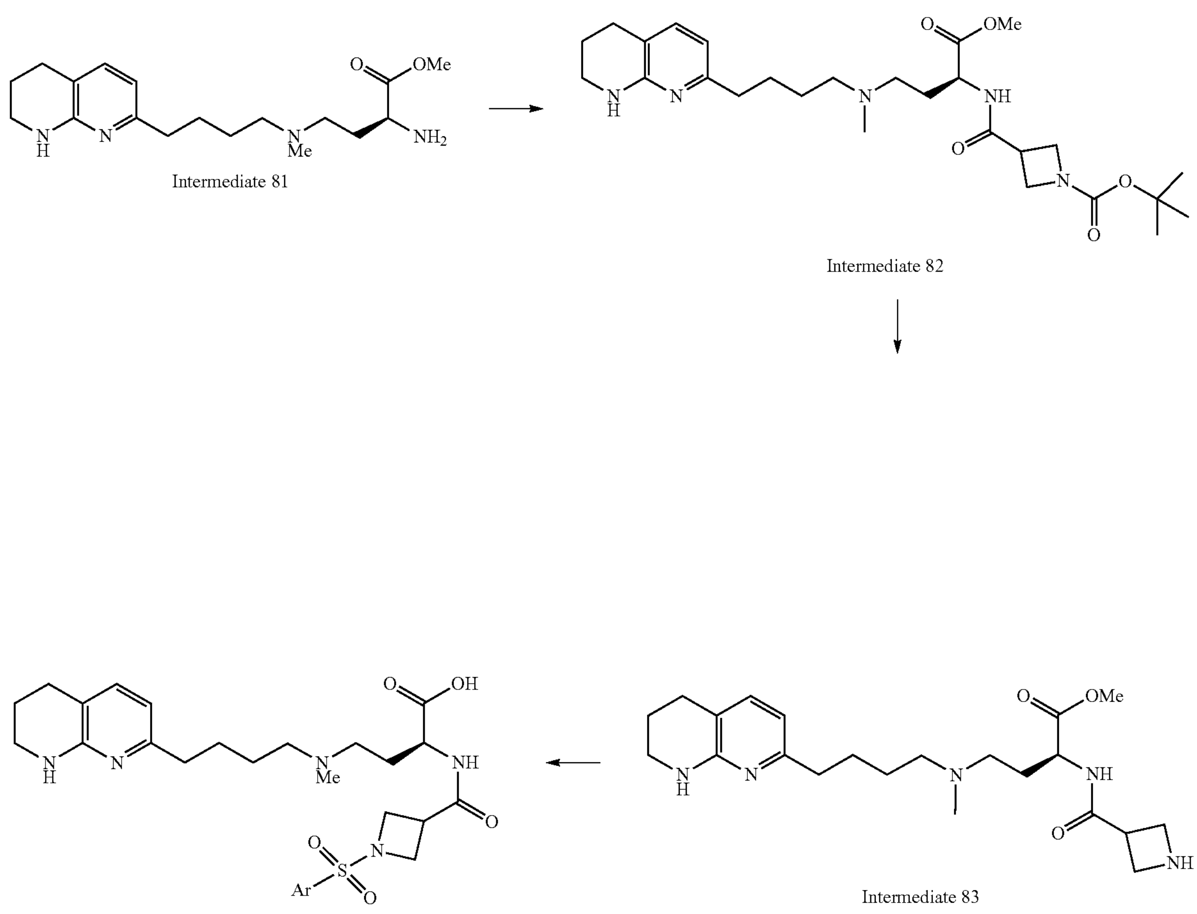

Intermediate 81

Intermediate 82

Intermediate 83

Examples 39-40

Example 39: (S)-2-(1-((3-chlorophenyl)sulfonyl)azetidine-3-carboxamido)-4-(methyl(4-(5,6,7,8-tetrahydro-1,8-naphthyridin-2-yl)butyl)amino)butanoic acid (a) Intermediate 82: tert-Butyl (S)-3-((1-methoxy-4-(methyl(4-(5,6,7,8-tetrahydro-1,8-naphthyridin-2-yl)butyl)amino)-1-oxobutan-2-yl)carbamoyl)azetidine-1-carboxylate

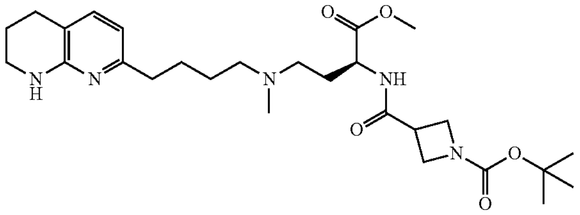 [SMILES: COC(=O)[C@H](CCN(C)CCCCc1ccc2c(n1)NCCC2)NC(=O)C1CN(C(=O)OC(C)(C)C)C1]

A solution of 1-(tert-butoxycarbonyl)azetidine-3-carboxylic acid (140 mg, 0.697 mmol), HATU (429 mg, 0.697 mmol) and DIPEA (0.552 mL, 3.17 mmol) in dichloromethane (2 mL) was stirred for 15 min and intermediate 81 (212 mg, 0.634 mmol) in dichloromethane (2 mL) added. LCMS showed that the reaction had gone to completion. The reaction mixture was concentrated in vacuo then dissolved in dichloromethane (2 mL) and loaded onto a 28 g KP-NH cartridge and purified by flash chromatography, eluting with 0-100% EtOAc in cyclohexane then 0-100% 3:1 EtOAc:EtOH in cyclohexane. The appropriate fractions were combined and concentrated in vacuo to give intermediate 82 (108 mg), as an orange solid used without purification. MS $[M+H]^+$ calculated for $C_{27}H_{43}N_5O_5$+H 517.32, found 518.4.

(b) Intermediate 83: Methyl (S)-2-(azetidine-3-carboxamido)-4-(methyl(4-(5,6,7,8-tetrahydro-1,8-naphthyridin-2-yl)butyl)amino)butanoate·3 trifluoroacetate

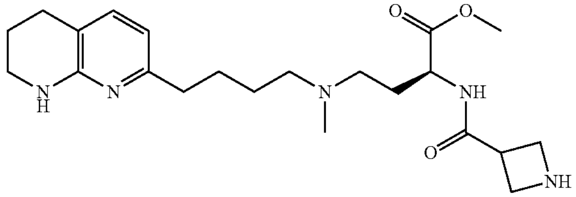 [SMILES: COC(=O)[C@H](CCN(C)CCCCc1ccc2c(n1)NCCC2)NC(=O)C1CNC1]

Figure 17:
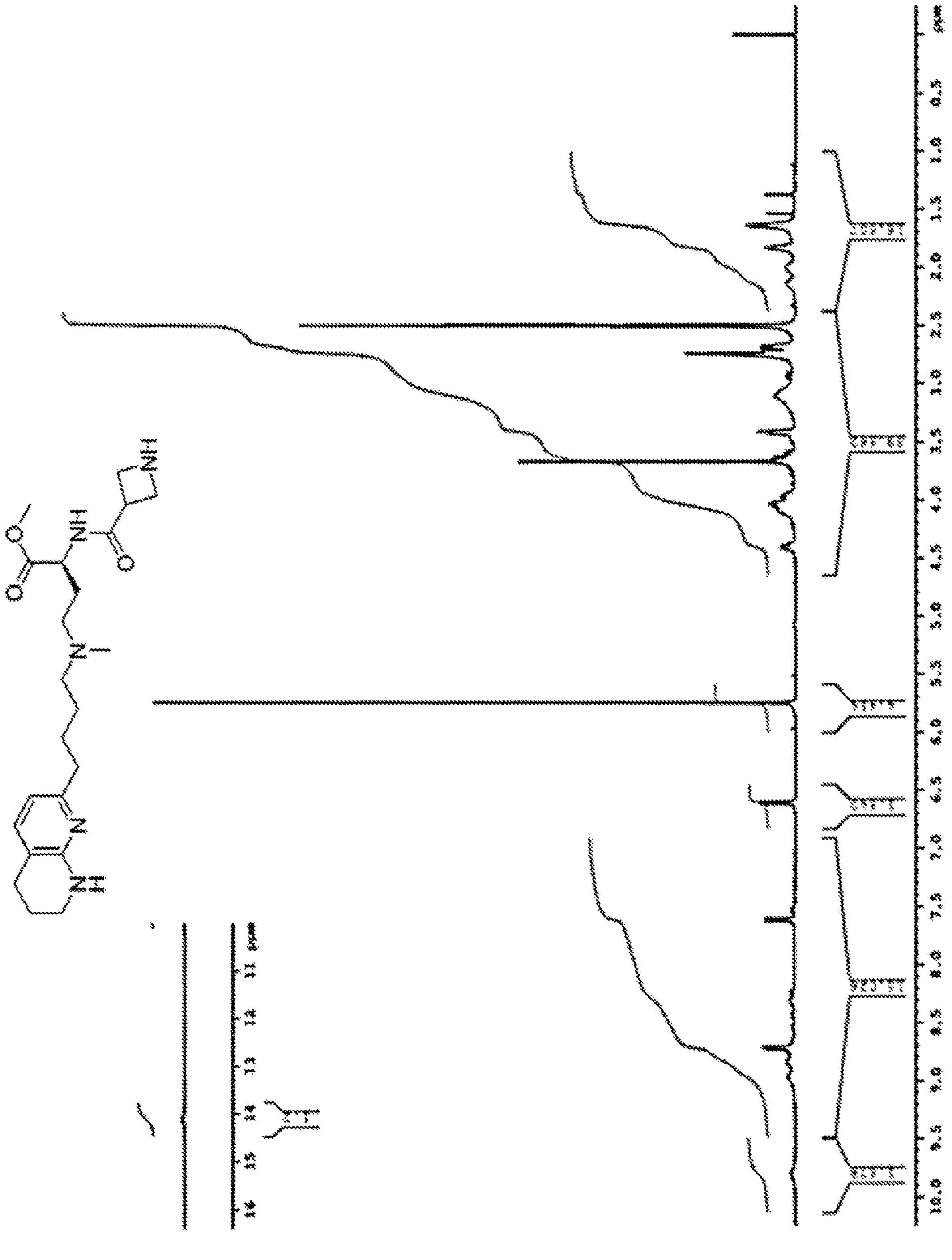
FIG. 17 is a $^1H$ NMR (400 MHz; DMSO-$d_6$) of Intermediate 83.

A solution of intermediate 82 (108 mg, 0.209 mmol) and trifluoroacetic acid (0.161 mL, 2.086 mmol) in dichloromethane (2 mL) was stirred at room temperature for 24 h. LCMS showed that the reaction had gone to near completion. The reaction mixture was concentrated in vacuo to give intermediate 83 as an orange gum. MS $[M+H]^+$ calculated for $C_{22}H_{35}N_5O_3$+H 418.28, found 418.4. $^1$H NMR (400 MHz; DMSO-$d_6$) is as shown in FIG. 17.

Example 39: (S)-2-(1-((3-chlorophenyl)sulfonyl)azetidine-3-carboxamido)-4-(methyl(4-(5,6,7,8-tetrahydro-1,8-naphthyridin-2-yl)butyl)amino)butanoic acid

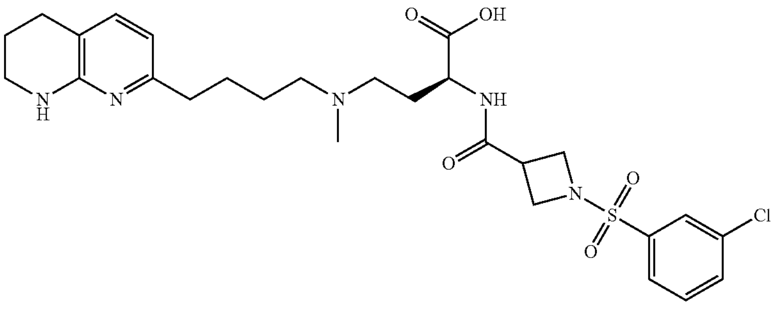 [SMILES: CN(CCCCc1ccc2c(n1)NCCC2)CC[C@H](NC(=O)C1CN(S(=O)(=O)c2cccc(Cl)c2)C1)C(=O)O]

Figure 18:
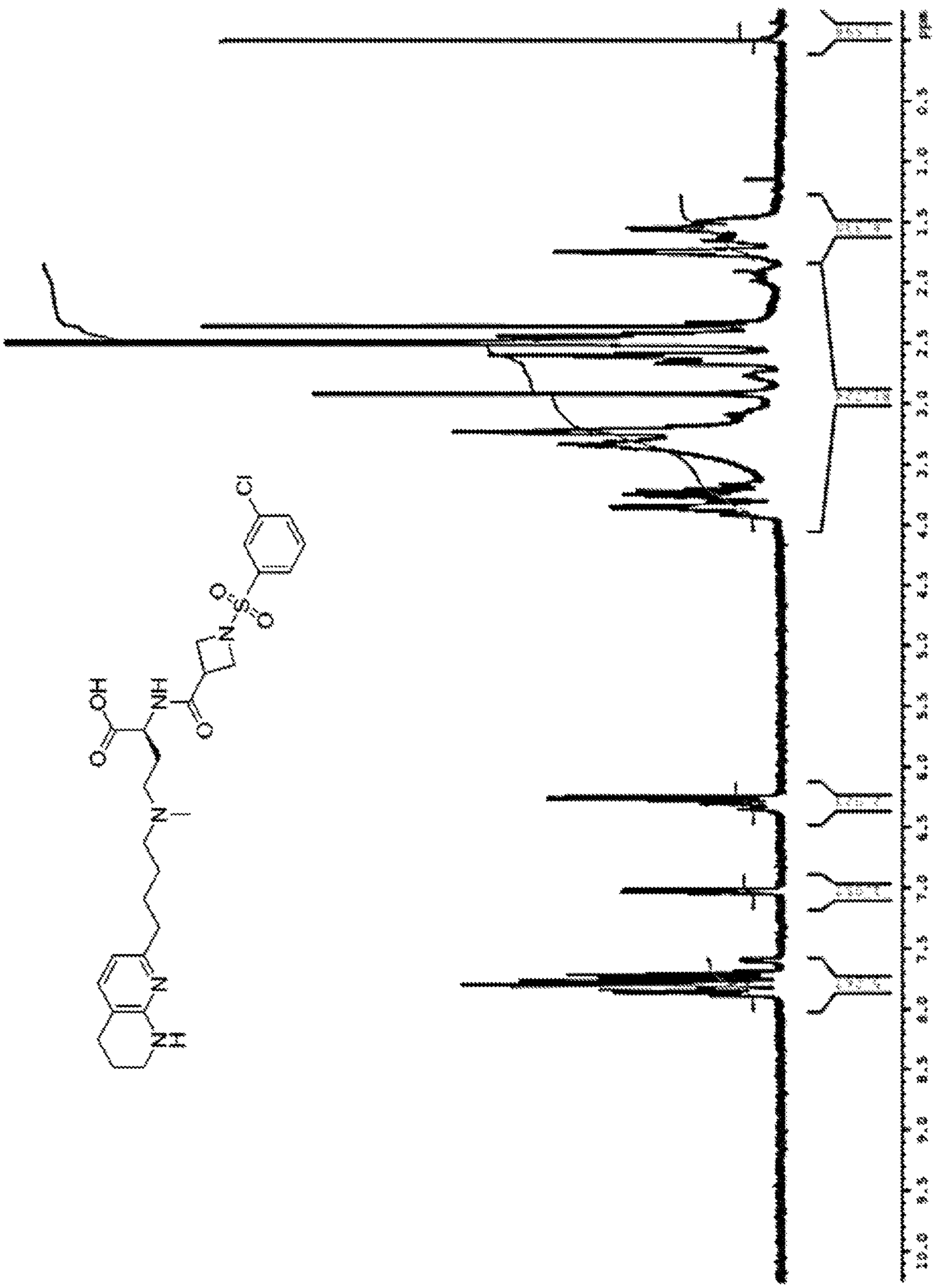
FIG. 18 is a $^1H$ NMR (400 MHz; DMSO-$d_6$) of Example 39.

A solution of intermediate 83 (57 mg, 0.075 mmol), THF (1 mL) and sodium hydroxide (2 M) (0.301 mL, 0.603 mmol) was cooled to 0° C. 3-Chlorobenzenesulfonyl chloride (0.013 mL, 0.090 mmol) was added to the reaction mixture and was stirred at 0° C. for 2 h. LCMS showed that the reaction had not gone to completion. Further 3-chlorobenzenesulfonyl chloride (0.013 mL, 0.090 mmol) was added and the reaction mixture stirred for a further 1.5 h. The reaction mixture was concentrated in vacuo to give a yellow solid which was dissolved in 1:1 DMSO:water then purified by MDAP. The appropriate fractions were combined and concentrated in vacuo then dried under a stream of nitrogen (40° C.) to give (S)-2-(1-((3-chlorophenyl)sulfonyl)azetidine-3-carboxamido)-4-(methyl(4-(5,6,7,8-tetrahydro-1,8-naphthyridin-2-yl)butyl)amino)butanoic acid (10 mg), as a white solid. MS $[M+H]^+$ calculated for $C_{27}H_{36}ClN_5O_5S+H$, 578.2 found 578.3. $^1H$ NMR (400 MHz; DMSO-$d_6$) is as shown in FIG. 18.

Example 40: (S)-4-(Methyl(4-(5,6,7,8-tetrahydro-1,8-naphthyridin-2-yl)butyl)amino)-2-(4-methylbenzenesulfonylazetidine-3-carboxamido)butanoic acid

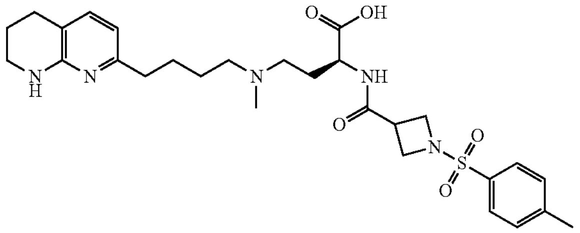 [SMILES: Cc1ccc(S(=O)(=O)N2CC(C(=O)N[C@@H](CCN(C)CCCCc3ccc4c(n3)NCCC4)C(=O)O)C2)cc1]

Figure 19:
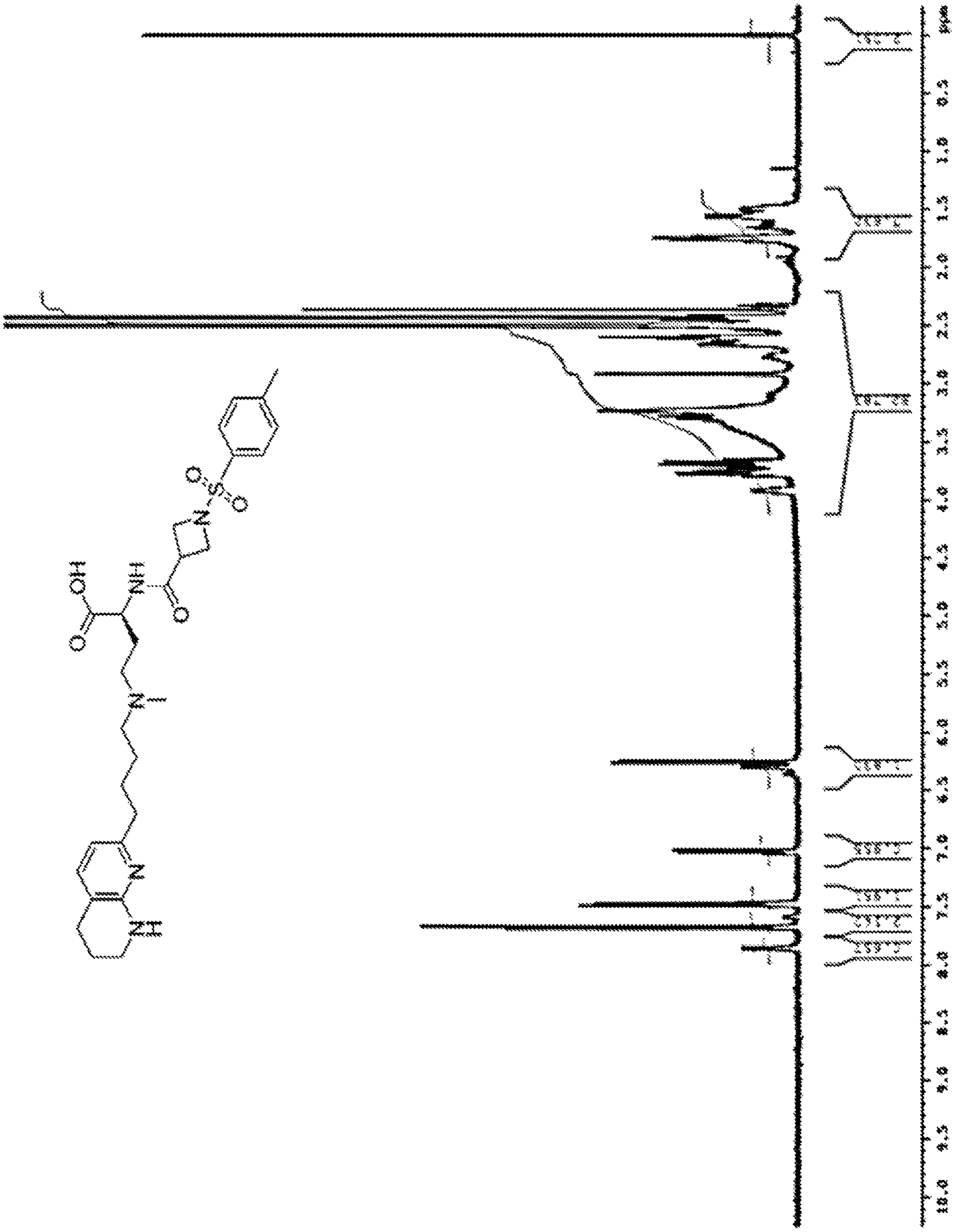
FIG. 19 is a $^1H$ NMR (400 MHz; DMSO-$d_6$) of Example 40.

A solution of intermediate 83 (57 mg, 0.075 mmol), THF (1 mL) and sodium hydroxide (2 M) (0.301 mL, 0.603 mmol) was cooled to 0° C. 4-Methylbenzenesulfonyl chloride (17.23 mg, 0.090 mmol) was added to the reaction mixture and was stirred at 0° C. for 1 h. The reaction mixture was concentrated in vacuo to give a yellow solid which was dissolved in 1:1 DMSO:water and purified by MDAP. The appropriate fractions were combined and concentrated in vacuo then dried under a stream of nitrogen (40° C.) to give (S)-4-(Methyl(4-(5,6,7,8-tetrahydro-1,8-naphthyridin-2-yl)butyl)amino)-2-(4-methylbenzenesulfonylazetidine-3-carboxamido)butanoic acid (10.5 mg), as a white solid. MS $[M+H]^+$ calculated for $C_{28}H_{39}N_5O_5S+H$, 557.26, found 558.3. $^1H$ NMR (400 MHz; DMSO-$d_6$) is as shown in FIG. 19.

Cell Adhesion Data

The assays were performed as described in the literature (P. A. Procopiou, N. A. Anderson, J. Barrett, T. N. Barrett, M. H. J. Crawford, B. J. Fallon, A. P. Hancock, J. Le, S. Lemma, R. P. Marshall, J. Morrell, J. M. Pritchard, J. E. Rowedder, P. Saklatvala, R. J. Slack, S. L. Sollis, C. J. Suckling, L. R. Thorp, G. Vitulli, et al., *J. Med. Chem.* 2018, 61, 8417-8443; S. B. Ludbrook, S. T. Barry, C. J. Delves, C. M. T. Horgan, *Biochem. J.* 2003, 369, 311-318).

| Example No | Structure | αvβ6 $IC_{50}$ nM |
|---|---|---|
| 1 | 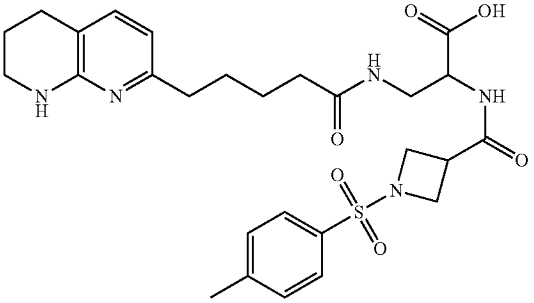 [SMILES: Cc1ccc(S(=O)(=O)N2CC(C(=O)NC(CNC(=O)CCCCc3ccc4c(n3)NCCC4)C(=O)O)C2)cc1] | <250 |
| 2 | 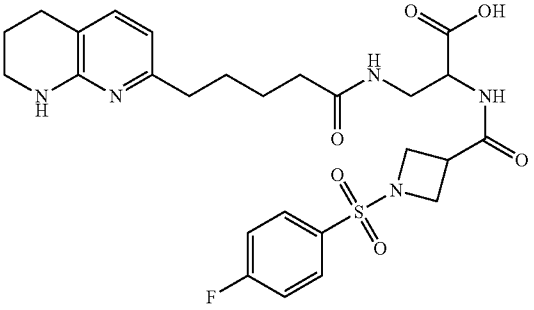 [SMILES: O=C(CCCCc1ccc2c(n1)NCCC2)NCC(NC(=O)C1CN(S(=O)(=O)c2ccc(F)cc2)C1)C(=O)O] | <250 |

-continued
| Example No | Structure | αvβ6 $IC_{50}$ nM |
| --- | --- | --- |
| 3 | 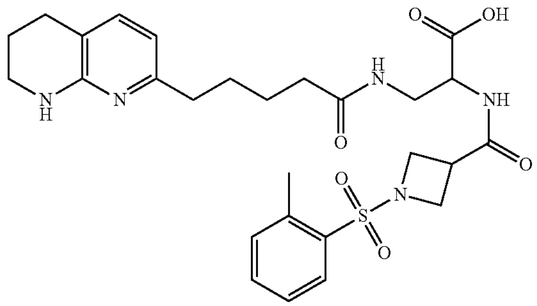 [SMILES: Cc1ccccc1S(=O)(=O)N1CC(C(=O)NC(CNC(=O)CCCCc2ccc3c(n2)NCCC3)C(=O)O)C1] | <250 |
| 4 | 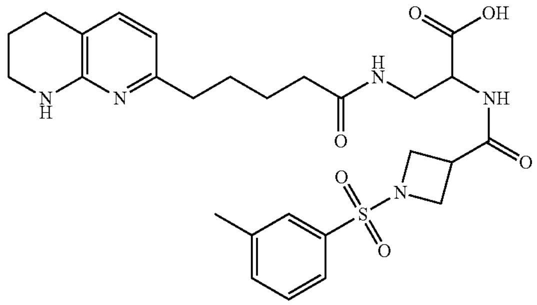 | <250 |
| 5 | 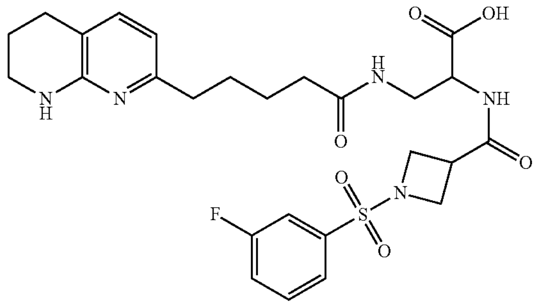 [SMILES: O=C(CCCCc1ccc2c(n1)NCCC2)NCC(NC(=O)C1CN(S(=O)(=O)c2cccc(F)c2)C1)C(=O)O] | <250 |
| 6A | 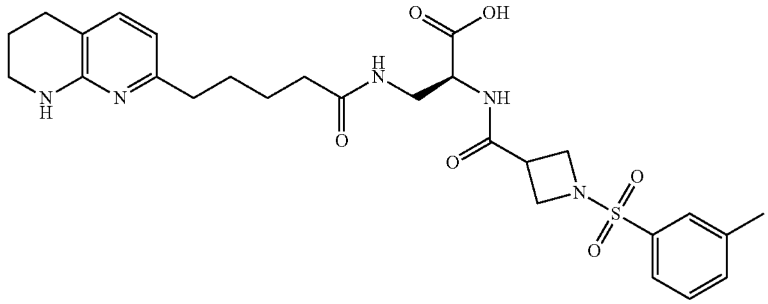 [SMILES: Cc1cccc(S(=O)(=O)N2CC(C(=O)N[C@@H](CNC(=O)CCCCc3ccc4c(n3)NCCC4)C(=O)O)C2)c1] | <250 |
| 6B | 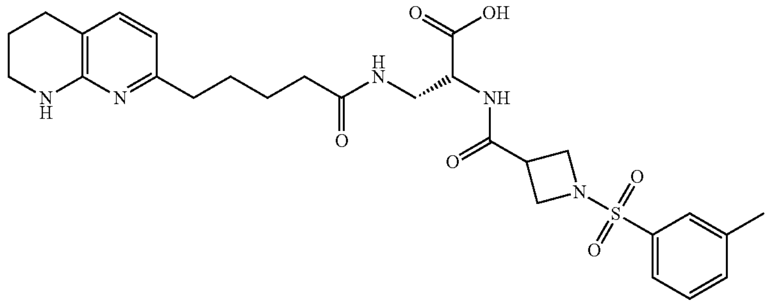 | >250 |

-continued
| Example No | Structure | αvβ6 $IC_{50}$ nM |
|---|---|---|
| 7 | 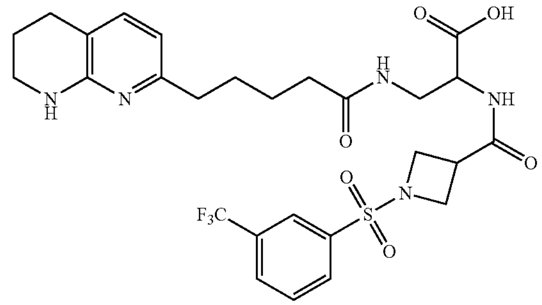 [SMILES: O=C(CCCCc1ccc2c(n1)NCCC2)NCC(NC(=O)C1CN(S(=O)(=O)c2cccc(C(F)(F)F)c2)C1)C(=O)O] | <250 |
| 8 | 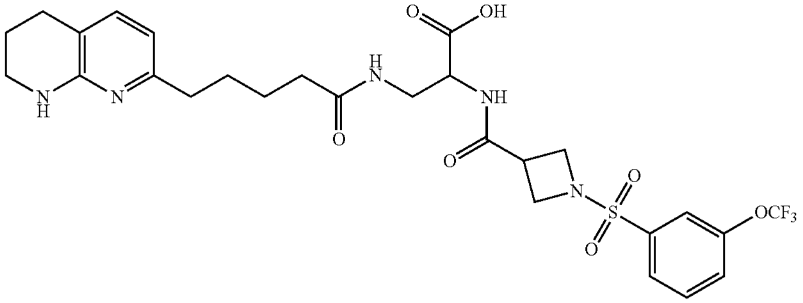 [SMILES: O=C(CCCCc1ccc2c(n1)NCCC2)NCC(NC(=O)C1CN(S(=O)(=O)c2cccc(OC(F)(F)F)c2)C1)C(=O)O] | <250 |
| 9 | 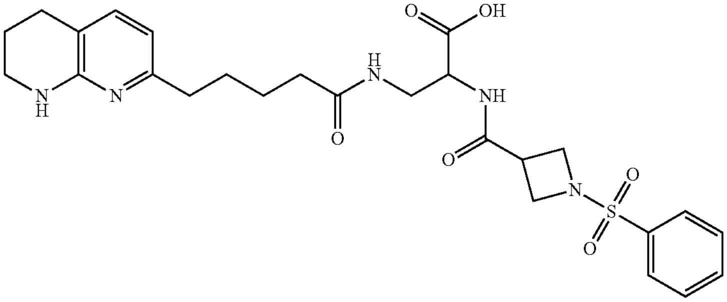 [SMILES: O=C(CCCCc1ccc2c(n1)NCCC2)NCC(NC(=O)C1CN(S(=O)(=O)c2ccccc2)C1)C(=O)O] | <250 |
| 10 | 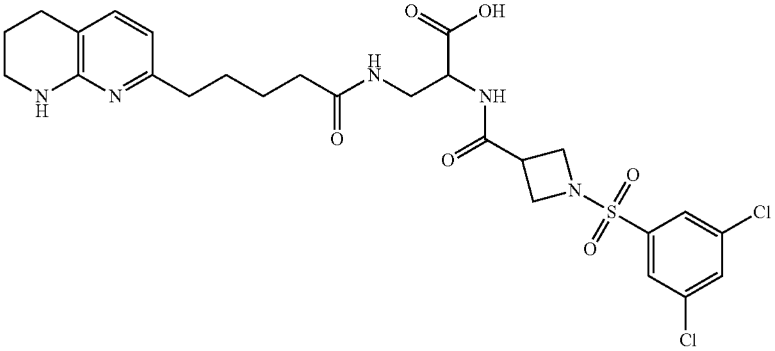 [SMILES: O=C(CCCCc1ccc2c(n1)NCCC2)NCC(NC(=O)C1CN(S(=O)(=O)c2cc(Cl)cc(Cl)c2)C1)C(=O)O] | <250 |

-continued
| Example No | Structure | αvβ6 $IC_{50}$ nM |
|---|---|---|
| 11 | 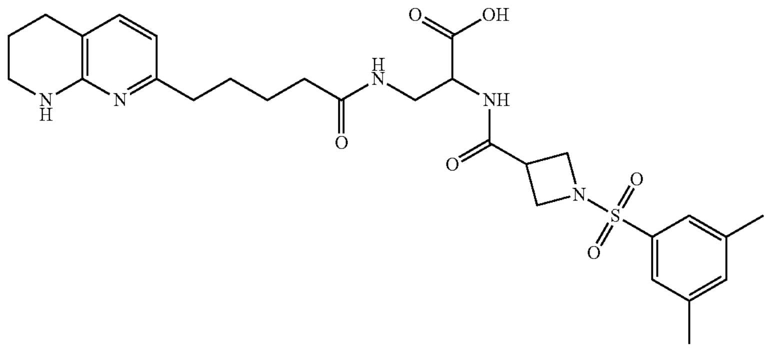 [SMILES: Cc1cc(C)cc(S(=O)(=O)N2CC(C(=O)NC(CNC(=O)CCCCc3ccc4c(n3)NCCC4)C(=O)O)C2)c1] | <250 |
| 12 | 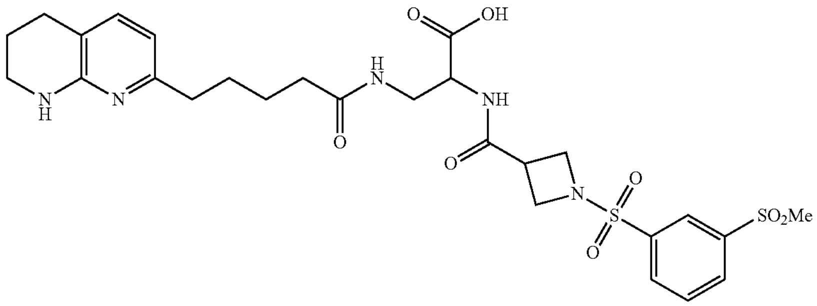 [SMILES: CS(=O)(=O)c1cccc(S(=O)(=O)N2CC(C(=O)NC(CNC(=O)CCCCc3ccc4c(n3)NCCC4)C(=O)O)C2)c1] | <250 |
| 13 | 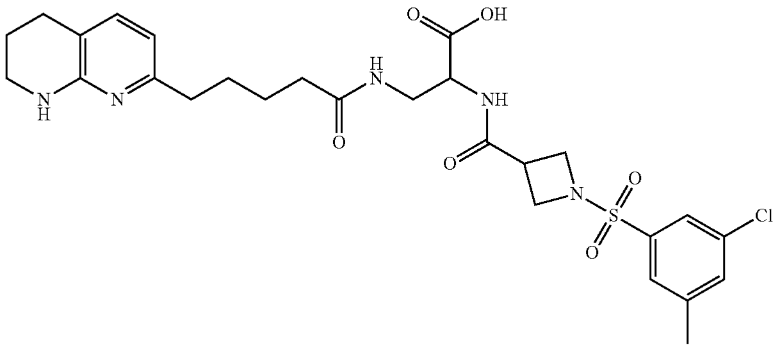 [SMILES: Cc1cc(Cl)cc(S(=O)(=O)N2CC(C(=O)NC(CNC(=O)CCCCc3ccc4c(n3)NCCC4)C(=O)O)C2)c1] | <250 |
| 14 | 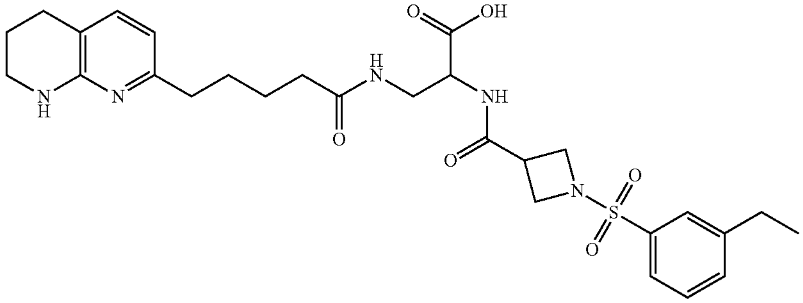 [SMILES: CCc1cccc(S(=O)(=O)N2CC(C(=O)NC(CNC(=O)CCCCc3ccc4c(n3)NCCC4)C(=O)O)C2)c1] | <250 |

-continued
| Example No | Structure | $\alpha v\beta 6$ $IC_{50}$ nM |
|---|---|---|
| 15 | 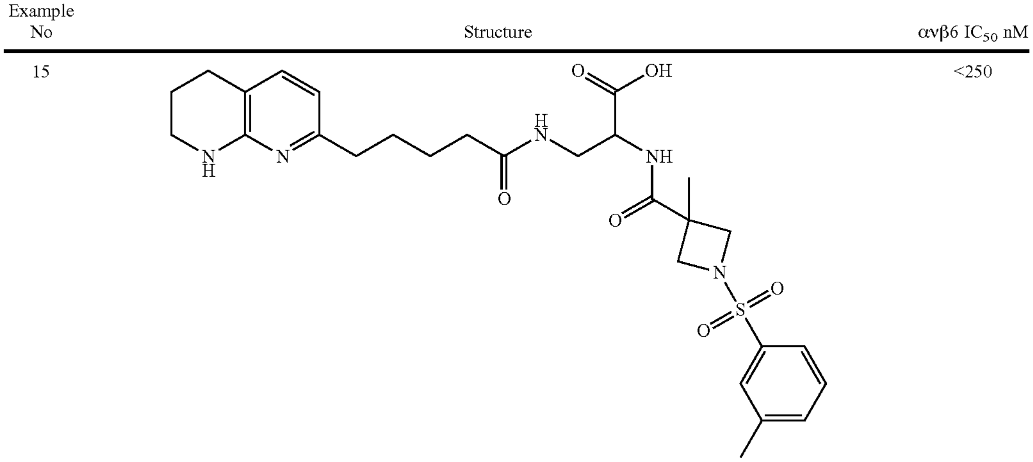 | <250 |
| 16 | 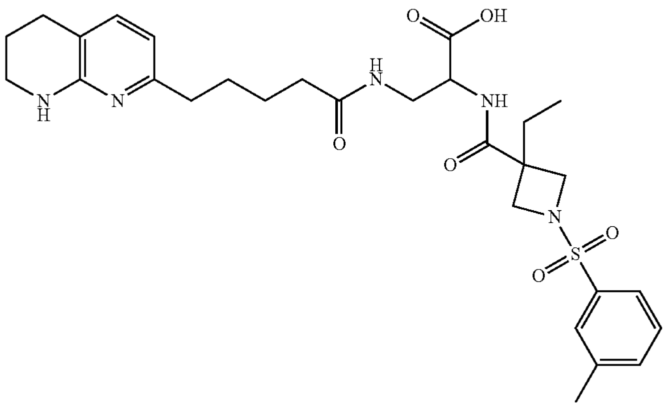 [SMILES: CCC1(C(=O)NC(CNC(=O)CCCCc2ccc3c(n2)NCCC3)C(=O)O)CN(S(=O)(=O)c2cccc(C)c2)C1] | <250 |
| 17 | 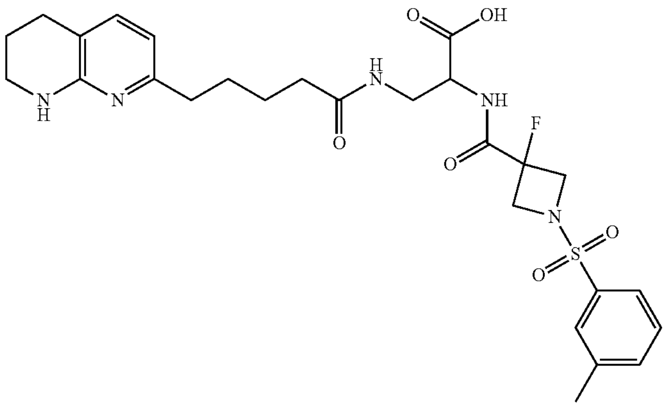 [SMILES: Cc1cccc(S(=O)(=O)N2CC(F)(C(=O)NC(CNC(=O)CCCCc3ccc4c(n3)NCCC4)C(=O)O)C2)c1] | <250 |

-continued
| Example No | Structure | αvβ6 $IC_{50}$ nM |
|---|---|---|
| 18 | 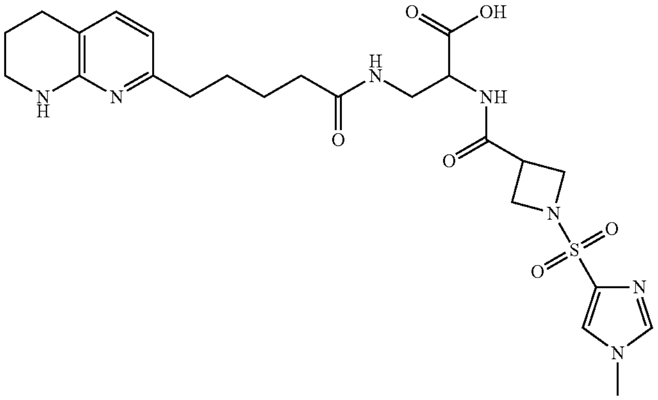 [SMILES: Cn1cnc(S(=O)(=O)N2CC(C(=O)NC(CNC(=O)CCCCc3ccc4c(n3)NCCC4)C(=O)O)C2)c1] | <250 |
| 19 | 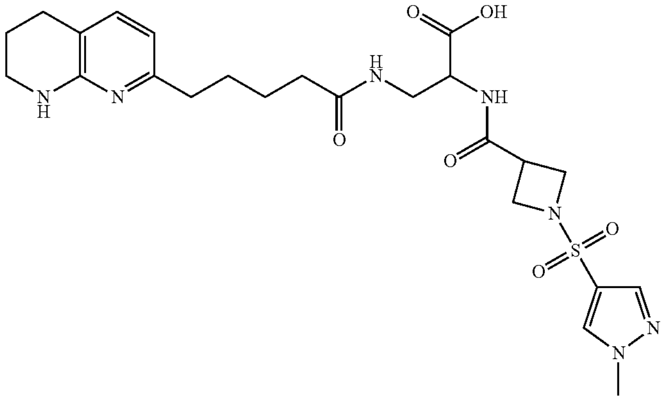 [SMILES: Cn1cc(S(=O)(=O)N2CC(C(=O)NC(CNC(=O)CCCCc3ccc4c(n3)NCCC4)C(=O)O)C2)cn1] | <250 |
| 20 | 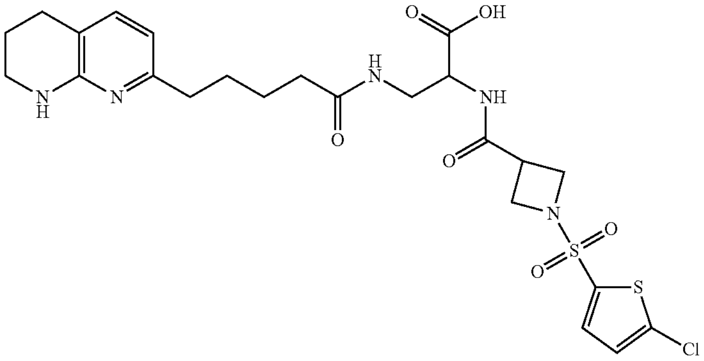 [SMILES: O=C(CCCCc1ccc2c(n1)NCCC2)NCC(NC(=O)C1CN(S(=O)(=O)c2ccc(Cl)s2)C1)C(=O)O] | <250 |
| 21 | 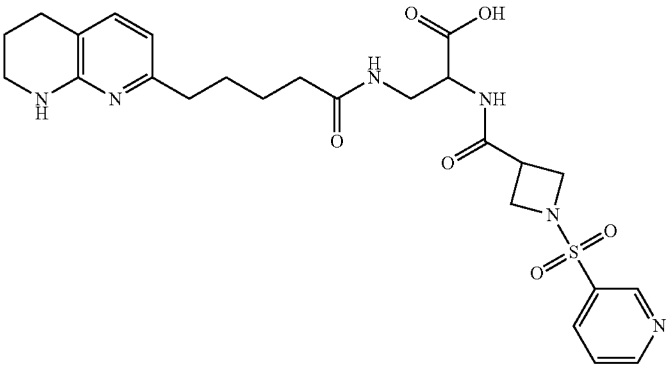 [SMILES: O=C(CCCCc1ccc2c(n1)NCCC2)NCC(NC(=O)C1CN(S(=O)(=O)c2cccnc2)C1)C(=O)O] | <250 |

-continued
| Example No | Structure | αvβ6 $IC_{50}$ nM |
|---|---|---|
| 22 | 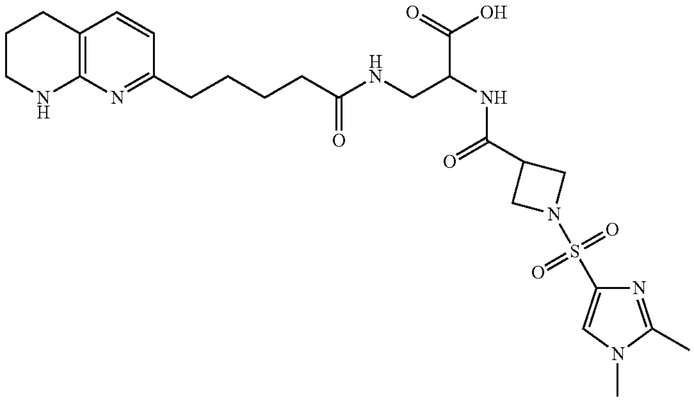 [SMILES: Cc1nc(S(=O)(=O)N2CC(C(=O)NC(CNC(=O)CCCCc3ccc4c(n3)NCCC4)C(=O)O)C2)cn1C] | <250 |
| 23 | 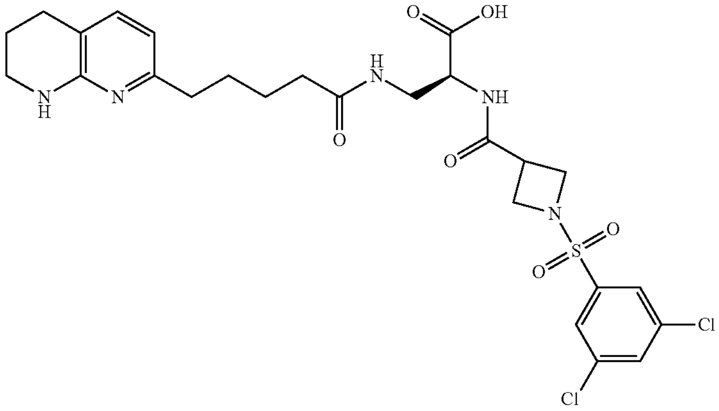 [SMILES: O=C(CCCCc1ccc2c(n1)NCCC2)NC[C@H](NC(=O)C1CN(S(=O)(=O)c2cc(Cl)cc(Cl)c2)C1)C(=O)O] | <250 |
| 24 | 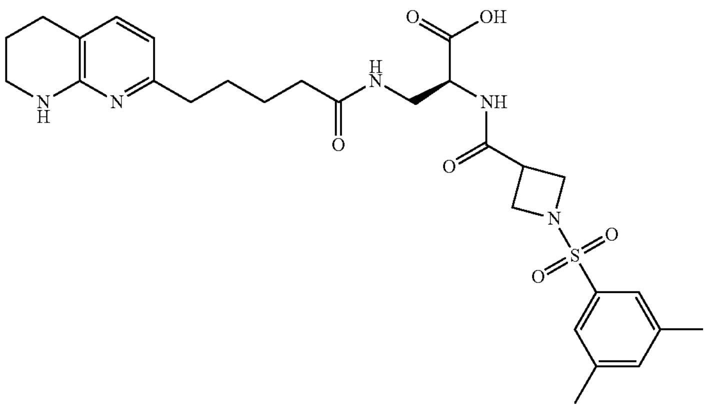 [SMILES: Cc1cc(C)cc(S(=O)(=O)N2CC(C(=O)N[C@@H](CNC(=O)CCCCc3ccc4c(n3)NCCC4)C(=O)O)C2)c1] | <250 |

-continued
| Example No | Structure | αvβ6 $IC_{50}$ nM |
|---|---|---|
| 25 | 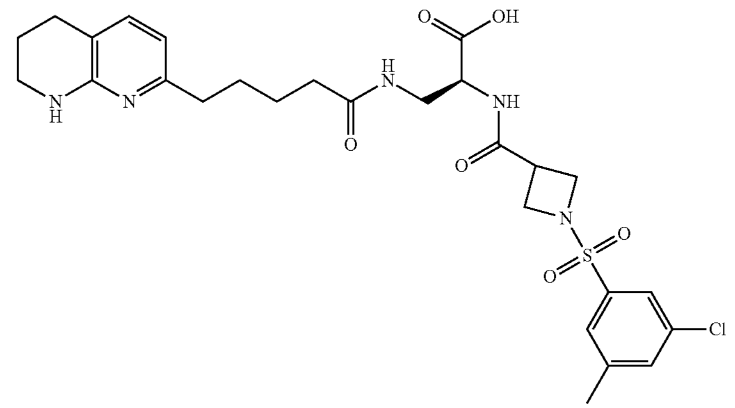 [SMILES: Cc1cc(Cl)cc(S(=O)(=O)N2CC(C(=O)N[C@@H](CNC(=O)CCCCc3ccc4c(n3)NCCC4)C(=O)O)C2)c1] | <250 |
| 26 | 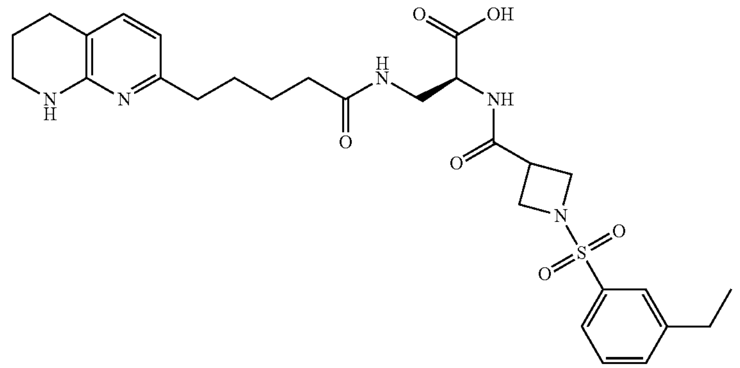 [SMILES: CCc1cccc(S(=O)(=O)N2CC(C(=O)N[C@@H](CNC(=O)CCCCc3ccc4c(n3)NCCC4)C(=O)O)C2)c1] | <250 |
| 27 | 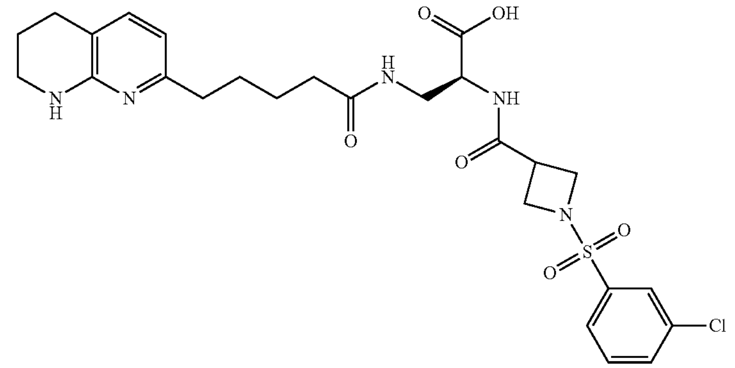 [SMILES: O=C(CCCCc1ccc2c(n1)NCCC2)NC[C@H](NC(=O)C1CN(S(=O)(=O)c2cccc(Cl)c2)C1)C(=O)O] | <250 |
| 28 | 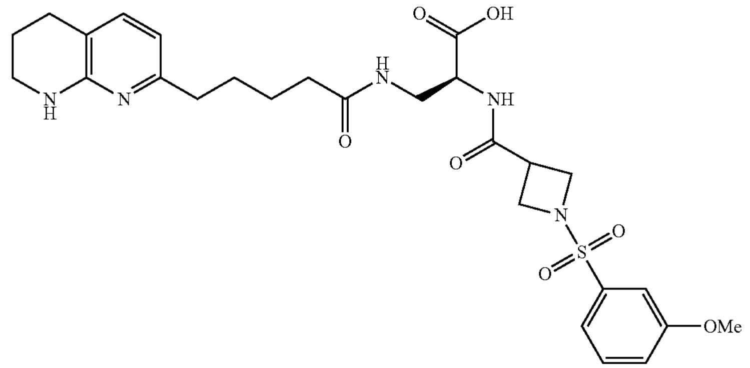 [SMILES: COc1cccc(S(=O)(=O)N2CC(C(=O)N[C@@H](CNC(=O)CCCCc3ccc4c(n3)NCCC4)C(=O)O)C2)c1] | <250 |

-continued
| Example No | Structure | αvβ6 $IC_{50}$ nM |
|---|---|---|
| 29 | 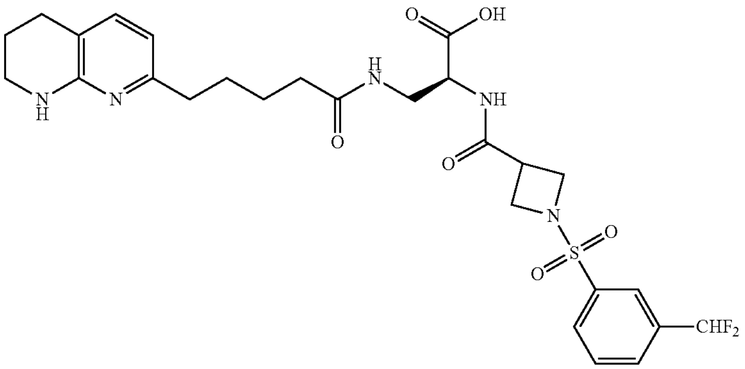 [SMILES: O=C(CCCCc1ccc2c(n1)NCCC2)NC[C@H](NC(=O)C1CN(S(=O)(=O)c2cccc(C(F)F)c2)C1)C(=O)O] | <250 |
| 30 | 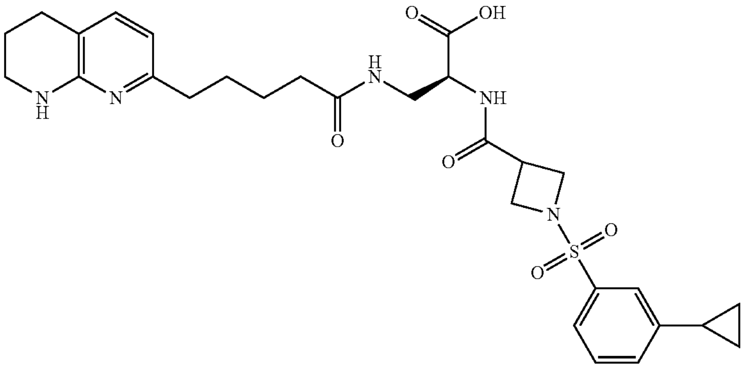 [SMILES: O=C(CCCCc1ccc2c(n1)NCCC2)NC[C@H](NC(=O)C1CN(S(=O)(=O)c2cccc(C3CC3)c2)C1)C(=O)O] | <250 |
| 31 | 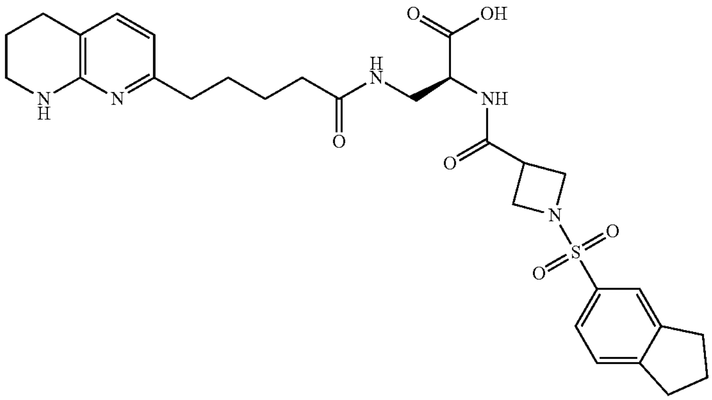 [SMILES: O=C(CCCCc1ccc2c(n1)NCCC2)NC[C@H](NC(=O)C1CN(S(=O)(=O)c2ccc3c(c2)CCC3)C1)C(=O)O] | <250 |
| 32 | 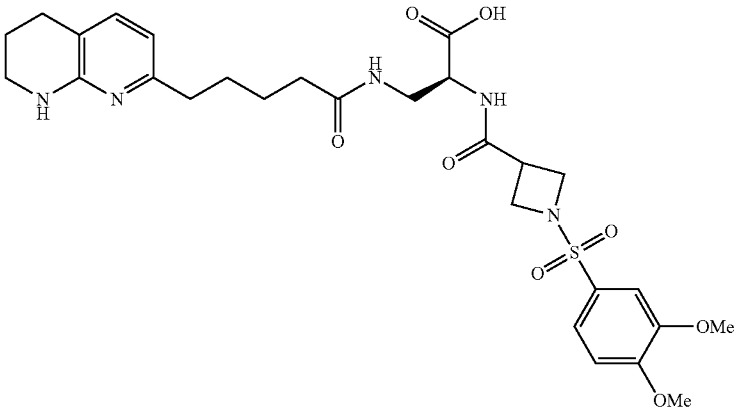 [SMILES: COc1ccc(S(=O)(=O)N2CC(C(=O)N[C@@H](CNC(=O)CCCCc3ccc4c(n3)NCCC4)C(=O)O)C2)cc1OC] | <250 |

-continued
| Example No | Structure | αvβ6 $IC_{50}$ nM |
|---|---|---|
| 33 | 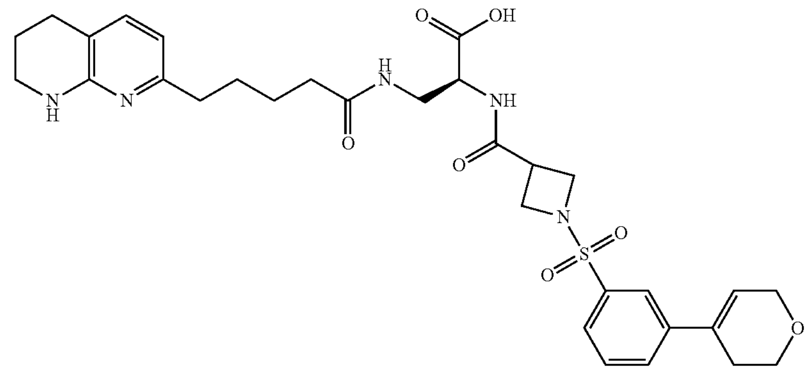 [SMILES: O=C(CCCCc1ccc2c(n1)NCCC2)NC[C@H](NC(=O)C1CN(S(=O)(=O)c2cccc(C3=CCOCC3)c2)C1)C(=O)O] | <250 |
| 34 | 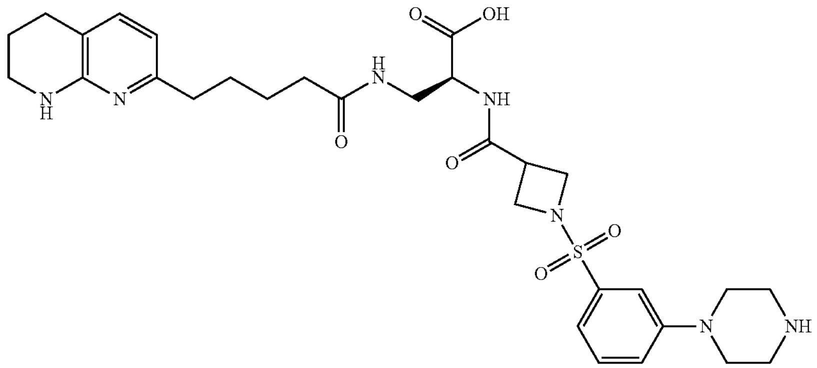 [SMILES: O=C(CCCCc1ccc2c(n1)NCCC2)NC[C@H](NC(=O)C1CN(S(=O)(=O)c2cccc(N3CCNCC3)c2)C1)C(=O)O] | <250 |
| 35 | 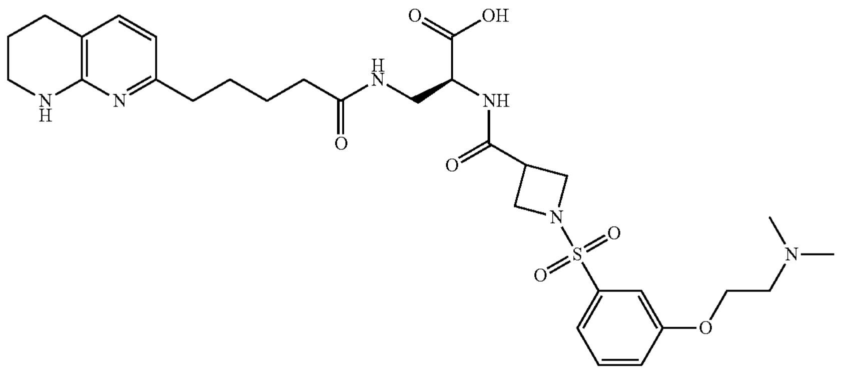 [SMILES: CN(C)CCOc1cccc(S(=O)(=O)N2CC(C(=O)N[C@@H](CNC(=O)CCCCc3ccc4c(n3)NCCC4)C(=O)O)C2)c1] | <250 |
| 36 | 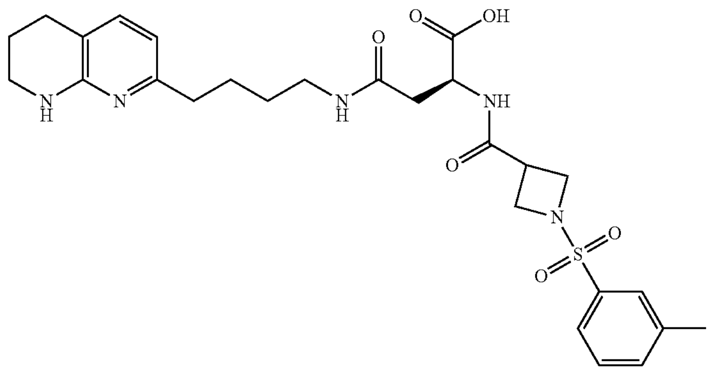 [SMILES: Cc1cccc(S(=O)(=O)N2CC(C(=O)N[C@@H](CC(=O)NCCCCc3ccc4c(n3)NCCC4)C(=O)O)C2)c1] | <250 |

-continued
| Example No | Structure | αvβ6 $IC_{50}$ nM |
|---|---|---|
| 37 | 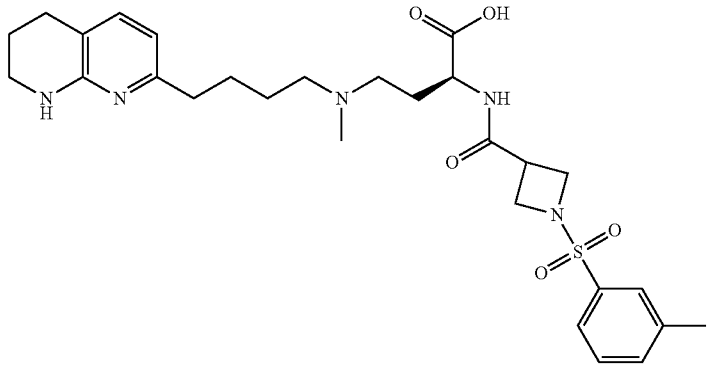 [SMILES: Cc1cccc(S(=O)(=O)N2CC(C(=O)N[C@@H](CCN(C)CCCCc3ccc4c(n3)NCCC4)C(=O)O)C2)c1] | <250 |
| 38 | 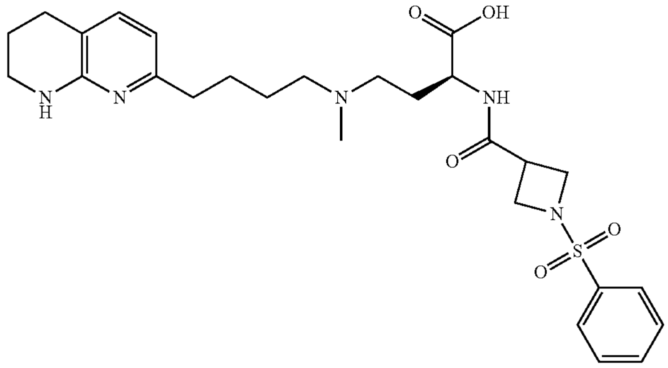 [SMILES: CN(CCCCc1ccc2c(n1)NCCC2)CC[C@H](NC(=O)C1CN(S(=O)(=O)c2ccccc2)C1)C(=O)O] | <250 |
| 39 | 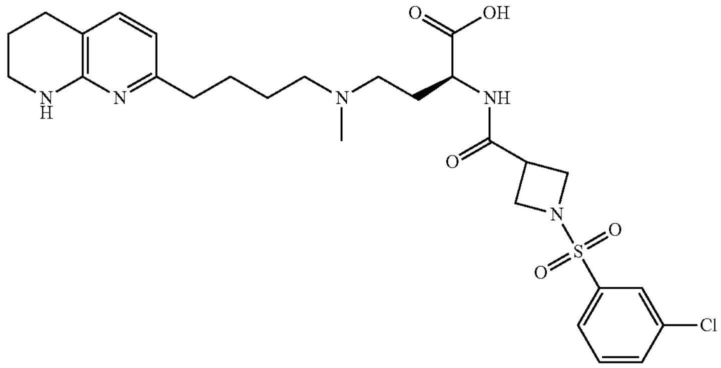 [SMILES: CN(CCCCc1ccc2c(n1)NCCC2)CC[C@H](NC(=O)C1CN(S(=O)(=O)c2cccc(Cl)c2)C1)C(=O)O] | <250 |
| 40 | 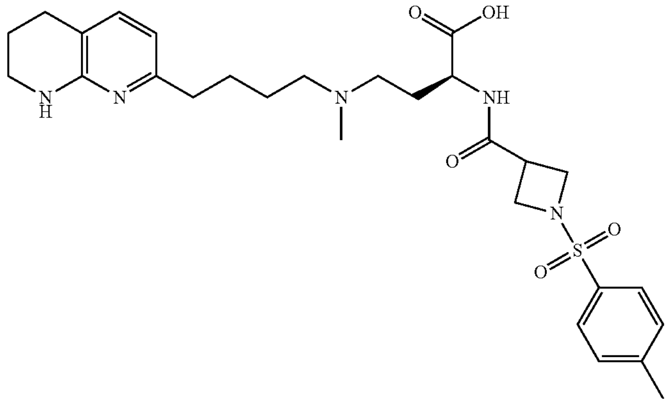 [SMILES: Cc1ccc(S(=O)(=O)N2CC(C(=O)N[C@@H](CCN(C)CCCCc3ccc4c(n3)NCCC4)C(=O)O)C2)cc1] | <250 |

Unless stereochemistry is specified, the compounds are racemic.

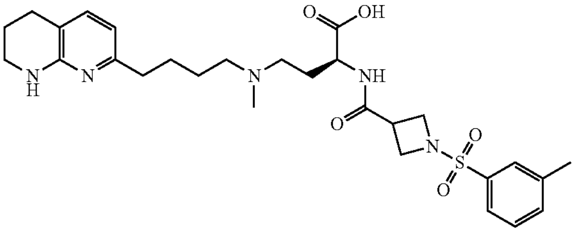

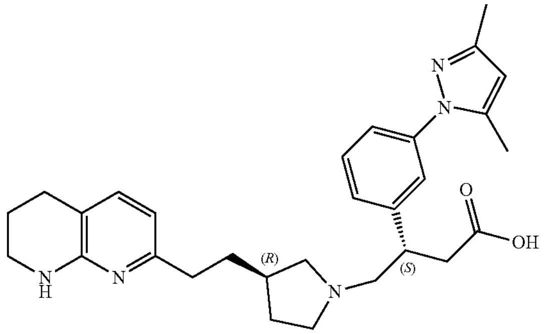

Comparison of Example 6A with GSK3008348

| | αvβ6 ($pIC_{50}$) | ChromlogD pH 7.4 | hERG Q-patch ($pIC_{50}$) |
|---|---|---|---|
| Example 6A | 8.3 | 2.27 | <4.5 |
| GSK3008348 | 8.4 | 2.82 | 4.9 |

ChromlogD

ChromlogD is a measure of lipophilicity of a compound (R. J. Young et al. *Drug Discovery Today* 2011, 116, 882-830). Lipophilicity is a key physicochemical property that plays a crucial role in determining ADMET (absorption, distribution, metabolism, excretion, and toxicity) properties and the overall suitability of drug candidates. There is increasing evidence to suggest that control of physicochemical properties such as lipophilicity, within a defined optimal range, can improve compound quality and the likelihood of therapeutic success (J. A. Arnott and S. L. Planey, *Expert Opinion on Drug Discovery,* 2012, 7:10, 863-875).

hERG Q-Patch

The human ether-a-go-go related gene (hERG) encodes the inward rectifying voltage gated potassium channel in the heart (IKr) that is involved in cardiac repolarisation. Inhibition of the hERG current causes QT interval prolongation resulting in potentially fatal ventricular tachyarrhythmia called Torsade de Pointes. A number of drugs have been withdrawn from late stage clinical trials due to these cardiotoxic effects, therefore it is important to identify inhibitors early in drug discovery (W. Haverkamp et al. *Eur Heart J.,* 2000, 21(15), 1216). A low potency in this screen is advantageous for compound development.

Data for GSK3008348 and a description of the assays can be found in: *J. Med. Chem.,* 2018, 61, 8417-8443.

The invention claimed is:

1. A compound according to formula I:

(I)

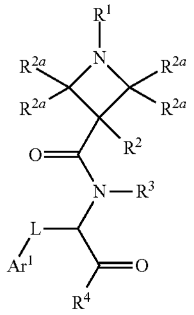

wherein $R^1$ is —$SO_2R^{1a}$, wherein $R^{1a}$ is selected from alkyl, alkenyl, alkynyl, aryl, heteroaryl, alkylaryl or alkylheteroaryl, each of which may be optionally substituted;

$R^2$ is selected from: hydrogen, halogen, optionally substituted alkyl or optionally substituted alkoxyl;

$R^{2a}$ are each independently selected from: hydrogen, halogen, optionally substituted alkyl or optionally substituted alkoxyl;

$R^3$ is selected from: hydrogen, optionally substituted alkyl or optionally substituted alkoxyl;

$R^4$ is hydroxyl;

L is a linker selected from any of formulae (II) to (VIII):

(II)

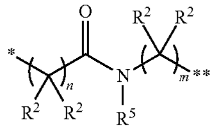

(III)

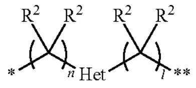

(IV)

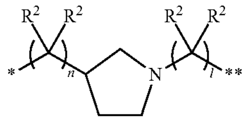

(V)

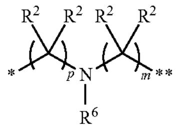

(VI)

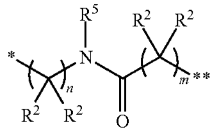

(VII)

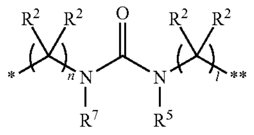

-continued (VIII)

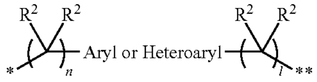

wherein:

Het is a 4, 5, 6 or 7 membered saturated heterocycle containing N, O, S or C linked through either N or C, typically selected from: azetidine, pyrrolidine, piperidine, piperazine, morpholine, thiomorpholine, homomorpholine, homopiperazine, azepane; $R^2$ is as described above: $R^5$, $R^6$ and $R^7$ are each independently selected from: hydrogen, optionally substituted alkyl or optionally substituted alkoxy: the length of the linker is between 2 to 12 bond lengths: 1, m, n and p are each independently an integer in the range of 0 to 10: the positions indicated with '*' and '**' represent the left-hand side and the right-hand side of the linker respectively; and in formula (VIII), the Aryl or Heteroaryl may be substituted; and:

$Ar^1$ is a group according to any of formulae (IXa) to (IXj):

(IXa)

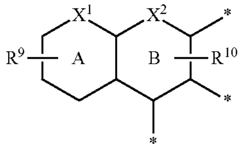

(IXb)

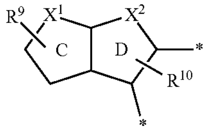

(IXc)

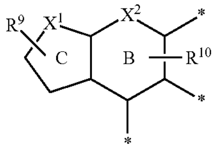

(IXd)

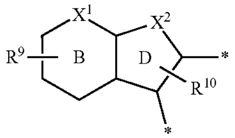

(IXe)

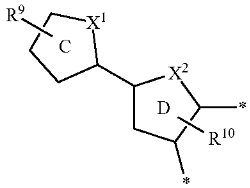

(IXf)

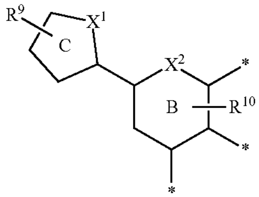

-continued (IXg)

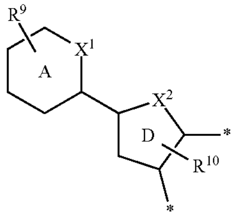

(IXh)

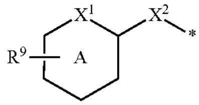

(IXi)

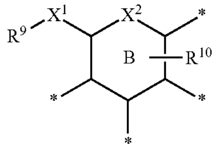

wherein:

$X^1$ and $X^2$ are each independently a donor atom wherein the donor atom is nitrogen;

* represents a possible connection point between $Ar^1$ and the linker described above;

rings A to D are each independently an aromatic heterocycle or a non-aromatic heterocycle, with the proviso that at least one ring is aromatic:

$R^9$ and $R^{10}$ are each independently selected from: hydrogen, halogen, optionally substituted alkyl, optionally substituted alkoxy, optionally substituted alkenyl, optionally substituted alkynyl, optionally substituted aryl, optionally substituted alkylalkoxy, optionally substituted heteroaryl, optionally substituted alkylaryl or optionally substituted alkylheteroaryl, or combinations thereof;

or a pharmaceutically acceptable salt thereof.

2. The compound according to claim 1, wherein the linker has a structure according to formulae (II), (V) or VI.

3. The compound according to claim 1, wherein $Ar^1$ is a group according to any of formulae (IXa), (IXb), (IXc), (IXd), IXh), or (IXi).

4. The compound according to claim 1, wherein $Ar^1$ is selected from one of the groups according to formulae (Xa) to (Xr):

(Xa)

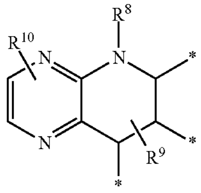

(Xb)

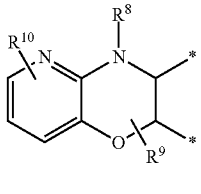

-continued (Xc)

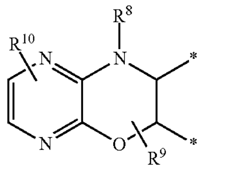

(Xd)

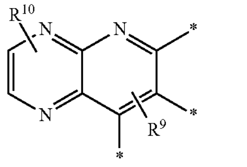

(Xe)

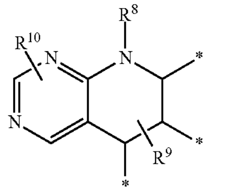

(Xf)

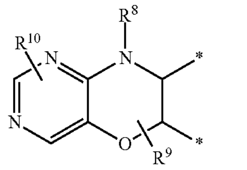

(Xh)

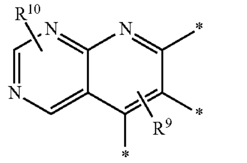

(Xj)

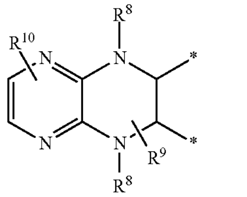

(Xl)

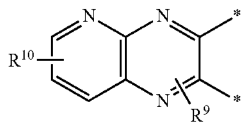

(Xm)

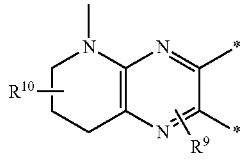

(Xn)

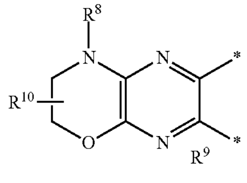

-continued (Xo)

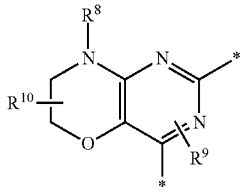

(Xp)

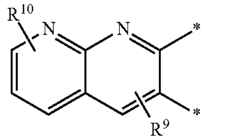

(Xq)

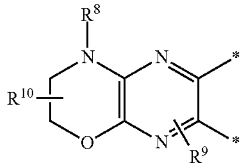

(Xr)

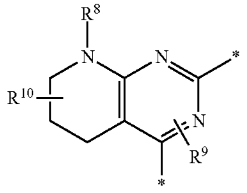

wherein:

$R^8$ is selected from: hydrogen or optionally substituted alkyl; and $R^9$ and $R^{10}$ are each independently selected from: hydrogen, halogen, optionally substituted alkyl, optionally substituted alkoxy, optionally substituted alkenyl, optionally substituted alkynyl, optionally substituted aryl, optionally substituted alkylalkoxy, optionally substituted heteroaryl, optionally substituted alkylaryl or optionally substituted alkylheteroaryl, or combinations thereof.

5. A compound according to 1 wherein $Ar^1$ is a group according to the formula (XIa) to (XIc);

(XIa)

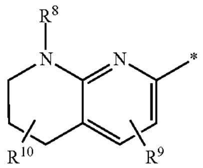

(XIb)

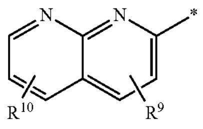

(XIc)

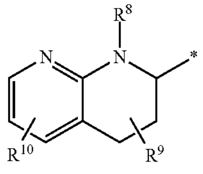

wherein $R^8$ is selected from: hydrogen or optionally substituted alkyl; and $R^9$ and $R^{10}$ are each independently selected from: hydrogen, halogen, optionally substituted alkyl, optionally substituted alkoxy, optionally substituted alkenyl, optionally substituted alkynyl, optionally substituted aryl, optionally substituted alkylalkoxy, optionally substituted heteroaryl, optionally substituted alkylaryl or optionally substituted alkylheteroaryl, or combinations thereof.

6. The compound according to claim 1, wherein l and m are each independently an integer in the range of 1 to 3.

7. The compound according to claim 1, wherein n and p are each integers independently in the range of 2 to 7.

8. The compound according to claim 1, wherein $R^{1a}$ is selected from: alkyl, alkenyl, alkynyl, aryl, heteroaryl, alkylaryl or alkylheteroaryl, each of which may be optionally substituted;

$R^2$ is selected from: hydrogen, halogen, optionally substituted alkyl or optionally substituted alkoxyl;

$R^2$ are each independently selected from: hydrogen, halogen, optionally substituted alkyl or optionally substituted alkoxyl;

$R^3$ is selected from: hydrogen, optionally substituted alkyl or optionally substituted alkoxyl;

$R^4$ is hydroxyl;

$Ar^1$ is (XIa)

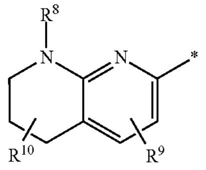

wherein $R^8$ is selected from: hydrogen or optionally substituted alkyl; and $R^9$ and $R^{10}$ are each independently selected from: hydrogen, halogen, optionally substituted alkyl, optionally substituted alkoxy, optionally substituted alkenyl, optionally substituted alkynyl, optionally substituted aryl, optionally substituted alkylalkoxy, optionally substituted heteroaryl, optionally substituted alkylaryl or optionally substituted alkylheteroaryl, or combinations thereof, and L is a linker selected from any of formulae (II), (V) and (VI)

(II)

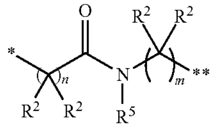

(V)

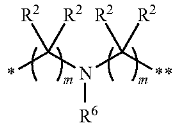

(VI)

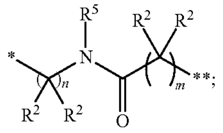

or a pharmaceutically acceptable salt thereof.

9. The compound according to claim 1 selected from:

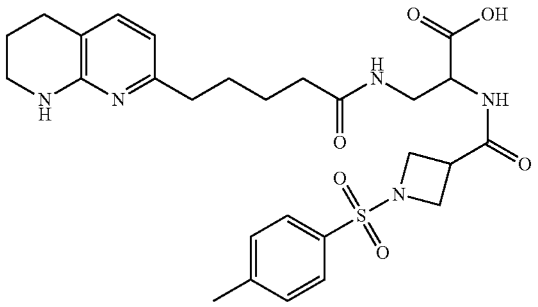

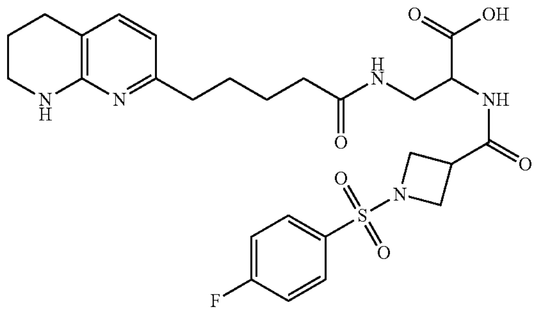

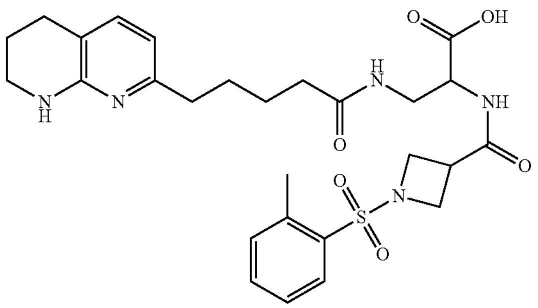

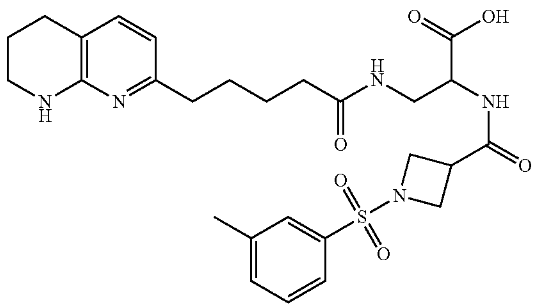

-continued
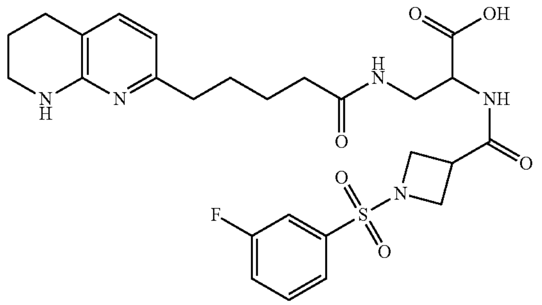
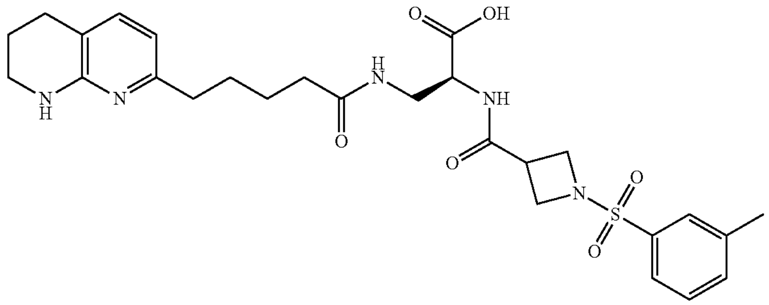
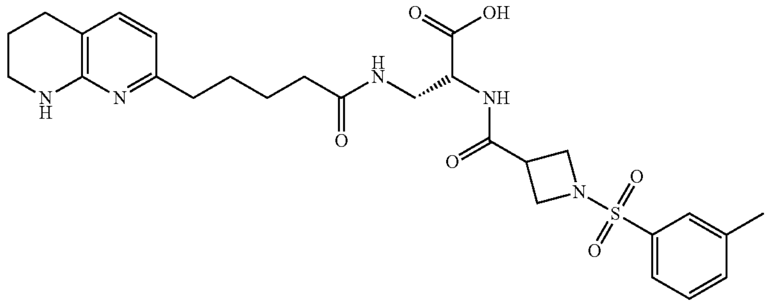
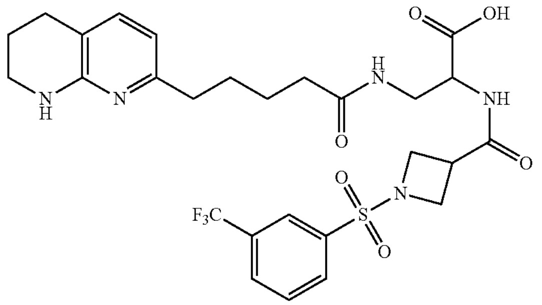
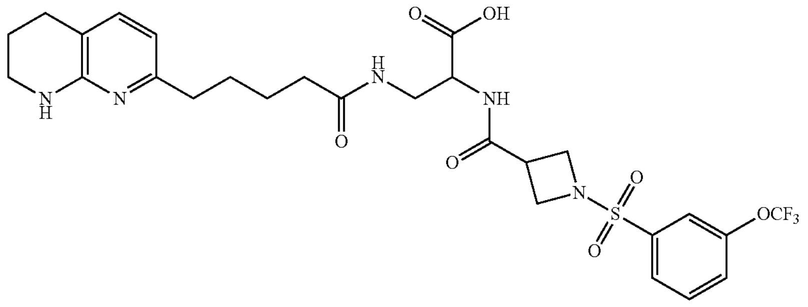

-continued
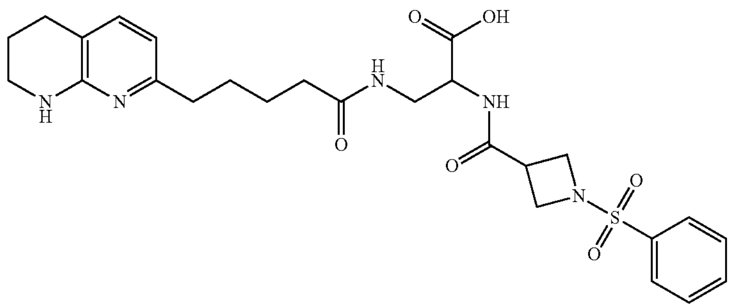
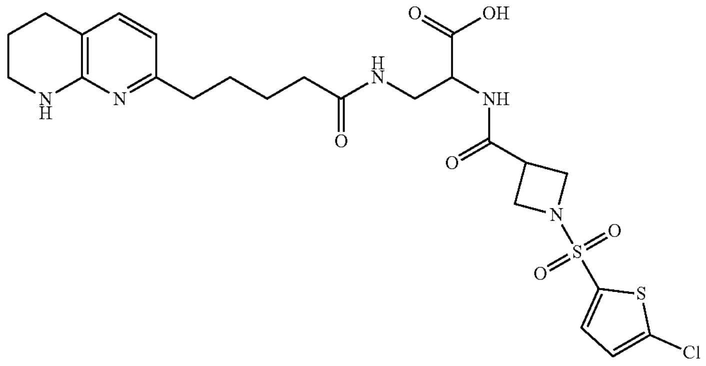
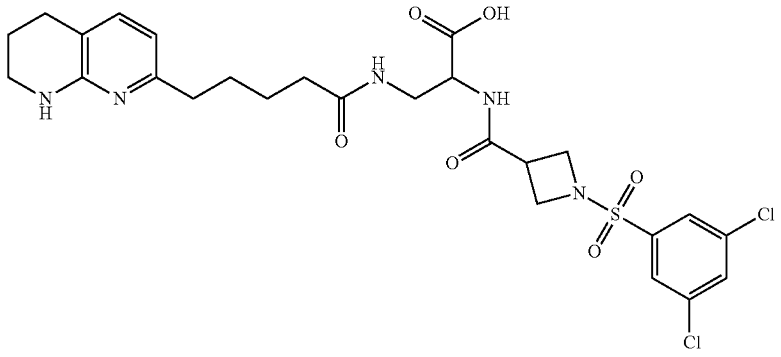
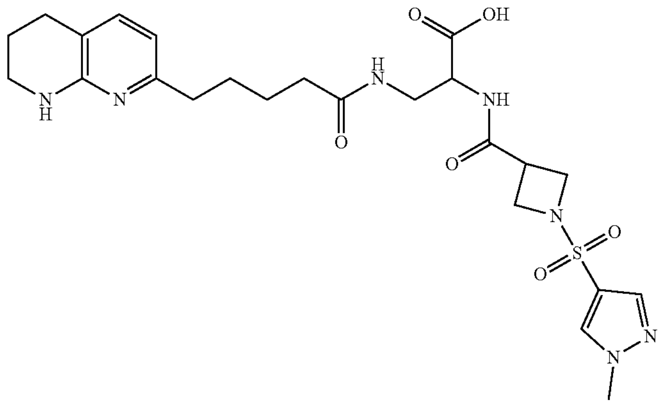

-continued
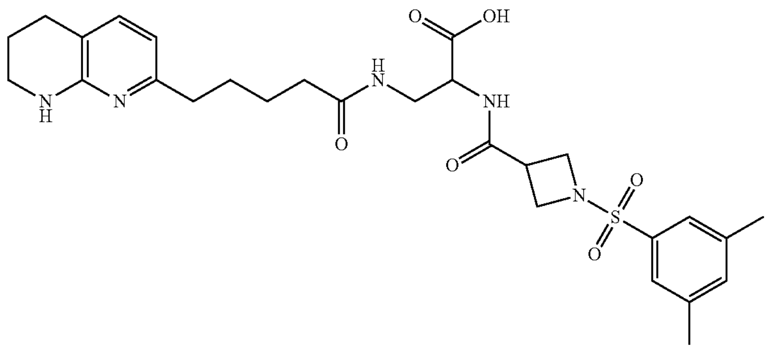
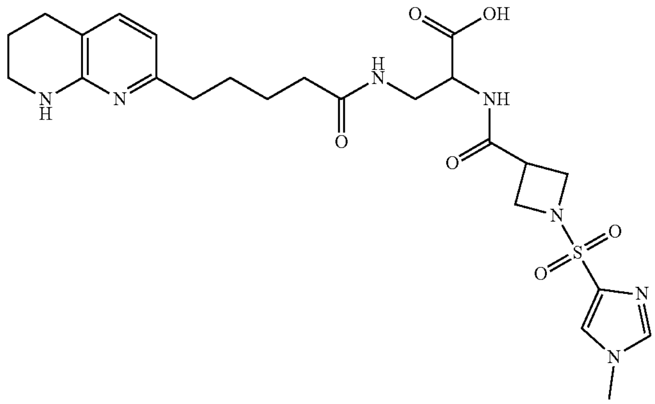
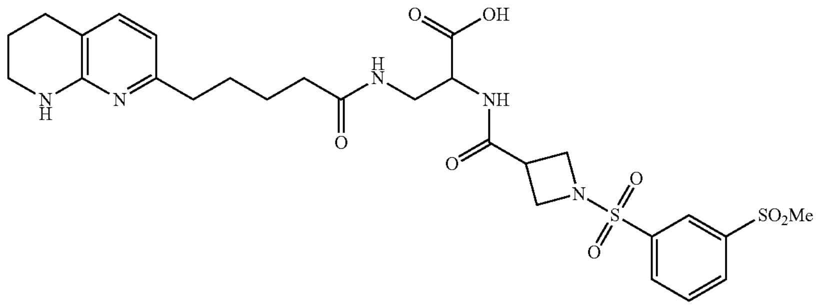
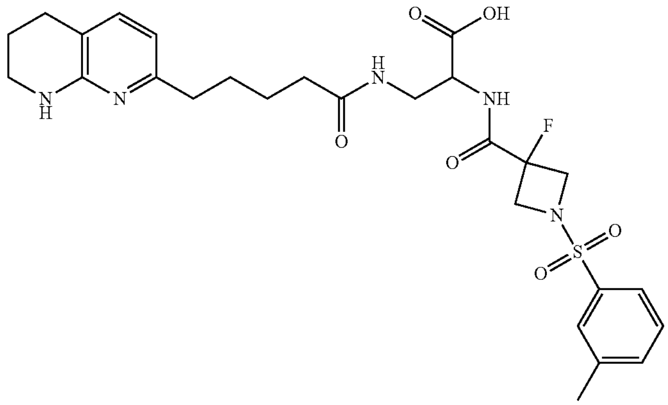

-continued
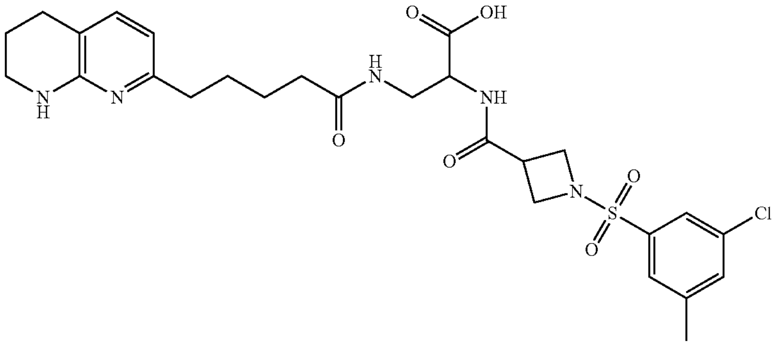
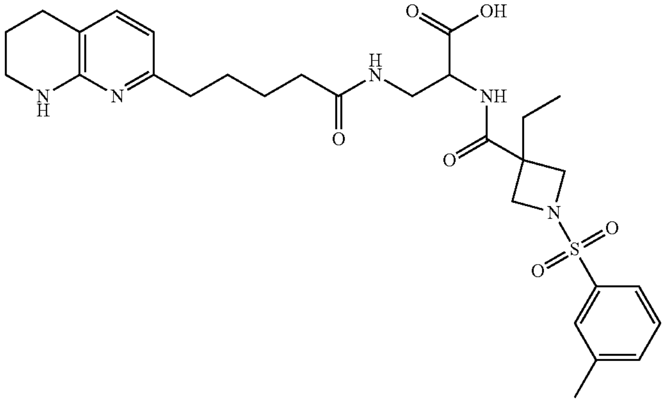
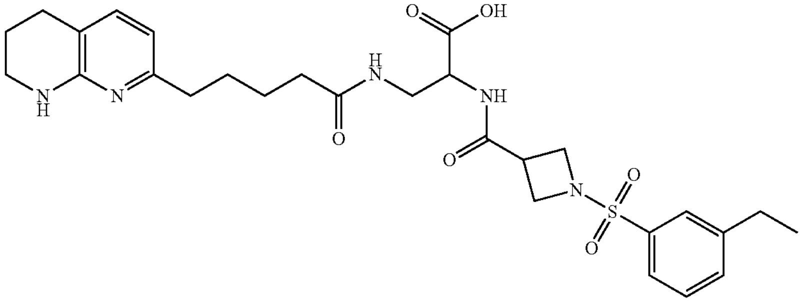
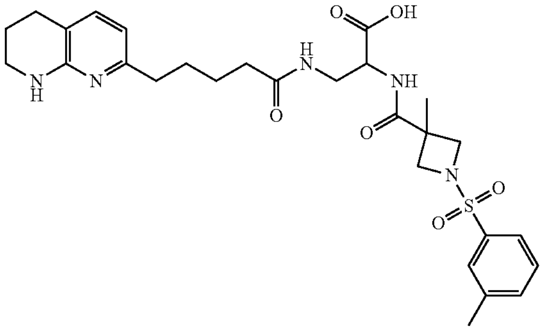
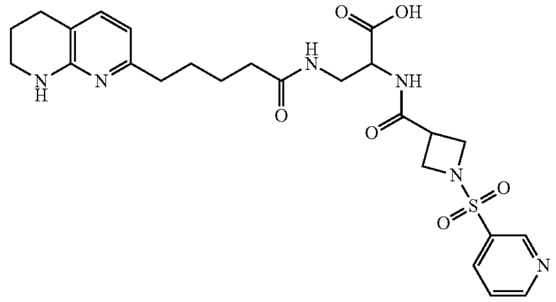
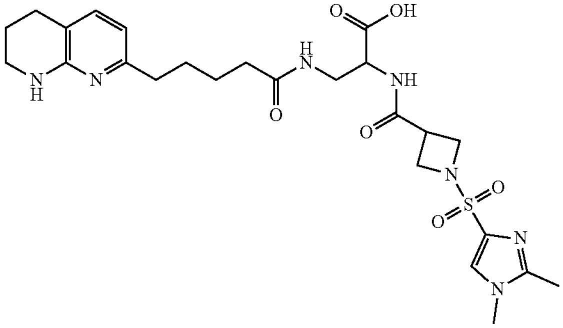
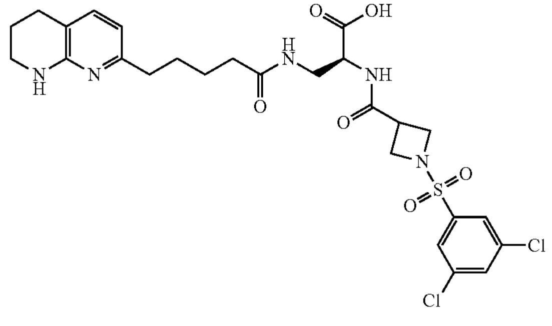

-continued
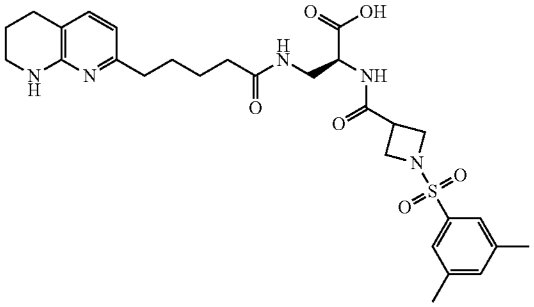
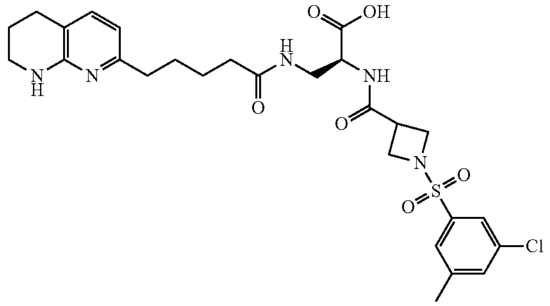
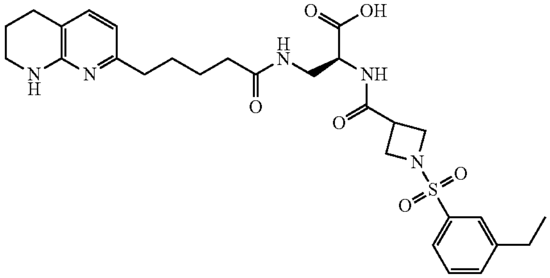
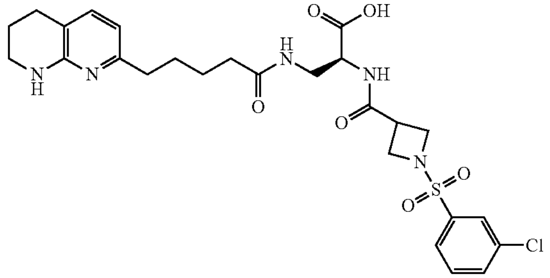
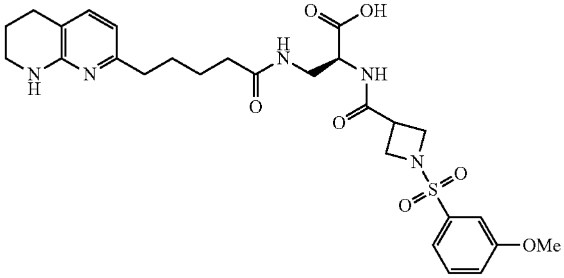
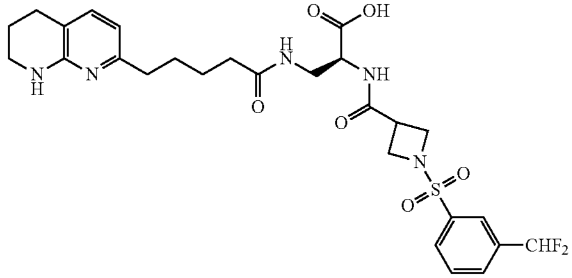
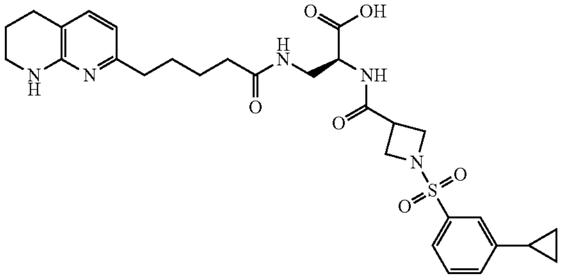
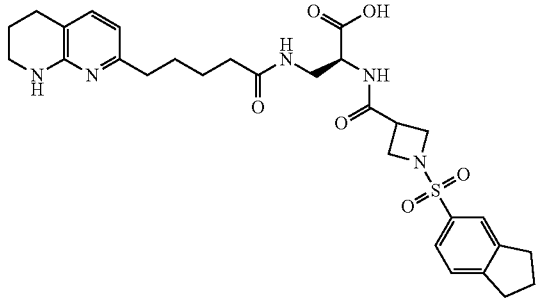
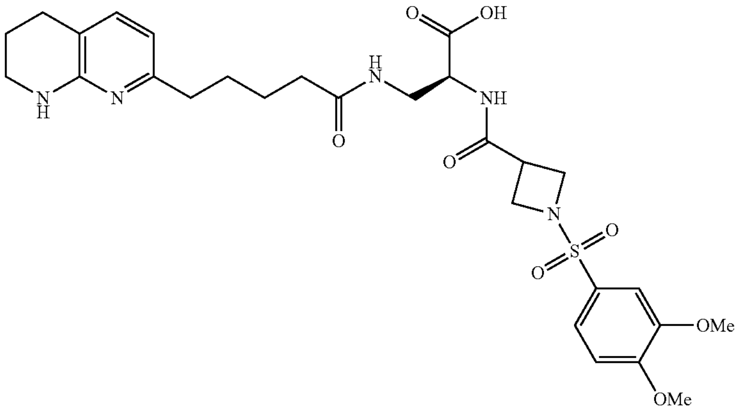

-continued
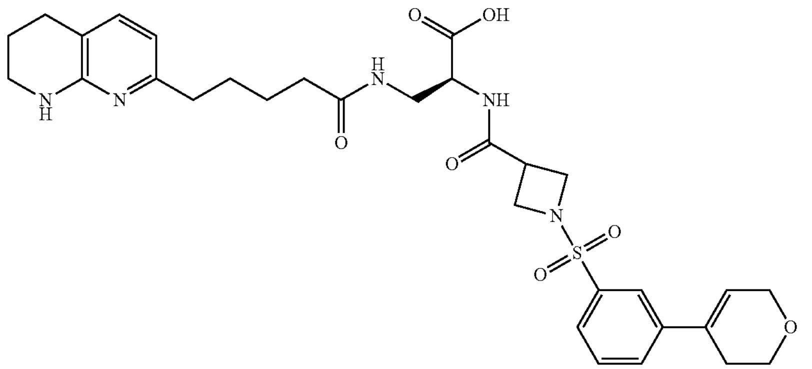
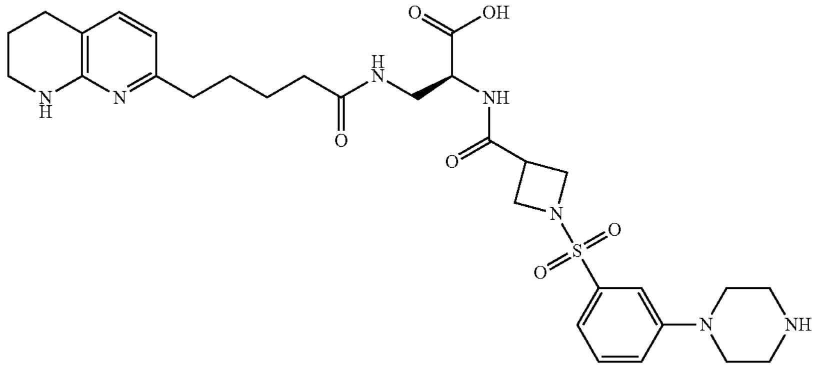
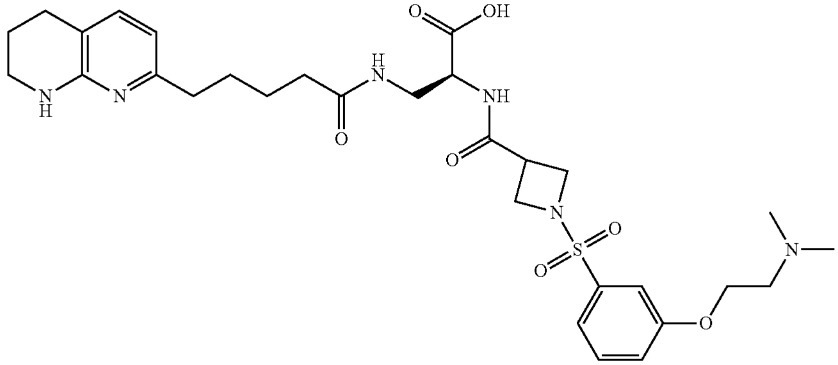
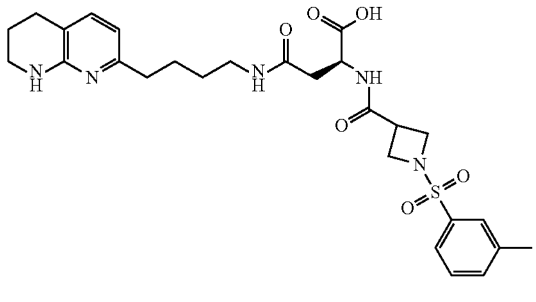
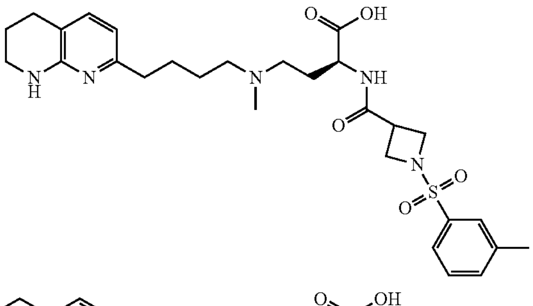
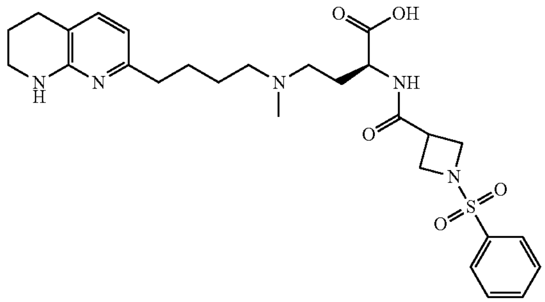
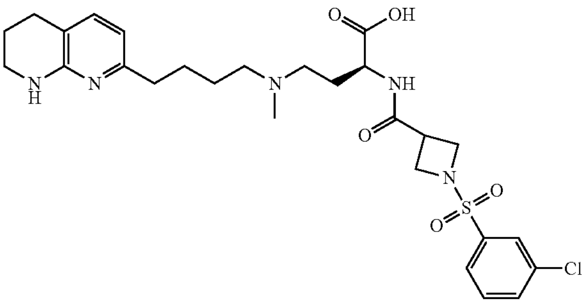

-continued
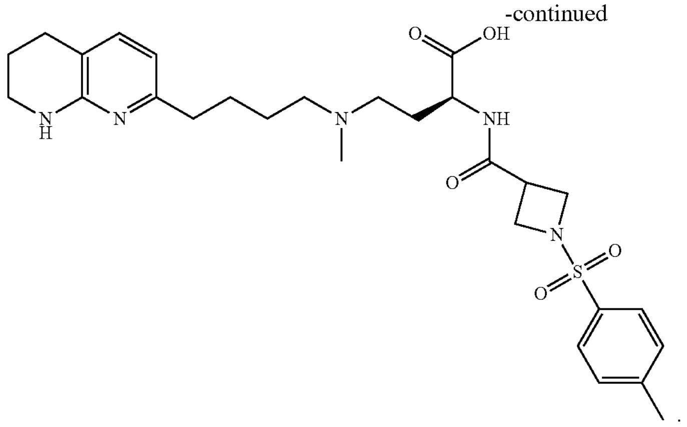
10. The compound according to claim 1 selected from:
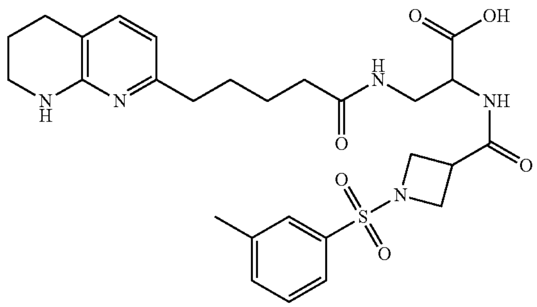
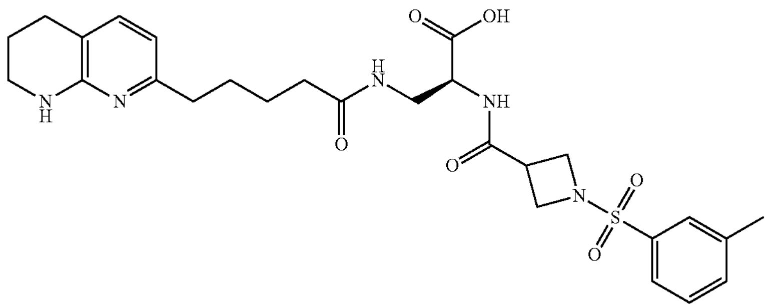
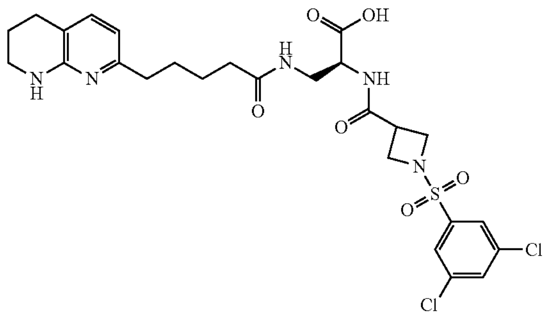
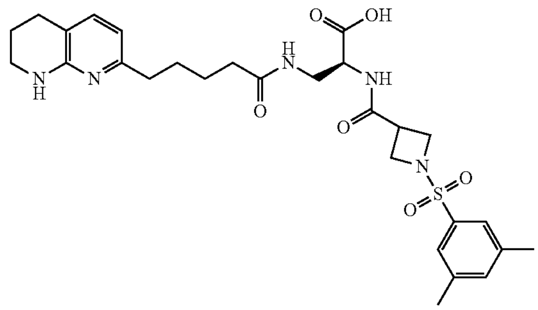

-continued
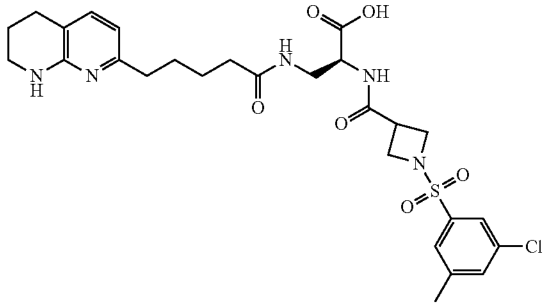
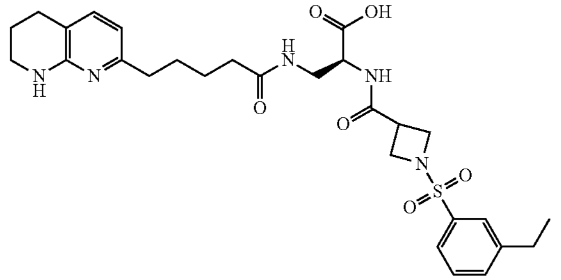
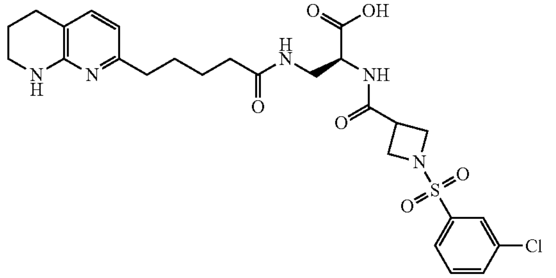
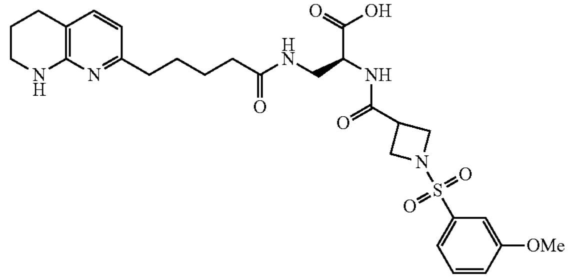
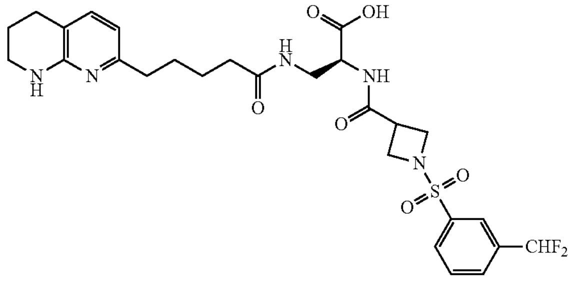
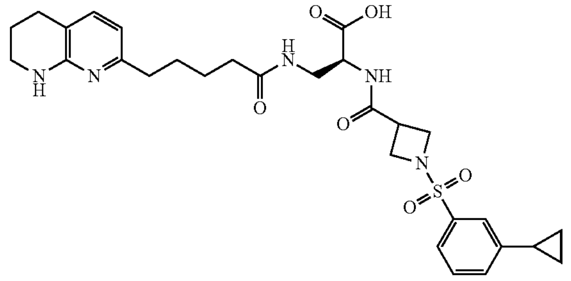
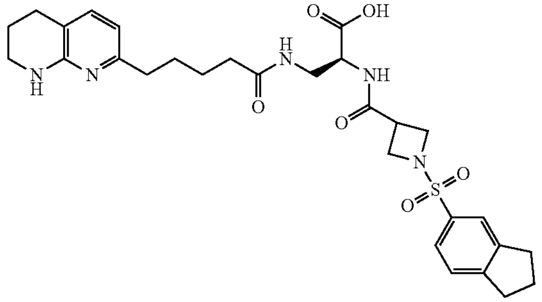
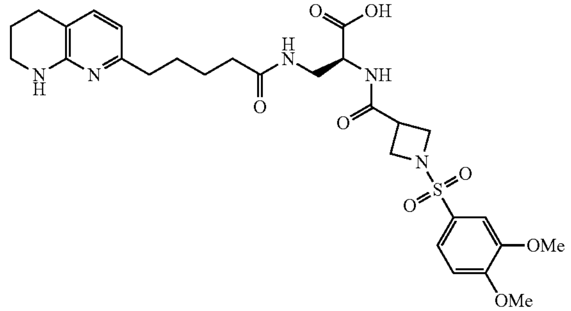
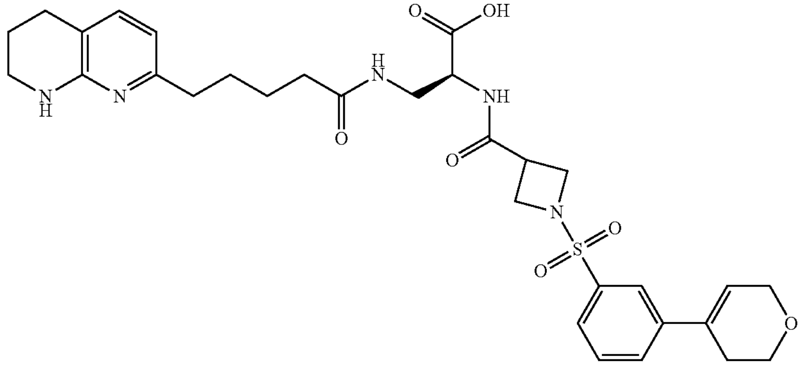

-continued
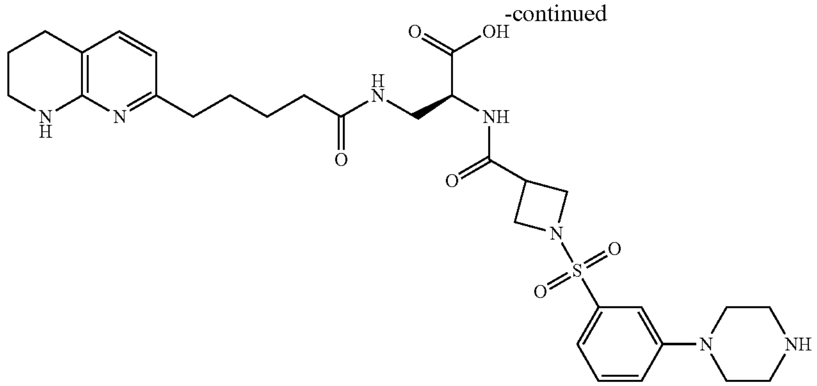
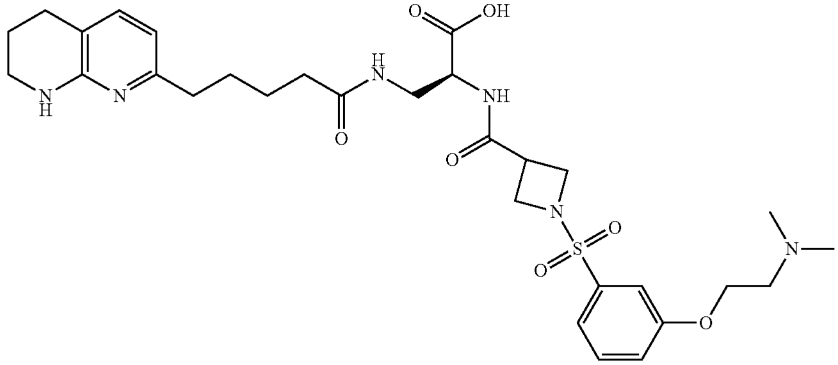
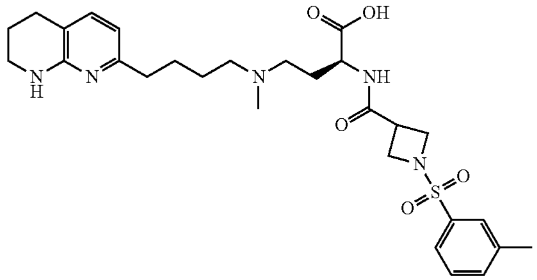
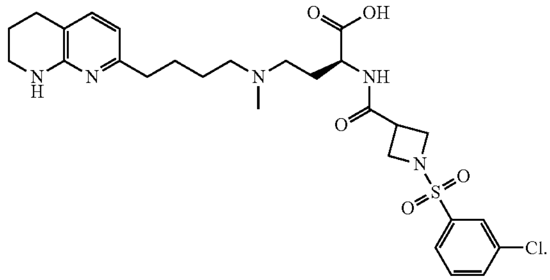
11. The compound according to claim 1, wherein the compound is (S)-3-(5-(5,6,7,8-Tetrahydro-1,8-naphthyridin-2-yl)pentanamido)-2-(1-(3-methylbenzenesulfonyl)azetidine-3-carboxamido)pentanoic acid.
* * * * *